(12) United States Patent
Zhang et al.

(10) Patent No.: US 9,121,007 B2
(45) Date of Patent: Sep. 1, 2015

(54) TREATMENT OF BONE-RELATED CANCERS USING PLACENTAL STEM CELLS

(75) Inventors: Xiaokui Zhang, Livingston, NJ (US); Shmuel Yaccoby, Little Rock, AR (US); Sascha Abramson, Hillsborough, NJ (US); Robert J. Hariri, Bernardsville, NJ (US)

(73) Assignee: ANTHROGENESIS CORPORATIN, Warren, NJ (US)

( * ) Notice: Subject to any disclaimer, the term of this patent is extended or adjusted under 35 U.S.C. 154(b) by 181 days.

(21) Appl. No.: 13/013,721

(22) Filed: Jan. 25, 2011

(65) Prior Publication Data
US 2011/0206645 A1 Aug. 25, 2011

Related U.S. Application Data

(60) Provisional application No. 61/298,517, filed on Jan. 26, 2010, provisional application No. 61/307,821, filed on Feb. 24, 2010, provisional application No. 61/352,768, filed on Jun. 8, 2010.

(51) Int. Cl.
*A01N 63/00* (2006.01)
*C12N 5/073* (2010.01)
*A61K 31/4545* (2006.01)
*A61K 35/50* (2015.01)
*A61K 35/12* (2015.01)

(52) U.S. Cl.
CPC .......... *C12N 5/0605* (2013.01); *A61K 31/4545* (2013.01); *A61K 35/50* (2013.01); *A61K 35/12* (2013.01); *C12N 2502/025* (2013.01); *C12N 2502/1142* (2013.01); *C12N 2502/30* (2013.01)

(58) Field of Classification Search
CPC ..................................................... A01N 63/00
USPC ........................................................ 424/93.7
See application file for complete search history.

(56) References Cited

U.S. PATENT DOCUMENTS

| | | |
|---|---|---|
| 3,862,002 A | 1/1975 | Sanders |
| 4,829,000 A | 5/1989 | Kleinman et al. |
| 5,004,681 A | 4/1991 | Boyse et al. |
| 5,192,553 A | 3/1993 | Boyse et al. |
| 5,197,985 A | 3/1993 | Caplan et al. |
| 5,226,914 A | 7/1993 | Caplan et al. |
| 5,272,071 A | 12/1993 | Chappel |
| 5,284,766 A | 2/1994 | Okano et al. |
| 5,372,581 A | 12/1994 | Anderson |
| 5,385,901 A | 1/1995 | Kaplan |
| 5,415,665 A | 5/1995 | Hessel et al. |
| 5,437,994 A | 8/1995 | Emerson et al. |
| 5,443,950 A | 8/1995 | Naughton et al. |
| 5,460,964 A | 10/1995 | McGlave et al. |
| 5,464,764 A | 11/1995 | Capecchi et al. |
| 5,487,992 A | 1/1996 | Capecchi et al. |
| 5,516,532 A | 5/1996 | Atala et al. |
| 5,580,777 A | 12/1996 | Bernard |
| 5,591,625 A | 1/1997 | Gerson et al. |
| 5,605,822 A | 2/1997 | Emerson et al. |
| 5,627,059 A | 5/1997 | Capecchi et al. |
| 5,635,386 A | 6/1997 | Palsson et al. |
| 5,643,741 A | 7/1997 | Tsukamoto et al. |
| 5,646,043 A | 7/1997 | Emerson et al. |
| 5,654,186 A | 8/1997 | Cerami et al. |
| 5,654,381 A | 8/1997 | Hrkach et al. |
| 5,665,557 A | 9/1997 | Murray et al. |
| 5,668,104 A | 9/1997 | Nakahata et al. |
| 5,670,147 A | 9/1997 | Emerson et al. |
| 5,670,351 A | 9/1997 | Emerson et al. |
| 5,672,346 A | 9/1997 | Srour et al. |
| 5,677,139 A | 10/1997 | Johnson |
| 5,709,854 A | 1/1998 | Griffith-Cima et al. |
| 5,716,616 A | 2/1998 | Prockop et al. |
| 5,716,794 A | 2/1998 | Tjota et al. |
| 5,716,827 A | 2/1998 | Tsukamoto |
| 5,733,541 A | 3/1998 | Taichman et al. |
| 5,733,542 A | 3/1998 | Haynesworth et al. |
| 5,736,396 A | 4/1998 | Bruder et al. |
| 5,744,361 A | 4/1998 | Hoffman et al. |
| 5,750,397 A | 5/1998 | Tsukamoto et al. |
| 5,763,197 A | 6/1998 | Tsukamoto et al. |
| 5,763,266 A | 6/1998 | Palsson et al. |
| 5,807,686 A | 9/1998 | Wagner et al. |
| 5,811,094 A | 9/1998 | Caplan et al. |
| 5,827,735 A | 10/1998 | Young et al. |
| 5,827,740 A | 10/1998 | Pittenger |
| 5,827,742 A | 10/1998 | Scadden |

(Continued)

FOREIGN PATENT DOCUMENTS

| | | |
|---|---|---|
| CN | 1407088 | 4/2003 |
| CN | 1548529 | 5/2003 |

(Continued)

OTHER PUBLICATIONS

U.S. Appl. No. 13/340,528, filed Dec. 29, 2011, Abramson.
U.S. Appl. No. 13/340,550, filed Dec. 29, 2011, Abramson et al.
U.S. Appl. No. 13/340,557, filed Dec. 29, 2011, Abramson et al.
U.S. Appl. No. 13/340,589, filed Dec. 29, 2011, Abbot et al.
U.S. Appl. No. 13/473,509, filed May 16, 2012, Edinger et al.
U.S. Appl. No. 13/480,370, filed May 24, 2012, Edinger et al.
U.S. Appl. No. 13/485,161, filed May 31, 2012, Herzberg et al.
Abkowitz, "Can Human Hematopoietic Stem Cells Become Skin, Gut, or Liver Cells?" N. Engl. J. Med. 346(10):770-2 (2002).
Aboagye-Mathiesen et al., "Isolation and Characterization of Human Placental Trophoblast Subpopulations from First-Trimester Chorionic Villi," Clinical and Diagnostic Laboratory Immunology 3(1):14-22 (1996).

(Continued)

*Primary Examiner* — Karen Cochrane Carlson
*Assistant Examiner* — Natalie Moss
(74) *Attorney, Agent, or Firm* — Jones Day

(57) ABSTRACT

Provided herein are methods of suppression of proliferation and growth of cells of bone-related cancers, e.g., multiple myeloma or chondrosarcoma cells, using placental cells, e.g., the placental stem cells described herein, and populations of such placental cells. Also provided herein are methods of treating individuals having cells of a bone-related cancer.

10 Claims, 17 Drawing Sheets

(56) References Cited

U.S. PATENT DOCUMENTS

Figure 1:
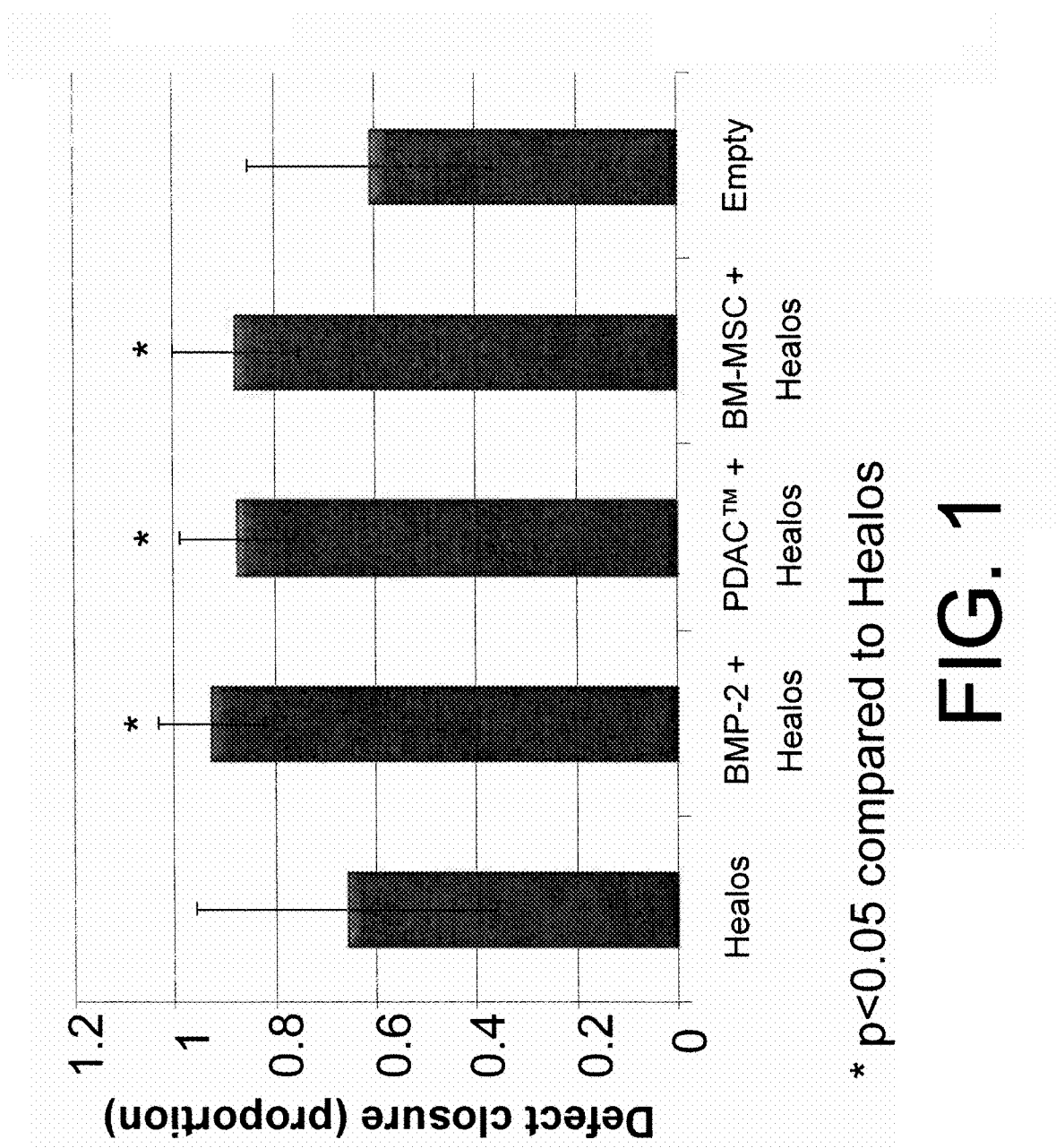

| | | | |
|---|---|---|---|
| 5,837,539 A | 11/1998 | Caplan et al. | |
| 5,849,553 A | 12/1998 | Anderson et al. | |
| 5,851,984 A | 12/1998 | Matthews et al. | |
| 5,855,619 A | 1/1999 | Caplan et al. | |
| 5,858,782 A | 1/1999 | Long et al. | |
| 5,866,414 A | 2/1999 | Badylak et al. | |
| 5,874,301 A | 2/1999 | Keller et al. | |
| 5,877,299 A | 3/1999 | Thomas et al. | |
| 5,879,318 A | 3/1999 | Van Der Heiden et al. | |
| 5,879,940 A | 3/1999 | Torok-Storb et al. | |
| 5,902,741 A | 5/1999 | Purchio et al. | |
| 5,905,041 A | 5/1999 | Beug et al. | |
| 5,906,934 A | 5/1999 | Grande et al. | |
| 5,908,782 A | 6/1999 | Marshak et al. | |
| 5,908,784 A | 6/1999 | Johnstone et al. | |
| 5,914,108 A | 6/1999 | Tsukamoto et al. | |
| 5,914,268 A | 6/1999 | Keller et al. | |
| 5,916,202 A | 6/1999 | Haswell | |
| 5,919,176 A | 7/1999 | Kuypers et al. | |
| 5,919,702 A | 7/1999 | Purchio et al. | |
| 5,922,597 A | 7/1999 | Varfaille et al. | |
| 5,925,567 A | 7/1999 | Kraus et al. | |
| 5,928,214 A | 7/1999 | Rubinstein et al. | |
| 5,928,947 A | 7/1999 | Anderson et al. | |
| 5,942,225 A | 8/1999 | Bruder et al. | |
| 5,942,496 A | 8/1999 | Bonadio et al. | |
| 5,958,767 A | 9/1999 | Snyder et al. | |
| 5,962,325 A | 10/1999 | Naughton et al. | |
| 5,968,829 A | 10/1999 | Carpenter | |
| 5,969,105 A | 10/1999 | Feng et al. | |
| 5,993,429 A | 11/1999 | Kuypers et al. | |
| 5,997,860 A | 12/1999 | Bauer et al. | |
| 6,001,654 A | 12/1999 | Anderson et al. | |
| 6,010,696 A | 1/2000 | Caplan et al. | |
| 6,011,000 A | 1/2000 | Faller et al. | |
| 6,020,469 A | 2/2000 | Hershenson | |
| 6,022,540 A | 2/2000 | Bruder et al. | |
| 6,022,743 A | 2/2000 | Naughton et al. | |
| 6,022,848 A | 2/2000 | Kozlov et al. | |
| 6,030,836 A | 2/2000 | Thiede | |
| 6,057,123 A | 5/2000 | Craig et al. | |
| 6,059,968 A | 5/2000 | Wolf, Jr. | |
| 6,077,708 A | 6/2000 | Collins et al. | |
| 6,087,113 A | 7/2000 | Caplan et al. | |
| 6,093,531 A | 7/2000 | Bjornson et al. | |
| 6,110,739 A | 8/2000 | Keller et al. | |
| 6,127,135 A | 10/2000 | Hill et al. | |
| 6,146,888 A | 11/2000 | Smith et al. | |
| 6,174,333 B1 | 1/2001 | Kadiyala et al. | |
| 6,179,819 B1 | 1/2001 | Haswel | |
| 6,184,035 B1 | 2/2001 | Csete et al. | |
| 6,190,368 B1 | 2/2001 | Kuypers et al. | |
| 6,214,369 B1 | 4/2001 | Grande et al. | |
| 6,224,860 B1 | 5/2001 | Brown | |
| 6,225,119 B1 | 5/2001 | Qasba et al. | |
| 6,227,202 B1 | 5/2001 | Matapurkar | |
| 6,231,880 B1 | 5/2001 | Perrine | |
| 6,239,157 B1 | 5/2001 | Mbalaviele et al. | |
| 6,248,587 B1 | 6/2001 | Rodgers et al. | |
| 6,251,383 B1 | 6/2001 | Upadhyay et al. | |
| 6,255,112 B1 | 7/2001 | Thiede et al. | |
| 6,280,718 B1 | 8/2001 | Kaufman et al. | |
| 6,281,012 B1 | 8/2001 | McIntosh et al. | |
| 6,291,240 B1 | 9/2001 | Mansbridge | |
| 6,300,314 B1 | 10/2001 | Wallner et al. | |
| 6,306,575 B1 | 10/2001 | Thomas et al. | |
| 6,312,950 B1 | 11/2001 | Ohmura et al. | |
| 6,322,784 B1 | 11/2001 | Pittenger et al. | |
| 6,326,019 B1 | 12/2001 | Tseng | |
| 6,326,198 B1 | 12/2001 | Emerson et al. | |
| 6,328,765 B1 | 12/2001 | Hardwick et al. | |
| 6,328,960 B1 | 12/2001 | McIntosh et al. | |
| 6,333,029 B1 | 12/2001 | Vyakamam et al. | |
| 6,335,195 B1 | 1/2002 | Rodgers et al. | |
| 6,337,387 B1 | 1/2002 | Sakano et al. | |
| 6,338,942 B2 | 1/2002 | Kraus et al. | |
| 6,355,239 B1 | 3/2002 | Bruder et al. | |
| 6,368,636 B1 | 4/2002 | McIntosh et al. | |
| 6,379,953 B1 | 4/2002 | Bruder et al. | |
| 6,387,367 B1 | 5/2002 | Davis-Sproul et al. | |
| 6,387,369 B1 | 5/2002 | Pittenger et al. | |
| 6,461,645 B1 | 10/2002 | Boyse et al. | |
| 6,497,875 B1 | 12/2002 | Sorrell et al. | |
| 6,534,084 B1 | 3/2003 | Vyakamam et al. | |
| 6,541,024 B1 | 4/2003 | Kadiyala et al. | |
| 6,548,299 B1 | 4/2003 | Pykett | |
| 6,685,936 B2 | 2/2004 | McIntosh et al. | |
| 6,709,864 B1 | 3/2004 | Pittenger et al. | |
| 6,797,269 B2 | 9/2004 | Mosca et al. | |
| 6,835,377 B2 | 12/2004 | Goldberg et al. | |
| 6,863,900 B2 | 3/2005 | Kadiyala et al. | |
| 6,875,430 B2 | 4/2005 | McIntosh et al. | |
| 6,875,607 B1 | 4/2005 | Reubinoff et al. | |
| 6,916,655 B2 | 7/2005 | Yasumoto | |
| 7,029,666 B2 | 4/2006 | Bruder et al. | |
| 7,045,148 B2 | 5/2006 | Hariri | |
| 7,091,353 B2 | 8/2006 | Robarge et al. | |
| 7,147,626 B2 | 12/2006 | Goodman et al. | |
| 7,244,759 B2 | 7/2007 | Muller et al. | |
| 7,255,879 B2 | 8/2007 | Hariri | |
| 7,311,904 B2 | 12/2007 | Hariri | |
| 7,311,905 B2 | 12/2007 | Hariri | |
| 7,468,276 B2 | 12/2008 | Hariri | |
| 7,498,171 B2 | 3/2009 | Hariri et al. | |
| 7,638,141 B2 | 12/2009 | Hariri | |
| 7,642,091 B2 | 1/2010 | Lee et al. | |
| 7,682,803 B2 | 3/2010 | Paludan et al. | |
| 7,700,090 B2 | 4/2010 | Heidaran et al. | |
| 7,909,806 B2 | 3/2011 | Goodman | |
| 7,914,779 B2 | 3/2011 | Hariri | |
| 7,928,280 B2 | 4/2011 | Hariri et al. | |
| 7,976,836 B2 | 7/2011 | Hariri | |
| 7,993,918 B2 * | 8/2011 | Paludan et al. | 435/375 |
| 8,057,788 B2 | 11/2011 | Hariri | |
| 8,057,789 B2 | 11/2011 | Hariri | |
| 8,071,135 B2 | 12/2011 | Liu et al. | |
| 8,071,376 B2 | 12/2011 | Heidaran | |
| 8,105,634 B2 | 1/2012 | Liu et al. | |
| 8,562,973 B2 * | 10/2013 | Edinger et al. | 424/93.7 |
| 2001/0005591 A1 | 6/2001 | Qasba et al. | |
| 2001/0038836 A1 | 11/2001 | During et al. | |
| 2002/0102239 A1 | 8/2002 | Koopmans | |
| 2002/0123141 A1 | 9/2002 | Hariri | |
| 2002/0132343 A1 | 9/2002 | Lum | |
| 2002/0160510 A1 | 10/2002 | Hariri | |
| 2003/0007954 A1 | 1/2003 | Naughton et al. | |
| 2003/0032179 A1 | 2/2003 | Hariri | |
| 2003/0044977 A1 | 3/2003 | Sakuragawa et al. | |
| 2003/0045552 A1 | 3/2003 | Robarge et al. | |
| 2003/0096841 A1 | 5/2003 | Robarge et al. | |
| 2003/0161818 A1 | 8/2003 | Weiss et al. | |
| 2003/0180269 A1 | 9/2003 | Hariri | |
| 2003/0187515 A1 | 10/2003 | Hariri | |
| 2003/0235563 A1 | 12/2003 | Strom et al. | |
| 2003/0235909 A1 | 12/2003 | Hariri | |
| 2004/0018617 A1 | 1/2004 | Hwang | |
| 2004/0028660 A1 | 2/2004 | Hariri et al. | |
| 2004/0048372 A1 | 3/2004 | Hariri | |
| 2004/0048796 A1 | 3/2004 | Hariri et al. | |
| 2004/0107453 A1 | 6/2004 | Furcht et al. | |
| 2004/0136967 A1 | 7/2004 | Weiss et al. | |
| 2004/0161419 A1 | 8/2004 | Strom et al. | |
| 2004/0171147 A1 | 9/2004 | Hariri | |
| 2004/0180040 A1 | 9/2004 | Phillips et al. | |
| 2004/0219136 A1 | 11/2004 | Hariri | |
| 2004/0229351 A1 | 11/2004 | Rodriguez et al. | |
| 2004/0241144 A1 | 12/2004 | Kaps et al. | |
| 2005/0019865 A1 | 1/2005 | Kihm et al. | |
| 2005/0019908 A1 | 1/2005 | Hariri | |
| 2005/0032209 A1 | 2/2005 | Messina et al. | |
| 2005/0037491 A1 | 2/2005 | Mistry et al. | |
| 2005/0042595 A1 | 2/2005 | Haas | |
| 2005/0054093 A1 | 3/2005 | Haas | |
| 2005/0054098 A1 | 3/2005 | Mistry et al. | |

(56) References Cited

U.S. PATENT DOCUMENTS

| | | |
|---|---|---|
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0085543 A1 | 4/2005 | Wallimann et al. |
| 2005/0089513 A1 | 4/2005 | Sakuragawa et al. |
| 2005/0112104 A1 | 5/2005 | Pittenger et al. |
| 2005/0118712 A1 | 6/2005 | Tsai et al. |
| 2005/0118715 A1 | 6/2005 | Hariri et al. |
| 2005/0124003 A1 | 6/2005 | Atala et al. |
| 2005/0143420 A1 | 6/2005 | Moutouh-de Parseval et al. |
| 2005/0148034 A1 | 7/2005 | Hariri et al. |
| 2005/0148074 A1 | 7/2005 | Davies et al. |
| 2005/0176139 A1 | 8/2005 | Chen et al. |
| 2005/0181502 A1 | 8/2005 | Furcht et al. |
| 2005/0186182 A1 | 8/2005 | Deisher et al. |
| 2005/0233452 A1 | 10/2005 | Ho et al. |
| 2005/0239897 A1 | 10/2005 | Pittenger et al. |
| 2005/0266391 A1 | 12/2005 | Bennett et al. |
| 2005/0272148 A1 | 12/2005 | Hariri |
| 2005/0276792 A1 | 12/2005 | Kaminski et al. |
| 2005/0282272 A1 | 12/2005 | Bhatia et al. |
| 2005/0283844 A1 | 12/2005 | Furcht et al. |
| 2006/0008450 A1 | 1/2006 | Verfaillie et al. |
| 2006/0024280 A1 | 2/2006 | West |
| 2006/0060494 A1 | 3/2006 | Goodman et al. |
| 2006/0078993 A1 | 4/2006 | Phan et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0222634 A1 | 10/2006 | Clarke et al. |
| 2006/0223177 A1 | 10/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2006/0263337 A1 | 11/2006 | Maziarz et al. |
| 2006/0281178 A1 | 12/2006 | Sakuragaw et al. |
| 2007/0009494 A1 | 1/2007 | Mistry et al. |
| 2007/0014771 A1 | 1/2007 | Mistry et al. |
| 2007/0020225 A1 | 1/2007 | Abramson et al. |
| 2007/0021704 A1 | 1/2007 | Hariri et al. |
| 2007/0021762 A1 | 1/2007 | Liu et al. |
| 2007/0031384 A1 | 2/2007 | Atala et al. |
| 2007/0036767 A1 | 2/2007 | Mistry et al. |
| 2007/0038298 A1 | 2/2007 | Sulner et al. |
| 2007/0041954 A1 | 2/2007 | Ichim |
| 2007/0043328 A1 | 2/2007 | Goodman et al. |
| 2007/0053888 A1 | 3/2007 | Hariri |
| 2007/0092497 A1 | 4/2007 | Hariri |
| 2007/0092967 A1 | 4/2007 | Han et al. |
| 2007/0116682 A1 | 5/2007 | Atala et al. |
| 2007/0122903 A1 | 5/2007 | Rezania et al. |
| 2007/0134210 A1 | 6/2007 | Heidaran |
| 2007/0141700 A1 | 6/2007 | Harmon |
| 2007/0160588 A1 | 7/2007 | Kihm |
| 2007/0190034 A1 | 8/2007 | Paludan et al. |
| 2007/0190042 A1 | 8/2007 | Edinger et al. |
| 2007/0190649 A1 | 8/2007 | Gage |
| 2007/0253931 A1 | 11/2007 | Varney et al. |
| 2007/0264269 A1 | 11/2007 | Harmon et al. |
| 2007/0275362 A1 | 11/2007 | Edinger et al. |
| 2007/0287176 A1 | 12/2007 | Rezania |
| 2007/0292399 A1 | 12/2007 | Heidaran et al. |
| 2007/0292910 A1 | 12/2007 | Heidaran et al. |
| 2008/0032401 A1* | 2/2008 | Edinger et al. ............... 435/366 |
| 2008/0044848 A1 | 2/2008 | Heidaran |
| 2008/0069895 A1 | 3/2008 | Liu et al. |
| 2008/0131410 A1 | 6/2008 | Hariri |
| 2008/0131522 A1 | 6/2008 | Liu et al. |
| 2008/0131966 A1 | 6/2008 | Hariri |
| 2008/0145934 A1 | 6/2008 | Harris et al. |
| 2008/0152624 A1* | 6/2008 | Paludan et al. ............... 424/93.7 |
| 2008/0152629 A1 | 6/2008 | Edinger et al. |
| 2008/0166328 A1 | 7/2008 | Harmon et al. |
| 2008/0175824 A1 | 7/2008 | Heidaran et al. |
| 2008/0181935 A1 | 7/2008 | Bhatia et al. |
| 2008/0181967 A1 | 7/2008 | Liu et al. |
| 2008/0206343 A1 | 8/2008 | Edinger et al. |
| 2008/0208158 A1 | 8/2008 | Goodman et al. |
| 2008/0213227 A1 | 9/2008 | Aggarwal et al. |
| 2008/0213228 A1* | 9/2008 | Edinger et al. ............... 424/93.7 |
| 2008/0226595 A1 | 9/2008 | Edinger et al. |
| 2009/0053805 A1 | 2/2009 | Hariri |
| 2009/0104164 A1 | 4/2009 | Zhang et al. |
| 2009/0136471 A1 | 5/2009 | Heidaran et al. |
| 2009/0142831 A1 | 6/2009 | Hariri |
| 2009/0226406 A1 | 9/2009 | Hariri |
| 2009/0252710 A1 | 10/2009 | Zhang et al. |
| 2009/0263361 A1 | 10/2009 | Lee et al. |
| 2010/0047213 A1 | 2/2010 | Zeitlin et al. |
| 2010/0047214 A1 | 2/2010 | Abramson et al. |
| 2010/0047351 A1 | 2/2010 | Zeitlin et al. |
| 2010/0120015 A1 | 5/2010 | Hariri |
| 2010/0124569 A1 | 5/2010 | Abbot |
| 2010/0143312 A1 | 6/2010 | Hariri |
| 2010/0172830 A1 | 7/2010 | Heidaran |
| 2010/0183571 A1 | 7/2010 | Paludan et al. |
| 2010/0260847 A1 | 10/2010 | Hariri |
| 2010/0291679 A1 | 11/2010 | Edinger et al. |
| 2010/0297689 A1 | 11/2010 | Edinger et al. |
| 2010/0323446 A1 | 12/2010 | Barnett |
| 2011/0003387 A1 | 1/2011 | Abbot et al. |
| 2011/0206645 A1 | 8/2011 | Zhang et al. |
| 2011/0217271 A1 | 9/2011 | Hariri |
| 2011/0217272 A1 | 9/2011 | Hariri |
| 2011/0223141 A1 | 9/2011 | Hariri |
| 2011/0250182 A1 | 10/2011 | Abbot |
| 2011/0250185 A1 | 10/2011 | Paludan et al. |
| 2011/0280843 A1 | 11/2011 | Edinger et al. |
| 2011/0280845 A1 | 11/2011 | Edinger et al. |
| 2011/0280849 A1 | 11/2011 | Zhang et al. |
| 2011/0311491 A1 | 12/2011 | Edinger et al. |
| 2011/0318401 A1 | 12/2011 | Hariri et al. |
| 2012/0020936 A1 | 1/2012 | Hariri |
| 2012/0034195 A1 | 2/2012 | Hariri |
| 2012/0058089 A1 | 3/2012 | Hariri |
| 2012/0121550 A1 | 5/2012 | Heidaran |
| 2012/0148553 A1 | 6/2012 | Hariri et al. |

FOREIGN PATENT DOCUMENTS

| | | |
|---|---|---|
| CN | 1786154 | 6/2006 |
| EP | 0333328 | 9/1989 |
| EP | 0529751 | 3/1993 |
| EP | 0552380 | 7/1993 |
| EP | 1264877 | 12/2002 |
| EP | 1288293 A1 | 3/2003 |
| EP | 1384775 A1 | 1/2004 |
| EP | 1405649 | 4/2004 |
| EP | 1535994 | 6/2005 |
| EP | 1775341 | 4/2007 |
| JP | 2003235549 | 12/2002 |
| JP | 2005151907 | 11/2003 |
| WO | WO 90/11354 | 10/1990 |
| WO | WO 91/01140 | 2/1991 |
| WO | WO 91/06667 | 5/1991 |
| WO | WO 93/04169 | 3/1993 |
| WO | WO 95/22611 | 8/1995 |
| WO | WO 96/34035 | 10/1996 |
| WO | WO 96/39101 | 12/1996 |
| WO | WO 98/37903 | 9/1998 |
| WO | WO 99/03973 | 1/1999 |
| WO | WO 99/64566 | 12/1999 |
| WO | WO 00/17325 | 3/2000 |
| WO | WO 00/27999 | 5/2000 |
| WO | WO 00/38762 | 7/2000 |
| WO | WO 00/73421 | 12/2000 |
| WO | WO 01/93909 | 12/2001 |
| WO | WO 02/46373 | 6/2002 |
| WO | WO 02/063962 | 8/2002 |

(56) References Cited

FOREIGN PATENT DOCUMENTS

| | | |
|---|---|---|
| WO | WO 02/064755 | 8/2002 |
| WO | WO 03/042405 | 5/2003 |
| WO | WO 03/068937 | 8/2003 |
| WO | WO 03/086373 | 10/2003 |
| WO | WO 03/087333 | 10/2003 |
| WO | WO 03/087392 | 10/2003 |
| WO | WO 03/089619 | 10/2003 |
| WO | WO 03/102151 | 12/2003 |
| WO | WO 2004/047770 | 6/2004 |
| WO | WO 2004/071283 | 8/2004 |
| WO | WO 2004/087896 | 10/2004 |
| WO | WO 2005/042703 | 5/2005 |
| WO | WO 2005/055929 | 6/2005 |
| WO | WO 2005/097190 | 10/2005 |
| WO | WO 2005/105992 | 11/2005 |
| WO | WO 2006/015214 | 2/2006 |
| WO | WO 2006/111706 | 10/2006 |
| WO | WO 2007/024441 | 3/2007 |
| WO | WO 2007/047465 | 4/2007 |
| WO | WO 2007/047468 | 4/2007 |
| WO | WO 2007/056578 | 5/2007 |
| WO | WO 2007/071048 | 6/2007 |
| WO | WO 2007/073552 | 6/2007 |
| WO | WO 2007/079183 | 7/2007 |
| WO | WO 2007/087293 | 8/2007 |
| WO | WO 2008/019148 | 2/2008 |
| WO | WO 2008/051568 | 5/2008 |
| WO | WO 2008/060541 | 5/2008 |
| WO | WO 2008/100497 | 8/2008 |
| WO | WO 2009/045360 | 4/2009 |
| WO | WO 2012/009422 | 1/2012 |

OTHER PUBLICATIONS

Addison, et al., "Metabolism of Prednisolone by the Isolated Perfused Human Placental Lobule," J. Ster. Biochem. Mol. Biol., 39(1):83-90 (1991).
Aggarwal, et al., "Human Mesenchymal Stem Cells Modulate Allogeneic Immune Cell Responses," Blood 105(4):1815-22 (2005).
Anker in'T P, et al., "Isolation of Mesenchymal Stem Cells of Fetal or Maternal Origin from Human Placenta," Stem Cells 22: 1338-45 (2004).
Aplin, "Implantation, trophoblast Differentiation and Haemochorial Placentation: Mechanistic Evidence in vivo and in vitro," Journal of Cell Science 99:681-692 (1991).
Ashihara, et al., "Successful Peripheral Blood Stem Cell Transplantation for Myelodysplastic Syndrome," Bone Marrow Transplantation 24(12): 1343-1345 (1999).
Bailo, et al., "Engraftment Potential of Human Amnion and Chorion Cells Derived from Term Placenta," Transplantation 78:1439-1448 (2004).
Ballin, et al., "Autologous Umbilical Cord Blood Transfusion," Arch. Dis. Child Fetal Neonatal. Ed. 73(3):F181-F183 (1995).
Barlogie et al., "High-dose therapy immunomodulatory drugs in multiple myeloma," *Seminars in Oncology*, 2002, 29 (6):26-33.
Barlow et al., "Comparison of Human Placenta- and Bone Marrow-Derived Multipotent Mesenchymal Stem Cells," Stem Cells and Development 17:1095-1108 (2008).
Barry et al., "The Monoclonal Antibody SH-2, Raised Against Human Mesenchymal Stem Cells, Recognizes an Epitope on Endoglin (CD105)," Osiris Therapeutics Inc., 2001 Aliceanna Street, Baltimore, MD 21231, Biochemical and Biophysical Research Communications 265:134-139 (1999).
Barry, "Where do all the placentas go?" Canadian Journal of Infection Control 9(1):8-10 (1994).
Battula et al., "Prospective Isolation and Characterization of Mesenchymal Stem Cells from Human Placenta Using a Firzzled-9-Specific Monoclonal Antibody," Differentiation 76:326-336 (2008).
Belvedere, et al., "Increased Blood Volume and CD34(+)CD38(-) Progenitor Cell Recovery Using a Novel Umbilical Cord Blood Collection System," Stem Cells 18(4):245-251 (2000).
Bloxam et al., "Culture of Syncytiotrophoblast for the Study of Human Placental Transfer. Part I: Isolation and Purification of Cytotrophoblast,"Placenta 18:93-98 (1997).
Bloxam, "Human Placental Trophoblast Culture: One-Sided and Two-Sided Models," Proceedings of the Nutrition Society 50:349-354 (1991).
Bullen et al., "Two-Sided Culture of Human Placental Trophoblast. Morphology, Immunocytochemistry and Permeability Properties," Placenta 11:431-450 (1990).
Campagnoli, et al., "Identification of Mesenchymal Stem/Progenitor Cells in Human First-Trimester Fetal Blood, Liver, and Bone Marrow." Blood 98(8):2396-402 (2001).
Caniggia et al., "Oxygen and Placental Development During the First Trimester: Implications for the Pathophysiology of Pre-Eclampsia," PubMed, Placenta 21(Suppl A):S25-30 (2000).
Caplan, "The Mesengenic Process," Clin. Plast. Surg. 21(3):429-435 (1994).
Carter, et al., "Characterization of MSC Potential to Treat GVHD Using Molecular Markers Linked to MSC-Mediated Immunosuppression in Vitro," Blood, 106(11) part 2, Abstract No. 4322,160B (2005).
Cester et al., "Cation Transport Across Cultured Trophoblast Membrane in Preeclampsia," Clin. and Exper. Hyper. In Pregnancy, B11(1):59-69 (1992).
Chang, et al., "Placenta-Derived Multipotent Cells Exhibit Immunosuppressive Properties That are Enhanced in the Presence of Interferon-gamma," Stem Cells 24:2466-2477 (2006).
Chao, et al., "Stem Cell Transplantation (Cord Blood Transplants)." American Society of Hematology p. 354-371 (2004).
Chen, et al. "Intravaneous Administration of Human Umbilical Cord Reduces Behavioral Deficits after Stroke in Rats," Stroke 32(11): 2682-2688 (2001).
Chen, et al., "The Potential for the Use of Mononuclear Cells from Human Umbilical Cord Blood in the Treatment of Amyotrophic Lateral Sclerosis is SOD1 Mice," J. Med. 31(1-2):21-30 (2000).
Chen, et al., "Therapeutic Benefit of Intravenous Administration of Bone Marrow Stromal Cells after Cerebral Ischemia in Rats," Stroke, 32(4):1005-11 (2001).
Chies et al., "Sickle Cell Disease: A Chronic Inflammatory Condition," Medical Hypotheses 57(1):46-50 (2001).
Chin, et al., "Enhanced Interferon Production and Lymphokine-Activated Cytotoxicity of Human Placental Cells," Cellular Immunology 113:1-9 (1988).
Clark, et al., "Placental Trophoblast from Successful Human Pregnancies Expresses the Tolerance Signaling Molecule, CD200 (OX-2)" Am. J. Reprod. Immunol., 50(3):187-195 (2003).
Contractor, et al., "A comparison of the effects of different perfusion regimens on the structure of the isolated human placental lobule," Cell Tissue Res. 237:609-617 (1984).
Cosma, et al., "Use and Application of Stem Cells in Toxicology," SOT 2003 Annual Meeting, p. 4, Abstract 19 (2003).
Cotte et al., "Preparation of Highly Purified Cytotrophoblast from Human Placenta with Subsequent Modulation to Form Syncytiotrophoblast in Monolayer Cultures," In Vitro 16(8):639-646 (1980).
Czarneski, et al., "Effects of Cord Blood Transfer on the Hematopoietic Recovery Following Sublethal Irradiation in MRL Ipr/Ipr Mice," Proc. Soc. Exp. Biol. Med. 220(2):79-87 (1999).
Database WPI Week 200357 Derwent Publications Ltd., London, GB, AN 2003-59905 & CN 1 407 888 A (Zhou S) Apr. 2, 2003.
Davani, et al., "Mesenchymal Progenitor Cells Differentiate into an Endothelial Phenotype, Enhance Vascular Density, and Improve Heart Function in a Rat Cellular Cardiomyoplasty Model," Circulation 108[suppl II]:II-253-II-258 (2003).
Davies, et al. "Thalidomide and Immunomodulatory Derivatives Augment Natural Killer Cell Cytotoxicity in Multiple Myeloma," Blood 98(1):210-216 (2001).
Davies, et al., "Engraftment and Survival After Unrelated-Donor Bone Marrow Transplantation: A Report from the National Marrow Donor Program," Blood, 96(13): 4096-4102, (2000).
Davila, et al., "Use and Application of Stem Cells in Toxicology," Toxicological Sciences 79:214-223 (2004).

(56) References Cited

OTHER PUBLICATIONS

De Coppi, et al., "Amniotic Fluid and Chorionic Villi Derived Human Stem Cells for the Engineering of Tissues in Vivo." The Journal of Urology, vol. 171, No. 4, Supplement, Saturday, May 8, p. 21, Abstract 81 (2004).
De Coppi, et al., "Human Embryonic and Fetal Stem-Cell Isolation from Amniotic Fluid and Placenta for Tissue Reconstruction." Urology and Reproductive Surgery, vol. 195, No. 3S, Sep. 2002, p. S93.
De Coppi, et al., "Human fetal stem cell isolation from amniotic fluid for tissue reconstruction," J. Urology 167(4 Supp.) 85 (Abstract 338) (2002).
De Coppi, et al., "Pluripotent Stem Cells Derived from Human Chorionic Villi and Amniotic Fluid for Tissue Engineering Applications." Experimental Biology/IUPS Meeting Abstracts, A1366, Abstract 781.7 (2005).
De Filippo, et al., "Total Penile Urethra Replacement with Autologous Cell-Seeded Collagen Matrices." Urology and Reproductive Surgery, vol. 195, No. 3S, Sep. 2002, p. S95.
De Wynter, et al., "CD34+AC133+ Cells Isolated from Cord Blood are Highly Enriched in Long-Term Culture-Initiating Cells, NOD/SCID-Repopulating Cells and Dendritic Cell Progenitors," Stem Cells 16(6):387-396 (1998).
Dominici, et al., "Minimal Criteria for Defining Multipotent Mesenchymal Stromal Cells. The International Society for Cellular Therapy Position Statement," Cytotherapy 8(4):315-317 (2006).
Drake, et al., "Human Placental Cytotrophoblasts Attract Monocytes and CD56 (Bright) Natural Killer Cells Via the Actions of Monocyte Inflammatory Protein 1Alpha," J. Exp. Med. 193(10):1199-1212 (2001).
Dushnik-Levinson, et al. "Embryogenesis in vitro: study of differentiation of embryonic stem cells." Biol Neonate. 67(2):77-83 (1995).
Elchalal, et al., "Postpartum Umbilical Cord Blood Collection for Transplantation: a Comparison of Three Methods," Am. J. of Obstetrics & Gyn. 182(1 Pt 1):227-232 (2000).
Ende, "Berashis Cells in Human Umbilical Cord Blood Vs. Embryonic Stem Cells," J. Med. 33(1-4):167-171 (2002).
Ende, "Collection of Umbilical Cord Blood for Transplantation," Blood 80(6):1623-1624 (1992).
Ende, "The Feasibility of Using Blood Bank Stored (4° C.) Cord Blood, Unmatched for HLA for Marrow Transplantation," Am. J. Clin. Pathol. 111:773-781 (1999).
Ende, et al., "Human Umbilical Cord Blood Cells Amerliorate Alzheimer's Disease in Transgenic Mice," J. Med. 32(3-4):241-7 (2001).
Ende, et al., "Human Umbilical Cord Blood Cells Ameliorate Huntington's Disease in Transgenic Mice," J. Med. 32(3-4):231-240 (2001).
Ende, et al., "Human Umbilical Cord Blood Effect on SOD Mice (Amyotrophic Lateral Sclerosis)," Life Sci. 67(1):53-59 (2001).
Ende, et al., "Parkinson's Disease Mice and Human Umbilical Cord Blood," Journal of Medicine 33(1-4):173-180 (2002).
Ende, et al., "Pooled Umbilical Cord Blood as a Possible Universal Donor for Marrow Reconstitution and Use in Nuclear Accidents," Life Sci. 69:1531-1539 (2001).
Ende, et al., "The Effect of Human Cord Blood on SJL/J Mice After Chemoablation and Irradiation and Its Possible Clinical Significance," Immunol. Invest. 24(6):999-1012 (1995).
Erices, et al., "Mesenchymal Progenitor Cells in Human Umbilical Cord Blood," Br. J. Haemotol. 109(1):235-242 Abstract (2000).
Evans, "Stem Cell Therapy: Moving towards Reality," Am. J. Obstet. Gynecol. 194:662-663 (2006).
Extended European Search Report dated Feb. 16, 2011 for EP Application No. 10184356.3-1222 (specification corresponding to U.S. Patent No. 7,311,905).
Extended European Search Report dated Jan. 21, 2011 for EP Application No. 10185142.6-1222 (specification corresponding to U.S. Patent No. 7,311,905).
Fasouliotis, et al., "Human umbilical cord blood banking and transplantation: a state of the art," Eur. J. Obstet. Gynecol. Reprod. Biol. 90(1):13-25 (2000).
Fisher et al., "Adhesive and Degradatie Properties of Human Placental Cytotrophoblast Cells In Vitro," Journal od Cell Biology 109:891-902 (1989).
Frank H G, et al., "Cell culture models of human trophoblast: primary culture of trophoblast—a workshop report." Placent Apr. 2001, vol. 22 Suppl A, pp. S107-S109, XP002443188 ISSN: 0143-4004 (Apr. 2001).
Genbacev et al., "Regulation of Human Placental Development by Oxygen Tension," 277(5332):1669-1672 (1997).
Gluckman, et al., "Cord Blood Heamatopoietic Stem Cells: Biology and Transplantation," In: Hematology, American Society of Hematology Education Program Book (1998) p. 1-14.
Gluckman, et al., "Results of Unrelated Umbilical Cord Blood Hematipoeietic Stem Cell Transplant," Transfusion Cinique et Biologique 8(3):146-154 (2001).
Greenwood et al., "Membrane Potential Difference and Intracellular Cation Concentrations in Human Placental Trophoblast Cells in Culture," Journal of Physiology 492.3:629-640 (1996).
Hadjantonakis, et al., "The Stem Cells of Early Embryos," Differentiation 68:159-166 (2001).
Hamada, et al., "Mesenchymal Stem Cells (MSC) as Therapeutic Cytoreagents for Gene Therapy," Cancer Sci 96:149-156 (2005).
Harbacheuski, et al., "Placenta Derived Adherent Cells (PDACs) Supress Tumor Cells of Diverse Origin." Blood 108(11):288 (2006).
Harun et al., "Cytotrophoblast Stem Cell Lines Derived from Human Embyonic Stem Cells and Their Capacityt o Mimic Invasive Implantation Events," Human Reproduction, Oxford University Press, pp. 1-10 (2006).
Hattori et al., "Molecular Cloning of Adipocyte-Derived Leucine Aminopeptidase Highly Related to Placental Leucine Aminopeptidase/Oxytocinase," J. Biochem. 125(5):931-938 (1999).
Hatzopoulos, et al. "Isolation and characterization of endothelial progenitor cells from mouse embryos," Development. 125(8):1457-68 (1998).
Heidaran, Disclosure Document No. 457045 for "A Method or Process for the Treatment of Degenerative Conditions or Cancer Employing Custom Fabricated Organ Tissue Grafts Using Cells Isolated, Expanded, and Stored at Birth", 15 pages, stamped received by OIPE on May 28, 1999, paper dated May 13, 1999.
Herrera, et al., "Mesenchymal Stem Cells Contribute to the Renal Repair of Acute Tubular Epithelial Injury," Int. J. Mol. Med., 2004: 14(6):1035-41.
Himori, et al., Chemotherapeutic susceptibility of human bone marrow progenitor cells and human myelogenous leukemia cells (HL-60) in co-culture: preliminary report. Int J Cell Cloning. 2(4):254-62 (1984).
Hirano et al., "CD9 is Expressied in Extravillous Trophoblasts in Association with Integrin α3 and integrin α5," Molecular Human Reproduction 5(2):162-167 (1999).
Hirashima, et al. "Maturation of embryonic stem cells into endothelial cells in an in vitro model of vasculogenesis," Blood. 93(4):1253-63 (1999).
Hoek R M, et al., "Down-regulation of the macrophage lineage though interaction with OX2 (CD200)" Science, American Association for the ADvancement of Science, US, vol. 290, No. 5497, Dec. 1, 2000, pp. 1768-1771, XP002263649 ISSN:0036-8075.
Hows, "Status of Umbilical Cord Blood Transplantation in the Year 2001," J Clin Pathol 54(6):428-434 (2001).
Hoynowski, et al., "Characterization and Differentiation of Equine Umbilical Cord-Derived Matrix Cells," Biochemical and Biophysical Research Communications, 2007; 362:347-53.
Huss, "Isolation of Primary and Immortalized CD34—Hematopoietic and Mesenchymal Stem Cells from Various Sources," Stem Cells 18:1-9 (2000).
Huss, "Perspectives on the Morphology and Biology of CD34—Negative Stem Cells," J. Hematother. Stem. Cell Res. 9(6):783-793 (2000).
Igura, et al., "Isolation and Characterization of Mesencymal Progenitor Cells from Chorionic Villi of Human Placenta," Cytotherapy 6(6): 543-553 (2004).

(56) References Cited

OTHER PUBLICATIONS

Ino et al., "Expression of Placental Leucine Aminopeptidase and Adipoctye-Derived Leucine Aminopeptidase in Human Normal and Malignant Invasive Trophoblastic Cells" Laboratory Investigation 83(12):1799-1809 (2003).
International Preliminary Report on Patentability from PCT/US2006/049491 dated Jan. 14, 2008.
International Search Report and Written Opinion from PCT/US2006/049491 dated Sep. 26, 2007.
Iwasaki, "Recent Advances in the Treatment of Graft-Versus-Host Disease,". Clin. Med. Res., 2004; 2(4):243-52.
Jaiswal, et al., "Osteogenic Differentiation of Purified, Culture-Expanded Human Mesenchymal Stem Cells in vitro," J. Cell Biochem. 64(2):295-312 (1997).
James et al., "Cytotrophobast Differentiation in the First Trimester of Pregnancy: Evidence for Separate Progenitros of Extravillous Trophoblasts and Syncytiotrophoblast," Reproduction 130:95-130 (2005).
Jiang et al., "Hypoxia Prevents Induction of Aromatase Expression in Human Trophoblast Cells in Culture: Potential Nihibitory Role of the Hypoxia-Inducible Transcription Factor Mash-2 (Mammalian Achaete-Scute Homologous Protein-20," Molecular Endocrinology 14(10):1661-1673 (2000).
Jones et al., "Isolation and Characterization of Bone Marrow Multipotential Mesenchymal Progenitor Cells," Arthritis Rheum. 46(12):3349-3360 (2002).
Jones et al., "Ultrastructure of the Normal Human Placenta," Electron Microsc. 4:129-178 (1991).
Kao et al., "The Human Villous Cytotrophoblast: Interactions with Extracellular Matrix Proteins, Endocrine Function, and Cytoplasmic Differentiation in the Absence of Syncytium Formation," Developmental Biology 130:693-702 (1988).
Kato et al., "Discordant Secretion of Placental Protein Hormones in Differentiating Trophoblasts in Vitro," Journal of Clinical Endocrinology and Metabolism 68(4):814-820 (1989).
Kaufmann et al., "Extravillous Trophoblast in the Human Placenta," Trophoblast Research 10:21-65 (1997).
Kawata et al., "Transcriptional Control of HLA-A,B,C Antigen in Human Placental Cytotrophoblast Isolated Using Trophoblast- and HLA-Specific Monoclonal Antibodies and the Fluorescence-Activated Cell Sorter," J. Exp. Med. 160(3):633-51 (1984).
Kliman et al., "Purification, Characterization, and In Vitro Differentiation of Cytotropholblasts from Human Term Placentae," Endocrinology 118(4):1567-1582 (1986).
Koc, et al., "Rapid Hematopoietic Recovery After Coinfusion of Autologous-Blood Stem Cells and Culture-Expanded Marrow Mesenchymal Stem Cells in Advanced Breast Cancer Patients Receiving High-Dose Chemotherapy," J Clin Oncol 18:307-316 (2000).
Koh, et al., "Parthenolgenetically Derived Stem Cells for Urologic Reconstruction." The Journal of Urology, vol. 171, No. 4, Supplement, Saturday, May 8, 2004, p. 21, Abstract 81.
Korbling, et al., "Hepatocytes and Epithelial Cells of Donor Origin in Recipients of Peripheral-Blood Stem Cells," N. Engl. J. Med. 346(10):738-746 (2002).
Kurtzberg, "Placental Bood as a Source of Hmatopoietic Sem Cells for Transplantation into Unrelated Recipients," N. Engl. J. Med. 335:157-166 (1996).
Landon et al., "The Effects of Ethanol Methotrexate and Diphenylhydantoin on [$^{14}$C] Leucine Incorporation by Human Trophoblasst Cells Cultured In Vitro," British Journal of Obstetrics and Gynaecology 94:252-255 (1987).
Law, E., et al., Stem Cell Symposium, State of New Jersey Commission on Science & Technology 2005 (Abstract).
Lazarus, et al., "Cotransplantation of HLA-Identical Sibling Culture-Expanded Mesenchymal Stem Cells and Hematopoietic Stem Cells in Hematologic Malignancy Patients," Biol Blood Marrow Transplant, 11(5):389-398 (2005).
Le Blanc et al., "Treatment of Severe Acute Graft-Versus-Host Disease With Third Party Haploidentical Mesenchvmal Stem Cells,"• Lancet, 363(9419):1439-41 (2004).
Lebkowski, et al., "Serum and Plasma Levels of FGF-2 and VEGF in Healthy Blood Donors," Cancer J. 7(Suppl 2):S83-S93 (2001).
Leonard, et al., "The Role of ABC Transporters in Clinical Practice," Oncologist. 8:411-424 (2003).
Li et al., "Human Placenta-Derived Adherent Stem Cells Prevent Bone Loss and Stimulate Bone Formation in Myelomatous Bones, and Suppress Growth of Primary Multiple Myeloma," Blood 112(11) p. 2PP, XP002631697 (2008).
Li et al., "Human Placenta-Derived Adherent Stem Cells Prevent Bone Loss, Stimulate Bone Formation, and Suppress Growth of Multiple Myeloma in Bone," XP002631698, Stem Cells 29(2):263-273 (2010).
Li et al., "Mesenchymal Stem Cells Derived from Human Placenta Suppress Allogenic Umbilical Cord Blood Lymphocyte Proliferation." Cell Res. 15: 539-547 (2005).
Lin, et al. "Murine CD200(+)CK7(+) trophoblasts in a poly (I:C)—induced embryo resorption model." Reproduction (Cambridge), vol. 130, No. 4, pp. 529-537, XP002443406 ISSN: 1470-1626 (Oct. 2005).
Lipinski et al., "Human Trophoblast Cell-Surface Antigen Defined by Monoclonal Antibodies," Proc. Natl. Acad. Sci. USA, Medical Sciences 78(8):5147-5150 (1981).
Loke et al., "Identification of Cytotrophoblast Colonies in Cultures of Human Placental Cells Using Monoclonal Antibodies," Placenta 7:221-231 (1986).
Lorkowski, et al., "ABCG Subfamily of Human ATP-Binding Cassette Proteins," Pure Appl. Chem. 74(11):2057-2081 (2002).
Lowy, et al. "Isolation of transforming DNA: cloning the hamster aprt gene," Cell. 22(3):817-23 (1980).
Ma et al., "Human Umbilical Cord Wharton's Jelly-Derived Mesenchymal Stem Cells Differentiation into Nerve-Like Cells," Chinese Med. Jour., 118(23):1987-1993 (2005).
Ma et al., "Development of an in vitro Human Placenta Model by the Cultivation of Human Trophoblasts in a Fiber-Based Bioreactor System," Tissue Engineering 5, 91-102 (1999).
Mackay, et al., "Chondrogenic Differentiation of Cultured Human Mesenchymal Stem Cells from Marrow," Tissue Engineering 4(4):415-28 (1998).
McMaster et al, "Human Placental HLA-G Expression is Restricted to Differentiated Cytotrophoblasts," J. Immunol. 154(8):3771-3778 (1995).
Melchner, et al., "Human Placental Conditioned Medium Reverses Apparent Commitment to Differentiation of Human Promyelocytic Leukemia Cells (HL60)," Blood 66(6):1469-1472 (1985).
Melnik, et al., "Evaluation of Eluants from Batch Separations of CD34(+) Cells from Human Cord Blood Using a Commercial, Immunomagnetic Cell Separation System," Biotechnol. Prog. 17(5):907-916 (2001).
Miki et al., "Isolation of Multipotent Stem Cells from Placenta." AASLD Abstracts, Hepatology, Abstract 279, p. 290A (Oct. 2003).
Miki et al., "Production of Hepatocytes from Human Amniotic Stem Cells." Hepatology, Abstract 20, vol. 36, No. 4, Pt. 2 (2002).
Miki et al., "Stem Cell Characteristics of Amniotic Epithelial Cells." Stem Cells Express, published online Aug. 9, 2005; doi:10. 1634/stemcells:2004-0357 (2005).
Minguell, et al., "Mesenchymal Stem Cells," Exp. Biol. Med. 226:507-520 (2001).
Moore, et al., "A Simple Perfusion Technique for Isolation of Maternal Intervillous Blood Mononuclear Cells from Human Placentae," J. Immunol. Methods 209(1):93-104 (1997).
Moreau et al., "Myofibroblastic Stromal Cells Isolated From Human Bone Marrow Indue the Proliferation of Both Early Myeloid and B-Lymphoid Cells," Blood 82:2396-2405 (1993).
Moreira et al., "Thalidomide Exerts Its Inhibitory Action on Tumor Necrosis Factoraby Enhancing mRNA Degradation," J. Expr. Med. 177: 1675-1680 (1993).
Morgan et al., "Long-Term Culture of Human Trophoblast Cells," British Journal of Obstetrics and Gynaecology 92:84-92 (1985).

(56) References Cited

OTHER PUBLICATIONS

Morigi, et al., "Mesenchymal Stem Cells are Renotropic, Helping to Repair the Kidney and Improve Function in Acute Renal Failure," J. Am. Soc. Nephrol., 2004; 15(7):1794-1804.
Morishima, et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," Blood, 2002; 99(11):4200-06.
Morrish et al., "Epidermal Growth Factor Induces Differentiation and Secretion of Human Chorionic Gonadotropin and Placental Lactogen in Normal Human Placenta," Journal of Clinical Endocrinology and Metabolism 65(6):1282-1290 (1987).
Morrish et al., "In Vitro Cultured Human Term Cytotrophoblast: A Model for Normal Primary Epitehlial Cells Demonstrating a Spontaneous Differentiation Programme that Requires EGF for Extensive Development of Syncytium," Placenta 18: 577-585 (1997).
Muhlemann, et al., "Cytomegalovirus in the Perfused Human Term Placenta in vitro," Placenta 16:367-373 (1995).
Myllynen "In Search of Models for Hepatic and Placental Pharmacokinetics," [Dissertation] University of Oulu, (2003).
Nagayama et al., "Immunological reconstitution after cord blood transplantation for an adult patient", Bone Marrow Transplantation 24: 211-213 (1999).
Ninichuk, et al., "Multipotent Mesenchymal Stem Cells Reduce Interstitial Fibrosis but do not Delay Progression of Chronic Kidney Disease in Collagen4a3-Deficient Mice," Kidney Int., 2006; 70(1):121-29.
Nishishita, et al., "A Potential Pro-Angiogenic Cell Therapy with Human Placenta-Derived Mesenchymal Cells," Biochem. Biophys. Res. Commun. 325(1):24-31 (2004).
Noort, et al., "Mesenchymal Stem Cells Promote Engraftment of Human Umbilical Cord Blood-Derived CD34+ Cells in NOD/SCID Mice," Experimental Hematology 30(8):870-878 (2002).
Notice of Opposition by Farmindustria S.A. to corresponding claims filed in Peru; English translation Jan. 18, 2008.
Oda et al., "Trophoblast Stem Cells," Methods in Enxymology 419(15):387-400 (2006).
Paludan, et al., "Immune Suppression by Placenta Derived Adherent Cells (PDAC) Correlate with Monocyte Chemoattractant Protein-1 and 1L-2 Secretion," Blood 108(11) Part II, p. 48B (2006) (abstract only).
Paludan, et al., "Placental Derived Stem Cells (PDAC) Suppress the Allo-MLR and the EBV Regression Assay," http://www.call4abstract.com/hem/finalpreview.php?absnum=552996 (2006).
Pande et al., "Isolation and Culture of Hamster Ectoplacental Cone Trophoblasts: an In Vitro Study on the Cell Types and Their Growth Pattern," Cell Prolif. 29:163-171 (1996).
Panepucci, et al., "Comparison of Gene Expression of Umbilical Cord Vein and Bone Marrow-Derived Mesenchvmal Stem Cells," Stem Cells, 2004; 22(7):1263-78.
Papaioannou, et al., "Stem Cells from Early Mammalian Embryos" Stem Cells Handbook:19-31 (2004).
Parolini, et al., "Concise Review: Isolation and Characterization of Cells from Human Term Placenta: Outcome of the First International Workshop on Placenta Derived Stem Cells," Stem Cells 26(2):300-311 (2008).
Pellegrini, et al., "FADD and Caspase-8 are Required for Cytokine-Induced Proliferation of Hemopoietic Progenitor Cells," Blood 106(5):1581-1589 (2005).
Pera, et al., "Human Embryonic Stem Cells," J. Cell. Sci. 113:5-10 (2000).
Petroff et al., "Isolation and Culture of Term Human Trophoblast Cells," Methods in Molecular Medicine, Placenta and Trophoblast, 1(16):203-217 (2006).
Pittenger et al., "Multilineage Potential of Adult Human Mesenchymal Stem Cells," Science 284(5411):143-147 (1999).
Portmann-Lanz, et al., "Placental Mesenchymal Stem Cells as Potential Autologous Graft for Pre- and Perinatal Neuroregeneration" Am. J. Obstet Gynecol. 194:664-673 (2006).
Potgens et al., "Human Trophoblast Contains an Intracellular Protein Reactive with and Antibody against CD133-A Novel Marker for Trophoblast," Placenta 22:639-645 (2001).
Potgens et al., "Monoclonal Antibody CD133-2 (AC141) Against Hematopoeietic Stem Cell Antigen CD133 Shows Crossactivity with Cytokeratin 18," Journal of Histochemistry & Cytochemistry 50(8):1131-1134 (2002).
Pountos, et al., "Mesenchymal Stem Cell Tissue Engineering: Techniques for Isolation, Expansion and Application," Injury Int. J. Care Injured, 2007; 38(Supp. 4):S23-33.
Quinn et al., "Mouse Trophoblast Stem Cells," Methods in Molecular Medicine 121(1):125-148 (2005).
Rachmilewitz et al., "Intermediate Cells During Cytotrphoblast Differentiation in Vitro," Cell Growth & Differentiation 4:395-402 (1993).
Reyes, et al., "Purification and ex vivo Expansion of Postnatal Human Marrow Mesodermanl Progenitor Cells," Blood 98(9):2615-2625 (2001).
Reyes, et al., Origin of endothelial progenitors in human postnatal bone marrow.J Clin Invest. 109(3):337-46 (2002).
Rielland et al., "Trophoblast Stem Cell Derivation, Cross-species Comparison and Use of Nuclear Transfer: New Tools to Study Trophoblast Growth and Differentiation," Developmental Biology 322:1-10 (2008).
Ringler et al., "In Vitro Systems for the Study of Human Placental Endocrine Function," Endocrine Reviews 11(1):105-123.
Rong-Hao et al., "Establishment and Characterization of a Cytotrophoblast Cell Line From Normal Placenta of Human Origin," Human Reproduction 11(6):1328-1333 (1996).
Rossant, "Stem Cells from the Mammalian Blastocyst," Stem Cell 19:477-482 (2001).
Roth, et al., "Human Placental Cytotrophoblats Produce the Immunosuppressive Cytokine Interliukin 10," J. Exp. Med. 184(2):539-548 (1996).
Rubinstein, et al., "Processing and Cryopreservation of Placental/Umbilical Cord Blood for Unrelated Bone Marrow Reconstitution," Proc. Natl. Acad. Sci. USA 92:10119-10122 (1995).
Russo, "Fighting Darwin's Battles. Symposium Marks Evolutionist Victory, Anti-Evolution Growth" The Scientist 15:6 (2001).
Sakuragawa, et al., "Expression of markers for both neuronal and glial cells in human amniotic epithelial cells," Neuroscience Letters 209:9-12 (1996).
Sakuragawa, et al., "Human amniotic epithelial cells are promising transgene carriers for allogeneic cell transplantation into liver," J. Hum. Genet. 45:171-176 (2000).
Sapin, "Esterification of Vitamin A by the Human Placenta Involves Villous Mesenchymal Fibrlboasts," pediatric Research 48(4):565-572 (2000).
Saric et al., "An IFN-γ-induced Aminopeptidase in the ER, ERAP I, Trims Precursors to MHC Class I-presented Peptides," Nature Immunology 3(12):1169-1176 (2002).
Schulz et al., "Human Embryonic Stem Cells as Models for Trophoblast Differentiation," Placenta 29(Suppl A):S10-S16 (2008).
Schutz, et al., "Isolation and Cultivation of Endothelial Cells Derived from Human Placenta," Eur. J. Cell Biol. 395-401 (1996).
Schwab, "Fast and Reliable Culture Method for Cells from 8-10 Week Trophoblast Tissue," Lancet 323:1082 (1984).
ScienCell—Human Amniotic Epithelial Cells. http://www.sciencellonline.com/products/7100.htm.
Shamblott, et al., "Derivation of Pluripotent Stem Cells from Cultured Human Primordial Germ Cells," Proc. Natl. Acad. Sci. USA 95(23):13726-13731 (1998).
Sherley, "Asymmetric Cell Kinetics Genes: The Key to Expansion of Adult Stem Cells in Culture", Stem Cell 20:561-72 (2002).
Sikkema-Raddatz, "Four Years' Cytogenetic Experience with the Culture of Chorionic Villi," Prenatal Diagnosis 20:950-955 (2000).
Slager, Transforming growth factor-beta in the early mouse embryo: implications for the regulation of muscle formation and implantation. Dev Genet. 14(3):212-24 (1993).
Soma, "Human Trophoblast in Tissue Culture," Obstetrics and Gynaecology 18(6):704-718 (1961).

(56) References Cited

OTHER PUBLICATIONS

Stromberg et al., "Isolation of Functional Human Trophoblast Cells and Their Partial Characterization in Primary Cell Culture," In Vitro 14(7):631-638 (1978).
Sunderland et al., "HLA A, B, C Antigens are Expressed on Nonvillous Trophoblast of the Early Human Placenta," Journal of Immunology 127(6):2614-2615 (1981).
Tarrade et al., "Characterization of Human Villous and Extravillous Trophoblasts Isolated from First Trimester Placenta," Laboratory Investigation 81(9):1199-1211 (2001).
Thomson, et al., Embryonic stem cell lines derived from human blastocysts. Science. 282 (5391): 1145-1147 (1998).
Toma et al., "Human Mesenchymal Stem Cells Differentiate to a Cardiomyocyte Phenotype in the Adult Murine Heart," Circulation 105:93-98 (2002).
Truman et al., "Human Placental Cytotrophoblast Cells: Identification and Culture," Arch Gynecol. Obstet. 246:39-49 (1989).
Truman et al., "The Effects of Substrate and Epidermal Growth Factor on Human Placental Trophoblast Cells in Culture," In Vitro Cellular & Developmental Biology 22(9):525-528 (1986).
Turner, et al., "A modified Harvest Technique for Cord Blood Hematopoietic Stem Cells," Bone Marrow Transplantation 10:89-91 (1992).
Ulloa-Montoya, et al., "Culture Systems for Pluripotent Stem Cells," Journal of Bioscience and Bioengineering, 2005; 100(1):12-27.
Viacord, Umblicical cord blood can save lives (Informational brochure), Boston: ViaCell Centr-Bro R1 10/01 (2001).
Wang et al., "Enhanced Recovery of Hematopoietic Progenitor and Stem Cells from Cultivated, Postpartum Human Placenta," Blood 98(11/1):183a Abstract No. 769 (2001).
Wang et al., "Mesenchymal Stem/Progenitor Cells in Human Cord Blood as Support for Ex Vivo Expansion of CD34+ Hematopoietic Stem Cells and for Chondrogenic Differentiation," Haematologica 89(7):837-844 (2004).
Watanabe et al, "Multilineage Potential of Human Placenta-Derived Mesenchymal Cells," Blood 100(11):517a, Abstract 2022 (2002).
Wiesmann, et al., "Effects of Caspase Inhibitors on Hematopoietic Engraftment After Short-Term Culture," Cell. Transplant. 11(4):351-358 (2002).
Xu et al., "BMP4 Initiates Human Embryonic Stem Cell Differentiation to Trophoblast," Nature Biology 20:1261-1264 (2002).
Xu et al., "High Sensitivity of Megakaryocytic Progenitor Cells Contained in Placental/Umbilical Cord Blood to the Stresses During Cryopreservation," Bone Marrow Transplantation 34: 537-543 (2004).
Ye et al., "Recovery of Placental-Derived Adherent Cells with Mesenchymal Stem Cell Characteristics," Blood 98(11):147b Abstract No. 4260 (2001).
Yeger et al., "Enzymatic Isolation of Human Trophoblast and Culture on Various Substrates: Comparison of First Trimester with Term Trophoblast," Placenta 10:137-151 (1989).
Yen et al, "Isolation of multipotent cells from human term placenta" Stem Cells (Dayton, Ohio) 2005, vol. 23(1):3-9, XP002443187 ISSN: 1065-5099 (Jan. 2005).
Young, et al., "Human Pluripotent and Progenitor Cells Display Cell Surface Cluster Differentiation Markers CD10, CD13, CD56, and MHC class-I," Proc Soc Exp Biol Med. 221(1):63-71 (1999).
Young, et al., "Use of Mesenchymal Stem Cells in a Collagen Matrix for Achilles Tendon Repair," 16:4:406-413 (1998).
Yui et al., "Functional, Long-term Cultures of Human Term Trophoblasts Purified by Column-elimination of CD9 Expressing Cells," Placenta 15:231-246 (1994).
Zhang, et al., "Comparison of Mesenchymal Stem Cells from Human Placenta and Bone Marrow," Chinese Medical Journal, 117(6):882-87 (2004).
Zhang, et al., "Efficient Adena-Associated Virus-Mediated Gene Expression in Human Placenta-Derived Mesenchvmal Cells," Microbiol. Immunol. 47(1):109-16 (2003).
Zhang, et al., "Human Placenta-Derived Mesenchymal Progenitor Cells Support Culture Expansion of Long-Term Culture-Initiating Cells from Cord Blood CD34+ Cells." Exp. Hematol. 32(7): 657-664 (2004).
Office Action dated Dec. 16, 2004 in U.S. Appl. No. 10/004,942, now US Patent No. 7,045,148.
Office Action dated Dec. 5, 2003 in U.S. Appl. No. 10/004,942, now US Patent No. 7,045,148.
Office Action dated Jun. 15, 2004 in U.S. Appl. No. 10/004,942, now US Patent No. 7,045,148.
Office Action dated Jun. 20, 2005 in U.S. Appl. No. 10/004,942, now US Patent No. 7,045,148.
Office Action dated May 7, 2003 in U.S. Appl. No. 10/004,942, now US Patent No. 7,045,148.
Notice of Allowance dated Sep. 15, 2005 in U.S. Appl. No. 10/004,942, now US Patent No. 7,045,148.
Office Action dated Mar. 22, 2007 in U.S. Appl. No. 10/074,976, now US Patent No. 7,311,904.
Notice of Allowance dated Aug. 16, 2007 in U.S. Appl. No. 10/074,976, now US Patent No. 7,311,904.
Office Action dated Jan. 5, 2006 in U.S. Appl. No. 10/074,976, now US Patent No. 7,311,904.
Office Action dated Sep. 20, 2006 in U.S. Appl. No. 10/074,976, now US Patent No. 7,311,904.
Office Action dated Sep. 23, 2004 in U.S. Appl. No. 10/074,976, now US Patent No. 7,311,904.
Advisory Action dated Jul. 12, 2004 in U.S. Appl. No. 10/076,180.
Office Action dated Aug. 28, 2003 in U.S. Appl. No. 10/076,180.
Office Action dated Jun. 20, 2005 in U.S. Appl. No. 10/076,180.
Office Action dated Mar. 18, 2004 in U.S. Appl. No. 10/076,180.
Office Action dated Oct. 20, 2004 in U.S. Appl. No. 10/076,180.
Office Action dated Jan. 19, 2006 in U.S. Appl. No. 10/366,671, now US Patent No. 7,311,905.
Advisory Action dated Feb. 2, 2007 in U.S. Appl. No. 10/366,671, now US Patent No. 7,311,905.
Notice of Allowance dated Sep. 10, 2007 in U.S. Appl. No. 10/366,671, now US Patent No. 7,311,905.
Office Action dated May 14, 2007 in U.S. Appl. No. 10/366,671, now US Patent No. 7,311,905.
Office Action dated Oct. 10, 2006 in U.S. Appl. No. 10/366,671, now US Patent No. 7,311,905.
Notice of Allowance dated Oct. 30, 2008 in U.S. Appl. No. 10/411,655, now US Patent No. 7,498,171.
Office Action dated Feb. 28, 2008 in U.S. Appl. No. 10/411,655, now US Patent No. 7,498,171.
Office Action dated Jul. 11, 2007 in U.S. Appl. No. 10/411,655, now US Patent No. 7,498,171.
Office Action dated May 18, 2006 in U.S. Appl. No. 10/411,655, now US Patent No. 7,498,171.
Office Action dated Nov. 20, 2006 in U.S. Appl. No. 10/411,655, now US Patent No. 7,498,171.
Advisory Action dated Oct. 25, 2007 in U.S. Appl. No. 10/449,248.
Office Action dated Apr. 26, 2007 in U.S. Appl. No. 10/449,248.
Office Action dated Aug. 29, 2006 in U.S. Appl. No. 10/449,248.
Office Action dated Feb. 7, 2008 in U.S. Appl. No. 10/449,248.
Notice of Allowance May 21, 2007 in U.S. Appl. No. 10/640,428, now US Patent No. 7,255,879.
Office Action dated Oct. 18, 2006 in U.S. Appl. No. 10/640,428, now US Patent No. 7,255,879.
Office Action dated Jan. 19, 2006 in U.S. Appl. No. 10/640,428 now Patent No. 7,255,879.
Advisory Action dated Feb. 20, 2007 in U.S. Appl. No. 10/640,428, now US Patent No. 7,255,879.
Office Action dated Apr. 2, 2009 in U.S. Appl. No. 10/721,144.
Final Office Action dated Dec. 15, 2011 in U.S. Appl. No. 10/721,144.
Non Final Office Action dated Feb. 1, 2011 in U.S. Appl. No. 10/721,144.
Final Office Action dated Sep. 14, 2010 in U.S. Appl. No. 10/721,144.
Office Action dated Mar. 18, 2010 in U.S. Appl. No. 10/721,144.
Advisory Action dated Oct. 7, 2009 in U.S. Appl. No. 10/721,144.
Advisory Action dated Aug. 17, 2009 in U.S. Appl. No. 10/721,144.

(56) References Cited

OTHER PUBLICATIONS

Office Action dated Feb. 5, 2008 in U.S. Appl. No. 10/721,144.
Final Office Action dated Jun. 27, 2007 in U.S. Appl. No. 10/721,144.
Office Action dated Dec. 28, 2006 in U.S. Appl. No. 10/721,144.
Office Action dated Jun. 14, 2006 in U.S. Appl. No. 10/721,144.
Advisory Action dated Feb. 6, 2006 in U.S. Appl. No. 10/721,144.
Final Office Action dated Jan. 11, 2006 in U.S. Appl. No. 10/721,144.
Office Action dated Oct. 4, 2005 in U.S. Appl. No. 10/721,144.
Notice of Allowance dated Oct. 14, 2008 in U.S. Appl. No. 10/874,828, now US Patent No. 7,468,276.
Office Action dated Sep. 9, 2008 in U.S. Appl. No. 10/874,828, now US Patent No. 7,468,276.
Office Action dated Dec. 13, 2007 in U.S. Appl. No. 10/874,828, now US Patent No. 7,468,276.
Office Action dated Apr. 6, 2007 in U.S. Appl. No. 10/874,828, now US Patent No. 7,468,276.
Office Action dated Jun. 12, 2006 in U.S. Appl. No. 10/874,828, now US Patent No. 7,468,276.
Notice of Allowance dated Aug. 12, 2009 in U.S. Appl. No. 11/187,400.
Office Action dated Feb. 20, 2009 in U.S. Appl. No. 11/187,400.
Advisory Action dated Sep. 8, 2008 in U.S. Appl. No. 11/187,400.
Office Action dated May 22, 2008 in U.S. Appl. No. 11/187,400.
Office Action dated Jan. 4, 2008 in U.S. Appl. No. 11/187,400.
Office Action dated Apr. 20, 2007 in U.S. Appl. No. 11/187,400.
Final Office Action dated Aug. 4, 2010 in U.S. Appl. No. 11/592,544.
Non Final Office Action dated Feb. 4, 2009 in U.S. Appl. No. 11/592,544.
Final Office Action dated Dec. 9, 2009 in U.S. Appl. No. 11/593,348.
Notice of Allowance dated Dec. 1, 2009 in U.S. Appl. No. 11/648,802.
Office Action dated Dec. 3, 2008 in U.S. Appl. No. 11/648,802.
Final Office Action dated Oct. 31, 2011 in U.S. Appl. No. 11/648,804.
Non-Final Office Action dated Apr. 21, 2011 in U.S. Appl. No. 11/648,804.
Final Office Action dated May 20, 2010 in U.S. Appl. No. 11/648,804.
Non-Final Office Action dated Oct. 21, 2009 in U.S. Appl. No. 11/648,804.
Notice of Allowance dated Sep. 29, 2011 in U.S. Appl. No. 11/648,813.
Notice of Allowance dated Jan. 10, 2011 in U.S. Appl. No. 11/648,813.
Final Office Action dated Oct. 27, 2009 in U.S. Appl. No. 11/648,813.
Non Final Office Action dated Jun. 7, 2010 in U.S. Appl. No. 11/648,813.
Office Action dated Jan. 26, 2009 in U.S. Appl. No. 11/648,813.
Non-Final Office Action dated Jan. 22, 2010 in U.S. Appl. No. 11/648,824.
Notice of Allowance dated Nov. 29, 2010 in U.S. Appl. No. 11/980,012.
Non Final Office Action dated Jun. 7, 2010 in U.S. Appl. No. 11/980,012.
Final Office Action dated Feb. 1, 2011 in U.S. Appl. No. 11/982,291.
Non Final Office Action dated Jul. 15, 2010 in U.S. Appl. No. 11/982,291.

* cited by examiner

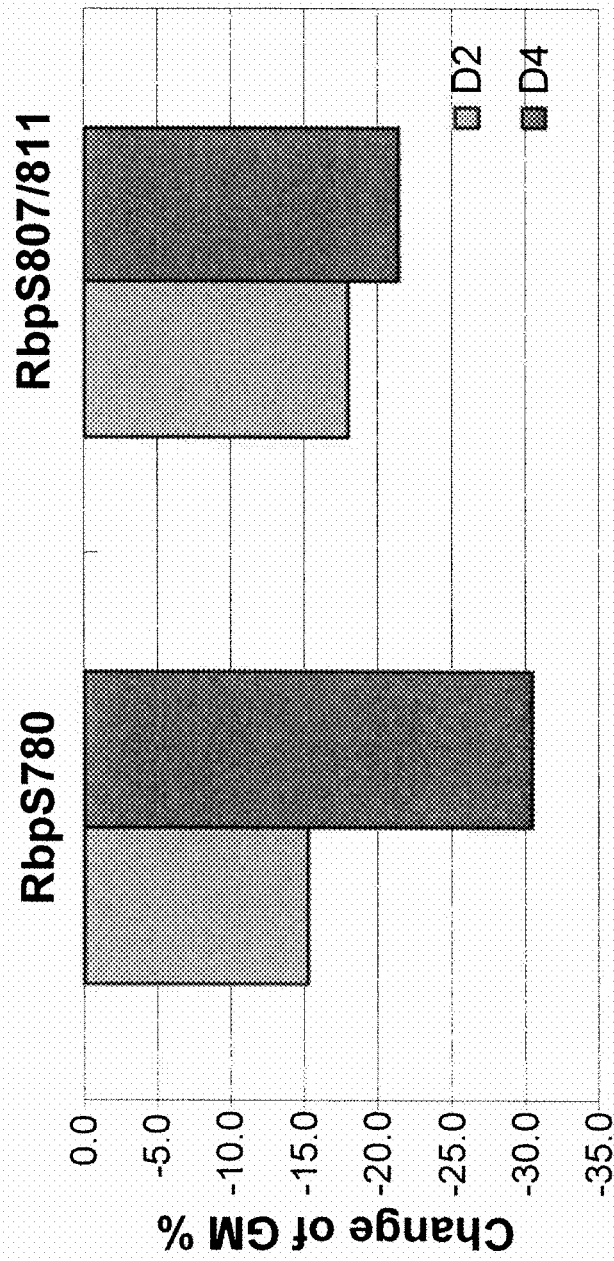

TREATMENT OF BONE-RELATED CANCERS USING PLACENTAL STEM CELLS

This application claims the benefit of U.S. Provisional Patent Application Ser. No. 61/298,517, filed Jan. 26, 2010; U.S. Provisional Patent Application Ser. No. 61/307,821, filed Feb. 24, 2010; and U.S. Provisional Patent Application Ser. No. 61/352,768, filed Jun. 8, 2010, each of which is incorporated by reference herein in its entirety.

1. FIELD

Provided herein are methods of using tissue culture plastic-adherent placental stem cells (referred to herein as PDACs), and/or bone marrow-derived mesenchymal stem cells (BM-MSCs) to treat bone related cancers, e.g., multiple myeloma, to suppress the proliferation of cells of bone-related cancers, e.g., multiple myeloma cells or chondrosarcoma cells, and to suppress the growth of bone-related cancers, e.g., multiple myeloma, chondrosarcoma, and other bone-related cancers, e.g., tumors.

2. BACKGROUND

Multiple myeloma (also known as MM, myeloma, plasma cell myeloma, or Kahler's disease) is a type of cancer of plasma cells, which are antibody-producing immune system cells. Symptoms of multiple myeloma include bone pain, infection, renal failure, anemia, and bone lesions. The disease is considered incurable, and only a few treatments, such as lenalidomide (REVLIMID®) are available and show promise. As such, a need exists for new treatments for multiple myeloma. To date, no one has described the ability of non-hematopoietic, tissue culture plastic-adherent placental stem cells to suppress the growth of bone-related cancers, e.g., multiple myeloma, or to suppress the proliferation of cells of bone-related cancers.

3. SUMMARY

In one aspect, provided herein are methods of treating an individual having a bone-related cancer, comprising administering to the individual a therapeutically effective amount of isolated tissue culture plastic-adherent placental stem cells, also referred to herein as PDACs (placenta derived adherent cells), isolated populations of such placental stem cells, or isolated populations of cells comprising the placental stem cells; and/or isolated bone marrow-derived mesenchymal stem cells (BM-MSCs) or bone marrow comprising BM-MSCs.

In one embodiment, provided herein is a method of treating an individual having a bone-related cancer, comprising administering to said individual a therapeutically effective amount of placental stem cells and/or BM-MSCs, wherein said therapeutically effective amount of placental stem cells and/or BM-MSCs improves, e.g., detectably improves, one or more symptoms of, or reduces, e.g., detectably reduces, the progression of, said bone-related cancer. In a specific embodiment, said bone-related cancer is multiple myeloma. In a specific embodiment, said bone-related cancer is chondrosarcoma. In other embodiments, said bone-related cancer is bone cancer, neuroblastoma, osteosarcoma, Ewing's sarcoma, chordoma, malignant fibrous histiocytoma of bone, prostate cancer, or fibrosarcoma of bone. In a specific embodiment, the bone-related cancer is not prostate cancer. In other embodiments, said bone-related cancer comprises a solid tumor. In another embodiment, said individual is a mammal. In another embodiment, said individual is a human. In another embodiment, said administering said placental stem cells results in a greater, e.g., detectably greater, improvement of said one or more symptoms than administering an equivalent number of bone marrow-derived mesenchymal stem cells. In certain embodiments, said bone marrow-derived mesenchymal stem cells are one or more of $CD34^-$, $CD45^-$, $CD73^+$ and/or $CD105^+$.

In certain embodiments, said individual exhibits a bone lesion, e.g., a bone lesion caused by said bone-related cancer, e.g., a bone lesion visible on an X-ray radiogram. In other embodiments, said individual does not exhibit a bone lesion, e.g., a bone lesion caused by said bone-related cancer, e.g., a bone lesion visible on an X-ray radiogram. In other embodiments, said administering results in a delay in the appearance of, or onset of, bone lesions, e.g., bone lesions caused by said bone-related cancer, e.g., as visible on an X-ray radiogram, or bone lesions caused by treatment of a cancer.

In certain embodiments, said placental stem cells, and/or said BM-MSCs, are administered to said individual intravenously. In other embodiments, the method of treatment comprises administering at least about $1\times10^7$, $5\times10^7$, $1\times10^8$, $5\times10^8$, $1\times10^9$, $5\times10^9$, $1\times10^{10}$, $5\times10^{10}$ or $1\times10^{11}$ placental stem cells, and/or BM-MSCs, to said individual, in terms of total number of cells. In another specific embodiment, said placental stem cells, said BM-MSCs, or both have been proliferated in vitro for no more than 2, 3, 4, 5, 6, 7, 8, 9, 10, 11, 12, 13, 14, 15, 16, 17, 18, 19, 20, 21, 22, 23, 24, 25, 26, 27, 28, 29 or 30 population doublings prior to said administering. In another embodiment, said placental stem cells, and/or BM-MSCs, are administered to said individual at or adjacent to a bone lesion, e.g., a bone lesion caused by said bone-related cancer. In another embodiment, the method of treatment additionally comprises administering to said individual one or more anticancer compounds. In another embodiment of any of the embodiments herein, said placental stem cells and/or BM-MSCs have been cryopreserved and thawed prior to said administering.

In one embodiment, the methods of treatment can comprise determining, once or a plurality of times before said administering, and/or once or a plurality of times after said administering, one or more of (1) a number or degree of bone lesions in said individual; (2) a number of osteoclast precursors in said individual; or (3) a number of multiple myeloma cells in said individual, e.g., at least once before and at least once after said administration. In certain embodiments, said therapeutically effective amount of placental stem cells, and/or BM-MSCs, reduces, e.g., detectably reduces, the number of, or degree of severity of, or reduces the rate of increase in the number of, or degree of severity, said bone lesions in said individual, e.g., as determinable by bone densitometry or X-rays. In other embodiments, said therapeutically effective amount of placental stem cells, and/or BM-MSCs, reduces, e.g., detectably reduces, the number of osteoclast precursors in said individual, e.g., as determined using an antibody specific for osteoclast precursors to detect osteoclast precursors in, e.g., the individual's peripheral blood or bone marrow. In other embodiments, said therapeutically effective amount of placental stem cells, and/or BM-MSCs, reduces the number of bone-related cancer cells, e.g., multiple myeloma cells, in said individual, e.g., as determinable by cell counting (e.g., by flow cytometry), or antibody staining, of nucleated blood cells from said individual using an antibody specific for such cells, e.g., multiple myeloma cells or plasma cells, e.g., an antibody specific for cellular markers CD28 or CD138, or as determinable by assessing the level of M proteins in blood from the individual. In other embodiments, said placental stem cells, and/or BM-MSCs, reduce the number of cells of said bone-related cancer, or said osteoclast precursors, by at least, e.g., 10%, 15%, 20%, 25%, 30%, 35%, 40%, 45%, 50%, 55%, 60%, 65%, 70%, 75%, 80%, 85%, 90%, 95%, 98% or 99%, compared to the number of said cells prior to administration of said placental stem cells.

In another embodiment, the individual has chondrosarcoma; e.g., the bone-related cancer is chondrosarcoma. In certain embodiments, the method of treatment comprises determining, once or a plurality of times before said administering, and/or once or a plurality of times after said administering, one or more of a number of chondrosarcoma cells in the individual or the number of bone lesions (e.g., chondrosarcoma-caused masses) in the individual.

In another aspect, provided herein is a method of suppressing proliferation of cells of a bone-related cancer, comprising contacting said cells of a bone-related cancer with a plurality of placental stem cells, and/or BM-MSCs, for a time sufficient for said placental stem cells and/or BM-MSCs to suppress, e.g., detectably suppress, proliferation of said cells of a bone-related cancer, as compared to a plurality of said cells of a bone-related cancer not contacted with placental stem cells and/or BM-MSCs, e.g., as determinable by a reduction, e.g., a detectable reduction, in the number of said bone-related cancer cells, or a detectable reduction in the increase in number of said bone-related cancer cells. In certain embodiments, said cells of a bone-related cancer are multiple myeloma cells. In another embodiment of the method, said cells of a bone-related cancer are chondrosarcoma cells. In other embodiments, said cells of a bone-related cancer are bone cancer cells, neuroblastoma cells, osteosarcoma cells, Ewing sarcoma cells, chordoma cells, cells of a malignant fibrous histiocytoma of bone, or cells of a fibrosarcoma of bone. In another specific embodiment, said cells of a bone-related cancer are part of a solid tumor.

In certain embodiments of the method, said contacting is performed in vitro. In certain other embodiments, said contacting is performed in vivo. In certain embodiments, said contacting is performed in an individual who comprises said cells of a bone-related cancer, e.g., in an individual having a disease caused by said cells. In other embodiments, said contacting is performed in an individual who comprises multiple myeloma cells, e.g., in an individual having multiple myeloma. In certain embodiments, said individual is a mammal, e.g. a human. In another specific embodiment, said contacting comprises administering said placental stem cells to said individual intravenously. In another specific embodiment, said contacting comprises administering said placental stem cells, and/or BM-MSCs, to said individual at or adjacent to a bone lesion in the individual.

In another embodiment, the methods of suppressing proliferation of cells of a bone-related cancer, e.g., multiple myeloma cells, additionally comprises contacting said cells of a bone-related cancer with one or more anticancer compounds, e.g., a therapeutically effective amount of one or more anticancer compounds. In another embodiment, the method comprises administering at least about $1 \times 10^7$, $5 \times 10^7$, $1 \times 10^8$, $5 \times 10^8$, $1 \times 10^9$, $5 \times 10^9$, or $1 \times 10^{10}$ placental stem cells, and/or BM-MSCs, to said individual. In certain embodiments, said placental stem cells and/or BM-MSCs, and/or BM-MSCs, have been proliferated in vitro for no more than 2, 3, 4, 5, 6, 7, 8, 9, 10, 11, 12, 13, 14, 15, 16, 17, 18, 19, 20, 21, 22, 23, 24, 25, 26, 27, 28, 29 or 30 population doublings. In other embodiments, said placental stem cells, and/or BM-MSCs, suppress proliferation of cells of said bone-related cancer by at least, e.g., 10%, 15%, 20%, 25%, 30%, 35%, 40%, 45%, 50%, 55%, 60%, 65%, 70%, 75%, 80%, 85%, 90%, 95%, 98% or 99%, compared to proliferation of an equivalent number of cells of said bone-related cancer in the absence of said placental stem cells and/or BM-MSCs, e.g., as determinable by a detectable reduction in the number of said bone-related cancer cells, or a detectable reduction in the increase in number of said bone-related cancer cells, or as determinable by a detectable decrease in the number and/or severity of bone lesions in an individual having said cancer cells.

In other embodiments, said placental stem cells or BM-MSCs, or both, have been cryopreserved and thawed prior to said contacting. In another embodiment, the method comprises determining that said placental stem cells suppress, e.g., detectably suppress, the proliferation of a sample of said cells of a bone-related cancer prior to said contacting.

In another embodiment, provided herein is a method of reducing maturation of osteoclast precursors, into osteoclasts, comprising contacting said osteoclast precursors with a plurality of placental stem cells and/or BM-MSCs, wherein said plurality of placental stem cells and/or BM-MSCs is a number of cells sufficient to reduce, e.g., detectably reduce, osteoclast maturation from said osteoclast precursors, e.g., as determinable by a detectable reduction of, or lack of increase in, the number of osteoclasts as a result of said contacting. In another embodiment, provided herein is a method of increasing apoptosis of osteoclast precursors, comprising contacting said osteoclast precursors with a plurality of placental stem cells and/or BM-MSCs wherein said plurality of placental stem cells and/or BM-MSCs is a number of cells sufficient to increase, e.g., detectably increase, osteoclast precursor apoptosis. In certain embodiments, said increase in osteoclast precursor apoptosis is detected by a detectable increase in annexin V and/or propidium iodide staining of osteoclast precursors from said individual. In certain embodiments, the osteoclast precursors are in an individual, e.g., an individual having a bone-related cancer, e.g., multiple myeloma, chondrosarcoma, or one of the other bone-related cancers described herein. In certain other embodiments, the method comprises contacting said osteoclast precursors with lenalidomide, e.g., administering lenalidomide to an individual having said osteoclast precursors.

In certain embodiments of the above methods, said contacting takes place in vitro. In other embodiments, said contacting takes place in vivo. In another embodiment, said contacting takes place in a human. In another embodiment, said contacting takes place in an individual having a bone-related cancer, e.g., an individual having cells of a bone related cancer, or a disease caused by such cells. In another embodiment, said individual is an individual having multiple myeloma or multiple myeloma cells. In another embodiment, said individual has at least one symptom of multiple myeloma. In another embodiment, said individual has at least one bone lesion caused by multiple myeloma.

In certain embodiments of any of the above methods, said placental stem cells are one or more of: (1) adherent to tissue culture plastic; (2) $CD34^-$, $CD10^+$, $CD105^+$ and $CD200^+$ as detectable by flow cytometry; and/or (3) have the capacity to differentiate into osteogenic or chondrogenic cells, e.g., either in vitro or in vivo, or both. In another embodiment, said placental stem cells are adherent to tissue culture plastic; $CD34^-$, $CD10^+$, $CD105^+$ and $CD200^+$ as detectable by flow cytometry; and have the capacity to differentiate into cells having one or more characteristics of osteogenic or chondrogenic cells, e.g., characteristics of osteocytes or chondrocytes, e.g., either in vitro or in vivo, or both. In other embodiments, the placental stem cells additionally have the ability to differentiate into cells having one or more characteristics of neural cells or neurogenic cells, e.g., characteristics of neurons; one or more characteristics of glial cells, e.g., characteristics of glia or astrocytes; one or more characteristics of adipocytic cells, e.g., characteristics of adipocytes; one or more characteristics of pancreatic cells; and/or one or more characteristics of cardiac cells. In a specific embodiment of each of the embodiments of placental stem cells herein, the placental stem cells are isolated placental stem cells.

In another embodiment, said placental stem cells are CD34$^-$, CD10$^+$, CD105$^+$ and CD200$^+$, and one or more of CD44$^+$, CD45$^-$, CD90$^+$, CD166$^+$, KDR$^-$, or CD133$^-$. In a more specific embodiment, said placental stem cells are CD34$^-$, CD10$^+$, CD105$^+$ and CD200$^+$, CD44$^+$, CD45$^-$, CD90$^+$, CD166$^+$, KDR$^-$, and CD133$^-$. In another embodiment, the placental stem cells are CD34$^-$, CD10$^+$, CD105$^+$ and CD200$^+$, and one or more of HLA ABC$^+$, HLA DR,DQ, DP$^-$, CD80$^-$, CD86$^-$, CD98$^-$, or PD-L1$^+$. In a more specific embodiment, said placental stem cells are CD34$^-$, CD10$^+$, CD105$^+$ and CD200$^+$, HLA ABC$^+$, HLA DR,DQ,DP$^-$, CD80$^-$, CD86$^-$, CD98$^-$, and PD-L1$^+$. In another embodiment, said placental stem cells are CD34$^-$, CD10$^+$, CD105$^+$ and CD200$^+$, and one or more of CD38$^-$, CD45$^-$, CD80$^-$, CD86$^-$, CD133$^-$, HLA-DR,DP,DQ$^-$, SSEA3$^-$, SSEA4$^-$, CD29$^+$, CD44$^+$, CD73$^+$, CD105$^+$, HLA-A,B,C$^+$, PDL1$^+$, ABC-p$^+$, and/or OCT-4$^+$, as detectable by flow cytometry and/or RT-PCR. In another embodiment, the placental stem cells are CD34$^-$, CD45$^-$, CD10$^+$, CD90$^+$, CD105$^+$ and CD200$^+$, as detectable by flow cytometry. In another embodiment, said placental stem cells CD34$^-$, CD45$^-$, CD10$^+$, CD80$^-$, CD86$^-$, CD90$^+$, CD105$^+$ and CD200$^+$, as detectable by flow cytometry. In another embodiment, said placental stem cells are CD34$^-$, CD45$^-$, CD10$^+$, CD80$^-$, CD86$^-$, CD90$^+$, CD105$^+$ and CD200$^+$, and additionally one or more of CD29$^+$, CD38$^-$, CD44$^+$, CD54$^+$, SH3$^+$ or SH4$^+$, as detectable by flow cytometry. In another embodiment, said placental stem cells are CD34$^-$, CD38$^-$, CD45$^-$, CD10$^+$, CD29$^+$, CD44$^+$, CD54$^+$, CD73$^+$, CD80$^-$, CD86$^-$, CD90$^+$, CD105$^+$, and CD200$^+$ as detectable by flow cytometry.

In another embodiment, said CD34$^-$, CD10$^+$, CD105$^+$ and CD200$^+$ placental stem cells are additionally one or more of CD3$^-$, CD9$^-$, CD117$^-$, CD133$^-$, CD146$^+$, CD166$^+$, KDR$^-$ (VEGFR2$^-$), HLA-A,B,C$^+$, HLA-DP,DQ,DR$^-$, or Programmed Death-1 Ligand (PDL1)$^+$, or any combination thereof. In another specific embodiment, said placental stem cells are CD3$^-$, CD9$^-$, CD34$^-$, CD38$^-$, CD45$^-$, CD10$^+$, CD29$^+$, CD44$^+$, CD54$^+$, CD73$^+$, CD80$^-$, CD86$^-$, CD90$^+$, CD105$^+$, CD117$^-$, CD133$^-$, CD146$^+$, CD166$^+$, CD200$^+$, KDR$^-$ (VEGFR2$^-$), HLA-A,B,C$^+$, HLA-DP,DQ,DR$^-$, or Programmed Death-1 Ligand (PDL1)$^+$, as detectable by flow cytometry.

In another embodiment, any of the placental stem cells described herein are additionally ABC-p$^+$, as detectable by flow cytometry, or OCT-4$^+$ (POU5F1$^+$), e.g., as determinable by RT-PCR, wherein ABC-p is a placenta-specific ABC transporter protein (also known as breast cancer resistance protein (BCRP) and as mitoxantrone resistance protein (MXR)). In another embodiment, any of the placental stem cells described herein are additionally SSEA3$^-$ or SSEA4$^-$, e.g., as determinable by flow cytometry, wherein SSEA3 is Stage Specific Embryonic Antigen 3, and SSEA4 is Stage Specific Embryonic Antigen 4. In another embodiment, any of the placental stem cells described herein are additionally SSEA3$^-$ and SSEA4$^-$.

In another embodiment of the methods described herein, any of the placental stem cells populations of isolated placental stem cells described herein are additionally one or more of MHC-I$^+$ (e.g., HLA-A,B,C$^+$), MHC-II$^-$ (e.g., HLA-DP,DQ, DR$^-$) or HLA-G$^-$. In another embodiment, any of the placental stem cells described herein are additionally each of MHC-I$^+$ (e.g., HLA-A,B,C$^+$), MHC-II$^-$ (e.g., HLA-DP,DQ,DR$^-$) and HLA-G$^-$.

In another embodiment, the CD34$^-$, CD10$^+$, CD105$^+$, CD200$^+$ placental stem cells are additionally one or more of CD3$^-$, CD9$^-$, CD29$^+$, CD38$^-$, CD44$^+$, CD54$^+$, CD80$^-$, CD86$^-$, CD146$^+$, CD166$^+$, SH3$^+$ or SH4$^+$. In another embodiment, the CD34$^-$, CD10$^+$, CD105$^+$, CD200$^+$ placental stem cells are additionally CD44$^+$. In another embodiment, the CD34$^-$, CD10$^+$, CD105$^+$, CD200$^+$ placental stem cells are additionally one or more of CD3$^-$, CD9$^-$, CD13$^+$, CD29$^+$, CD33$^+$, CD38$^-$, CD44$^+$, CD45$^-$, CD54$^+$, CD62E$^-$, CD62L$^-$, CD62P$^-$, SH3$^+$ (CD73$^+$), SH4$^+$ (CD73$^+$), CD80$^-$, CD86$^-$, CD90$^+$, SH2$^+$ (CD105$^+$), CD106/VCAM$^+$, CD117$^-$, CD144/VE-cadherin$^{low}$, CD184/CXCR4$^-$, CD133$^-$, OCT-4$^+$, SSEA3$^-$, SSEA4$^-$, ABC-p$^+$, KDR$^-$ (VEGFR2$^-$), HLA-A,B, C$^+$, HLA-DP,DQ,DR$^-$, HLA-G$^-$, or Programmed Death-1 Ligand (PDL1)$^+$, or any combination thereof. In another embodiment, the CD34$^-$, CD10$^+$, CD105$^+$, CD200$^+$ placental stem cells are additionally CD13$^+$, CD29$^+$, CD33$^+$, CD38$^-$, CD44$^+$, CD45$^-$, CD54/ICAM$^+$, CD62E$^-$, CD62L$^-$, CD62P$^-$, SH3$^+$ (CD73$^+$), SH4$^+$ (CD73$^+$), CD80$^-$, CD86$^-$, CD90$^+$, SH2$^+$ (CD105$^+$), CD106/VCAM$^+$, CD117$^-$, CD144/VE-cadherin$^{dim}$, CD146$^+$, CD166$^+$, CD184/CXCR4$^-$, CD133$^-$, OCT-4$^+$, SSEA3$^-$, SSEA4$^-$, ABC-p$^+$, KDR$^-$ (VEGFR2$^-$), HLA-A,B,C$^+$, HLA-DP,DQ,DR$^-$, HLA-G$^-$, and Programmed Death-1 Ligand (PDL1)$^+$.

In other embodiments of the methods disclosed herein, the isolated placental stem cells are CD200$^+$ and HLA-G$^-$; CD73$^+$, CD105$^+$, and CD200$^+$; CD200$^+$ and OCT-4$^+$; CD73$^+$, CD105$^+$ and HLA-G$^-$; CD73$^+$ and CD105$^+$; or OCT-4$^+$; or any combination thereof.

In certain embodiments of the methods disclosed herein, the placental stem cells are one or more of CD10$^+$, CD29$^+$, CD34$^-$, CD38$^-$, CD44$^+$, CD45$^-$, CD54$^+$, CD90$^+$, SH2$^+$, SH3$^+$, SH4$^+$, SSEA3$^-$, SSEA4$^-$, OCT-4$^+$, MHC-I$^+$ or ABC-p$^+$, where ABC-p is a placenta-specific ABC transporter protein (also known as breast cancer resistance protein (BCRP) and as mitoxantrone resistance protein (MXR)). In another embodiment, the placental stem cells are CD10$^+$, CD29$^+$, CD34$^-$, CD38$^-$, CD44$^+$, CD45$^-$, CD54$^+$, CD90$^+$, SH2$^+$, SH3$^+$, SH4$^+$, SSEA3$^-$, SSEA4$^-$, and OCT-4$^+$. In another embodiment, the placental stem cells are CD10$^+$, CD29$^+$, CD34$^-$, CD38$^-$, CD45$^-$, CD54$^+$, SH2$^+$, SH3$^+$, and SH4$^+$. In another embodiment, the placental stem cells are CD10$^+$, CD29$^+$, CD34$^-$, CD38$^-$, CD45$^-$, CD54$^+$, SH2$^+$, SH3$^+$, SH4$^+$ and OCT-4$^+$. In another embodiment, the placental stem cells are CD10$^+$, CD29$^+$, CD34$^-$, CD38$^-$, CD44$^+$, CD45$^-$, CD54$^+$, CD90$^+$, MHC-1$^+$, SH2$^+$, SH3$^+$, SH4$^+$. In another embodiment, the placental stem cells are OCT-4$^+$ and ABC-p$^+$. In another embodiment, the placental stem cells are SH2$^+$, SH3$^+$, SH4$^+$ and OCT-4$^+$. In another embodiment, the placental stem cells are OCT-4$^+$, CD34$^-$, SSEA3$^-$, and SSEA4$^-$. In a specific embodiment, said OCT-4$^+$, CD34$^-$, SSEA3$^-$, and SSEA4$^-$ placental stem cells are additionally CD10$^+$, CD29$^+$, CD34$^-$, CD44$^+$, CD45$^-$, CD54$^+$, CD90$^+$, SH2$^+$, SH3$^+$, and SH4$^+$. In another embodiment, the placental stem cells are OCT-4$^+$ and CD34$^-$, and either SH3$^+$ or SH4$^+$. In another embodiment, the placental stem cells are CD34$^-$ and either CD10$^+$, CD29$^+$, CD44$^+$, CD54$^+$, CD90$^+$, or OCT-4$^+$. In certain embodiments, the placental stem cells are CD10$^+$, CD34$^-$, CD105$^+$ and CD200$^+$.

In another embodiment, the placental stem cells are one or more of CD10$^+$, CD29$^+$, CD44$^+$, CD45$^-$, CD54/ICAM$^-$, CD62-E$^-$, CD62-L$^-$, CD62-P$^-$, CD80$^-$, CD86$^-$, CD103⁻, CD104⁻, CD105⁺, CD106/VCAM⁺, CD144/VE-cadherin$^{dim}$, CD184/CXCR4⁻, β2-microglobulin$^{dim}$, MHC-I$^{dim}$, MHC-II⁻, HLA-G$^{dim}$, and/or PDL1$^{dim}$. In certain embodiments, such placental stem cells or population of isolated placental stem cells are at least CD29⁺ and CD54⁻. In another embodiment, such placental stem cells are at least CD44⁺ and CD106⁺. In another embodiment, such placental stem cells are at least CD29⁺.

In certain embodiments of any of the above characteristics, expression of the cellular marker (e.g., cluster of differentiation or immunogenic marker) is determined by flow cytometry. In certain other embodiments, expression of the cellular marker is determined by RT-PCR.

In another embodiment, the placental stem cells, e.g., said CD10⁺, CD34⁻, CD105⁺, CD200⁺ cells, e.g., the cells in the aggregate, express one or more genes at a higher leve, e.g., a detectably higher level, than an equivalent number of bone marrow-derived mesenchymal stem cells, wherein said one or more genes are one or more of, or all of, ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A, and wherein said bone marrow-derived mesenchymal stem cells have undergone a number of passages in culture equivalent to the number of passages said isolated placental stem cells have undergone. In certain embodiments, said expression of said one or more genes is determined, e.g., by RT-PCR or microarray analysis, e.g, using a U133-A microarray (Affymetrix). In another embodiment, said placental stem cells express, e.g., differentially express, said one or more genes when cultured for, e.g., anywhere from about 3 to about 35 population doublings, in a medium comprising 60% DMEM-LG (e.g., from Gibco) and 40% MCDB-201 (e.g., from Sigma); 2% fetal calf serum (e.g., from Hyclone Labs.); 1× insulin-transferrin-selenium (ITS); 1× linoleic acid-bovine serum albumin (LA-BSA); 10⁻⁹ M dexamethasone (e.g., from Sigma); 10⁻⁴ M ascorbic acid 2-phosphate (e.g., from Sigma); epidermal growth factor 10 ng/mL (e.g., from R&D Systems); and platelet-derived growth factor (PDGF-BB) 10 ng/mL (e.g., from R&D Systems). In another embodiment, said placental stem cells express, e.g., differentially express, said one or more genes when cultured for from about 3 to about 35 population doublings in a medium comprising 60% DMEM-LG (e.g., from Gibco) and 40% MCDB-201 (e.g., from Sigma); 2% fetal calf serum (e.g., from Hyclone Labs.); 1× insulin-transferrin-selenium (ITS); 1× linoleic acid-bovine serum albumin (LA-BSA); 10⁻⁹ M dexamethasone (e.g., from Sigma); 10⁻⁴ M ascorbic acid 2-phosphate (Sigma); epidermal growth factor 10 ng/mL (e.g., from R&D Systems); and platelet-derived growth factor (PDGF-BB) 10 ng/mL (e.g., from R&D Systems).

In certain embodiments, the placental stem cells express CD200 and ARTS1 (aminopeptidase regulator of type 1 tumor necrosis factor); ARTS-1 and LRAP (leukocyte-derived arginine aminopeptidase); IL6 (interleukin-6) and TGFB2 (transforming growth factor, beta 2); IL6 and KRT18 (keratin 18); IER3 (immediate early response 3), MEST (mesoderm specific transcript homolog) and TGFB2; CD200 and IER3; CD200 and IL6; CD200 and KRT18; CD200 and LRAP; CD200 and MEST; CD200 and NFE2L3 (nuclear factor (erythroid-derived 2)-like 3); or CD200 and TGFB2 at a higher level, e.g., a detectably higher level, than an equivalent number of bone marrow-derived mesenchymal stem cells (BM-MSCs) wherein said bone marrow-derived mesenchymal stem cells have undergone a number of passages in culture equivalent to the number of passages said placental stem cells have undergone. In other embodiments, the placental stem cells express ARTS-1, CD200, IL6 and LRAP; ARTS-1, IL6, TGFB2, IER3, KRT18 and MEST; CD200, IER3, IL6, KRT18, LRAP, MEST, NFE2L3, and TGFB2; ARTS-1, CD200, IER3, IL6, KRT18, LRAP, MEST, NFE2L3, and TGFB2; or IER3, MEST and TGFB2 at a higher level, e.g., a detectably higher level, than an equivalent number of bone marrow-derived mesenchymal stem cells BM-MSCs, wherein said bone marrow-derived mesenchymal stem cells have undergone a number of passages in culture equivalent to the number of passages said placental stem cells have undergone.

In various embodiments, said placental stem cells useful in the methods disclosed herein are contained within a population of cells, at least 10%, 15%, 20%, 25%, 30%, 35%, 40%, 45%, 50%, 55%, 60%, 65%, 70%, 75%, 80%, 85%, 90%, 95%, 98% or 99% of the cells of which are said placental stem cells. In certain other embodiments, the placental stem cells in said population of cells are substantially free of cells having a maternal genotype; e.g., at least 40%, 45%, 50%, 55%, 60%, 65%, 70%, 75%, 80%, 85%, 90%, 95%, 98% or 99% of the placental stem cells in said population have a fetal genotype, i.e., are fetal in origin. In certain other embodiments, the population of cells comprising said placental stem cells are substantially free of cells having a maternal genotype; e.g., at least 40%, 45%, 50%, 55%, 60%, 65%, 70%, 75%, 80%, 85%, 90%, 95%, 98% or 99% of the cells in said population have a fetal genotype, i.e., are fetal in origin. In certain other embodiments, the population of cells comprising said placental stem cells comprise cells having a maternal genotype; e.g., at least 10%, 15%, 20%, 25%, 30%, 35%, 40%, 45%, 50%, 55%, 60%, 65%, 70%, 75%, 80%, 85%, 90%, 95%, 98% or 99% of the cells in said population have a maternal genotype, i.e., are maternal in origin.

In an embodiment of any of the embodiments of placental stem cells herein, the placental stem cells facilitate the formation of one or more embryoid-like bodies in a population of placental cells comprising said isolated placental stem cells when said population is cultured under conditions that allow the formation of an embryoid-like body e.g., culture under proliferation conditions).

In certain embodiments of any of the placental stem cells or BM-MSCs disclosed herein, the cells are mammalian, e.g., human.

In certain embodiments, any of the placental stem cells and/or BM-MSCs described herein are autologous to a recipient, e.g., an individual who has a bone-related cancer, e.g., an individual who has multiple myeloma, or has a symptom of a bone-related cancer, e.g., a symptom of multiple myeloma. In certain other embodiments, the placental stem cells and/or BM-MSCs are allogeneic to a recipient, e.g., an individual who has a bone-related cancer, e.g., an individual who has multiple myeloma, or has a symptom of a bone-related cancer, e.g., a symptom of multiple myeloma.

In certain embodiments of the methods of treatment or methods of suppressing bone-related cancer cell proliferation disclosed herein, the placental stem cells and/or BM-MSCs are cryopreserved prior to said administering. In another embodiment, said placental stem cells are obtained from a cell bank, e.g., a placental stem cell bank. In another embodiment, said BM-MSCs are obtained from a bank of bone marrow-derived mesenchymal stem cells.

In any of the embodiments of placental stem cells herein, the placental stem cells generally do not differentiate during culturing in growth medium, i.e., medium formulated to promote proliferation, e.g., during proliferation in growth medium. In another embodiment, said placental stem cells do not require a feeder layer in order to proliferate, e.g., do not require a feeder layer to proliferate when cultured in growth medium. In another embodiment, said placental stem cells do not differentiate in culture solely as the result of culture in the absence of a feeder cell layer.

In any of the embodiments of isolated BM-MSCs herein, the cells generally do not differentiate during culturing in growth medium, i.e., medium formulated to promote proliferation, e.g., during proliferation in growth medium. In another embodiment, said isolated BM-MSCs do not require a feeder layer in order to proliferate, e.g., do not require a feeder layer to proliferate when cultured in growth medium. In another embodiment, said isolated BM-MSCs do not differentiate in culture solely as the result of culture in the absence of a feeder cell layer.

In certain embodiments, said placental stem cells are obtained by perfusion of a post-partum placenta that has been drained of blood and perfused to remove residual blood; drained of blood but not perfused to remove residual blood; or neither drained of blood nor perfused to remove residual blood. In another specific embodiment, said placental stem cells are obtained by physical and/or enzymatic disruption of placental tissue. In another specific embodiment, said placental stem cells are obtained by culturing a portion of a placenta and allowing the placental stem cells to proliferate out of said portion of a placenta.

Cell surface, molecular and genetic markers characteristic of placental stem cells useful in the methods provided herein are described in detail in Section 5.2, below.

In another specific embodiment of the method, a therapeutically effective amount of said placental stem cells and/or BM-MSCs is a number of cells that results in elimination of, a detectable improvement in, lessening of the severity of, or slowing of the progression of one or more symptoms of, a bone-related cancer, e.g., multiple myeloma. In a specific embodiment, said symptom of a bone-related cancer, e.g., said symptom of multiple myeloma, is a bone lesion. In another specific embodiment, said therapeutically effective amount of placental stem cells and/or BM-MSCs increases, e.g., detectably increases, bone mineral density (BMD) in at least one bone of an individual receiving the cells, e.g., as measured by densitometry, or bone mineral content (BMC), e.g., as measured by densitometry. In another specific embodiment, said therapeutically effective amount of placental stem cells and/or BM-MSCs reduces, e.g., detectably reduces, a bone lesion, e.g., at least one bone lesion, caused by said bone-related cancer, e.g., as visible by X-ray, MRI, or CAT scan, or the like.

In another specific embodiment, said placental stem cells and/or BM-MSCs are administered to an individual having a bone-related cancer, e.g., multiple myeloma, at or adjacent to a bone lesion caused by said bone-related cancer, i.e., intralesionally. In another specific embodiment of the methods described above, said isolated placental stem cells and/or BM-MSCs are administered by bolus injection. In another specific embodiment, said placental stem cells and/or BM-MSCs are administered by intravenous infusion. In a specific embodiment, said intravenous infusion is intravenous infusion over about 1 to about 8 hours. In another specific embodiment, said placental stem cells and/or BM-MSCs are administered intracranially. In another specific embodiment, said isolated placental stem cells are administered intraperitoneally. In another specific embodiment, said placental stem cells and/or BM-MSCs are administered intra-arterially. In another specific embodiment of the method of treatment, said placental stem cells and/or BM-MSCs are administered intramuscularly, intradermally, subcutaneously, or intraocularly.

In another embodiment of the methods described above, said placental stem cells and/or BM-MSCs are administered by surgical implantation into said individual of a composition of matter comprising said cells, e.g., at or adjacent to a bone lesion caused by a bone-related cancer. In a specific embodiment, said composition of matter is a matrix or scaffold. In another specific embodiment, said matrix or scaffold is a hydrogel. In another specific embodiment, said matrix or scaffold is a decellularized tissue. In another specific embodiment, said matrix or scaffold is a synthetic biodegradable composition. In another specific embodiment, said matrix or scaffold is a foam. In another specific embodiment, said matrix or scaffold is a physiologically-acceptable ceramic material, e.g., mono-, di-, tri-, alpha-tri-, beta-tri-, and tetra-calcium phosphate, hydroxyapatite, a fluoroapatite, a calcium sulfate, a calcium fluoride, a calcium oxide, a calcium carbonate, a magnesium calcium phosphate, a biologically active glass (e.g., BIOGLASS®), or a mixture of any thereof. In another specific embodiment, said matrix or scaffold is a porous biocompatible ceramic material (e.g., SURGIBONE®, ENDOBON®, CEROS® or the like), or a mineralized collagen bone grafting product (e.g., HEALOS™, VITOSS®, RHAKOSS™, and CORTOSS®, or the like).

In another specific embodiment of the methods described above, said placental stem cells and/or BM-MSCs are administered once to said individual. In another specific embodiment, said placental stem cells and/or BM-MSCs are administered to said individual in two or more separate administrations. In another specific embodiment, said administering comprises administering between about $1 \times 10^4$ and $1 \times 10^5$ placental stem cells and/or BM-MSCs, e.g., per kilogram of said individual. In another specific embodiment, said administering comprises administering between about $1 \times 10^5$ and $1 \times 10^6$ placental stem cells and/or BM-MSCs per kilogram of said individual. In another specific embodiment, said administering comprises administering between about $1 \times 10^6$ and $1 \times 10^7$ placental stem cells and/or BM-MSCs per kilogram of said individual. In another specific embodiment, said administering comprises administering between about $1 \times 10^7$ and $1 \times 10^8$ placental stem cells and/or BM-MSCs per kilogram of said individual. In other specific embodiments, said administering comprises administering between about $1 \times 10^6$ and about $2 \times 10^6$ placental stem cells and/or BM-MSCs per kilogram of said individual; between about $2 \times 10^6$ and about $3 \times 10^6$ placental stem cells and/or BM-MSCs per kilogram of said individual; between about $3 \times 10^6$ and about $4 \times 10^6$ placental stem cells and/or BM-MSCs per kilogram of said individual; between about $4 \times 10^6$ and about $5 \times 10^6$ placental stem cells and/or BM-MSCs per kilogram of said individual; between about $5 \times 10^6$ and about $6 \times 10^6$ placental stem cells and/or BM-MSCs per kilogram of said individual; between about $6 \times 10^6$ and about $7 \times 10^6$ placental stem cells and/or BM-MSCs per kilogram of said individual; between about $7 \times 10^6$ and about $8 \times 10^6$ placental stem cells and/or BM-MSCs per kilogram of said individual; between about $8 \times 10^6$ and about $9 \times 10^6$ placental stem cells and/or BM-MSCs per kilogram of said individual; or between about $9 \times 10^6$ and about $1 \times 10^7$ placental stem cells and/or BM-MSCs per kilogram of said individual. In another specific embodiment, said administering comprises administering between about $1 \times 10^7$ and about $2 \times 10^7$ placental stem cells and/or BM-MSCs per kilogram of said individual to said individual. In another specific embodiment, said administering comprises administering between about $1.3 \times 10^7$ and about $1.5 \times 10^7$ placental stem cells and/or BM-MSCs per kilogram of said individual to said individual. In another specific embodiment, said administering comprises administering up to about $3 \times 10^7$ placental stem cells and/or BM-MSCs per kilogram of said individual to said individual. In a specific embodiment, said administering comprises administering between about $5 \times 10^6$ and about $2 \times 10^7$ placental stem cells and/or BM-MSCs to said individual. In another specific embodiment, said administering comprises administering about $150 \times 10^6$ placental stem cells and/or BM-MSCs in about 20 milliliters of solution to said individual.

In certain embodiments of the methods described above, said BM-MSCs are used in an amount, by numbers of cells, generally at least 50% greater than for said placental stem cells.

In a specific embodiment, said administering comprises administering between about $5 \times 10^6$ and about $2 \times 10^7$ placental stem cells and/or BM-MSCs to said individual, wherein said cells are contained in a solution comprising 10% dextran, e.g., dextran-40, 5% human serum albumin, and optionally an immunosuppressant.

In another specific embodiment, said administering comprises administering between about $5 \times 10^7$ and $3 \times 10^9$ placental stem cells and/or BM-MSCs intravenously. In specific embodiments, said administering comprises administering about $9 \times 10^8$ placental stem cells and/or BM-MSCs or about $1.8 \times 10^9$ placental stem cells and/or BM-MSCs intravenously. In another specific embodiment, said administering comprises administering between about $5 \times 10^7$ and $1 \times 10^8$ placental stem cells and/or BM-MSCs intralesionally. In another specific embodiment, said administering comprises administering about $9 \times 10^7$ placental stem cells and/or BM-MSCs intralesionally.

In another specific embodiment of the method of treatment, said placental stem cells and/or BM-MSCs are administered to said individual within 21-30, e.g., 21 days; within 7 days; within 48 hours; or within 24 hours of diagnosis of a bone-related cancer, e.g., multiple myeloma, or development of one or more symptoms of a bone-related cancer.

The placental stem cells and/or BM-MSCs used in the methods provided herein can, in certain embodiments, be genetically engineered to produce one or more proteins that suppress the growth or proliferation of cells of a bone-related cancer, e.g., multiple myeloma cells. For example, in certain embodiments, said one or more proteins can comprise osteoprotegerin, one or more bone morphogenetic proteins (BMPs); one or more connexins, e.g., connexin 26 (Cx26) and/or connexin 43 (Cx43); osteocontin; or activin A. In other embodiments, the placental stem cells and/or BM-MSCs have been engineered to express exogenous IFN-β or IL-2, e.g., in an amount that results in greater, e.g., detectably greater, suppression of tumor cell proliferation, when said tumor cells are contacted with said placental stem cells and/or BM-MSCs compared to such cells not expressing exogenous IFN-β or IL-2. Also provided herein are pharmaceutical compositions comprising such genetically-engineered placental stem cells and/or BM-MSCs for use in suppressing the growth or proliferation of bone-related cancer cells, e.g., multiple myeloma cells, or for treating an individual having bone-related cancer cells, e.g., multiple myeloma cells.

3.1 DEFINITIONS

As used herein, the term "about," when referring to a stated numeric value, indicates a value within plus or minus 10% of the stated numeric value.

As used herein, "bone lesion," in the context of a bone-related cancer, means an anomaly in the growth or structure of a bone, which is caused by, or is a symptom of, the bone-related cancer. In a non-limiting example, multiple myeloma generally causes lytic bone lesions, which are hollowed-out areas of a bone caused by demineralization of the bone. In another non-limiting example, chondrosarcoma generally causes lesions characterized by a growth on one or more bones, usually comprising a cartilaginous growth that may be calcified.

As used herein, "bone marrow-derived mesenchymal stem cells," also referred to as BM-MSCs, refers to mesenchymal stem cells obtained from bone marrow, or cultured from mesenchymal stem cells obtained from bone marrow, e.g., the cells disclosed in U.S. Pat. No. 5,486,359, the disclosure of which is incorporated by reference herein.

As used herein, the term "bone-related cancer" refers to a cancer that, in any phase of the disease, affects or metastasizes to one or more bones in an individual having the cancer. For example, multiple myeloma is a bone-related cancer because the cancer affects bones; one aspect of multiple myeloma is the development of bone lesions due at least in part to upregulation of osteoclast activity resulting from cytokines secreted by multiple myeloma cells.

As used herein, "contacting," in the context of contacting placental stem cells with cells of a bone-related cancer, encompasses, but does not require, placing the cells in such proximity such that they actually physically contact each other (e.g., in co-culture in a multiwell plate or the like), and placing the cells in the same space, without actual physical contact, but in the same space, e.g., in a TRANSWELL® culture system or administration to an individual, e.g, a human. "Contacting" as used herein encompasses bringing the placental stem cells and bone-related cancer cells together in vitro, e.g., in a single container (e.g., culture dish, flask, vial, etc.). "Contacting" also encompasses bringing placental stem cells and tumor cells together or in vivo, for example, in the same individual (e.g., mammal, for example, mouse, rat, dog, cat, sheep, goat, horse, human, etc.). For example, placental stem cells can be contacted with bone-related cancer cells by administering the placental stem cells intravenously to an individual having said bone-related cancer, or by direct injection into the site of a tumor, e.g., a bone lesion caused by a bone-related cancer, or the like. Placental stem cells can be contacted with bone-related cancer cells by administering the placental stem cells and bone-related cancer cells intravenously to, for example, an experimental animal.

As used herein, the term "SH2" refers to an antibody that binds an epitope on the cellular marker CD105. Thus, cells that are referred to as SH2$^+$ are CD105$^+$.

As used herein, the terms "SH3" and "SH4" refer to antibodies that bind epitopes present on the cellular marker CD73. Thus, cells that are referred to as SH3$^+$ and/or SH4$^+$ are CD73$^+$.

A placenta has the genotype of the fetus that develops within it, but is also in close physical contact with maternal tissues during gestation. As such, as used herein, the term "fetal genotype" means the genotype of the fetus, e.g., the genotype of the fetus associated with the placenta from which particular isolated placental stem cells, as described herein, are obtained, as opposed to the genotype of the mother that carried the fetus. As used herein, the term "maternal genotype" means the genotype of the mother that carried the fetus, e.g., the fetus associated with the placenta from which particular isolated placental stem cells, as described herein, are obtained.

As used herein, stem cells, e.g., placental stem cells, are "isolated" if at least 50%, 60%, 70%, 80%, 90%, 95%, or at least 99% of the other cells with which the stem cells are naturally associated are removed from the stem cells, e.g., during collection and/or culture of the stem cells.

As used herein, "multipotent," when referring to a cell, means that the cell has the ability to differentiate into some, but not necessarily all, types of cells of the body, or into cells having characteristics of some, but not all, types of cells of the body, or into cells of one or more of the three germ layers. In certain embodiments, for example, isolated placental stem cells (PDAC), as described in Section 5.2, below, that have the capacity to differentiate into cells having characteristics of neurogenic, chondrogenic and/or osteogenic cells are multipotent cells.

As used herein, the term "population of isolated cells" means a population of cells that is substantially separated from other cells of the tissue, e.g., placenta, from which the population of cells is derived or isolated. In certain embodiments, the population of cells is separated from at least 50%, 55%, 60%, 65%, 70%, 75%, 80%, 85%, 90%, 95%, 98% or 99% of other cells of the tissue, e.g., placenta, from which the population of cells is derived or isolated.

As used herein, the term "placental stem cell" refers to a stem cell or progenitor cell that is derived from a mammalian placenta, e.g., as described below, either as a primary isolate or a cultured cell regardless of whether the cell is a primary cell, part of a primary cell culture, or has been passaged after a primary culture. A cell e.g., a "placental stem cell," is considered a "stem cell" if the cell displays one, two, or all three of a marker or gene expression profile associated with one or more types of stem cells; the ability to replicate at least 10-40 times in culture; and the ability to differentiate into cells displaying characteristics of differentiated cells of one or more of the three germ layers. Unless otherwise noted herein, the term "placental" includes the umbilical cord. The isolated placental cells, e.g., placental stem cells, disclosed herein, in certain embodiments, differentiate in vitro under differentiating conditions), differentiate in vivo, or both.

As used herein, a cell or population of cells is "positive" for a particular marker when that marker is detectable above background, via, for example, antibody-mediated or nucleic acid-mediated detection. Detection of a particular marker can, for example, be accomplished either by use of antibodies, or by oligonucleotide probes or primers based on the sequence of the gene or mRNA encoding the marker. For example, a placental stem cell is positive for, e.g., CD73 because CD73 is detectable on placental stem cells in an amount greater, e.g., detectably greater, than background (in comparison to, e.g., an antibody isotype control). A cell is also positive for a marker when that marker can be used to distinguish the cell from at least one other cell type, or can be used to select or isolate the cell when present or expressed by the cell. In the context of, e.g., antibody-mediated detection, "positive," as an indication a particular cell surface marker is present, means that the marker is detectable using an antibody, e.g., a fluorescently-labeled antibody, specific for that marker; "positive" also refers to a cell exhibiting the marker in an amount that produces a signal, e.g., in a cytometer, that is above, e.g., detectably above, background. For example, a cell is "CD200$^+$" where the cell is labeled, e.g., detectably labeled, with an antibody specific to CD200, and the signal from the antibody is higher, e.g., detectably higher than that of a control (e.g., background or an isotype control). For example, a cell or population of cells can be determined to be OCT-4$^+$ if the amount of OCT-4 RNA detected in RNA from the cell or population of cells is detectably greater than background as determined, e.g., by a method of detecting RNA such as RT-PCR, slot blots, etc. In certain embodiments, OCT-4 is determined to be present, and a cell is "OCT-4$^+$" if OCT-4 is detectable using RT-PCR. Unless otherwise noted herein, cluster of differentiation ("CD") markers are detected using antibodies. With respect to HLA-G, a population of placental stem cell is, in certain embodiments, positive for HLA-G if more than 5% the cells in the population are positive for HLA-G, e.g., detectably stain with an antibody against HLA-G.

As used herein for all markers except HLA-G, a placental stem cell is "negative" for a particular cellular marker if the cellular marker is not detectable, e.g., using an antibody specific for that marker compared to a control (e.g., background or an isotype control), or is not detectable using a nucleic acid-based detection method, e.g., RT-PCR. For example, a cell is "CD34$^-$" where the cell is not reproducibly detectably labeled with an antibody specific to CD34 to a greater degree than a control (e.g., background or an isotype control). Markers, e.g., markers not detected, or not detectable, using antibodies, can be determined to be positive or negative in a similar manner, using an appropriate control, using other, for example, nucleic acid-mediated detection methods. Unless otherwise noted herein, cluster of differentiation ("CD") markers are detected using antibodies. With respect to HLA-G, a population of placental stem cell is, in certain embodiments, negative for HLA-G if 5% or fewer of the cells in the population are positive for HLA-G, e.g., detectably stain with an antibody against HLA-G.

As used herein, the designation "low" or "dim," when referring to the expression of a marker detectable in flow cytometry, means that the marker is expressed by fewer than 10% of cells tested, or that fluorescence attributable to the marker in, e.g., flow cytometry, is less than 1 log above background.

As used herein, "treat" encompasses the cure of, remediation of, improvement of, lessening of the severity of, or reduction in the time course of, a disease, disorder or condition, or any parameter or symptom thereof.

4. BRIEF DESCRIPTION OF THE FIGURES

FIG. 1: Placental stem cells improve repair of bone defects in experimental rats. Y axis: degree of skull bone defect closure, as assessed by area. X axis—conditions: HEALOS® alone; HEALOS® in combination with bone morphogenetic protein-2 (BMP-2); HEALOS® and placental stem cells; HEALOS® and bone marrow-derived mesenchymal stem cells (BM-MSCs); or no repair (empty). Asterisk indicates significant ($p<0.05$) improvement in repair of the defect in HEALOS® in combination with bone morphogenetic protein-2 (BMP-2); HEALOS® in combination with placental stem cells; and HEALOS® in combination with BM-MSCs, versus controls.

Figure 2:
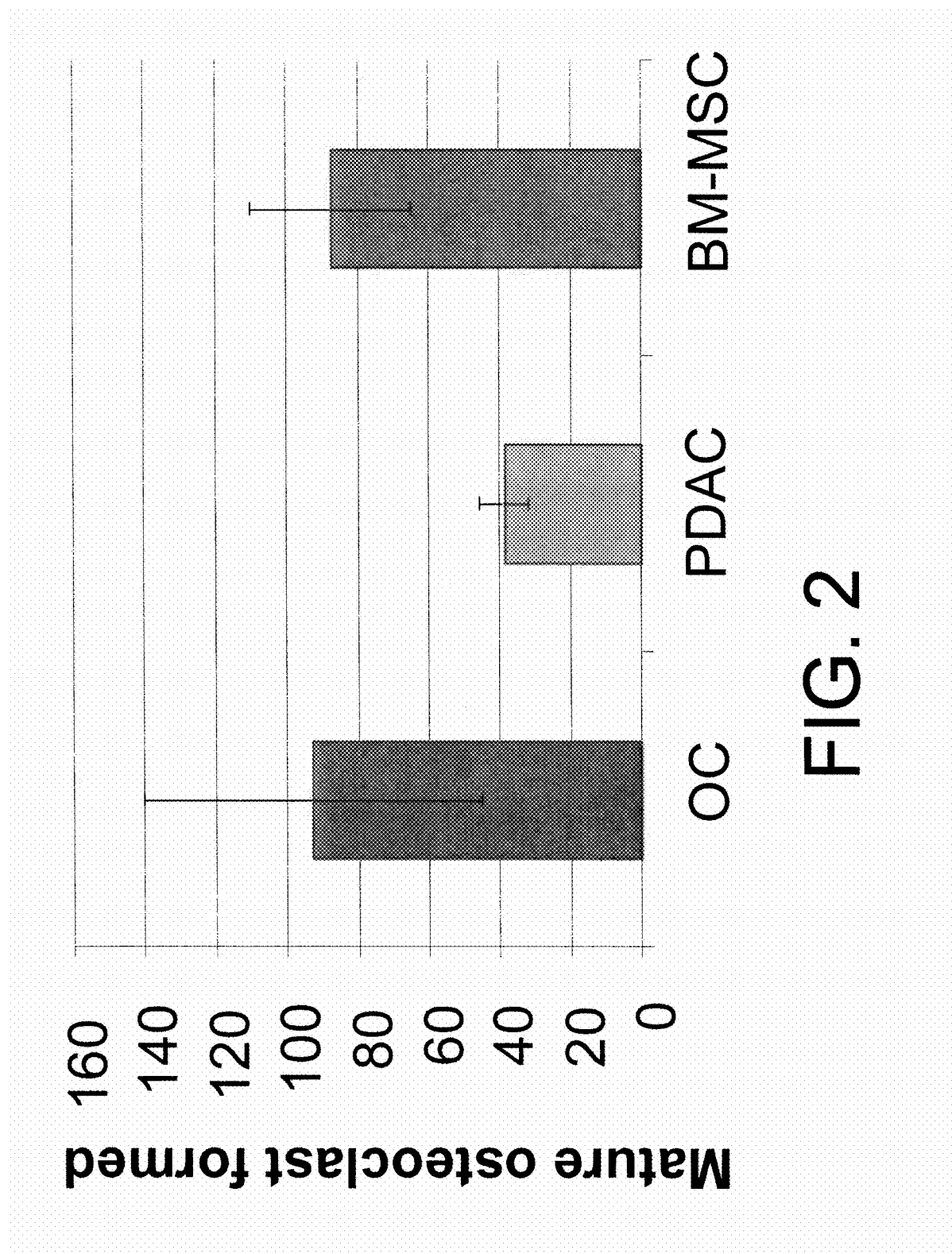

FIG. 2: Placental stem cells suppress the differentiation of osteoclast precursors. X axis: osteoclasts (OC); osteoclast precursors not co-cultured with placental stem cells, or bone marrow-derived mesenchymal stem cells (BM-MSCs). Y axis: numbers of mature osteoclasts formed.

Figure 3:
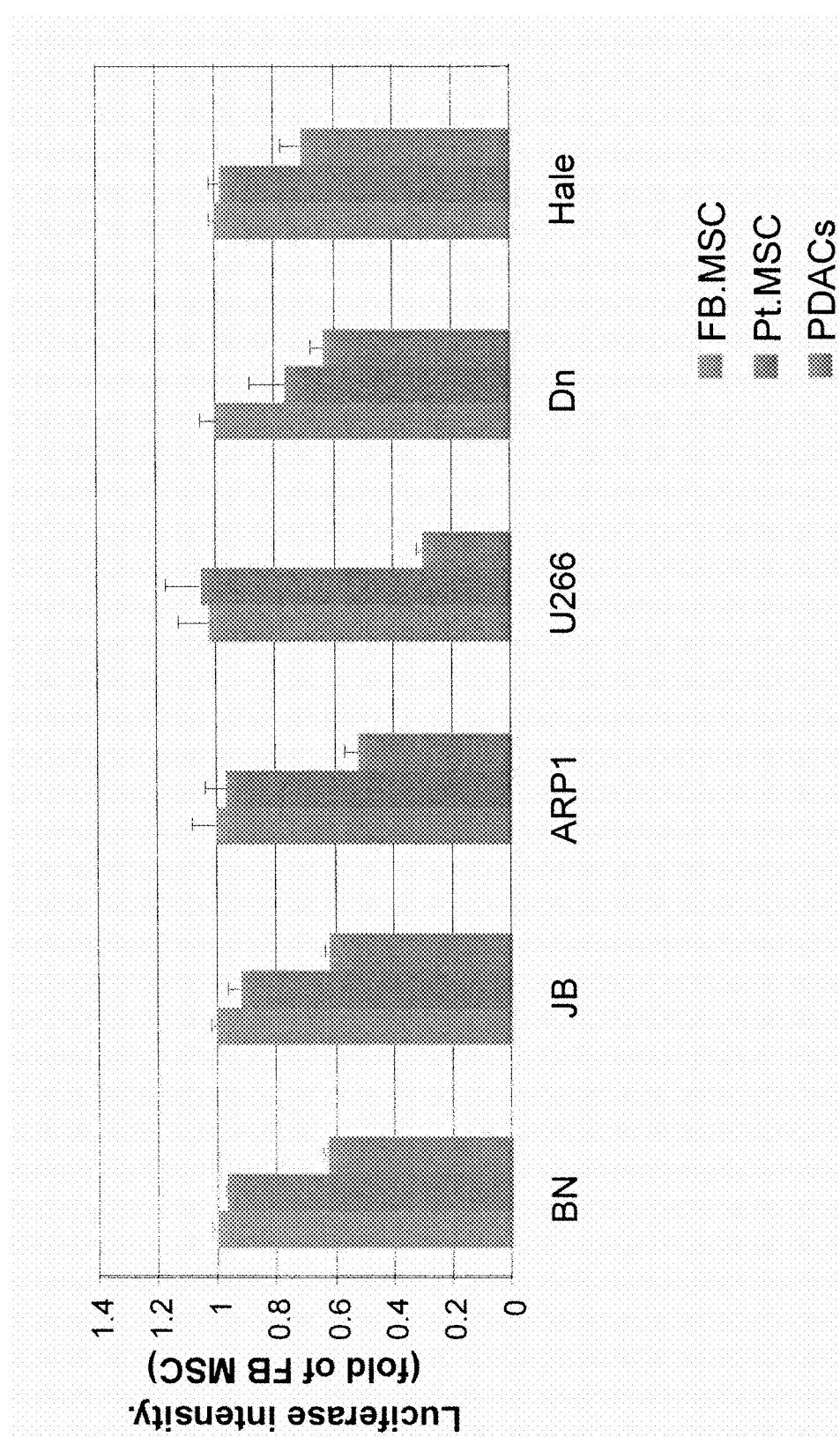

FIG. 3: Placental stem cells reduce the growth of tumor cells from different individuals. Multiple myeloma cells (cell lines BN, JB, ARP1, U266, Dn and Hale) were transfected with a gene encoding luciferase and co-cultured with (from left to right in each condition) fetal mesenchymal stem cells (FB-MSC), patient bone marrow-derived mesenchymal stem cells (Pt-MSC), or placental stem cells. Reduction of multiple myeloma cell growth after several weeks was expressed as fold-value of luciferase expression in multiple myeloma cells co-cultured with placental stem cells or Pt-MSC compared to luciferase expression by multiple myeloma cells co-cultured with FB-MSCs.

Figure 4:
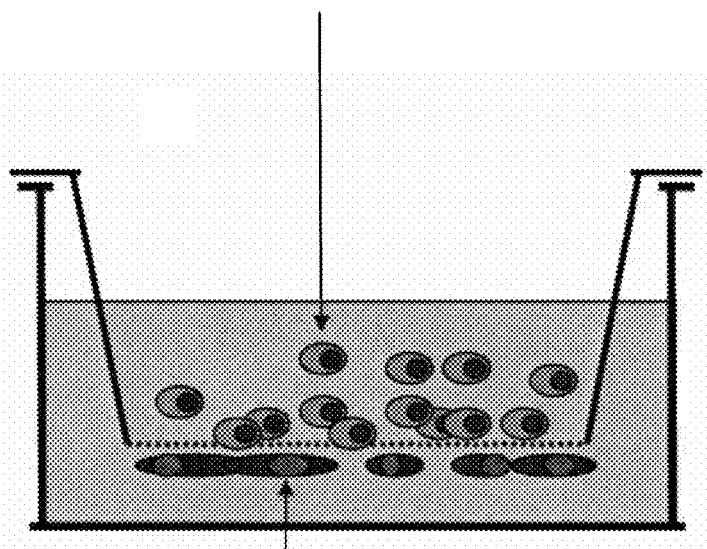

FIG. 4: Diagram of a TRANSWELL® experiment, in which placental stem cells or mesenchymal stem cells are cultured on the underside of a membrane, and multiple myeloma cells are cultured on the upper side of the membrane.

Figure 5:
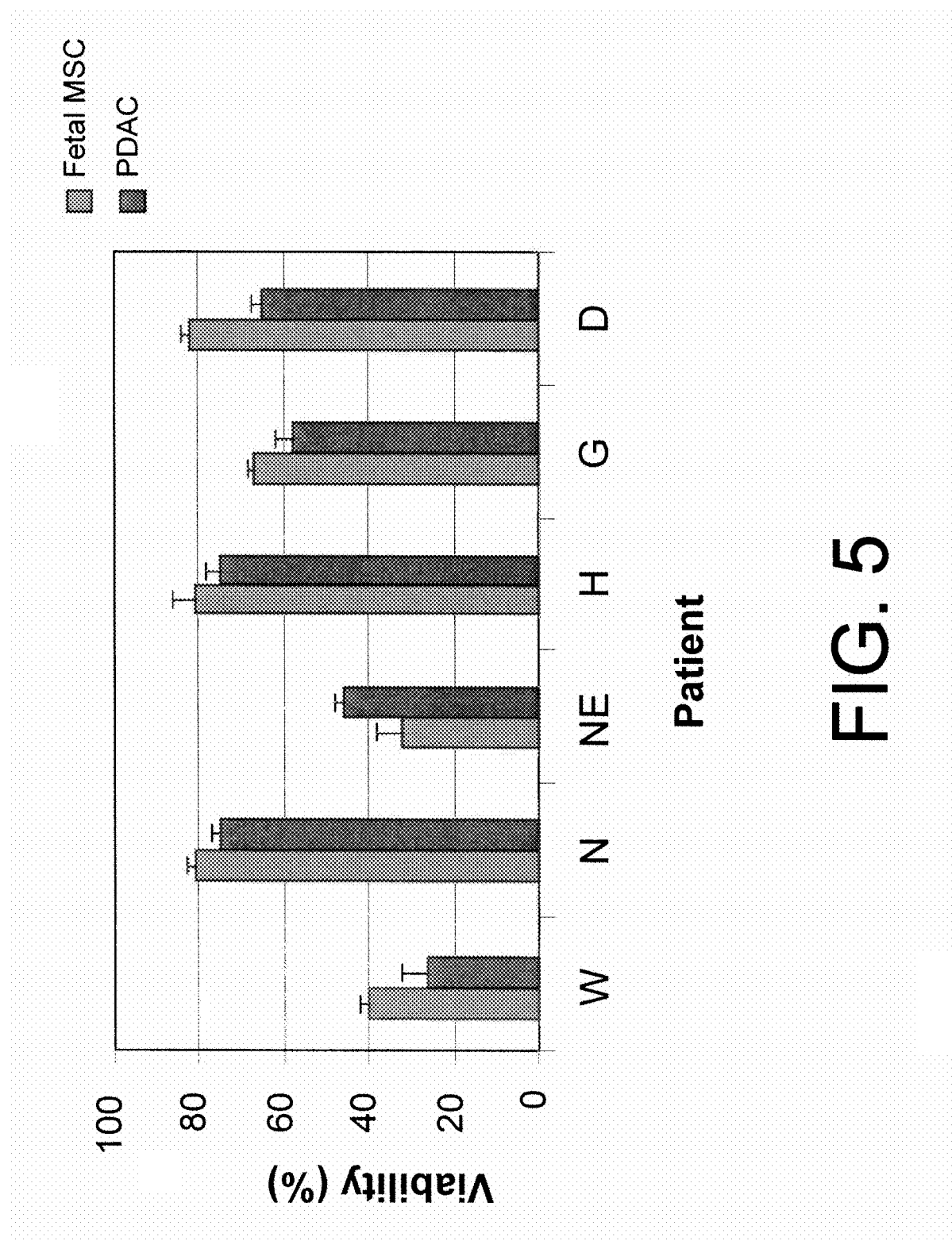

FIG. 5: Suppression of multiple myeloma cells from six different patients (X-axis) by placental stem cells (PDACs) and fetal bone marrow-derived mesenchymal stem cells (Fetal MSCs). Y-axis: percent viability compared to myeloma cells cultured in the absence of placental stem cells.

Figure 6:
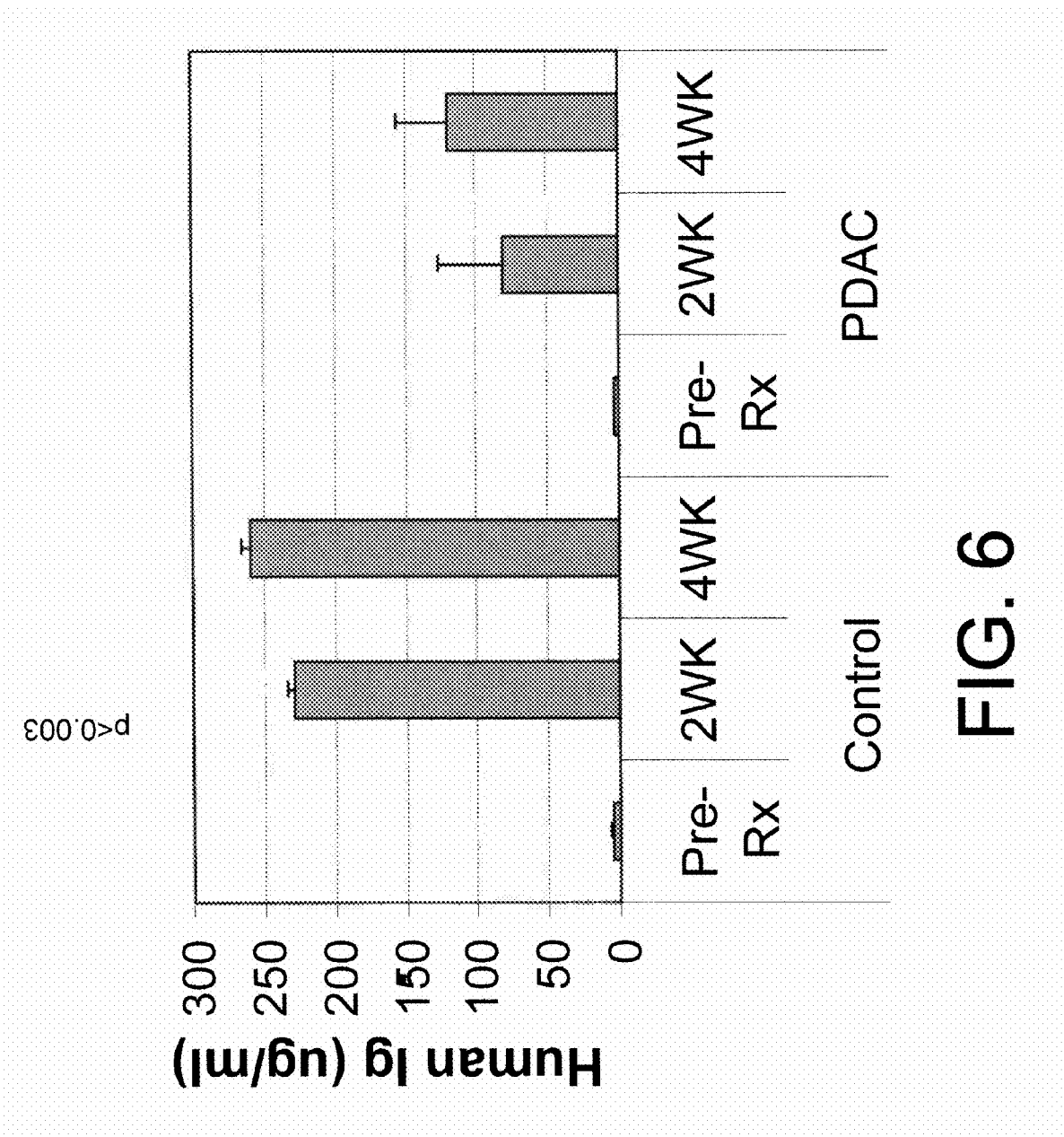

FIG. 6: Placental stem cells reduce multiple myeloma cell growth in SCID-rab/SCID-hu mice. The number of multiple myeloma cells was assessed by the titer of human antibody present in sera from the mice, as assessed by ELISA. Pre-Rx: titer of human antibody before administration of myeloma cells. 2 WK, 4 WK: titer of human antibody two weeks and four weeks post-administration of multiple myeloma cells, either alone (control) or with placental stem cells.

Figure 7:
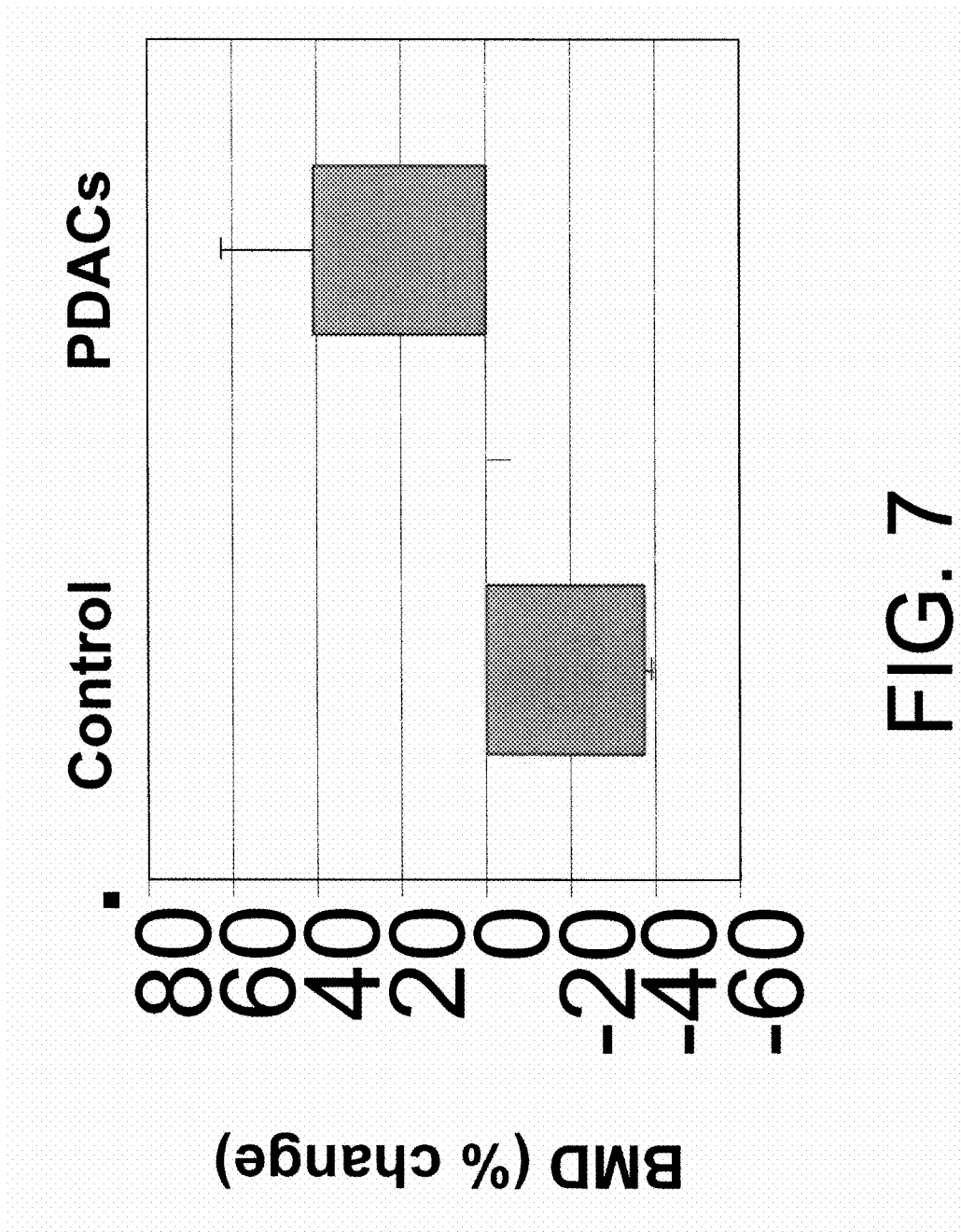

FIG. 7: Change in bone mass density, as assessed by X-rays, of bone implants in SCID-rab/SCID-hu mice. BMD: bone mineral density.

Figure 8:
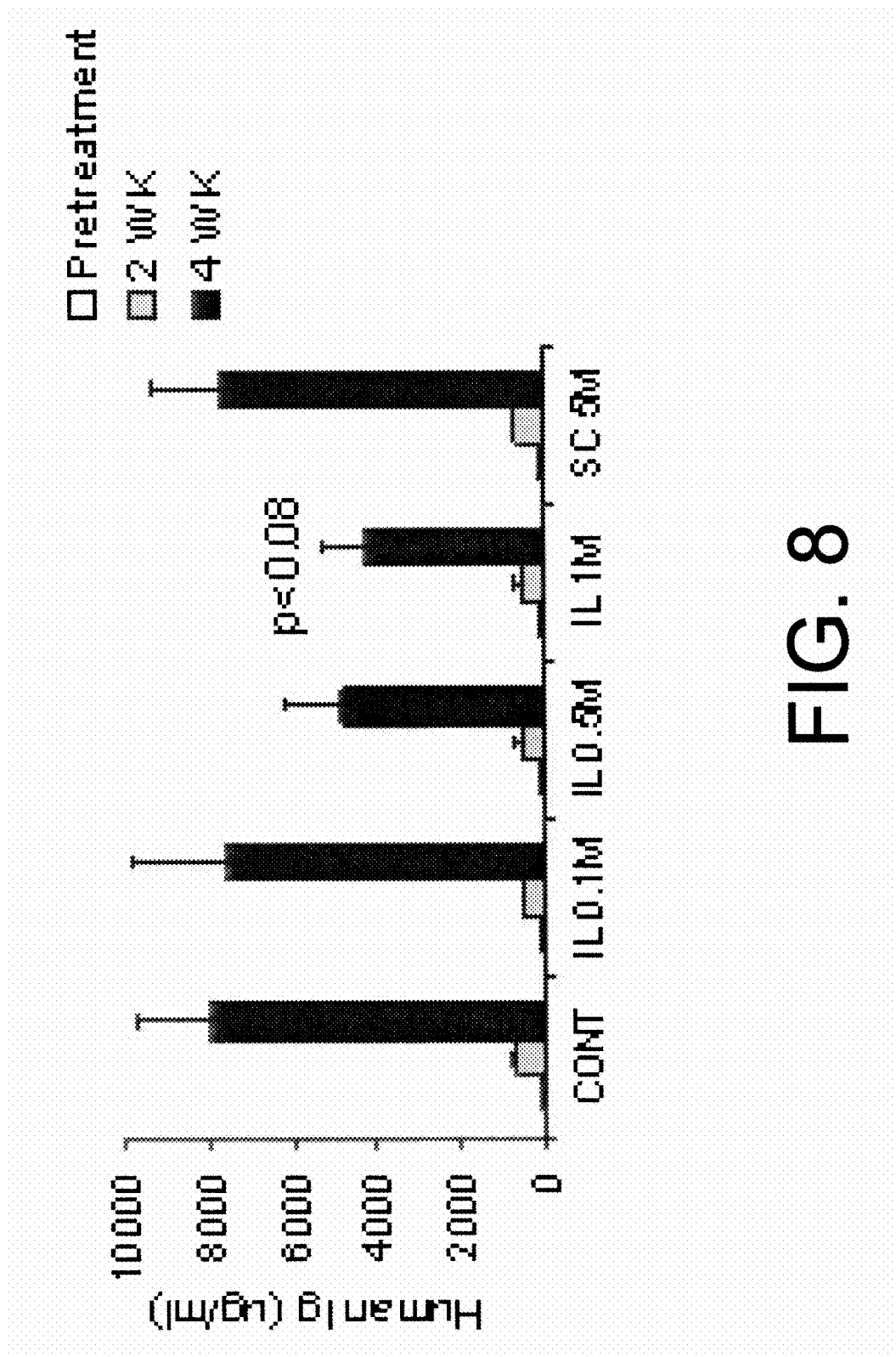
Figure 9:
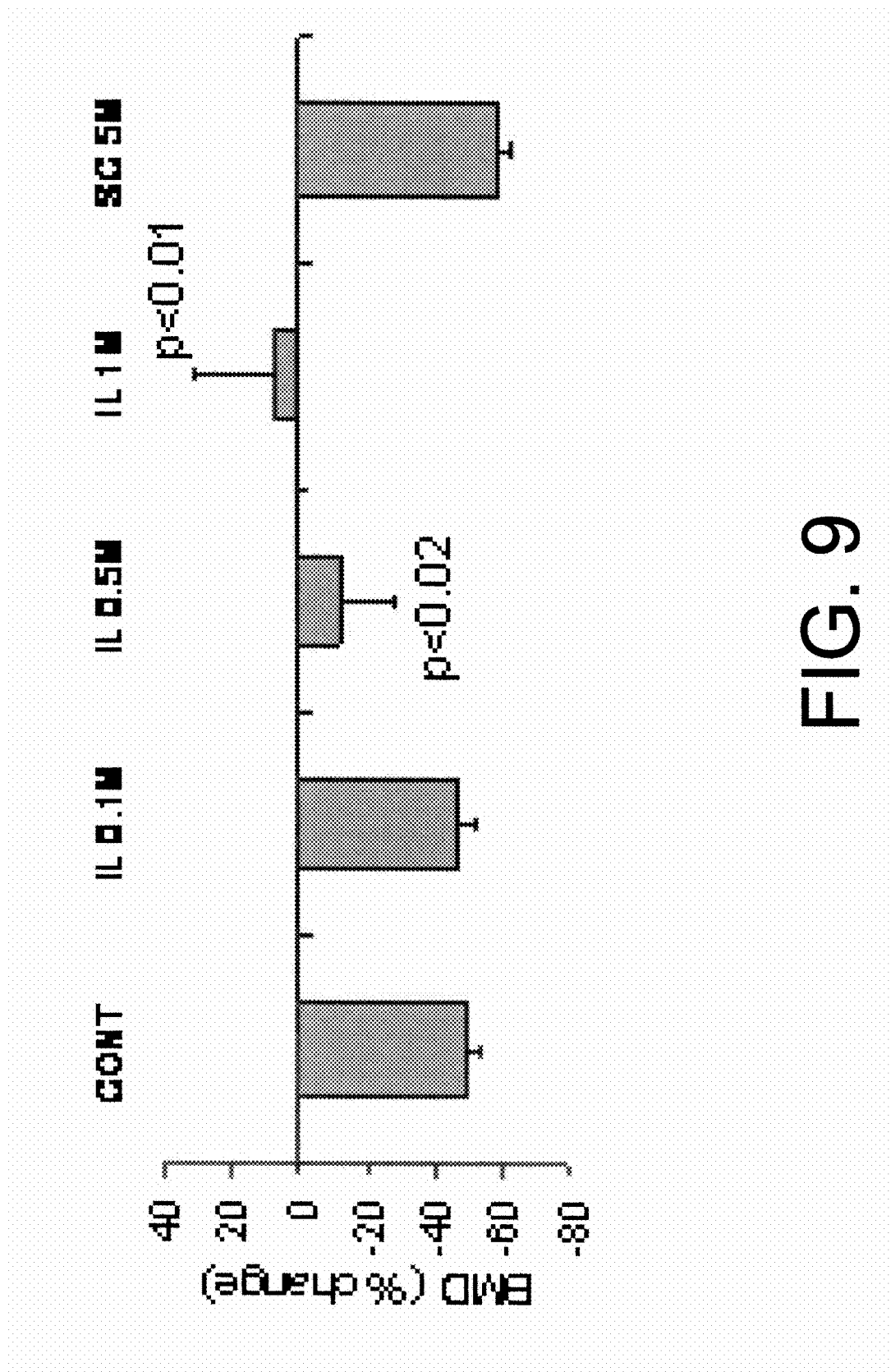

FIGS. 8-9: Placental stem cells effects on myeloma bone disease and tumor growth is dose dependent and comparable with fetal MSCs. SCID-rab mice engrafted with patient's 2 myeloma cells. (A-C) Upon establishment of high tumor burden hosts were intralesionally injected with vehicle, with 0.1, 0.5 and 1×10$^6$ placental stem cells, or subcutaneously engrafted with 5×10$^6$ placental stem cells using HyStem-C hydrogel carrier (see Methods for details) (6-7 mice/group).

FIG. 8: Changes in human immunoglobulin (Ig) prior to treatment (Pre-Rx), 2 and 4 weeks after treatment with placental stem cells. IL=intralesional administration of 0.1, 0.5 or 1×10$^6$ cells. SC=subcutaneous administration of cells. CONT=control (no cells).

FIG. 9: Changes in bone mineral density from pretreatment levels of the implanted myelomatous bone. IL=intralesional administration of 0.1, 0.5 or 1×10$^6$ cells. SC=subcutaneous administration of cells. CONT=control (no cells).

Figure 10:
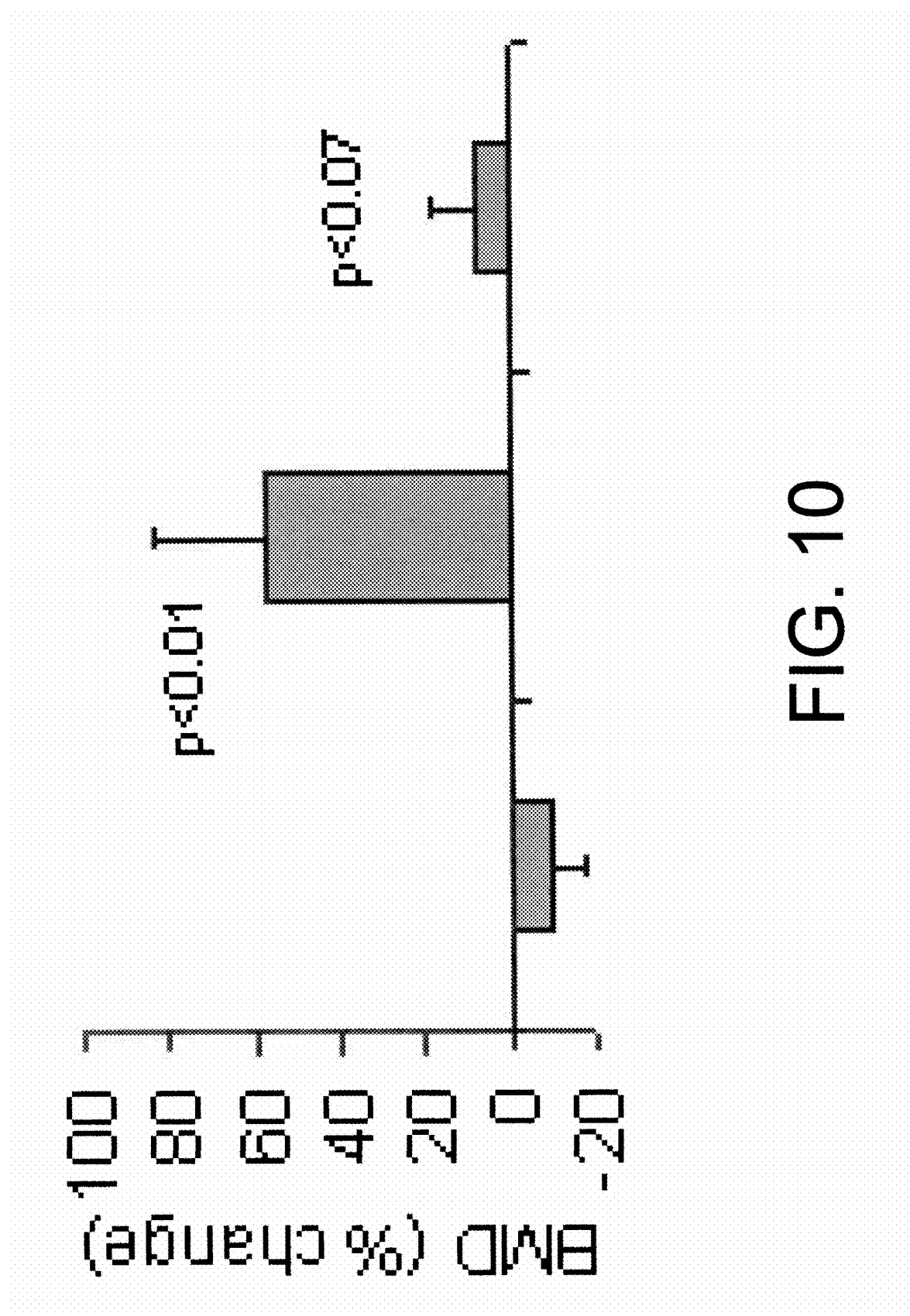

FIG. 10: Hosts were intralesionally injected with vehicle, or with 1×10$^6$ placental stem cells or MSCs. FIG. 10 depicts changes in bone mineral density from pretreatment levels of the implanted myelomatous bone. Left condition: control (no cells); middle condition: placental stem cells; right condition: bone marrow-derived mesenchymal stem cells.

Figure 11:
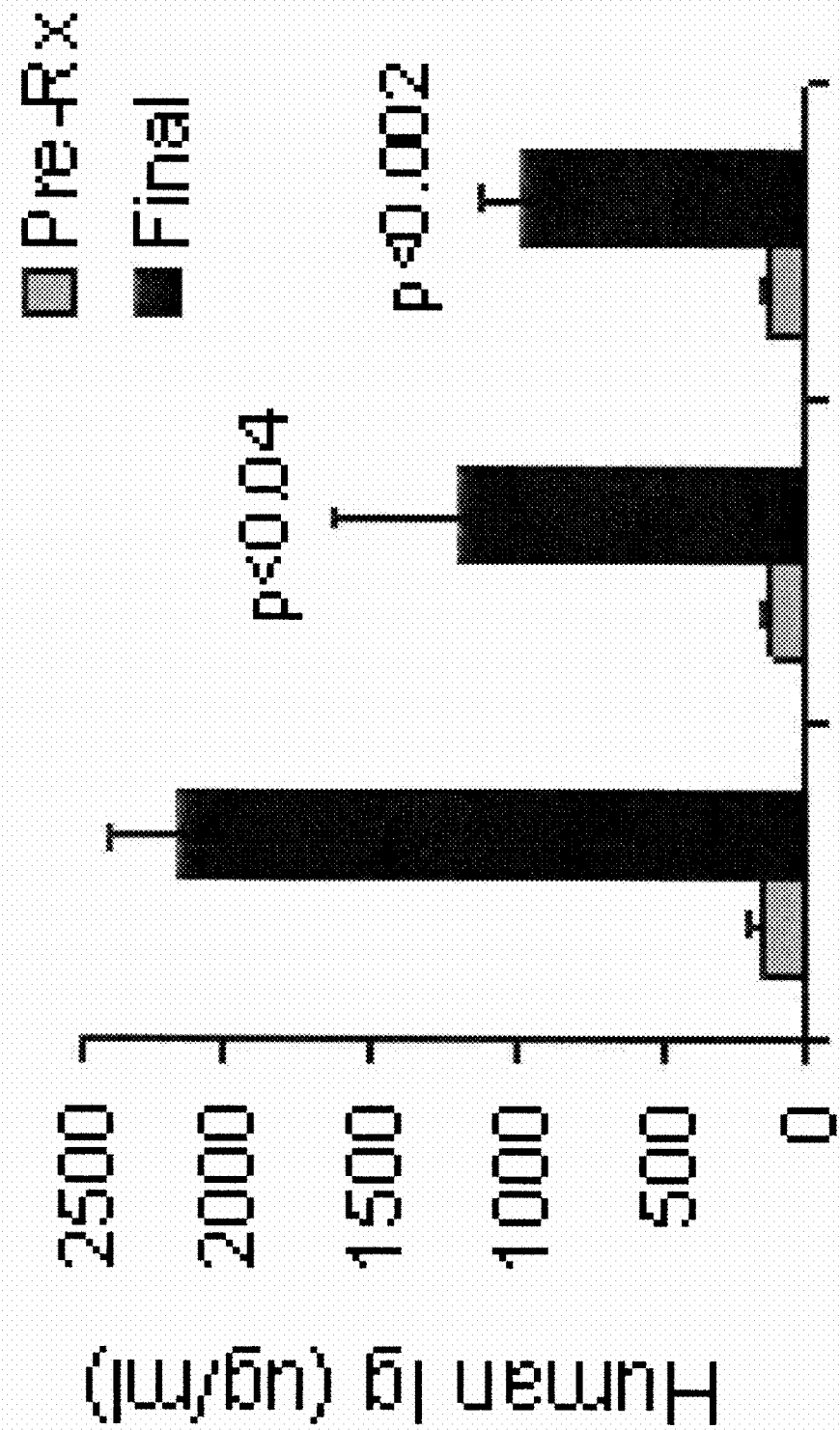

FIG. 11: Hosts were intralesionally injected with vehicle, or with 1×10$^6$ placental stem cells or MSCs. FIG. 11 depicts changes in human Ig prior to treatment (Pre-Rx) and experiment's end. Left condition: control (no cells); middle condition: placental stem cells; right condition: bone marrow-derived mesenchymal stem cells.

Figure 12:
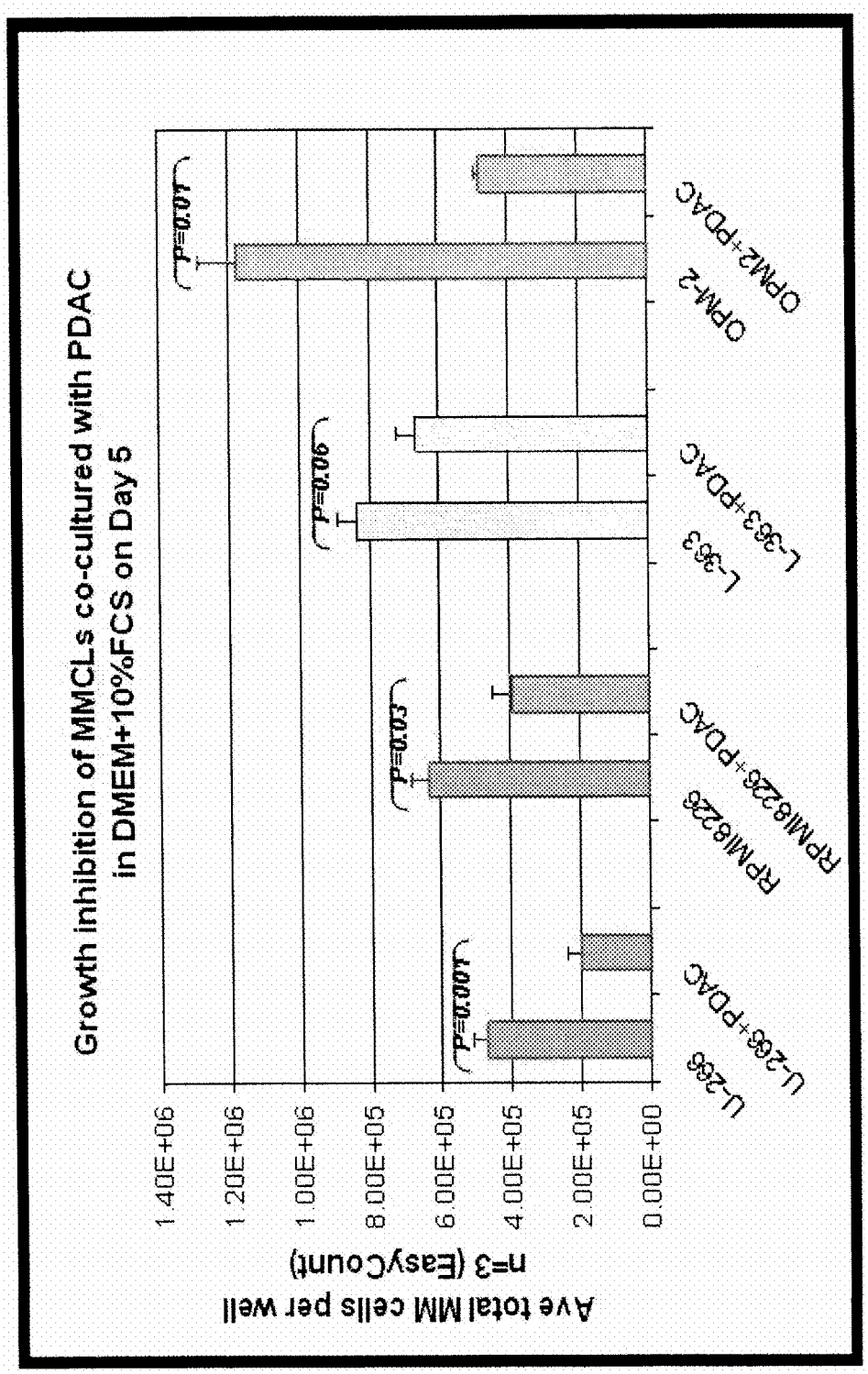

FIG. 12: Comparison of the average number (n=3) of multiple myeloma cell line cells (U-266, RPMI-8226, L363 and OMP-2) per well in the presence or absence of placental stem cells on day 5 of culture or co-culture. P-values are provided for control and experimental conditions for each multiple myeloma cell line.

Figure 13B:
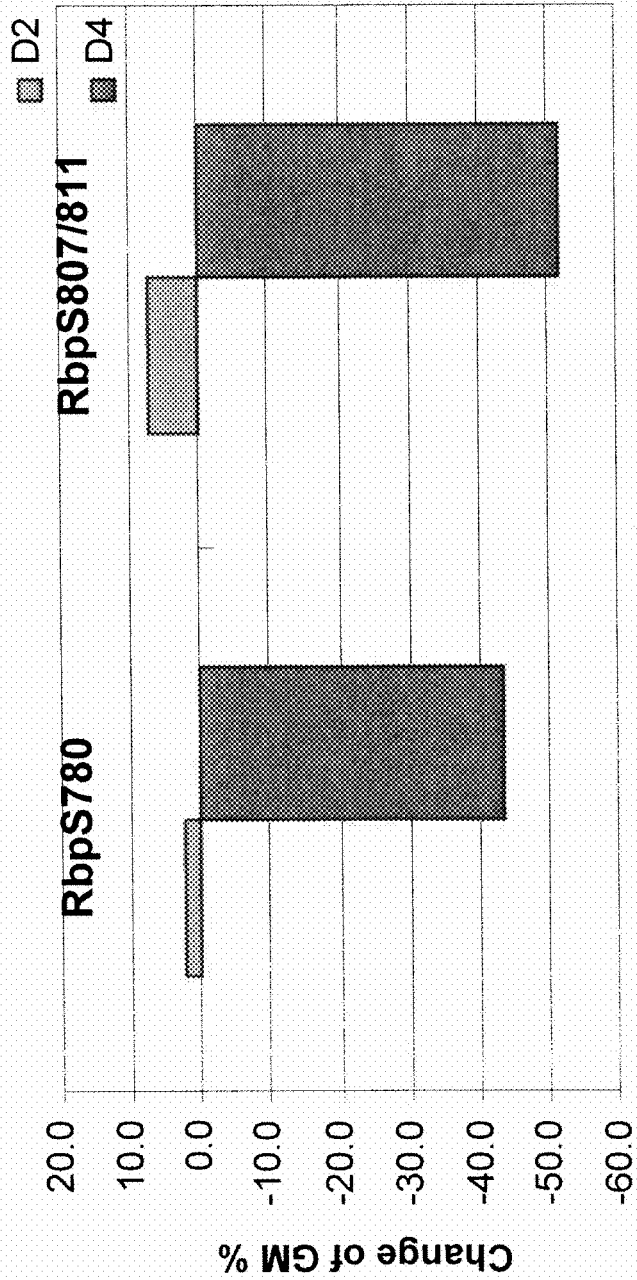
Figure 13C:
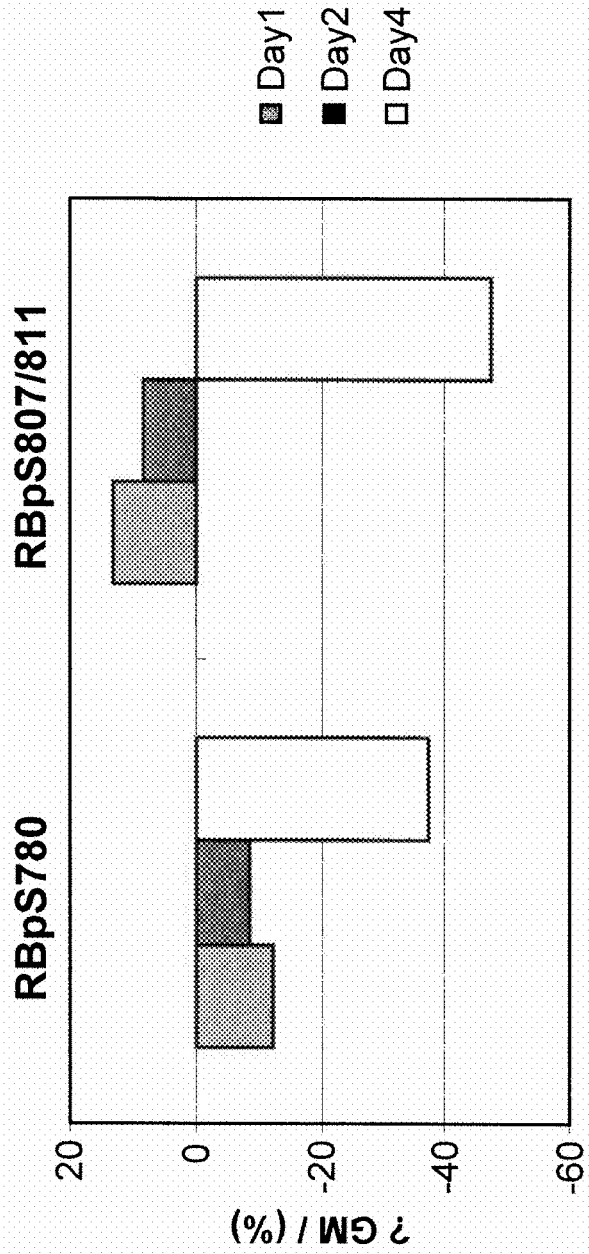

FIGS. 13A-13C: Reduction in the phosphorylation of retinoblastoma (Rb) protein at Serine 780 (S780), or at serines 807 and 811 (S807/S811) for multiple myeloma cell lines H929 (FIG. 13A), OPM-2 (FIG. 13B) and LP1 (FIG. 13C). D2: Day 2 of co-culture. D4: Day 4 of co-culture. GM: geometric mean of increase/decrease in Rb phosphorylation. Δ: Change in geometric mean.

Figure 14:
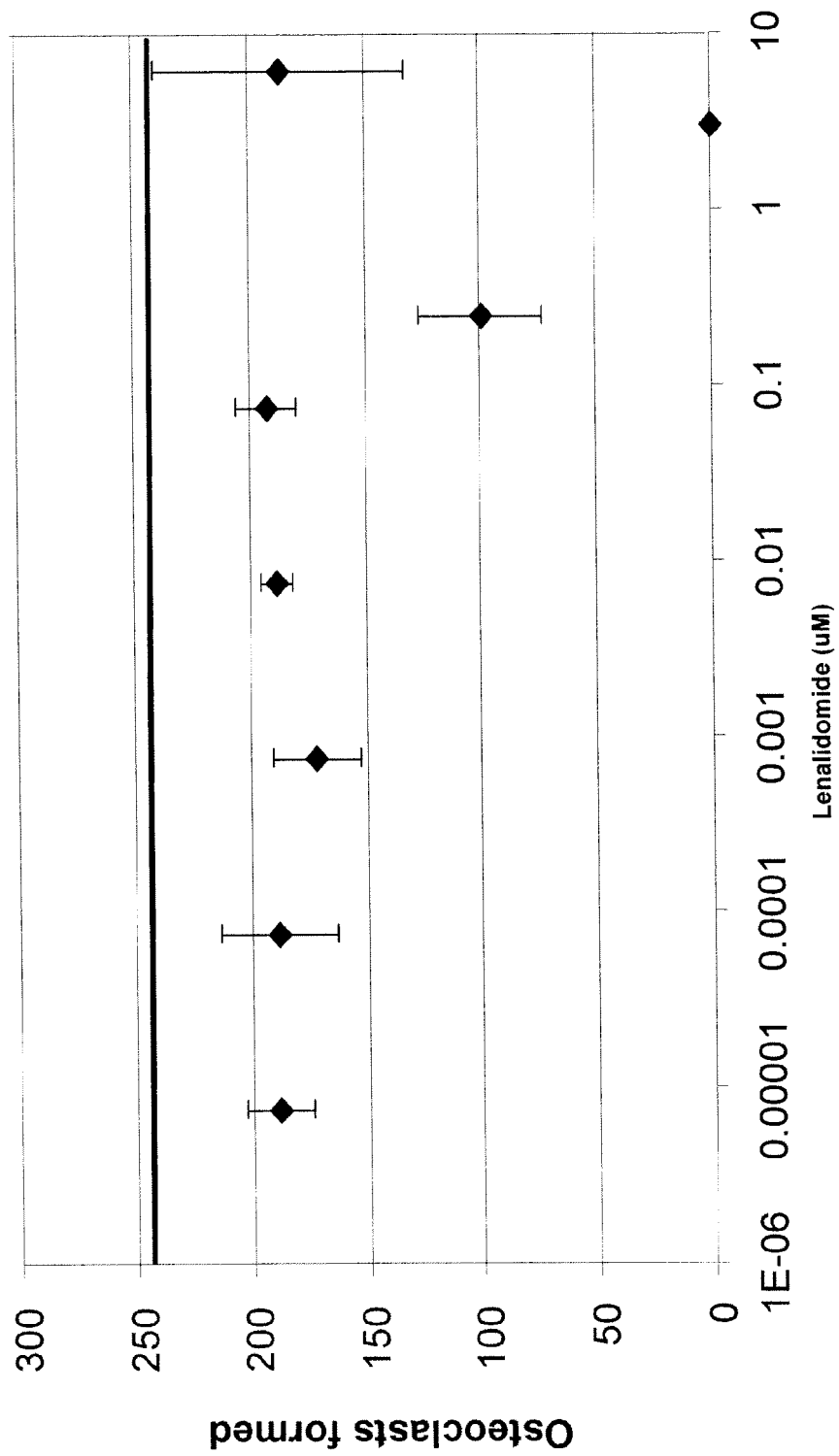

FIG. 14: Number of osteoclasts formed when cultured in the presence of 1 μM lenalidomide. Thick horizontal line represents the number of osteoclasts formed in the control wells.

Figure 15:
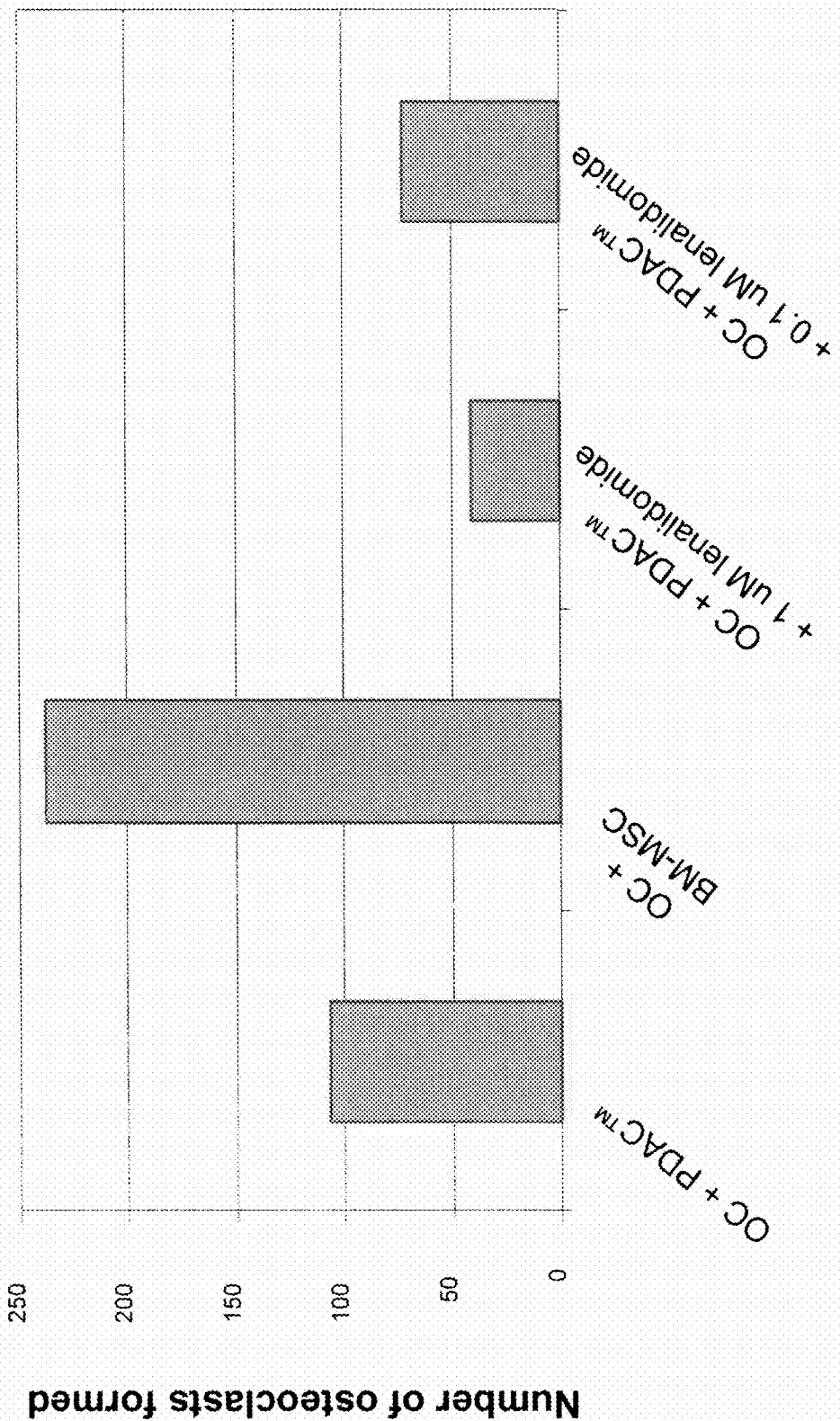

FIG. 15: Number of osteoclasts formed when co-cultured with placental stem cells (PDACs) alone, bone marrow-derived mesenchymal stem cells (BM-MCS), or the combination of PDACs and lenalidomide.

5. DETAILED DESCRIPTION

5.1 Treatment of Bone-Related Cancers Using Isolated Placental Stem Cells and/or Mesenchymal Stem Cells Provided herein are methods of treating an individual having a bone-related cancer comprising administering to the individual isolated placental stem cells, in particular, the isolated placental stem cells described in detail in Section 5.2, below, also referred to herein as PDACs (Placenta Derived Adherent Cells), and/or bone marrow-derived mesenchymal stem cells (BM-MSCs), e.g., a therapeutically effective amount of either or both of said cells. Bone-related cancers include, without limitation, multiple myeloma, bone cancer, neuroblastoma, osteosarcoma, Ewing's sarcoma, chondrosarcoma, chordoma, malignant fibrous histiocytoma of bone, fibrosarcoma of bone, prostate cancer, and any form of metastatic cancer characterized by bone metastases. In certain embodiments, the bone-related cancer does not include prostate cancer. In certain embodiments, administration of isolated placental stem cells and/or BM-MSCs is therapeutically effective to reduce, ameliorate or reverse one or more symptoms associated with the bone-related cancer, e.g., a symptom caused by, associated with, or related to an effect of the cancer on one or more bones in the individual, e.g, a bone defect attributable to the bone-related cancer. Treatment of bone-related cancers with placental stem cells and/or BM-MSCs as provided herein, can occur before, after, or concurrently with a second anti-cancer therapy, as discussed below. Accordingly, in one embodiment, bone defects that are a symptom of a bone-related cancer are treated before the cancer is treated with a second anti-cancer therapy. In another embodiment, bone defects that are a symptom of a bone-related cancer are treated at the same time, or near the same time, that the cancer is treated with a second anti-cancer therapy. In another embodiment, bone defects that are a symptom of a bone-related cancer are treated after the cancer is treated with a second anti-cancer therapy.

In one aspect, provided herein are methods of treating an individual having a bone-related cancer, comprising administering to the individual a therapeutically effective amount of placental stem cells and/or BM-MSCs. In one embodiment, provided herein is a method of treating an individual having a bone-related cancer, comprising administering to said individual a therapeutically effective amount of placental stem cells and/or BM-MSCs for a time sufficient for said placental stem cells and/or BM-MSCs to improve, e.g., detectably improve, one or more symptoms of, or reduce, e.g., detectably reduce, the progression of, said bone-related cancer. In a specific embodiment, said bone-related cancer is multiple myeloma. In another specific embodiment, the bone-related cancer is sarcoma. In other specific embodiments, said bone-related cancer is bone cancer, neuroblastoma, osteosarcoma, Ewing's sarcoma, chordoma, malignant fibrous histiocytoma of bone, or fibrosarcoma of bone. In another specific embodiment, said bone-related cancer comprises a solid tumor. In another specific embodiment, said bone-related cancer is not prostate cancer.

As used herein, "administering for a time sufficient," and the like, encompasses, for example, administration of cells, e.g., a unit of cells, followed by evaluation of the one or more symptoms of bone-related cancer, e.g., multiple myeloma, over a time sufficient to determine any change in the one or more symptoms, e.g., over the course of 1, 2, 3, 4, 5, 6, 7, 8, 9, 10, 11, 12, 13, 14, 15, 16, 17, 18, 19, 20, 21, 22 or 23 hours, or 1, 2, 3, 4, 5, or 6 days, or over 1, 2, 3, or 4 weeks, or the like. If no change is detected, one or more subsequent administrations of cells can take place.

In certain embodiments, treatment of bone-related cancers, e.g., multiple myeloma, comprises administering an amount, e.g., a therapeutically effective amount, of isolated placental stem cells and/or BM-MSCs, to an individual having bone-related cancer cells, e.g., multiple myeloma cells, wherein at least some of said placental stem cells and/or BM-MSCs directly contact at least some of the bone-related cancer cells, e.g., there is direct cell-cell contact between at least some of said placental stem cells and/or BM-MSCs, and at least some of said bone-related cancer cells. In certain other embodiments, treatment of bone-related cancers, e.g., multiple myeloma, comprises administering an amount, e.g., a therapeutically effective amount, of placental stem cells and/or BM-MSCs to an individual having bone-related cancer cells, e.g., multiple myeloma cells, wherein none, or substantially none, of said placental stem cells and/or BM-MSCs directly contact said bone-related cancer cells, e.g., there is no, or substantially no, direct cell-cell contact between most, or any, of said placental stem cells and/or BM-MSCs, and said bone-related cancer cells.

In certain embodiments, the placental stem cells and/or BM-MSCs, are administered intralesionally, e.g., directly into, or adjacent to (e.g., within about 1-5 cm of) one or more bone lesions caused by the bone-related cancer. In certain embodiments, the placental stem cells and/or BM-MSCs, are administered in combination with a matrix, e.g., an injectable matrix. In certain other embodiments, the placental stem cells and/or BM-MSCs, are administered to an individual having a bone-related cancer in combination with alginate, or with platelet-rich plasma. In certain other embodiments, the placental stem cells and/or BM-MSCs are administered to an individual having a bone-related cancer in combination with a solid matrix, e.g., a bone substitute, a matrix or bone substitute described in Section 5.7.4, below.

In certain other embodiments, the placental stem cells and/or BM-MSCs are administered intravenously to the individual. The placental stem cells and/or BM-MSCs can be administered from any container, and by any delivery system, medically suitable for the delivery of fluids, e.g., fluids comprising cells, to an individual. Such containers can be, for example, a sterile plastic bag, flask, jar, or other container from which the placental stem cells or BM-MSCs can be easily dispensed. For example, the container can be a blood bag or other plastic, medically-acceptable bag suitable for the intravenous administration of a liquid to a recipient.

Intralesional or intravenous administration can comprise, e.g., about, at least, or no more than $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$ or more isolated placental stem cells and/or BM-MSCs in a single dose. In certain embodiments, a dose of BM-MSCs comprises approximately 50% more cells than a dose of placental stem cells, e.g., PDACs.

In one embodiment, intralesional or intravenous administration can comprise about $2 \times 10^8$ placental stem cells in a single dose. In another embodiment, intralesional or intravenous administration can comprise about $8 \times 10^8$ placental stem cells in a single dose. The isolated placental stem cells may be administered once, or more than once, during a course of therapy. Preferably, the administered placental stem cells comprise at least 50% viable cells or more (that is, at least about 50%, 60%, 70%, 80%, 90%, 95%, 98% or 99% of the placental stem cells in a population of placental stem cells are functional or living). Preferably, at least about 60% of the cells in the population are viable. More preferably, at least about 70%, 80%, 90%, 95%, or 99% of the cells in the population in the pharmaceutical composition are viable.

Administration of isolated placental stem cells and/or BM-MSCs, in addition to treating symptoms of bone-related cancers, e.g., symptoms of multiple myeloma, such as bone lesions, can suppress the proliferation or growth of cells of the bone-related cancer, e.g., multiple myeloma cells. Suppression of proliferation can encompass, e.g., reducing the growth or proliferation rate of tumor cells, or killing some or all of the tumor cells. Thus, in another aspect, provided herein is a method of suppressing proliferation of cells of a bone-related cancer, comprising contacting said plurality of tumor cells with a plurality of placental stem cells and/or BM-MSCs for a time sufficient for said placental stem cells and/or BM-MSCs to suppress, e.g., detectably suppress, proliferation of said cells of a bone-related cancer, as compared to a plurality of said cells of a bone-related cancer not contacted with placental stem cells and/or BM-MSCs, e.g., as determinable by a detectable reduction in the number of such cells after treatment, a detectable reduction in the increase in the number of such cells after treatment, or the like. In specific embodiments, said cells of a bone-related cancer are multiple myeloma cells, bone cancer cells, neuroblastoma cells, osteosarcoma cells, Ewing's sarcoma cells, chondrosarcoma cells, chordoma cells, cells of a malignant fibrous histiocytoma of bone, cells of a cancer that metastasizes to the bone, prostate cancer cells, or cells of a fibrosarcoma of bone. In another specific embodiment, said cells of a bone-related cancer are cells of or within a solid tumor. In another specific embodiment, said cells of a bone-related cancer are not prostate cancer cells.

In another specific embodiment, said contacting is performed in vitro. In another specific embodiment, said contacting is performed in vivo, e.g., by administration of the cells to an individual having cells of a bone-related cancer, e.g., multiple myeloma or a chondrosarcoma. In another specific embodiment, said individual is a mammal. In another specific embodiment, said mammal is a human. In another specific embodiment, said contacting comprises administering said placental stem cells and/or BM-MSCs to said individual intravenously. In another specific embodiment, said contacting comprises administering said placental stem cells and/or BM-MSCs to said individual at or adjacent to a bone lesion caused by said bone-related cancer, e.g., intralesionally or intraosseously.

In another embodiment, the method of suppressing proliferation of cells of a bone-related cancer, e.g., multiple myeloma cells, by contacting said cells of a bone-related cancer with placental stem cells and/or BM-MSCs additionally comprises contacting said cells of a bone-related cancer with one or more anticancer compounds, e.g., one or more of the anticancer compounds in Section 5.1.3, e.g., administering one or more of said anticancer compounds to said individual.

In another embodiment, the method comprises administering at least $1 \times 10^7$ placental stem cells and/or BM-MSCs to said individual, by total numbers of cells. In another specific embodiment, the method comprises administering at least $1 \times 10^8$ placental stem cells and/or BM-MSCs to said individual, by total numbers of cells. In another specific embodiment, said placental stem cells and/or BM-MSCs have been proliferated in vitro prior to administration for no more than 30 population doublings. In another specific embodiment, said placental stem cells and/or BM-MSCs have been proliferated in vitro prior to administration for no more than 10 population doublings. In another specific embodiment, said placental stem cells and/or BM-MSCs have been cryopreserved and thawed prior to said contacting.

In another specific embodiment of the method, said placental stem cells and/or BM-MSCs suppress proliferation of said cells of a bone-related cancer, e.g., by at least 10%, 20%, 30%, 40%, 50%, 60%, 70%, 80% or 90%, e.g., as compared to proliferation of an equivalent number of cells of a bone-related cancer in the absence of said placental stem cells and/or BM-MSCs. In certain embodiments, the percent reduction in proliferation can be assessed by, for example, comparing a number of bone-related cancer cells in a tissue (e.g., blood) sample from an individual having the bone-related cancer before and after administration of the placental stem cells and/or BM-MSCs. In another specific embodiment, the method comprises determining, prior to said contacting, that said placental stem cells and/or BM-MSCs suppress, e.g., detectably suppress, the proliferation of a sample of said cells of a bone-related cancer. In such an embodiment, for example, the placental stem cells and/or BM-MSCs could be determined to suppress the proliferation of a sample of said cells of a bone-related cancer by, e.g., taking a sample of a population of placental stem cells and/or BM-MSCs (for example, a sample from a unit or lot from a stem cell bank, or the like).

In any of the methods disclosed herein, e.g., methods of treatment, methods of suppressing tumor growth, or methods of suppressing osteoclast maturation, disclosed herein, placental stem cells, e.g., PDACs, or BM-MSCs may be used alone, or the placental stem cells and BM-MSCs may be used in combination. When used in combination, the cells may be combined so as to be administrable at the same time, e.g., in the same unit of cells; or may be administrable separately, e.g., maintained in separate cell units, for example, in separate blood-type bags. When used in combination, administration of the placental stem cells and BM-MSCs can take place together, at the same time, or can take place at separate times.

Further provided herein is a method of reducing the maturation of osteoclast precursors into osteoclasts, comprising contacting said osteoclast precursors with a plurality of isolated placental stem cells and/or BM-MSCs (e.g., isolated BM-MSCs or BM-MSCs in bone marrow), wherein said plurality of placental stem cells and/or BM-MSCs is a number of placental stem cells and/or BM-MSCs, sufficient to reduce, e.g., detectably reduce, osteoclast maturation from said osteoclast precursors. In a specific embodiment, said contacting takes place in vitro. In another specific embodiment, said contacting takes place in vivo. In another specific embodiment, said contacting takes place in a mammal, e.g., in a human. In another specific embodiment, said contacting takes place in an individual having multiple myeloma, or comprising multiple myeloma cells, or who has one or more symptoms of multiple myeloma. In another specific embodiment, said one or more symptoms of multiple myeloma comprise one or more bone lesions, or bone pain resulting from osteoclast activity.

In another embodiment, provided herein is a method of increasing apoptosis of osteoclast precursors, comprising contacting said osteoclast precursors with a plurality of placental stem cells and/or BM-MSCs (e.g., isolated BM-MSCs or BM-MSCs in bone marrow), wherein said plurality of placental stem cells and/or BM-MSCs, is a number of placental stem cells and/or BM-MSCs, sufficient to increase, e.g., detectably increase, osteoclast precursor apoptosis. In a specific embodiment, said contacting takes place in vitro. In another specific embodiment, said contacting takes place in vivo. In another specific embodiment, said contacting takes place in a human. In another specific embodiment, said contacting takes place in an individual having multiple myeloma, or comprising multiple myeloma cells, or who has one or more symptoms of multiple myeloma. In another specific embodiment, said one or more symptoms of multiple myeloma comprise one or more bone lesions, or bone pain resulting from osteoclast activity. In another specific embodiment, said increase in osteoclast precursor apoptosis is detected by a detectable increase in annexin V and propidium iodide staining of osteoclast precursors from said individual.

In any of the above embodiments, the placental stem cells and/or BM-MSCs can be genetically engineered placental stem cells, e.g., the genetically engineered cells described in Section 5.7.2, below.

In any of the methods disclosed herein, said individual is a mammal. In a specific embodiment, said mammal is a human.

In any of the methods disclosed herein, the BM-MSCs can be isolated bone marrow-derived mesenchymal stem cells, e.g., BM-MSCs that have been cultured or purchased from a commercial source, or can be BM-MSCs contained within bone marrow, e.g., bone marrow aspirate, crude bone marrow, or the like.

5.1.1 Treatment of Multiple Myeloma

Provided herein are methods of treating an individual having multiple myeloma, comprising administering to said individual placental stem cells and/or BM-MSCs, wherein said isolated placental stem cells have any combination of, or all of, the characteristics described in Section 5.2, below.

Multiple myeloma is a cancer of plasma cells, which are antibody-producing cells of the immune system. The disease typically presents with three main characteristics: bone lesions, the development of which can result in bone pain and elevated blood calcium; anemia; and renal failure.

In certain embodiments, provided herein are methods of treating individuals having one or more multiple myeloma-related diseases or conditions, or symptoms thereof. In specific embodiments, said multiple myeloma-related diseases or conditions are monoclonal gammopathy of unknown significance (MGUS), smoldering myeloma (e.g., smoldering multiple myeloma), solitary plasmacytoma, benign monoclonal gammopathy, asymptomatic monoclonal gammopathy, non-myelomatous monoclonal gammopathy, discrete monoclonal gammopathy, cryptogenic monoclonal gammopathy, lanthanic monoclonal gammopathy, rudimentary monoclonal gammopathy, dysimmunoglobulinemia, asymptomatic paraimmunoglobulinemia, or idiopathic paraproteinemia. In certain embodiments, a person having smoldering myeloma exhibits blood paraprotein, but no other symptoms of multiple myeloma.

In certain embodiment, the symptoms are as follows.

Bone Lesions and Bone Pain—

Myeloma cells secrete osteoclast activating factor, which is a cytokine that activates osteoclasts to break down bone, creating painful bone lesions. These bone lesions, visible, e.g., in X-ray radiographs, are lytic in nature and typically appear as one or more regions in which the bone appears absent or "punched out." Myeloma bone pain usually involves the spine and ribs, and worsens with activity. Persistent localized pain may be present, and can indicate a pathological bone fracture. Involvement of the vertebrae may lead to spinal cord compression. The breakdown of bone also leads to release of calcium into the blood, leading to hypercalcemia and its associated symptoms.

Anemia—

The anemia found in myeloma is usually normocytic and normochromic, and results from the replacement of normal bone marrow by infiltrating tumor cells and inhibition of normal red blood cell production (hematopoiesis) by cytokines.

Renal Failure—

Multiple myeloma also tends to result in renal failure, which may develop both acutely and chronically. Renal failure in multiple myeloma is largely attributable to hypercalcemia, which develops as osteoclasts dismantle existing bone. Renal failure is also caused by tubular damage from excretion of light chains, also called Bence Jones proteins, which can manifest as the Fanconi syndrome (type II renal tubular acidosis). Other causes include glomerular deposition of amyloid, hyperuricemia, recurrent infections (e.g., pyelonephritis), and local infiltration of tumor cells. Renal failure can be associated with elevated levels of serum creatinin.

Multiple myeloma can present with other symptoms, as well, as follows.

Infection—

Another common symptom of multiple myeloma is infection, as the immune system is disrupted. The increased risk of infection is due to immune deficiency resulting from diffuse hypogammaglobulinemia, which is due to decreased production and increased destruction of normal antibodies. The most common infections are pneumonias and pyelonephritis. Common pneumonia pathogens causing disease in multiple myeloma patients include *Streptococcus pneumoniae, Staphylococcus aureus*, and *Klebsiella pneumoniae*, while common pathogens causing pyelonephritis include *Escherichia coli*. Typically, infection occurs in the initial few months after the start of chemotherapy.

Neurological Symptoms—

Symptoms of multiple myeloma include a spectrum of neurological conditions, including weakness, confusion and fatigue due to hypercalcemial headache, visual changes and retinopathy, which can be the result of hyperviscosity of the blood depending on the properties of paraprotein (see below). Other neurological symptoms include radicular pain, loss of bowel or bladder control (for example, due to involvement of spinal cord leading to cord compression), and carpal tunnel syndrome and other neuropathies (for example, due to infiltration of peripheral nerves by amyloid). Multiple myeloma may give rise to paraplegia in late presenting cases.

Presence of Paraprotein—

A diagnostic symptom of multiple myeloma is the presence in the blood and/or urine of paraprotein, which is a monoclonal protein (M protein), e.g., an immunoglobulin light-chain that is produced by the clonal proliferation of plasma cells, or immunoglobulin fragments. Presence of paraprotein can be determined by analyzing protein from urine and/or serum from an individual by agarose gel electrophoresis, or by immunofixation using one or more antibodies to an immunoglobulin light or heavy chain.

Symptomatic multiple myeloma, in certain embodiments, is diagnosed when the following symptoms or signs are present: clonal plasma cells constituting greater than 10% of cells on bone marrow biopsy or, in any quantity in a biopsy from other tissues (e.g., plasmacytoma); paraprotein in either serum or urine; evidence of end-organ damage (related organ or tissue impairment), for example, hypercalcemia (e.g., corrected calcium greater than about 12 mg per deciliter of blood, or greater than about 2.75 mmol in the blood), renal insufficiency attributable to myeloma, anemia defined as hemoglobin<10 g/dL blood, bone lesions (e.g., lytic lesions or osteoporosis with compression fractures, frequent severe infections (>2 a year), amyloidosis (the deposition of amyloid protein) of other organs, and hyperviscosity syndrome (increase in the viscosity of blood), e.g., a blood viscosity of above 1.8 centipoises, e.g., a blood viscosity of at least 2, 3, 4, or 5 centipoises.

Individuals having multiple myeloma, in certain embodiments, fall into one of the following groups. In one embodiment, the individual having multiple myeloma has never been treated for the disease. In another embodiment, the individual has responsive myeloma; that is, multiple myeloma that is responding to therapy. In a specific embodiment, such an individual exhibits a decrease in M protein (paraprotein) of at least 50% as a result of treatment. In another specific embodiment, the individual exhibits a decrease in M protein of between 25% and 50% as a result of treatment. In another embodiment, the individual has stable multiple myeloma, which refers to myeloma that has not responded to treatment (for example, the decrease in M protein has not reached 50%), but has not progressed or gotten worse. In another embodiment, the individual has progressive multiple myeloma, which refers to active myeloma that is worsening (for example, increasing M protein and worsening organ or tissue impairment or end organ damage). In another embodiment, the individual has relapsed multiple myeloma, which refers to myeloma disease that initially responded to therapy but has then begun to progress again. In specific embodiments, the individual has relapsed after initial therapy or has relapsed after subsequent therapy. In another embodiment, the individual has refractory multiple myeloma. In a specific embodiment, the refractory multiple myeloma is multiple myeloma that has not responded to initial therapy. In another specific embodiment, the refractory multiple myeloma is relapsed multiple myeloma that has not responded to subsequent treatment. In another specific embodiment, the refractory multiple myeloma is non-responding progressing refractory disease, which refers to refractory disease that is progressing. In another specific embodiment, the refractory multiple myeloma is non-responding non-progressing refractory disease, which refers to refractory disease that is not worsening.

Thus, in one embodiment, provided herein is a method of treating an individual having multiple myeloma, comprising administering to the individual isolated placental stem cells and/or BM-MSCs (e.g., isolated BM-MSCs or BM-MSCs in bone marrow), wherein said administration results in the detectable reduction of progression, detectable lessening of worsening, and/or detectable improvement, of one or more symptoms of multiple myeloma, e.g, any one or more of the symptoms of multiple myeloma described herein, without limitation. In specific embodiments, said one or more symptoms comprise elevated blood or urine calcium compared to normal, the presence of bone lesions, anemia, or renal failure. In another specific embodiment, said one or more symptoms comprise plasma cells, e.g., clonal plasma cells constituting greater than 10% of cells on bone marrow biopsy or, in any quantity in a biopsy from other tissues (e.g., plasmacytoma); paraprotein in either serum or urine; and/or evidence of end-organ damage. In another specific embodiment, said one or more symptoms is a concentration of calcium in the blood of greater than about 2.75 mmol/L, renal insufficiency, less than about 10 g hemoglobin per deciliter of blood, the presence of bone lesions, or amyloidosis of one or more organs other than bone marrow.

In another specific embodiment, said symptom is infection, e.g., infection caused by hypergammaglobulinemia. In certain embodiments, the infection is pneumonia or pyelonephritis. In certain embodiments, said infection occurs within 1, 2, 3, 4, 5, 6, 7, 8, 9, 10, 11 or 12 months following the start of chemotherapy, e.g., chemotherapy to treat said multiple myeloma.

In another specific embodiment, said symptom is a neurological symptom. In other specific embodiments, said neurological symptoms are weakness, confusion, fatigue, headache, visual changes, retinopathy, radicular pain, loss of bowel or bladder control, carpal tunnel syndrome, and/or paraplegia.

In a specific embodiment, provided herein is a method of treating an individual having multiple myeloma, comprising administering to the individual placental stem cells and/or BM-MSCs (e.g., isolated BM-MSCs or BM-MSCs in bone marrow), wherein said administration results in the detectable reduction in number of multiple myeloma cells, e.g., clonal multiple myeloma cells, in one or more organs or tissues of the individual.

In a specific embodiment, provided herein is a method of treating an individual having multiple myeloma, comprising administering to the individual isolated placental stem cells and/or BM-MSCs (e.g., isolated BM-MSCs or BM-MSCs in bone marrow), wherein said administration results in the detectable increase in hemoglobin in the blood of the individual, e.g., an increase to within normal limits. Normal hemoglobin levels vary by the age and sex of the individual, as shown in Table 1A, below:

TABLE 1A

| Newborns | 17-22 gm/dl |
|---|---|
| One (1) week of age | 15-20 gm/dl |
| One (1) month of age | 11-15 gm/dl |
| Children | 11-13 gm/dl |
| Adult males | 14-18 gm/dl |
| Adult women | 12-16 gm/dl |
| Men after middle age | 12.4-14.9 gm/dl |
| Women after middle age | 11.7-13.8 gm/dl |

Thus, in another specific embodiment, provided herein is a method of treating an individual having multiple myeloma, comprising administering to the individual isolated placental stem cells and/or BM-MSCs (e.g., isolated BM-MSCs or BM-MSCs in bone marrow), wherein said administration results in the increase of blood hemoglobin levels in said individual to between 11 g/dL blood and 20 g/dL blood. In another specific embodiment, said administering results in the increase of blood hemoglobin levels in said individual to between 11 g/dL blood and 13 g/dL blood. In another specific embodiment, said administering results in the increase of blood hemoglobin levels in said individual to between 12 g/dL blood and 16 g/dL blood. In another specific embodiment, said administering results in the increase of blood hemoglobin levels in said individual to between 14 g/dL blood and 18 g/dL blood. In another embodiment, provided herein is a method of treating an individual having anemia, e.g., having less than about 10 g hemoglobin per deciliter of blood, comprising administering to the individual a therapeutically effective amount of placental stem cells, wherein said anemia is caused by multiple myeloma, and wherein said therapeutically effective amount is an amount sufficient to cause a rise in hemoglobin in blood from the individual to about 10 grams per deciliter or more.

In another embodiment, provided herein is a method of treating an individual having multiple myeloma, comprising administering to the individual isolated placental stem cells, a population of isolated placental stem cells or a population of cells comprising isolated placental stem cells, wherein said administration results in detectable reduction in the level of paraprotein in blood or urine from said individual. In a specific embodiment, said administering results in the reduction of paraprotein in blood or urine of said individual to an undetectable level. In another embodiment, provided herein is a method of treating an individual having paraprotein in the individual's blood, comprising administering to the individual a therapeutically effective amount of placental stem cells and/or BM-MSCs, wherein the presence of paraprotein is caused by multiple myeloma, and wherein said therapeutically effective amount is an amount sufficient to cause a detectable drop in paraprotein in the individual's blood.

In another embodiment, provided herein is a method of treating an individual having a number of clonal plasma cells greater than 10%, out of all nucleated cells, in a bone marrow biopsy or blood sample from said individual, comprising administering to the individual a therapeutically effective amount of placental stem cells and/or BM-MSCs, wherein said number of clonal plasma cells is caused by multiple myeloma, and wherein said therapeutically effective amount is an amount sufficient to cause a detectable drop in said number of clonal plasma cells in a bone marrow biopsy or blood sample to below 10%.

In another embodiment, provided herein is a method of treating an individual having hypercalcemia comprising administering to the individual a therapeutically effective amount of placental stem cells and/or BM-MSCs, wherein said hypercalcemia is caused by multiple myeloma, and wherein said therapeutically effective amount is an amount sufficient to cause a detectable drop in calcium in blood from the individual. In another embodiment, provided herein is a method of treating an individual having high blood calcium levels (e.g., corrected calcium greater than about 12 mg per deciliter of blood, or greater than about 2.75 mmol), comprising administering to the individual a therapeutically effective amount of placental stem cells and/or BM-MSCs, wherein the high blood calcium levels are caused by multiple myeloma, and wherein said therapeutically effective amount is an amount sufficient to cause a detectable drop in said blood calcium levels, e.g., a drop in said blood calcium levels to below about 12 mg per deciliter of blood, or below about 2.75 mmol.

In another embodiment, provided herein is a method of treating an individual having anemia, wherein said anemia is caused by multiple myeloma, wherein said anemia is defined as blood hemoglobin of less than 10 g/dL blood, comprising administering to the individual a therapeutically effective amount of placental stem cells and/or BM-MSCs, wherein said therapeutically effective amount is an amount sufficient to cause a detectable increase in hemoglobin in blood from the individual. In a specific embodiment, said therapeutically effective amount is an amount that results in an increased of hemoglobin in blood from the individual to 10 g/dL or greater.

In another embodiment, provided herein is a method of treating an individual having blood hyperviscosity syndrome, wherein said blood has a viscosity of above 1.8 centipoises, wherein said blood hyperviscosity syndrome is caused by multiple myeloma, comprising administering to the individual a therapeutically effective amount of placental stem cells and/or BM-MSCs, wherein said therapeutically effective amount is an amount sufficient to cause a detectable decrease in viscosity of blood from the individual. In specific embodiments, said therapeutically effective amount is an amount that results in a decrease in viscosity of blood in the individual to below 5, 4, 3, 2, or 1.8 centipoises.

In another embodiment, provided herein is a method of treating an individual having greater than, e.g., 6%, 8%, 10%, 12%, 14%, 16%, 18% or 20% plasma cells in bone marrow of said individual, comprising administering to the individual a therapeutically effective amount of placental stem cells and/or BM-MSCs, wherein said therapeutically effective amount is an amount sufficient to cause a detectable decrease in the percentage of plasma cells in bone marrow from the individual.

In another embodiment, provided herein is a method of treating an individual having multiple myeloma, comprising administering to the individual isolated placental stem cells and/or BM-MSCs (e.g., isolated BM-MSCs or BM-MSCs in bone marrow), wherein said administration results in detectable reduction in the severity and/or number of bone lesions caused by multiple myeloma in said individual, as determinable by, e.g., bone scan or radiography. In another embodiment, provided herein is a method of treating an individual having multiple myeloma, comprising administering to the individual isolated placental stem cells and/or BM-MSCs, wherein said administration results in detectable reduction in loss of bone mass or bone mineral content, cessation of loss of bone mass or bone mineral content, or increase in bone mass or bone mineral content, in said individual.

In another specific embodiment of the method of treatment, said one or more symptoms of multiple myeloma are bone pain, osteocytic lesions (e.g., visible by X-ray or magnetic resonance imaging (MRI)), osteoporosis, anemia, hypercalcemia or a symptom due to hypercalcemia, or renal failure. In other specific embodiments, said individual has never been treated for multiple myeloma; said individual has been treated for multiple myeloma and responds to non-placental stem cell and/or BM-MSC therapy; said individual has been treated for multiple myeloma and has not responded to non-placental stem cell and/or BM-MSC therapy, but the course of multiple myeloma in said individual has not progressed; or said individual has progressive multiple myeloma.

In another embodiment, administration of the placental stem cells and/or BM-MSCs (e.g., isolated BM-MSCs or BM-MSCs in bone marrow), are sufficient to cause a detectable increase in one or more markers of bone formation in said individual. For instance, bone formation may be assessed by analysis of levels of bone specific alkaline phosphatase (BSAP) and/or serum intact procollagen type I N-terminal peptide (PINP) in, e.g., a serum sample from said individual. A detectable increase in serum BSAP and/or PINP after administration of placental stem cells and/or BM-MSCs to an individual having multiple myeloma is an indication of an increase in bone formation. Thus, in another embodiment, provided herein is a method of treating an individual having multiple myeloma, comprising administering to the individual isolated placental stem cells and/or BM-MSCs, wherein said administering results in a detectable increase in either BSAP or PINP in serum from the individual.

In another embodiment, administration of isolated placental stem cells and/or BM-MSCs, is sufficient to cause a detectable decrease in one or more markers of bone resorption. For instance, bone resorption may be assessed by analysis of levels of serum C-terminal type I collagen telopeptide (CTX) and/or serum tartrate-resistant acid phosphatase isoform-5b (TRACP-5b). A detectable decrease in CTX or TRACP-5b after administration of placental stem cells and/or BM-MSCs, to an individual having multiple myeloma is an indication of a decrease in bone resorption. Thus, in another embodiment, provided herein is a method of treating an individual having multiple myeloma, comprising administering to the individual isolated placental stem cells and/or BM-MSCs (e.g., isolated BM-MSCs or BM-MSCs in bone marrow), wherein said administering results in a detectable decrease in either CTX or TRACP-5b in serum from the individual.

In another embodiment, provided herein is a method of treating an individual having Stage I multiple myeloma, comprising administering to the individual a therapeutically effective amount of isolated placental stem cells and/or BM-MSCs (e.g., isolated BM-MSCs or BM-MSCs in bone marrow), wherein said Stage I multiple myeloma is characterized by: (i) hemoglobin level of 10 g/dL or more; (ii) normal bone, or only 1-2 lesions, as seen on a radiogram; (iii) less than 12 mg/dL blood calcium; and detectable levels of paraprotein; wherein said therapeutically effective amount of said placental stem cells and/or BM-MSCs is an amount sufficient to result in improvement of one or more of said symptoms, and/or a detectable reduction in the number of plasma cells in blood from the individual.

In another embodiment, provided herein is a method of treating an individual having Stage II multiple myeloma, comprising administering to the individual a therapeutically effective amount of isolated placental stem cells and/or BM-MSCs (e.g., isolated BM-MSCs or BM-MSCs in bone marrow), wherein said Stage II multiple myeloma is characterized by the symptoms: (i) blood hemoglobin below 8.5 g/dL; (ii) blood calcium level above 12 mg/dL; (iii) 3 or more areas of bone lesions as seen on a radiogram; and (iv) high levels of paraprotein; wherein said therapeutically effective amount of said isolated placental stem cells and/or BM-MSCs is an amount sufficient to result in improvement of one or more of said symptoms, and/or a detectable reduction in the number of plasma cells in blood from the individual.

In another embodiment, provided herein is a method of treating an individual having Stage I multiple myeloma, comprising administering to the individual a therapeutically effective amount of isolated placental stem cells and/or BM-MSCs (e.g., isolated BM-MSCs or BM-MSCs in bone marrow), wherein said Stage I multiple myeloma is characterized by serum beta-2 microglobulin less than 3.5 mg/L and a serum albumin level of 3.5 g/dL or higher, and wherein said therapeutically effective amount of said placental stem cells and/or BM-MSCs is an amount sufficient to reduce, e.g., detectably reduce, the level of serum beta-2 microglobulin, or increase, e.g., detectably increase, the blood albumin level in said individual.

In another embodiment, provided herein is a method of treating an individual having Stage II multiple myeloma, comprising administering to the individual a therapeutically effective amount of isolated placental stem cells and/or BM-MSCs (e.g., isolated BM-MSCs or BM-MSCs in bone marrow), wherein said Stage II multiple myeloma is characterized by serum beta-2 microglobulin of between about 3.3 mg/L and 5.5 mg/L with any level of serum albumin, or serum albumin level of below about 3.5 g/dL and serum beta-2 microglobulin less than about 3.5 g/L, and wherein said therapeutically effective amount of said placental stem cells and/or BM-MSCs is an amount sufficient to reduce, e.g., detectably reduce, the level of serum beta-2 microglobulin, e.g., to below about 3.3 mg/L, or increase, e.g., detectably increase, the blood albumin level, in said individual.

In another embodiment, provided herein is a method of treating an individual having Stage III multiple myeloma, comprising administering to the individual a therapeutically effective amount of isolated placental stem cells and/or BM-MSCs (e.g., isolated BM-MSCs or BM-MSCs in bone marrow), wherein said Stage III multiple myeloma is characterized by serum beta-2 microglobulin of greater than 5.5 mg/L with any level of serum albumin, wherein said therapeutically effective amount of said placental stem cells and/or BM-MSCs, is an amount sufficient to reduce, e.g., detectably reduce, the amount of serum beta-2 microglobulin in blood or serum of said individual, e.g., to below about 5.5 mg/L, or to below about 3.5 mg/L.

In certain other specific embodiments of any of the above, the individual having multiple myeloma is refractory to one or more non-cell multiple myeloma therapies, e.g., melphalan (with or without prednisolone), cyclophosphamide (with or without prednisolone), alkylating agents, VAD (vincristine, adriamycin and high-dose dexamethasone), ABCM (vincristine, adriamycin, prednisolone and carmustine), high-dose dexamethasone, thalidomide, biphosphonates, etc.

In another aspect, provided herein is a method of suppressing the proliferation of multiple myeloma cells, comprising contacting said multiple myeloma cells with isolated placental stem cells, e.g., the isolated placental stem cells described in Section 5.2, below, a population of such isolated placental stem cells, or a population of cells comprising the isolated placental stem cells, and/or isolated BM-MSCs or bone marrow comprising BM-MSCs, such that proliferation of said multiple myeloma cells is suppressed, e.g., detectably suppressed. In certain embodiments, provided herein is a method of suppressing the proliferation of multiple myeloma cells in vivo, comprising administering a therapeutically effective amount of placental stem cells and/or BM-MSCs, to an individual comprising multiple myeloma cells, wherein said administering reduces, e.g., detectably reduces, proliferation of said multiple myeloma cells. In a specific embodiment, said administering reduces, e.g., detectably reduces (e.g., improves), one or more symptoms or signs of multiple myeloma, or lessens the worsening of said one or more symptoms or signs of multiple myeloma. A reduction in the proliferation of multiple myeloma cells after administration of placental stem cells and/or BM-MSCs, can be assessed, e.g., by detecting a reduction in the number of plasma cells from blood or bone marrow of an individual having multiple myeloma, e.g., using one or more antibodies specific to plasma cells or multiple myeloma cells, for example, antibodies to CD28 or CD138.

In another aspect, provided herein is a method of reducing a number of multiple myeloma cells, e.g., in an individual having multiple myeloma, comprising contacting said multiple myeloma cells with isolated placental stem cells and/or BM-MSCs (e.g., isolated BM-MSCs or BM-MSCs in bone marrow), such that the number of multiple myeloma cells in said individual is suppressed, e.g., detectably suppressed, after said contacting. In a specific embodiment, said contacting is performed by administering said placental stem cells and/or BM-MSCs, to said individual. In another specific embodiment, said administering reduces, e.g., detectably reduces (e.g., improves), one or more symptoms or signs of multiple myeloma, or lessens the worsening of said one or more symptoms or signs of multiple myeloma. A reduction in the number of multiple myeloma cells after administration of placental stem cells and/or BM-MSCs, as compared to before administration, can be assessed, e.g., by detection of a reduction in the number of plasma cells from blood or bone marrow of an individual having multiple myeloma, e.g., using one or more antibodies specific to plasma cells or multiple myeloma cells, for example, antibodies to CD28 or CD138.

Typically, an individual presenting with one or more symptoms of multiple myeloma is assessed for multiple myeloma at least once before a final diagnosis of multiple myeloma, e.g., as a part of tests performed to arrive at a diagnosis of multiple myeloma. Also, typically, an individual diagnosed with multiple myeloma is assessed at least once, usually more than once, after a diagnosis of multiple myeloma, for symptoms of multiple myeloma to gauge progress of the disease. Such an assessment may comprise a determination of the extent and/or number of bone lesions using, e.g. X-ray analysis, magnetic resonance imaging (MRI), computerized tomography (CT) scanning, positron emission tomography (PET) scanning, or the like; a determination of the level of calcium in the blood; a determination of the level of M proteins (antibodies or fragments of antibodies) in the blood or urine, and the like. Effectiveness of treatment of multiple myeloma, e.g., effectiveness of administering placental stem cells and/or BM-MSCs, can be assessed by any one, or more, of such symptoms of multiple myeloma, e.g., by improvement in any one, or more, of such symptoms of multiple myeloma. Effectiveness can also be assessed by determining the number of multiple myeloma cells in blood or bone marrow of said individual, before and after administration of said placental stem cells and/or BM-MSCs.

Thus, in specific embodiments, any of the above methods comprises determining, once or a plurality of times before said administering, and, optionally, once or a plurality of times after said administering, one or more of (1) a number or degree of bone lesions in said individual; (2) a level of M proteins (paraprotein) in blood or urine from the individual; (3) a level of calcium in blood from the individual; and/or (4) a number of multiple myeloma cells in blood or bone marrow from the individual. In certain embodiments, if the level of calcium in blood from the individual, or the level of M proteins in the blood or urine from the individual, drops, e.g., detectably drops, after administration of isolated placental stem cells and/or BM-MSCs, compared to the level before administration, the placental stem cells and/or BM-MSCs, are therapeutically effective. Similarly, in certain embodiments, administration of the placental stem cells and/or BM-MSCs is therapeutically effective if the number of bone lesions, or the degree of severity of bone lesions, in the individual, is lessened after said administration relative to the number of bone lesions, or the degree of severity of bone lesions before said administration. In certain other embodiments, administration of the placental stem cells and/or BM-MSCs is also therapeutically effective, e.g., if administration of the placental stem cells and/or BM-MSCs results in a lessening of an increase in the level of M protein in the blood or urine of the individual, or lessening in an increase in the level of calcium in the blood of the individual, or a lessening in an increase in the number or severity of bone lesions in the individual. In certain specific embodiments, if there is no detectable change in the number or severity of bone lesions in the individual, the level of M protein in blood or urine of the individual, or the level of blood calcium in the individual, after administration of said placental stem cells and/or BM-MSCs, administration of either the placental stem cells, BM-MSCs, or both is repeated.

Effectiveness of administration of isolated placental stem cells and/or BM-MSCs may also be assessed by determining that an amount, e.g., a therapeutically effective amount, of the placental stem cells and/or BM-MSCs reduces, e.g., detectably reduces, the number of osteoclast precursors or multiple myeloma cells in the individual following administration. Reduction of the number of osteoclast precursors in said individual may be determined by any medically-acceptable method. For example, the number of osteoclast precursors may be determined using an antibody specific for osteoclast precursors to detect osteoclast precursors in, e.g., a sample of the individual's peripheral blood or bone marrow; the number of labeled cells may be assessed, e.g., by histology, counting cells under a microscope, sorting labeled cells by flow cytometry, or the like. In another specific embodiment, said therapeutically effective amount of placental stem cells and/or BM-MSCs reduces the number of multiple myeloma cells in said individual, e.g., as determinable by cell counting (e.g., by flow cytometry), or antibody staining, of nucleated blood cells from said individual using an antibody specific for multiple myeloma cells or plasma cells, e.g., an antibody specific for cellular markers CD28 or CD138.

In any of the methods of treating multiple myeloma, treating a symptom of multiple myeloma, or suppressing proliferation of multiple myeloma cells, as described herein, the multiple myeloma cells exhibit a translocation of genetic material from chromosome 4 to chromosome 14 (e.g., a t(4:14) translocation). In other embodiments, the multiple myeloma cells exhibit a t(14:16) translocation, a t(11:14) translocation, and/or an illegitimate IgH rearrangement with an unknown chromosomal partner. In certain other embodiments, the multiple myeloma cells do not secrete detectable amounts of immunoglobulin. In certain other embodiments, the multiple myeloma cells secrete only, or substantially only, light chain immunoglobulin, e.g., κ (kappa) light chain, λ (lambda) light chain, or both. In certain other embodiments, the multiple myeloma cells secrete immunoglobulin comprising a heavy chain and a light chain. In other embodiments, the multiple myeloma cells produce IgG immunoglobulin, IgA immunoglobulin, or both.

In any of the above embodiments, the isolated placental stem cells can be, e.g., the genetically engineered placental stem cells described below. In any of the above embodiments, the BM-MSCs can be genetically engineered BM-MSCs. BM-MSCs can be genetically engineered in any manner as described for genetic engineering of placental stem cells, as described Section 5.7.2, below.

In certain embodiments, the individual having multiple myeloma is additionally treated with a chemotherapeutic compound, e.g., an anticancer compounds described in Section 5.1.3, below, for example one or more of the anticancer compounds as well as with placental stem cells and/or BM-MSCs. Placental stem cells and/or BM-MSCs can be administered to said individual to treat multiple myeloma, e.g., at the same time as, or within 1, 2, 3, 4, 5, 6, 7, 8, 9, 10, 11 or 12 months following the start of chemotherapy, e.g., chemotherapy to treat said multiple myeloma. In other embodiments, the anticancer compound is administered within 1, 2, 3, 4, 5, 6, 7, 8, 9, 10, 11 or 12 months following administration of said placental stem cells and/or BM-MSCs.

5.1.2 Treatment of Chondrosarcoma

In another respect, provided herein is a method of treating an individual having a chondrosarcoma, comprising administering to said individual isolated placental stem cells and/or BM-MSCs (e.g., isolated BM-MSCs or BM-MSCs in bone marrow). As elsewhere herein, said isolated placental stem cells can have any combination of, or all of, the characteristics described in Section 5.2, below. Additionally, the BM-MSCs may be isolated or present in, e.g., bone marrow comprising BM-MSCs.

Thus, in one embodiment, provided herein is a method of treating an individual having a chondrosarcoma, comprising administering to the individual isolated placental stem cells and/or BM-MSCs, wherein said administration results in the detectable reduction of progression, detectable lessening of worsening, and/or detectable improvement, of one or more symptoms of chondrosarcoma. In specific embodiments, said symptoms include, but are not limited to, bone pain, one or more bone lesions visible, e.g., on an X-ray, swelling of the bone, e.g., at the site of the tumor, or enlargement of one or more bones.

In a specific embodiment, the chondrosarcoma is a clear cell chondrosarcoma. In another specific embodiment, the chondrosarcoma is a benign chondrosarcoma (enchondroma). In another specific embodiment, the chondrosarcoma is a low-grade malignant chondrosarcoma (Grade I chondrosarcoma; characterized by tumors resembling normal cartilage; tumors may surround areas of lamellar bone and/or show atypical cells including binucleate cells). In another specific embodiment, the chondrosarcoma is an intermediate grade malignant chondrosarcoma (Grade II chondrosarcoma; characterized by significant cellularity with many atypical cells, many of which have hyperchromasia (an abundance of darkly-staining DNA in the nucleus) and increased nuclear size, compared to Grade I). In another specific embodiment, the chondrosarcoma is a high grade malignant chondrosarcoma (Grade III chondrosarcoma; characterized by areas of marked pleomorphism, large cells with significant hyperchromasia, occasional giant cells and abundant necrosis. In another specific embodiment, the chondrosarcoma is a dedifferentiated chondrosarcoma (a chondrosarcoma comprising a well-differentiated cartilage tumor (enchondroma or Grade II or II chondrosarcoma) adjacent to a high-grade non-cartilaginous sarcoma). In another specific embodiment, the condrosarcoma is a mesenchymal chondrosarcoma.

In certain embodiments, said placental stem cells and/or BM-MSCs are administered to the individual without any further treatment of the chondrosarcoma. In certain other embodiments, said placental stem cells and/or BM-MSCs are administered to the individual after surgery to remove part or all of the chondrosarcoma tumor, or to remove part or all of a bone affected by chondrosarcoma. In certain other embodiments, said placental stem cells and/or BM-MSCs are administered to the individual prior to, or at the time of, surgery to remove part or all of the chondrosarcoma tumor, or to remove part or all of a bone affected by chondrosarcoma. In certain other embodiments, the placental stem cells and/or BM-MSCs are administered systemically to the individual, e.g., at a site or by a route other than the site of the chondrosarcoma in the individual; e.g., intravenously, intraarterially, peritoneally, or the like. In certain other embodiments, the placental stem cells and/or BM-MSCs are administered at or adjacent to the site of the chondrosarcoma (if the tumor has not been removed), e.g., the site of the chondrosarcoma in the individual, or the site from which the chondrosarcoma was removed, if surgical removal has taken place.

5.1.3 Combination Therapies

Treatment of a bone-related cancer, e.g., multiple myeloma, chondrosarcoma, or one of the other bone-related cancers noted herein, can comprise administration of placental stem cells and/or BM-MSCs (e.g., isolated BM-MSCs or BM-MSCs in bone marrow) in combination with a second therapy, to the individual having the cancer. In various embodiments, the second therapy is administered at the same time as said placental stem cells and/or BM-MSCs in the same course of treatment as said placenta cells, after said placental stem cells and/or BM-MSCs have been administered (e.g., after completion of a course of treatment comprising administering placental stem cells and/or BM-MSCs), or before administration of placental stem cells and/or BM-MSCs (e.g., before initiation of a course of treatment comprising administering placental stem cells and/or BM-MSCs). In certain embodiments, the placental stem cells and/or BM-MSCs, and second therapy, are formulated together to be administered, e.g., from the same package or container. In certain other embodiments, the placental stem cells and/or BM-MSCs, and second therapy, are each formulated for separate administration.

Thus, in another aspect, provided herein is a method of treating an individual having a bone-related cancer, e.g., multiple myeloma or chondrosarcoma, or one of the other bone-related cancers listed herein, comprising administering to the individual isolated placental stem cells and/or BM-MSCs, in combination with one or more other anticancer therapies, e.g., one or more chemotherapies or chemotherapeutic compounds. Such other anticancer therapies can be administered to the individual at the same time as, during the same course of treatment as, or separately from, said administration of placental stem cells and/or BM-MSCs. In a specific embodiment, the one or more anticancer therapies is/are administered sequentially with administration of said placental stem cells and/or BM-MSCs. In another specific embodiment, said other anticancer therapy or anticancer therapies are administered to said individual before administration of said placental stem cells and/or BM-MSCs; e.g., a course of such other anticancer therapies is administered to the individual, and completed, prior to administration to the individual of placental stem cells and/or BM-MSCs. In another specific embodiment, said placental stem cells and/or BM-MSCs are administered to the individual before administration of said other anticancer therapies; e.g., a course of placental stem cells and/or BM-MSCs is administered to said individual before administration of said other anticancer therapies, and completed, prior to administration to the individual said other anticancer therapy or anticancer therapies.

As used herein, "anticancer agent" or "anticancer therapy" is an agent or therapy that has been identified, e.g., in clinical, pre-clinical or scientific studies (including anecdotal studies) to have a tumoristatic or tumoricidal effect on one or more types of tumor or cancer cells.

In a specific embodiment, the anticancer agent is melphalan (also known as L-phenylalanine mustard or L-PAM; trade name Albertan). Thus, in one embodiment, the method of treating an individual having multiple myeloma comprises administering to said individual melphalan, e.g., a therapeutically effective dose or doses of melphalan (e.g., ALKERAN®). Administration is typically oral or intravenous. In another specific embodiment, the anticancer agent is thalidomide. In another specific embodiment, the anticancer agent is an amino-substituted thalidomide analog or an amino-substituted imidazole. In another specific embodiment, the anticancer agent is pomalidomide (sold under the trade name ACTIMID®); lenalidomide (sold under the trade name REVLIMID®); or lenalidomide in combination with dexamethasone. In another specific embodiment, the anticancer treatment is bortezomib (e.g., VELCADE®). In another specific embodiment, the anticancer agent comprises a combination of melphalan, prednisone, and thalidomide (administered separately or together). In another specific embodiment, the anticancer agent is the combination of bortezomib, melphalan and prednisone (administered separately or together). In other specific embodiments, the anticancer agent is one or more of cyclophosphamide (e.g., CYTOXAN®), vincristine (e.g., ONCOVIN®, VINCASAR PFS®), doxorubicin (e.g., ADRIAMYCIN RDF®, ADRIAMYCIN PFS®), or liposomal doxorubicin (e.g., DOXIL®).

Other anticancer agents are well-known in the art. Thus, in other specific embodiments, the anticancer agents include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cytarabine; dacarbazine; dactinomycin; daunorubicin hydrochloride; decitabine; dexormaplatin; dezaguanine; dezaguanine mesylate; diaziquone; docetaxel; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidenmin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., GLEEVEC®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (e.g., GENASENSE®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

In other embodiments, the combination therapy comprises administration of placental stem cells and/or BM-MSCs, to an individual in combination with an inhibitor of osteoclasts, e.g., an inhibitor of osteoclast formation or differentiation of osteoclast precursors into osteoclasts. In a specific embodiment, the osteoclast inhibitor is an inhibitor of RANKL, e.g., Denosumab. In another specific embodiment, the osteoclast inhibitor is an integrin or cathepsin K inhibitor.

In another embodiment, the combination therapy comprises administration of placental stem cells and/or BM-MSCs in combination with bisphosphonates. In specific embodiments, the bisphosphonates are aledronate (e.g., at a dosage of about 5 mg to about 10 mg per day, or about 35 mg to about 70 mg once a week; with or without supplemental vitamin D), ibandronate, risedronate, clodronate and/or pamidronate. In another embodiment, the combination therapy comprises administration of placental stem cells and/or BM-MSCs in combination with one or more of calcitonin, estrogen, parathyroid hormone (e.g., teriparatide, e.g, FORTEO®) or raloxifene.

In another embodiment, provided herein is a method of treating an individual having a bone-related cancer, e.g., multiple myeloma, chondrosarcoma, or one of the other bone-related cancers listed herein, comprising administering to the individual isolated placental stem cells and/or BM-MSCs, in combination with a compound having activin antagonist or activin receptor RIIa (ActRIIa) antagonist activity, e.g., an ActRIIa antagonist. In a specific embodiment, said ActRIIa antagonist is a soluble activin receptor type IIA IgC-Fc fusion protein (e.g., ACE-011®). See, e.g., U.S. Patent Application Publication No. 2009/0142333, which is incorporated by reference herein in its entirety.

In another embodiment, provided herein is a method of treating an individual having a bone-related cancer, e.g., multiple myeloma, chondrosarcoma, or one of the other bone-related cancers listed herein, comprising administering to the individual isolated placental stem cells and/or BM-MSCs, in combination with radiotherapy. In certain embodiments, the radiotherapy comprises administering X-rays to an organ or tissue in the individual having the bone-related cancer, which is affected by the bone-related cancer. In specific embodiments, for example, said radiotherapy, e.g., X-rays, is administered to a bone lesion caused by multiple myeloma, or a bone lesion caused by chondrosarcoma. In other specific embodiments, said radiotherapy, e.g., X-rays, is administered to a half of the individual's body that is affected by said bone-related cancer. In other specific embodiments, said radiotherapy, e.g., X-rays, is administered to the whole of the affected individual's body. In other embodiments, said radiation therapy comprises administering a proton beam or an electron beam to an organ or tissue in the individual having the bone-related cancer, which is affected by the bone-related cancer. In certain other embodiments, said radiotherapy is administered in preparation for hematopoietic stem cell replacement therapy (e.g., radiotherapy to kill the individual's existing hematopoietic system).

In another embodiment, isolated placental stem cells and/or BM-MSCs are combined with a bone substitute, e.g., to treat a bone lesion associated with a bone-related cancer, e.g., by administration at or adjacent to a bone lesion caused by a bone-related cancer. In a specific embodiment, said bone substitute is a physiologically-acceptable ceramic material, e.g., mono-, di-, tri-, alpha-tri-, beta-tri-, and tetra-calcium phosphate, hydroxyapatite, a fluoroapatite, a calcium sulfate, a calcium fluoride, a calcium oxide, a calcium carbonate, a magnesium calcium phosphate, a biologically active glass (e.g., BIOGLASS®), or a mixture of any thereof. In another specific embodiment, said bone substitute is a porous biocompatible ceramic material (e.g., SURGIBONE®, ENDOBON®, CEROS® or the like), or a mineralized collagen bone grafting product (e.g., HEALOS™, VITOSS®, RHAKOSS™, and CORTOSS®, or the like)

5.2 Placental Stem Cells

The isolated placental stem cells useful in the treatment of individuals having a bone-related cancer, e.g., multiple myeloma, or having cells of a bone-related cancer, e.g., multiple myeloma cells, are cells, obtainable from a placenta or part thereof, that adhere to a tissue culture substrate (e.g., uncoated tissue culture plastic), and have characteristics of multipotent cells or stem cells. In certain embodiments, the isolated placental stem cells useful in the methods disclosed herein have the capacity to differentiate into one or more non-placental cell types. Placental stem cells useful in the methods disclosed herein are described herein and, e.g., in U.S. Pat. No. 7,486,276, and in U.S. Patent Application Publication No. 2007/0275362, the disclosures of which are hereby incorporated by reference in their entireties. Placental stem cells are not trophoblasts, cytotrophoblasts, embryonic germ cells, or embryonic stem cells, as those cells are understood by persons of skill in the art The isolated placental stem cells useful in the methods disclosed herein can be either fetal or maternal in origin (that is, can have the genotype of either the fetus or mother, respectively). Preferably, the isolated placental stem cells and populations of isolated placental stem cells are fetal in origin. Isolated placental stem cells, or populations of cells comprising the isolated placental stem cells, can comprise isolated placental stem cells that are solely fetal or maternal in origin, or can comprise a mixed population of isolated placental stem cells of both fetal and maternal origin. In certain embodiments of any of the placental stem cells described herein, said isolated placental stem cells are non-maternal in origin. In certain other embodiments, said placental stem cells are substantially free of maternal cells; e.g., at least about 40%, 45%, 5-0%, 55%, 60%, 65%, 70%, 75%, 90%, 85%, 90%, 95%, 98% or 99% of said cells are non-maternal in origin.

The isolated placental stem cells, and populations of cells comprising the isolated placental stem cells, can be identified and selected by the morphological, marker, and culture characteristics discussed below. In certain embodiments, any of the placental stem cells described herein, are autologous to a recipient, e.g., an individual who has a bone-related cancer, or cells of a bone-related cancer, e.g., multiple myeloma or multiple myeloma cells, or chondrosarcoma or chondrosarcoma cells, or another bone related cancer of cells of another bone-related cancer. In certain other embodiments, any of the placental stem cells described herein, are heterologous to a recipient, e.g., an individual who has a bone-related cancer, or cells of a bone-related cancer, e.g., multiple myeloma or multiple myeloma cells, or chondrosarcoma or chondrosarcoma cells, or another bone related cancer of cells of another bone-related cancer.

In certain embodiments, the placental stem cells useful in the methods of the invention, e.g., the placental stem cells described herein, are obtained from term placenta, that is, a post-partum mammalian, e.g., human, placenta. In certain other embodiments, the placental stem cells useful in the methods of the invention, e.g., the placental stem cells described herein, are obtained from preterm mammalian, e.g., human, placenta.

5.2.1 Physical and Morphological Characteristics

The isolated placental stem cells described herein (PDACs), when cultured in primary cultures or in cell culture, adhere to the tissue culture substrate, e.g., tissue culture container surface (e.g., tissue culture plastic), or to a tissue culture surface coated with extracellular matrix or ligands such as laminin, collagen (e.g., native or denatured), gelatin, fibronectin, ornithine, vitronectin, and extracellular membrane protein (e.g., MATRIGEL® (BD Discovery Labware, Bedford, Mass.)). The isolated placental stem cells in culture assume a generally fibroblastoid, stellate appearance, with a number of cytoplasmic processes extending from the central cell body. The cells are, however, morphologically distinguishable from fibroblasts cultured under the same conditions, as the isolated placental stem cells exhibit a greater number of such processes than do fibroblasts. Morphologically, isolated placental stem cells are also distinguishable from hematopoietic stem cells, which generally assume a more rounded, or cobblestone, morphology in culture, and do not adhere to tissue culture plastic. Morphologically, the placental stem cells are also distinguishable from trophoblasts or cytotrophoblasts, which tend to appear rounded or epitheloid, and, in the case of cytotrophoblasts, multinucleate as compared to the uninucleate placental stem cells. The placental stem cells are unicellular and remain unicellular during culture and over multiple passages, and do not form, e.g., multinuclear cells in culture, e.g., in culture in growth medium in air, or culture in growth medium in 95% air/5% $CO_2$.

In certain embodiments, the isolated placental stem cells useful in the methods disclosed herein, e.g., the methods of treatment or methods of suppressing the growth of bone-related cancer cells or suppressing differentiation of osteoclast precursors into osteoclasts, when cultured in a growth medium, develop embryoid-like bodies. Embryoid-like bodies are well-known in the art, and are noncontiguous clumps of cells that can grow on top of an adherent layer of proliferating isolated placental stem cells. The term "embryoid-like" is used because the clumps of cells resemble embryoid bodies, clumps of cells that grow from cultures of embryonic stem cells. Growth medium in which embryoid-like bodies can develop in a proliferating culture of isolated placental stem cells includes medium comprising, e.g., DMEM-LG (e.g., from Gibco); 2% fetal calf serum (e.g., from Hyclone Labs.); 1× insulin-transferrin-selenium (ITS); 1× linoleic acid-bovine serum albumin (LA-BSA); $10^{-9}$ M dexamethasone (e.g., from Sigma); $10^{-4}$ M ascorbic acid 2-phosphate (e.g., from Sigma); epidermal growth factor 10 ng/mL (e.g., from R&D Systems); and platelet-derived growth factor (PDGF-BB) 10 ng/mL (e.g., from R&D Systems).

5.2.2 Cell Surface, Molecular and Genetic Markers

The isolated placental stem cells are tissue culture plastic-adherent human placental stem cells that have characteristics of multipotent cells or stem cells, and express a plurality of markers that can be used to identify and/or isolate the cells, or populations of cells that comprise the stem cells. The isolated placental stem cells include cells and placental stem cell-containing cell populations obtained directly from the placenta, or a part thereof. Isolated placental stem cell populations also include populations of (that is, two or more) isolated placental stem cells in culture, and a population in a container, e.g., a bag. The isolated placental stem cells described herein are not bone marrow-derived mesenchymal cells, adipose-derived mesenchymal stem cells, or mesenchymal cells obtained from umbilical cord blood, placental blood, or peripheral blood. Placental stem cells useful in the methods and compositions described herein are described, e.g., in U.S. Pat. Nos. 7,311,904; 7,311,905; and 7,468,276; and in U.S. Patent Application Publication No. 2007/0275362, the disclosures of which are hereby incorporated by reference in their entireties. In a specific embodiments of any of the embodiments of the placental stem cells described herein, the cells are mammalian, e.g., human.

In certain embodiments, the isolated placental stem cells are isolated placental stem cells. In certain other embodiments, the isolated placental cells are isolated placental multipotent cells. In one embodiment, isolated placental stem cells useful in the methods described herein are $CD34^-$, $CD10^+$ and $CD105^+$ as detectable by flow cytometry. As used herein, the phrase "as detectable by," "as determinable by," and the like, does not indicate that the cells need to be assessed for expression of the recited markers in order for the cells to be "isolated," nor to the cells need to be isolated using the markers. In another specific embodiment, the isolated $CD34^-$, $CD10^+$, $CD105^+$ placental stem cells have the potential to differentiate into cells of a neural phenotype, cells of an osteogenic phenotype, and/or cells of a chondrogenic phenotype, e.g., either in vitro or in vivo, or both. In another specific embodiment, the isolated $CD34^-$, $CD10^+$, $CD105^+$ placental stem cells are additionally $CD200^+$. In another specific embodiment, the isolated $CD34^-$, $CD10^+$, $CD105^+$ placental stem cells are additionally $CD45^-$ or $CD90^+$. In another specific embodiment, the isolated $CD34^-$, $CD10^+$, $CD105^+$ placental stem cells are additionally $CD45^-$ and $CD90^+$, as detectable by flow cytometry. In another specific embodiment, the isolated $CD34^-$, $CD10^+$, $CD105^+$, $CD200^+$ placental stem cells are additionally $CD90^+$ or $CD45^-$, as detectable by flow cytometry. In a specific embodiment, the isolated $CD34^-$, $CD10^+$, $CD105^+$, $CD200^+$ placental stem cells are additionally one or more of $CD44^+$, $CD45^-$, $CD90^+$, $CD166^+$, $KDR^+$, or $CD133^-$. In another specific embodiment, the isolated $CD34^-$, $CD10^+$, $CD105^+$, $CD200^+$ placental stem cells are additionally $CD44^+$, $CD45^-$, $CD90^+$, $CD166^+$, $KDR^+$, and $CD133^-$. In another specific embodiment, the isolated $CD34^-$, $CD10^+$, $CD105^+$, $CD200^+$ placental stem cells are additionally $CD90^+$ and $CD45^-$, as detectable by flow cytometry, i.e., the placental stem cells are $CD34^-$, $CD10^+$, $CD45^-$, $CD90^+$, $CD105^+$ and $CD200^+$. In another specific embodiment, said $CD34^-$, $CD10^+$, $CD45^-$, $CD90^+$, $CD105^+$, $CD200^+$ placental stem cells are additionally $CD44^+$, $CD80^-$ and/or $CD86^-$. In another specific embodiment, said $CD34^-$, $CD10^+$, $CD44^+$, $CD45^-$, $CD90^+$, $CD105^+$, $CD200^+$ placental stem cells are additionally one or more of $CD80^-$, $CD86^-$, $CD117^-$, $CD133^-$, cytokeratin$^+$, $KDR^+$, $HLA-A,B,C^+$, $HLA-DR,DP,DQ^-$, and $HLA-G^-$. In another specific embodiment, the $CD34^-$, $CD10^+$, $CD105^+$ placental stem cells are additionally one or more of $SSEA1^-$, $SSEA3^-$ and/or $SSEA4^-$. In another specific embodiment, the $CD34^-$, $CD10^+$, $CD105^+$ placental stem cells are additionally $SSEA1^-$, $SSEA3^-$ and $SSEA4^-$.

In another embodiment, said placental stem cells are $CD34^-$, $CD10^+$, $CD105^+$ and $CD200^+$, and one or more of $CD44^+$, $CD45^-$, $CD90^+$, $CD166^+$, $KDR^-$, or $CD133^-$. In a more specific embodiment, said placental stem cells are $CD34^-$, $CD10^+$, $CD105^+$ and $CD200^+$, $CD44^+$, $CD45^-$, $CD90^+$, $CD166^+$, $KDR^-$, and $CD133^-$. In another embodiment, said placental stem cells are $CD34^-$, $CD10^+$, $CD105^+$ and $CD200^+$, and one or more of HLA ABC$^+$, HLA DR,DQ, DP$^-$, $CD80^-$, $CD86^-$, $CD98^-$, or PD-L1$^+$. In a more specific embodiment, said placental stem cells are $CD34^-$, $CD10^+$, $CD105^+$ and $CD200^+$, HLA ABC$^+$, HLA DR,DQ,DP$^-$, $CD80^-$, $CD86^-$, $CD98^-$, and PD-L1$^+$. In certain embodiments, said placental stem cells are $CD34^-$, $CD10^+$, $CD105^+$ and $CD200^+$, and one or more of $CD3^-$, $CD9^-$, $CD38^-$, $CD45^-$, $CD80^-$, $CD86^-$, $CD133^-$, HLA-DR,DP,DQ$^-$, $SSEA3^-$, $SSEA4^-$, $CD29^+$, $CD44^+$, $CD73^+$, $CD90^+$, $CD105^+$, $HLA-A,B,C^+$, PDL1$^+$, ABC-p$^+$, and/or OCT-4$^+$, as detectable by flow cytometry. In other embodiments, any of the $CD34^-$, $CD10^+$, $CD105^+$ placental stem cells described above are additionally one or more of $CD29^+$, $CD38^-$, $CD44^+$, $CD54^+$, $SH3^+$ or $SH4^+$. In another specific embodiment, the placental stem cells are additionally $CD44^+$. In another specific embodiment of any of the isolated $CD34^-$, $CD10^+$, $CD105^+$ placental stem cells above, the cells are additionally one or more of $CD117^-$, $CD133^-$, $KDR^-$ (VEGFR2$^-$), HLA-A,B, C$^+$, HLA-DP,DQ,DR$^-$, or Programmed Death-1 Ligand (PDL1)$^+$, or any combination thereof.

In another embodiment, the isolated $CD34^-$, $CD10^+$, $CD105^+$ placental stem cells are additionally one or more of $CD3^-$, $CD9^-$, $CD13^+$, $CD29^+$, $CD33^+$, $CD38^-$, $CD44^+$, $CD45^-$, $CD54^+$, $CD62E^-$, $CD62L^-$, $CD62P^-$, $SH3^+$ ($CD73^+$), $SH4^+$ ($CD73^+$), $CD80^-$, $CD86^-$, $CD90^+$, $SH2^+$ ($CD105^+$), CD106/VCAM$^+$, $CD117^-$, CD144/VE-cadherin$^{low}$, $CD146^+$, $CD166^+$, CD184/CXCR4$^-$, $CD200^+$, $CD133^-$, OCT-4$^+$, $SSEA3^-$, $SSEA4^-$, ABC-p$^+$, $KDR^-$ (VEGFR2$^-$), HLA-A,B,C$^+$, HLA-DP,DQ,DR$^-$, HLA-G$^-$, or Programmed Death-1 Ligand (PDL1)$^+$, or any combination thereof. In another embodiment, the $CD3^-$, $CD9^-$, $CD34^-$, $CD10^+$, $CD105^+$ placental stem cells are additionally $CD13^+$, $CD29^+$, $CD33^+$, $CD38^-$, $CD44^+$, $CD45^-$, CD54/ICAM$^+$, $CD62E^-$, $CD62L^-$, $CD62P^-$, $SH3^+$ ($CD73^+$), $SH4^+$ ($CD73^+$), $CD80^-$, $CD86^-$, $CD90^+$, $SH2^+$ ($CD105^+$), CD106/VCAM$^+$, $CD117^-$, CD144/VE-cadherin$^{low}$, $CD146^+$, $CD166^+$, CD184/CXCR4$^-$, $CD200^+$, $CD133^-$, OCT-4$^+$, $SSEA3^-$, $SSEA4^-$, ABC-p$^+$, $KDR^-$ (VEGFR2$^-$), HLA-A,B,C$^+$, HLA-DP,DQ, DR$^-$, HLA-G$^-$, and Programmed Death-1 Ligand (PDL1)$^+$.

In another specific embodiment, any of the isolated placental stem cells described herein are ABC-p$^+$, as detectable by flow cytometry, and/or OCT-4$^+$ (POU5F1$^+$), as determinable by RT-PCR, wherein ABC-p is a placenta-specific ABC transporter protein (also known as breast cancer resistance protein (BCRP) and as mitoxantrone resistance protein (MXR)), and OCT-4 is the Octamer-4 protein (POU5F1). In another specific embodiment, any of the placental stem cells described herein are additionally SSEA3$^-$ or SSEA4$^-$, as determinable by flow cytometry, wherein SSEA3 is Stage Specific Embryonic Antigen 3, and SSEA4 is Stage Specific Embryonic Antigen 4. In another specific embodiment, any of the placental stem cells described herein are additionally SSEA3$^-$ and SSEA4$^-$.

In another specific embodiment, any of the placental stem cells described herein are one or more of MHC-I$^+$ (e.g., HLA-A,B,C$^+$), MHC-II$^-$ (e.g., HLA-DP,DQ,DR$^-$) or HLA-G$^-$. In another specific embodiment, any of the placental stem cells described herein are one or more of MHC-I$^+$ (e.g., HLA-A, B,C$^+$), MHC-II$^-$ (e.g., HLA-DP,DQ,DR$^-$) and HLA-G$^-$.

Also provided herein are populations of cells comprising, e.g., that are enriched for, the isolated placental stem cells, that are useful in the methods and compositions disclosed herein. Preferred populations of cells comprise the isolated placental stem cells, wherein at least 10%, 15%, 20%, 25%, 30%, 35%, 40%, 45%, 50%, 55%, 60%, 65%, 70%, 75%, 80%, 85%, 90%, 95% or 98% of the cells in said population of cells are isolated CD10$^+$, CD105$^+$ and CD34$^-$ placental stem cells. In a specific embodiment, the isolated CD34$^-$, CD10$^+$, CD105$^+$ placental stem cells are additionally CD200$^+$. In another specific embodiment, the isolated CD34$^-$, CD10$^+$, CD105$^+$, CD200$^+$ placental stem cells are additionally CD90$^+$ or CD45$^-$, as detectable by flow cytometry. In another specific embodiment, the isolated CD34$^-$, CD10$^+$, CD105$^+$, CD200$^+$ placental stem cells are additionally CD90$^+$ and CD45$^-$, as detectable by flow cytometry. In another specific embodiment, any of the isolated CD34$^-$, CD10$^+$, CD105$^+$ placental stem cells described above are additionally one or more of CD29$^+$, CD38$^-$, CD44$^+$, CD54$^+$, SH3$^+$ or SH4$^+$. In another specific embodiment, the isolated CD34$^-$, CD10$^+$, CD105$^+$ placental stem cells, or isolated CD34$^-$, CD10$^+$, CD105$^+$, CD200$^+$ placental stem cells, are additionally CD44$^+$. In a specific embodiment of any of the populations of cells comprising isolated CD34$^-$, CD10$^+$, CD105$^+$ placental stem cells above, the isolated placental stem cells are additionally one or more of CD13$^+$, CD29$^+$, CD33$^+$, CD38$^-$, CD44$^+$, CD45$^-$, CD54$^+$, CD62E$^-$, CD62L$^-$, CD62P$^-$, SH3$^+$ (CD73$^+$), SH4$^+$ (CD73$^+$), CD80$^-$, CD86$^-$, CD90$^+$, SH2$^+$ (CD105$^+$), CD106/VCAM$^+$, CD117$^-$, CD144/VE-cadherin$^{low}$, CD184/CXCR4$^-$, CD200$^+$, CD133$^-$, OCT-4$^+$, SSEA3$^-$, SSEA4$^-$, ABC-p$^+$, KDR$^-$ (VEGFR2$^-$), HLA-A, B,C$^+$, HLA-DP,DQ,DR$^-$, HLA-G$^-$, or Programmed Death-1 Ligand (PDL1)$^+$, or any combination thereof. In another specific embodiment, the CD34$^-$, CD10$^+$, CD105$^+$ cells are additionally CD13$^+$, CD29$^+$, CD33$^+$, CD38$^-$, CD44$^+$, CD45$^-$, CD54/ICAM$^+$, CD62E$^-$, CD62L$^-$, CD62P$^-$, SH3$^+$ (CD73$^+$), SH4$^+$ (CD73$^+$), CD80$^-$, CD86$^-$, CD90$^+$, SH2$^+$ (CD105$^+$), CD106/VCAM$^+$, CD117$^-$, CD144/VE-cadherin$^{low}$, CD184/CXCR4$^-$, CD200$^+$, CD133$^-$, OCT-4$^+$, SSEA3$^-$, SSEA4$^-$, ABC-p$^+$, KDR$^-$ (VEGFR2$^-$), HLA-A,B,C$^+$, HLA-DP,DQ, DR$^-$, HLA-G$^-$, and Programmed Death-1 Ligand (PDL1)$^+$.

In certain embodiments, the isolated placental stem cells useful in the methods and compositions described herein are one or more, or all, of CD10$^+$, CD29$^+$, CD34$^-$, CD38$^-$, CD44$^+$, CD45$^-$, CD54$^+$, CD90$^+$, SH2$^+$, SH3$^+$, SH4$^+$, SSEA3$^-$, SSEA4$^-$, OCT-4$^+$, and ABC-p$^+$, wherein said isolated placental stem cells are obtained by physical and/or enzymatic disruption of placental tissue. In a specific embodiment, the isolated placental stem cells are OCT-4$^+$ and ABC-p$^+$. In another specific embodiment, the isolated placental stem cells are OCT-4$^+$ and CD34$^-$, wherein said isolated placental stem cells have at least one, or all, of the following characteristics: CD10$^+$, CD29$^+$, CD44$^+$, CD45$^-$, CD54$^+$, CD90$^+$, SH3$^+$, SH4$^+$, SSEA3$^-$, and SSEA4$^-$. In another specific embodiment, the isolated placental stem cells are OCT-4$^+$, CD34$^-$, CD10$^+$, CD29$^+$, CD44$^+$, CD45$^-$, CD54$^+$, CD90$^+$, SH3$^+$, SH4$^+$, SSEA3$^-$, and SSEA4$^-$. In another embodiment, the isolated placental stem cells are OCT-4$^+$, CD34$^-$, SSEA3$^-$, and SSEA4$^-$. In another specific embodiment, the isolated placental stem cells are OCT-4$^+$ and CD34$^-$, and is either SH2$^+$ or SH3$^+$. In another specific embodiment, the isolated placental stem cells are OCT-4$^+$, CD34$^-$, SH2$^+$ and SH3$^+$. In another specific embodiment, the isolated placental stem cells are OCT-4$^+$, CD34$^-$, SSEA3$^-$, and SSEA4$^-$, and are either SH2$^+$ or SH3$^+$. In another specific embodiment, the isolated placental stem cells are OCT-4$^+$ and CD34$^-$, and either SH2$^+$ or SH3$^+$, and is at least one of CD10$^+$, CD29$^+$, CD44$^+$, CD45$^-$, CD54$^+$, CD90$^+$, SSEA3$^-$, or SSEA4$^-$. In another specific embodiment, the isolated placental stem cells are OCT-4$^+$, CD34$^-$, CD10$^+$, CD29$^+$, CD44$^+$, CD45$^-$, CD54$^+$, CD90$^+$, SSEA3$^-$, and SSEA4$^-$, and either SH2$^+$ or SH3$^+$.

In another embodiment, the isolated placental stem cells useful in the methods and compositions disclosed herein are SH2$^+$, SH3$^+$, SH4$^+$, and OCT-4$^+$. In another specific embodiment, the isolated placental stem cells are CD10$^+$, CD29$^+$, CD44$^+$, CD54$^+$, CD90$^+$, CD34$^-$, CD45$^-$, SSEA3$^-$, or SSEA4$^-$. In another embodiment, the isolated placental stem cells are SH2$^+$, SH3$^+$, SH4$^+$, SSEA3$^-$ and SSEA4$^-$. In another specific embodiment, the isolated placental stem cells are SH2$^+$, SH3$^+$, SH4$^+$, SSEA3$^-$ and SSEA4$^-$, CD10$^+$, CD29$^+$, CD44$^+$, CD54$^+$, CD90$^+$, OCT-4$^+$, CD34$^-$ or CD45$^-$.

In another embodiment, the isolated placental stem cells useful in the methods and compositions disclosed herein are CD10$^+$, CD29$^-$, CD34$^-$, CD44$^+$, CD45$^-$, CD54$^+$, CD90$^-$, SH2$^+$, SH3$^+$, and SH4$^+$; wherein said isolated placental stem cells are additionally one or more of OCT-4$^+$, SSEA3$^-$ or SSEA4$^-$.

In certain embodiments, isolated placental stem cells useful in the methods and compositions disclosed herein are CD200$^+$ or HLA-G$^-$. In a specific embodiment, the isolated placental stem cells are CD200$^+$ and HLA-G$^-$. In another specific embodiment, the isolated placental stem cells are additionally CD73$^+$ and CD105$^+$. In another specific embodiment, the isolated placental stem cells are additionally CD34$^-$, CD38$^-$ or CD45$^-$. In another specific embodiment, the isolated placental stem cells are additionally CD34$^-$, CD38$^-$ and CD45$^-$. In another specific embodiment, said isolated placental stem cells are CD34$^-$, CD38$^-$, CD45$^-$, CD73$^+$ and CD105$^+$. In another specific embodiment, said isolated CD200$^+$ or HLA-G$^-$ placental stem cells facilitate the formation of embryoid-like bodies in a population of placental cells comprising the isolated placental stem cells, under conditions that allow the formation of embryoid-like bodies. In another specific embodiment, the isolated placental stem cells are isolated away from placental cells that are not stem or multipotent cells. In another specific embodiment, said isolated placental stem cells are isolated away from placental cells that do not display these markers.

In another embodiment, a cell population useful in the methods and compositions described herein is a population of cells comprising, e.g., that is enriched for, CD200$^+$, HLA-G$^-$ placental stem cells. In a specific embodiment, said population is a population of placental cells. In various embodiments, at least about 10%, at least about 20%, at least about 30%, at least about 40%, at least about 50%, or at least about 60% of cells in said cell population are isolated CD200$^+$, HLA-G$^-$ placental stem cells. In certain embodiments, at least about 70% of cells in said cell population are isolated CD200$^+$, HLA-G$^-$ placental stem cells. In certain other embodiments, at least about 90%, 95%, or 99% of said cells are isolated CD200$^+$, HLA-G$^-$ placental stem cells. In a specific embodiment of the cell populations, said isolated CD200$^+$, HLA-G$^-$ placental stem cells are also CD73$^+$ and CD105$^+$. In another specific embodiment, said isolated CD200$^+$, HLA-G$^-$ placental stem cells are also CD34$^-$, CD38$^-$ or CD45$^-$. In another specific embodiment, said isolated CD200$^+$, HLA-G$^-$ placental stem cells are also CD34$^-$, CD38$^-$, CD45$^-$, CD73$^+$ and CD105$^+$. In another specific embodiment, said cell population is isolated away from placental cells that are not stem cells. In another specific embodiment, said isolated CD200$^+$, HLA-G$^-$ placental stem cells are isolated away from placental cells that do not display these markers.

In another embodiment, the isolated placental stem cells useful in the methods and compositions described herein are CD73$^+$, CD105$^+$, and CD200$^+$. In another specific embodiment, the isolated placental stem cells are HLA-G$^-$. In another specific embodiment, the isolated placental stem cells are CD34$^-$, CD38$^-$ or CD45$^-$. In another specific embodiment, the isolated placental stem cells are CD34$^-$, CD38$^-$ and CD45$^-$. In another specific embodiment, the isolated placental stem cells are CD34$^-$, CD38$^-$, CD45$^-$, and HLA-G$^-$. In another specific embodiment, the isolated placental stem cells are isolated away from placental cells that are not the isolated placental stem cells. In another specific embodiment, the isolated placental stem cells are isolated away from placental cells that do not display these markers.

In another embodiment, a cell population useful in the methods and compositions described herein is a population of cells comprising, e.g., that is enriched for, isolated CD73$^+$, CD105$^+$, CD200$^+$ placental stem cells. In various embodiments, at least about 10%, at least about 20%, at least about 30%, at least about 40%, at least about 50%, or at least about 60% of cells in said cell population are isolated CD73$^+$, CD105$^+$, CD200$^+$ placental stem cells. In another embodiment, at least about 70% of said cells in said population of cells are isolated CD73$^+$, CD105$^+$, CD200$^+$ placental stem cells. In another embodiment, at least about 90%, 95% or 99% of cells in said population of cells are isolated CD73$^+$, CD105$^+$, CD200$^+$ placental stem cells. In a specific embodiment of said populations, the isolated placental stem cells are HLA-G$^-$. In another specific embodiment, the isolated placental stem cells are additionally CD34$^-$, CD38$^-$ or CD45$^-$. In another specific embodiment, the isolated placental stem cells are additionally CD34$^-$, CD38$^-$ and CD45$^-$. In another specific embodiment, the isolated placental stem cells are additionally CD34$^-$, CD38$^-$, CD45$^-$, and HLA-G$^-$. In another specific embodiment, said population of placental cells is isolated away from placental cells that are not stem cells. In another specific embodiment, said population of placental stem cells is isolated away from placental cells that do not display these characteristics.

In certain other embodiments, the isolated placental stem cells are one or more of CD10$^+$, CD29$^+$, CD34$^-$, CD38$^-$, CD44$^+$, CD45$^-$, CD54$^+$, CD90$^+$, SH2$^+$, SH3$^+$, SH4$^+$, SSEA3$-$, SSEA4$^-$, OCT-4$^+$, HLA-G$^-$ or ABC-p$^+$. In a specific embodiment, the isolated placental stem cells are CD10$^+$, CD29$^+$, CD34$^-$, CD38$^-$, CD44$^+$, CD45$^-$, CD54$^+$, CD90$^+$, SH2$^+$, SH3$^+$, SH4$^+$, SSEA3$-$, SSEA4$^-$, and OCT-4$^+$. In another specific embodiment, the isolated placental stem cells are CD10$^+$, CD29$^+$, CD34$^-$, CD38$^-$, CD45$^-$, CD54$^+$, SH2$^+$, SH3$^+$, and SH4$^+$. In another specific embodiment, the isolated placental stem cells are CD10$^+$, CD29$^+$, CD34$^-$, CD38$^-$, CD45$^-$, CD54$^+$, SH2$^+$, SH3$^+$, SH4$^+$ and OCT-4$^+$. In another specific embodiment, the isolated placental stem cells are CD10$^+$, CD29$^+$, CD34$^-$, CD38$^-$, CD44$^+$, CD45$^-$, CD54$^+$, CD90$^+$, HLA-G$^-$, SH2$^+$, SH3$^+$, SH4$^+$. In another specific embodiment, the isolated placental stem cells are OCT-4$^+$ and ABC-p$^+$. In another specific embodiment, the isolated placental stem cells are SH2$^+$, SH3$^+$, SH4$^+$ and OCT-4$^+$. In another embodiment, the isolated placental stem cells are OCT-4$^+$, CD34$^-$, SSEA3$^-$, and SSEA4$^-$. In a specific embodiment, said isolated OCT-4$^+$, CD34$^-$, SSEA3$^-$, and SSEA4$^-$ placental stem cells are additionally CD10$^+$, CD29$^+$, CD34$^-$, CD44$^+$, CD45$^-$, CD54$^+$, CD90$^+$, SH2$^+$, SH3$^+$, and SH4$^+$. In another embodiment, the isolated placental stem cells are OCT-4$^+$ and CD34$^-$, and either SH3$^+$ or SH4$^-$. In another embodiment, the isolated placental stem cells are CD34$^-$ and either CD10$^+$, CD29$^+$, CD44$^+$, CD54$^+$, CD90$^+$, or OCT-4$^+$.

In another embodiment, the isolated placental stem cells useful in the methods and compositions described herein are CD200$^+$ and OCT-4$^+$. In a specific embodiment, the isolated placental stem cells are CD73$^+$ and CD105$^+$. In another specific embodiment, said isolated placental stem cells are HLA-G$^-$. In another specific embodiment, said isolated CD200$^+$, OCT-4$^+$ placental stem cells are CD34$^-$, CD38$^-$ or CD45$^-$. In another specific embodiment, said isolated CD200$^+$, OCT-4$^+$ placental stem cells are CD34$^-$, CD38$^-$ and CD45$^-$. In another specific embodiment, said isolated CD200$^+$, OCT-4$^+$ placental stem cells are CD34$^-$, CD38$^-$, CD45$^-$, CD73$^+$, CD105$^+$ and HLA-G$^-$. In another specific embodiment, said isolated CD200$^+$, OCT-4$^+$ placental stem cells are isolated away from placental cells that are not stem cells. In another specific embodiment, said isolated CD200$^+$, OCT-4$^+$ placental stem cells are isolated away from placental cells that do not display these characteristics.

In another embodiment, a cell population useful in the methods and compositions described herein is a population of cells comprising, e.g., that is enriched for, CD200$^+$, OCT-4$^+$ placental stem cells. In various embodiments, at least about 10%, at least about 20%, at least about 30%, at least about 40%, at least about 50%, or at least about 60% of cells in said cell population are isolated CD200$^+$, OCT-4$^+$ placental stem cells. In another embodiment, at least about 70% of said cells are said isolated CD200$^+$, OCT-4$^+$ placental stem cells. In another embodiment, at least about 80%, 90%, 95%, or 99% of cells in said cell population are said isolated CD200$^+$, OCT-4$^+$ placental stem cells. In a specific embodiment of the isolated populations, said isolated CD200$^+$, OCT-4$^+$ placental stem cells are additionally CD73$^+$ and CD105$^+$. In another specific embodiment, said isolated CD200$^+$, OCT-4$^+$ placental stem cells are additionally HLA-G$^-$. In another specific embodiment, said isolated CD200$^+$, OCT-4$^+$ placental stem cells are additionally CD34$^-$, CD38$^-$ and CD45$^-$. In another specific embodiment, said isolated CD200$^+$, OCT-4$^+$ placental stem cells are additionally CD34$^-$, CD38$^-$, CD45$^-$, CD73$^+$, CD105$^+$ and HLA-G$^-$. In another specific embodiment, said cell population is isolated away from placental cells that are not isolated CD200$^+$, OCT-4$^+$ placental stem cells. In another specific embodiment, said cell population is isolated away from placental cells that do not display these markers.

In another embodiment, the isolated placental stem cells useful in the methods and compositions described herein are CD73$^+$, CD105$^+$ and HLA-G$^-$. In another specific embodiment, the isolated CD73$^+$, CD105$^+$ and HLA-G$^-$ placental stem cells are additionally CD34$^-$, CD38$^-$ or CD45$^-$. In another specific embodiment, the isolated CD73$^+$, CD105$^+$, HLA-G⁻ placental stem cells are additionally CD34⁻, CD38⁻ and CD45⁻. In another specific embodiment, the isolated CD73⁺, CD105⁺, HLA-G⁻ placental stem cells are additionally OCT-4⁺. In another specific embodiment, the isolated CD73⁺, CD105⁺, HLA-G⁻ placental stem cells are additionally CD200⁺. In another specific embodiment, the isolated CD73⁺, CD105⁺, HLA-G⁻ placental stem cells are additionally CD34⁻, CD38⁻, CD45⁻, OCT-4⁺ and CD200⁺. In another specific embodiment, said the isolated CD73⁺, CD105⁺, HLA-G⁻ placental stem cells are isolated away from placental cells that are not the isolated CD73⁺, CD105⁺, HLA-G⁻ placental stem cells. In another specific embodiment, said the isolated CD73⁺, CD105⁺, HLA-G⁻ placental stem cells are isolated away from placental cells that do not display these markers.

In another embodiment, a cell population useful in the methods and compositions described herein is a population of cells comprising, e.g., that is enriched for, isolated CD73⁺, CD105⁺ and HLA-G⁻ placental stem cells. In various embodiments, at least about 10%, at least about 20%, at least about 30%, at least about 40%, at least about 50%, or at least about 60% of cells in said population of cells are isolated CD73⁺, CD105⁺, HLA-G⁻ placental stem cells. In another embodiment, at least about 70% of cells in said population of cells are isolated CD73⁺, CD105⁺, HLA-G⁻ placental stem cells. In another embodiment, at least about 90%, 95% or 99% of cells in said population of cells are isolated CD73⁺, CD105⁺, HLA-G⁻ placental stem cells. In a specific embodiment of the above populations, said isolated CD73⁺, CD105⁺, HLA-G⁻ placental stem cells are additionally CD34⁻, CD38⁻ or CD45⁻. In another specific embodiment, said isolated CD73⁺, CD105⁺, HLA-G⁻ placental stem cells are additionally CD34⁻, CD38⁻ and CD45⁻. In another specific embodiment, said isolated CD73⁺, CD105⁺, HLA-G⁻ placental stem cells are additionally OCT-4⁺. In another specific embodiment, said isolated CD73⁺, CD105⁺, HLA-G⁻ placental stem cells are additionally CD200⁺. In another specific embodiment, said isolated CD73⁺, CD105⁺, HLA-G⁻ placental stem cells are additionally CD34⁻, CD38⁻, CD45⁻, OCT-4⁺ and CD200⁺. In another specific embodiment, said cell population is isolated away from placental cells that are not CD73⁺, CD105⁺, HLA-G⁻ placental stem cells. In another specific embodiment, said cell population is isolated away from placental cells that do not display these markers.

In another embodiment, the isolated placental stem cells useful in the methods and compositions described herein are isolated HLA-A,B,C⁺, CD45⁻, CD133⁻ and CD34⁻ placental stem cells. In another embodiment, a cell population useful in the methods and compositions described herein is a population of cells comprising isolated placental cells, wherein at least about 70%, at least about 80%, at least about 90%, at least about 95% or at least about 99% of cells in said isolated population of cells are isolated HLA-A,B,C⁺, CD45⁻, CD133⁻ and CD34⁻ placental stem cells. In a specific embodiment, said isolated placental stem cells or population of isolated placental stem cells are isolated away from placental cells that are not HLA-A,B,C⁺, CD45⁻, CD133⁻ and CD34⁻ placental stem cells. In another specific embodiment of any of the placental stem cells described herein, said isolated placental stem cells are non-maternal in origin. In another specific embodiment, said isolated population of placental stem cells are substantially free of maternal components; e.g., at least about 40%, 45%, 5-0%, 55%, 60%, 65%, 70%, 75%, 90%, 85%, 90%, 95%, 98% or 99% of said cells in said isolated population of placental cells are non-maternal in origin.

In another embodiment, the isolated placental stem cells useful in the methods and compositions described herein are isolated CD10⁺, CD13⁺, CD33⁺, CD45⁻, CD117⁻ and CD133⁻ placental stem cells. In another embodiment, a cell population useful in the methods and compositions described herein is a population of cells comprising said isolated placental stem cells, wherein at least about 70%, at least about 80%, at least about 90%, at least about 95% or at least about 99% of cells in said population of cells are said isolated CD10⁺, CD13⁺, CD33⁺, CD45⁻, CD117⁻ and CD133⁻ placental stem cells. In a specific embodiment, said isolated placental stem cells or population of isolated placental stem cells are isolated away from placental cells that are not said isolated placental cells. In another specific embodiment, said isolated CD10⁺, CD13⁺, CD33⁺, CD45⁻, CD117⁻ and CD133⁻ placental stem cells are non-maternal in origin, i.e., have the fetal genotype. In another specific embodiment, at least about 40%, 45%, 50%, 55%, 60%, 65%, 70%, 75%, 90%, 85%, 90%, 95%, 98% or 99% of said cells in said isolated population of placental stem cells, are non-maternal in origin. In another specific embodiment, said isolated placental stem cells or population of isolated placental stem cells are isolated away from placental cells that do not display these characteristics.

In another embodiment, the isolated placental stem cells useful in the methods and compositions described herein are isolated CD10⁻, CD33⁻, CD44⁺, CD45⁻, and CD117⁻ placental stem cells. In another embodiment, a cell population useful for the in the methods and compositions described herein is a population of cells comprising, e.g., enriched for, said isolated placental stem cells, wherein at least about 70%, at least about 80%, at least about 90%, at least about 95% or at least about 99% of cells in said population of cells are isolated CD10⁻, CD33⁻, CD44⁺, CD45⁻, and CD117⁻ placental stem cells. In a specific embodiment, said isolated placental stem cells or population of isolated placental stem cells are isolated away from placental cells that are not said placental stem cells. In another specific embodiment, said isolated placental stem cells are non-maternal in origin. In another specific embodiment, at least about 40%, 45%, 50%, 55%, 60%, 65%, 70%, 75%, 90%, 85%, 90%, 95%, 98% or 99% of said placental stem cells in said cell population are non-maternal in origin. In another specific embodiment, said isolated placental stem cells or population of isolated placental stem cells are isolated away from placental cells that do not display these markers.

In another embodiment, the isolated placental stem cells useful in the methods and compositions described herein are isolated CD10⁻, CD13⁻, CD33⁻, CD45⁻, and CD117⁻ placental stem cells. In another embodiment, a cell population useful for in the methods and compositions described herein is a population of cells comprising, e.g., enriched for, isolated CD10⁻, CD13⁻, CD33⁻, CD45⁻, and CD117⁻ placental stem cells, wherein at least about 70%, at least about 80%, at least about 90%, at least about 95% or at least about 99% of cells in said population are CD 10⁻, CD 13⁻, CD33⁻, CD45⁻, and CD117⁻ placental stem cells. In a specific embodiment, said isolated placental stem cells or population of isolated placental stem cells are isolated away from placental cells that are not said placental stem cells. In another specific embodiment, said isolated placental stem cells are non-maternal in origin. In another specific embodiment, at least about 40%, 45%, 50%, 55%, 60%, 65%, 70%, 75%, 90%, 85%, 90%, 95%, 98% or 99% of said cells in said cell population are non-maternal in origin. In another specific embodiment, said isolated placental stem cells or population of isolated placental stem cells is isolated away from placental cells that do not display these characteristics.

In another embodiment, the isolated placental stem cells useful in the methods and compositions described herein are HLA A,B,C$^+$, CD45$^-$, CD34$^-$, and CD133$^-$, and are additionally CD10$^+$, CD13$^+$, CD38$^+$, CD44$^+$, CD90$^+$, CD105$^+$, CD200$^+$ and/or HLA-G$^-$, and/or negative for CD117. In another embodiment, a cell population useful in the methods described herein is a population of cells comprising said isolated placental stem cells, wherein at least about 20%, 25%, 30%, 35%, 40%, 45%, 50%, 55%, 60%, 65%, 70%, 75%, 80%, 85%, 90%, 95%, 98% or about 99% of the cells in said population are isolated placental stem cells that are HLA A,B,C$^-$, CD45$^-$, CD34$^-$, CD133$^-$, and that are additionally positive for CD10, CD13, CD38, CD44, CD90, CD105, CD200, and/or negative for CD117 and/or HLA-G. In a specific embodiment, said isolated placental stem cells or population of isolated placental stem cells are isolated away from placental cells that are not said placental stem cells. In another specific embodiment, said isolated placental stem cells are non-maternal in origin. In another specific embodiment, at least about 40%, 45%, 50%, 55%, 60%, 65%, 70%, 75%, 90%, 85%, 90%, 95%, 98% or 99% of said cells in said cell population are non-maternal in origin. In another specific embodiment, said isolated placental stem cells or population of isolated placental stem cells are isolated away from placental cells that do not display these markers.

In another embodiment, the isolated placental stem cells useful in the methods and compositions described herein are CD200$^+$ and CD10$^+$, as determinable by antibody binding, and CD117$^-$, as determinable by both antibody binding and RT-PCR. In another embodiment, the isolated placental stem cells useful in the methods and compositions described herein are CD10$^+$, CD29$^-$, CD54$^+$, CD200$^+$, HLA-G$^-$, MHC class I$^+$ and β-2-microglobulin$^+$. In another embodiment, isolated placental stem cells useful in the methods and compositions described herein are placental cells wherein the expression of at least one cellular marker is at least two-fold higher than for a mesenchymal stem cell (e.g., a bone marrow-derived mesenchymal stem cell). In another specific embodiment, said isolated placental stem cells are non-maternal in origin. In another specific embodiment, at least about 40%, 45%, 50%, 55%, 60%, 65%, 70%, 75%, 90%, 85%, 90%, 95%, 98% or 99% of said cells in said cell population are non-maternal in origin.

In another embodiment, the isolated placental stem cells useful in the methods and compositions described herein are one or more of CD10$^+$, CD29$^+$, CD44$^+$, CD45$^-$, CD54/ICAM$^+$, CD62E$^-$, CD62L$^-$, CD62P$^-$, CD80$^-$, CD86$^-$, CD103$^-$, CD104$^-$, CD105$^+$, CD106/VCAM$^+$, CD144/VE-cadherin$^{low}$, CD184/CXCR4$^-$, β2-microglobulin$^{low}$, MHC-I$^{low}$, MHC-II$^-$, HLA-G$^{low}$, and/or PDL1$^{low}$. In a specific embodiment, the isolated placental stem cells are at least CD29$^+$ and CD54$^+$. In another specific embodiment, the isolated placental stem cells are at least CD44$^+$ and CD106$^+$. In another specific embodiment, the isolated placental stem cells are at least CD29$^+$.

In another embodiment, a cell population useful in the methods and compositions described herein comprises isolated placental stem cells, wherein at least 50%, 60%, 70%, 80%, 90%, 95%, 98% or 99% of the cells in said cell population are isolated placental stem cells that are one or more of CD10$^+$, CD29$^+$, CD44$^+$, CD45$^-$, CD54/ICAM$^+$, CD62E$^-$, CD62L$^-$, CD62P$^-$, CD80$^-$, CD86$^-$, CD103$^-$, CD104$^-$, CD105$^+$, CD106/VCAM$^+$, CD144/VE-cadherin$^{dim}$, CD184/CXCR4$^-$, β2-microglobulin$^{dim}$, HLA-I$^{dim}$, HLA-II$^-$, HLA-G$^{dim}$, and/or PDL1$^{dim}$. In another specific embodiment, at least 50%, 60%, 70%, 80%, 90%, 95%, 98% or 99% of cells in said cell population are CD10$^+$, CD29$^+$, CD44$^+$, CD45$^-$, CD54/ICAM$^+$, CD62-E$^-$, CD62-L$^-$, CD62P$^-$, CD80$^-$, CD86$^-$, CD103$^-$, CD104$^-$, CD105$^+$, CD106/VCAM$^+$, CD144/VE-cadherin$^{dim}$, CD184/CXCR4$^-$, β2-microglobulin$^{dim}$, MHC-I$^{dim}$, MHC-II$^-$, HLA-G$^{dim}$, and PDL1$^{dim}$ placental stem cells.

In another embodiment, the isolated placental stem cells useful in the methods and compositions described herein are one or more, or all, of CD10$^+$, CD29$^+$, CD34$^-$, CD38$^-$, CD44$^+$, CD45$^-$, CD54$^+$, CD90$^+$, SH2$^+$, SH3$^+$, SH4$^+$, SSEA3$^-$, SSEA4$^-$, OCT-4$^+$, and ABC-p$^+$, where ABC-p is a placenta-specific ABC transporter protein (also known as breast cancer resistance protein (BCRP) and as mitoxantrone resistance protein (MXR)), wherein said isolated placental stem cells are obtained by perfusion of a mammalian, e.g., human, placenta that has been drained of cord blood and perfused to remove residual blood.

In another specific embodiment of any of the embodiments of placental stem cells described herein, the cells are negative for telomerase gene expression, negative for telomerase activity, or both. Telomerase gene expression can be detected using, e.g., detection of telomerase RNA using, e.g., dot blots or slot blots; or a telomere repeat amplification protocol (TRAP) assay (e.g., TRAPEZE® ELISA, fluorometric or gel-based assay kits from Millipore).

In another specific embodiment of any of the embodiments of placental stem cells described herein, the placental stem cells are positive for vimentin, e.g., at least 50%, 55%, 60%, 65%, 70%, 75%, 80%, 85%, 90%, 95%, or 98% of said placental stem cells express vimentin. Vimentin can be detected, e.g., by flow cytometry using one or more antibodies to vimentin, e.g., that are available from Abcam; by in situ fluorescent staining, or the like.

In another specific embodiment of any of the embodiments of placental stem cells described herein, the placental stem cells do not secrete detectable amounts of human chorionic gonadotropin (hCG). Human chorionic gonadotropin can be detected, e.g., by ELISA or immunofluorescence using, for example, hCG monoclonal antibody HCG1 (Abeam), or polyclonal anti-hCG antibodies (Abcam, Novus Biologicals).

In another embodiment of any of the isolated placental stem cells described herein, a population of the isolated placental stem cells comprises CD56$^+$ tissue culture plastic-adherent placental cells that are not natural killer cells. In a specific embodiment, the population comprises about 1% to about 30% of said CD56$^+$ placental cells in said population of isolated placental stem cells, as determinable by flow cytometry using CD56-FITC (fluorescein isothiocyanate). In another specific embodiment, the population comprises about 16% to about 62% of said CD56$^+$ placental cells in said population of isolated placental stem cells, as determinable by flow cytometry using CD56-APC (allophycocyanin).

In another specific embodiment of any of the above characteristics, expression of the cellular marker (e.g., cluster of differentiation or immunogenic marker) is determinable by flow cytometry; in another specific embodiment, expression of the marker is determinable by RT-PCR.

Gene profiling confirms that isolated placental stem cells are distinguishable from other cells, e.g., mesenchymal stem cells, e.g., bone marrow-derived mesenchymal stem cells. The isolated placental stem cells described herein can be distinguished from, e.g., mesenchymal stem cells on the basis of the expression of one or more genes, the expression of which is significantly higher in the isolated placental stem cells, or in certain isolated umbilical cord stem cells, in comparison to bone marrow-derived mesenchymal stem cells. In particular, the isolated placental stem cells, useful in the methods of treatment provided herein, can be distinguished from mesenchymal stem cells, e.g., bone marrow-derived mesenchymal stem cells, on the basis of the expression of one or more genes, the expression of which is significantly higher (that is, at least twofold higher) in the isolated placental stem cells than in an equivalent number of bone marrow-derived mesenchymal stem cells, wherein the one or more genes are ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, ZC3H12A, or a combination of any of the foregoing, when the cells are grown under equivalent conditions. See, e.g., U.S. Patent Application Publication No. 2007/0275362, the disclosure of which is incorporated herein by reference in its entirety. In certain specific embodiments, said expression of said one or more genes is determined, e.g., by RT-PCR or microarray analysis, e.g, using a U133-A microarray (Affymetrix). In another specific embodiment, said isolated placental stem cells express said one or more genes when cultured for a number of population doublings, e.g., anywhere from about 3 to about 35 population doublings, in a medium comprising DMEM-LG (e.g., from Gibco); 2% fetal calf serum (e.g., from Hyclone Labs.); 1× insulin-transferrin-selenium (ITS); 1× linoleic acid-bovine serum albumin (LA-BSA); $10^{-9}$ M dexamethasone (e.g., from Sigma); $10^{-4}$ M ascorbic acid 2-phosphate (e.g., from Sigma); epidermal growth factor 10 ng/mL (e.g., from R&D Systems); and platelet-derived growth factor (PDGF-BB) 10 ng/mL (e.g., from R&D Systems). In another specific embodiment, the isolated placental stem cell-specific gene is CD200. It should be understood that generally, expression of a particular gene, e.g., any of the genes listed herein, is assessed by analysis of the aggregate expression of the gene in a population of placental stem cells.

Specific sequences for these genes can be found in GenBank, e.g., at accession nos. NM_001615 (ACTG2), BC065545 (ADARB1), (NM_181847 (AMIGO2), AY358590 (ARTS-1), BC074884 (B4GALT6), BC008396 (BCHE), BC020196 (C11orf9), BC031103 (CD200), NM_001845 (COL4A1), NM_001846 (COL4A2), BC052289 (CPA4), BC094758 (DMD), AF293359 (DSC3), NM_001943 (DSG2), AF338241 (ELOVL2), AY336105 (F2RL1), NM_018215 (FLJ10781), AY416799 (GATA6), BC075798 (GPR126), NM_016235 (GPRC5B), AF340038 (ICAM1), BC000844 (IER3), BC066339 (IGFBP7), BC013142 (IL1A), BT019749 (IL6), BC007461 (IL18), (BC072017) KRT18, BC075839 (KRT8), BC060825 (LIPG), BC065240 (LRAP), BC010444 (MATN2), BC011908 (MEST), BC068455 (NFE2L3), NM_014840 (NUAK1), AB006755 (PCDH7), NM_014476 (PDLIM3), BC126199 (PKP-2), BC090862 (RTN1), BC002538 (SERPINB9), BC023312 (ST3GAL6), BC001201 (ST6GALNAC5), BC126160 or BC065328 (SLC12A8), BC025697 (TCF21), BC096235 (TGFB2), BC005046 (VTN), and BC005001 (ZC3H12A) as of March 2008.

In certain specific embodiments, said isolated placental stem cells express each of ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A at a higher level, e.g., a detectably higher level, than an equivalent number of bone marrow-derived mesenchymal stem cells, when the cells are grown under equivalent conditions.

In specific embodiments, the placental stem cells express CD200 and ARTS1 (aminopeptidase regulator of type 1 tumor necrosis factor); CD200 and NUAK1, ARTS-1 and LRAP (leukocyte-derived arginine aminopeptidase); IL6 (interleukin-6) and TGFB2 (transforming growth factor, beta 2); IL6 and KRT18 (keratin 18); IER3 (immediate early response 3), MEST (mesoderm specific transcript homolog) and TGFB2; CD200 and IER3; CD200 and IL6; CD200 and KRT18; CD200 and LRAP; CD200 and MEST; CD200 and NFE2L3 (nuclear factor (erythroid-derived 2)-like 3); or CD200 and TGFB2 at a higher level, e.g., a detectably higher level, than an equivalent number of bone marrow-derived mesenchymal stem cells (BM-MSCs) wherein said bone marrow-derived mesenchymal stem cells have undergone a number of passages in culture equivalent to the number of passages said isolated placental stem cells have undergone. In other specific embodiments, the placental stem cells express ARTS-1, CD200, IL6 and LRAP; ARTS-1, IL6, TGFB2, IER3, KRT18 and MEST; CD200, IER3, IL6, KRT18, LRAP, MEST, NFE2L3, and TGFB2; ARTS-1, CD200, IER3, IL6, KRT18, LRAP, MEST, NFE2L3, and TGFB2; or IER3, MEST and TGFB2 at a higher level, e.g., a detectably higher level, than an equivalent number of bone marrow-derived mesenchymal stem cells BM-MSCs, wherein said bone marrow-derived mesenchymal stem cells have undergone a number of passages in culture equivalent to the number of passages said isolated placental stem cells have undergone.

Expression, e.g., differential expression as compared to bone marrow-derived mesenchymal stem cells, of the above-referenced genes can be assessed by standard techniques. For example, probes based on the sequence of the gene(s) can be individually selected and constructed by conventional techniques. Expression of the genes can be assessed, e.g., on a microarray comprising probes to one or more of the genes, e.g., an Affymetrix GENECHIP® Human Genome U133A 2.0 array, or an Affymetrix GENECHIP® Human Genome U133 Plus 2.0 (Santa Clara, Calif.). Expression of these genes can be assessed even if the sequence for a particular GenBank accession number is amended because probes specific for the amended sequence can readily be generated using well-known standard techniques.

The level of expression of these genes can be used to confirm the identity of a population of isolated placental stem cells, to identify a population of cells as comprising at least a plurality of isolated placental stem cells, or the like. Populations of isolated placental stem cells, the identity of which is confirmed, can be clonal, e.g., populations of isolated placental stem cells expanded from a single isolated placental stem cell, or a mixed population of stem cells, e.g., a population of cells comprising isolated placental stem cells that are expanded from multiple isolated placental stem cells, or a population of cells comprising isolated placental stem cells, as described herein, and at least one other type of cell.

The level of expression of these genes can be used to select populations of isolated placental stem cells. For example, a population of placental stem cells, e.g., clonally-expanded placental stem cells, may be selected if the expression of one or more of the genes listed above is significantly higher in a sample from the population of placental stem cells than in an equivalent population of mesenchymal stem cells, e.g., bone marrow-derived mesenchymal stem cells.

Isolated placental stem cells can be selected on the basis of the level of expression of one or more such genes as compared to the level of expression in said one or more genes in, e.g., a mesenchymal stem cell control, for example, the level of expression in said one or more genes in an equivalent number of bone marrow-derived mesenchymal stem cells. In one embodiment, the level of expression of said one or more genes in a sample comprising an equivalent number of mesenchymal stem cells is used as a control. In another embodiment, the control, for isolated placental stem cells tested under certain conditions, is a numeric value representing the level of expression of said one or more genes in mesenchymal stem cells under said conditions.

The isolated placental stem cells described herein, in certain embodiments, display the above characteristics (e.g., combinations of cell surface markers and/or gene expression profiles) in primary culture, or during proliferation in medium comprising, e.g., DMEM-LG (Gibco), 2% fetal calf serum (FCS) (Hyclone Laboratories), 1× insulin-transferrin-selenium (ITS), 1× lenolenic-acid-bovine-serum-albumin (LA-BSA), $10^{-9}$M dexamethasone (Sigma), $10^{-4}$M ascorbic acid 2-phosphate (Sigma), epidermal growth factor (EGF) 10 ng/ml (R&D Systems), platelet derived-growth factor (PDGF-BB) 10 ng/ml (R&D Systems), and 100 U penicillin/ 1000 U streptomycin.

In certain embodiments of any of the placental stem cells disclosed herein, the cells are human. In certain embodiments of any of the placental stem cells disclosed herein, the cellular marker characteristics or gene expression characteristics are human markers or human genes.

In another specific embodiment of said isolated placental stem cells or populations of cells comprising the isolated placental stem cells, said placental stem cells or population have been expanded, for example, passaged at least, about, or no more than, 1, 2, 3, 4, 5, 6, 7, 8, 9, 10, 11, 12, 13, 14, 15, 16, 17, 18, 19, or 20 times, or proliferated for at least, about, or no more than, 1, 2, 3, 4, 5, 6, 7, 8, 9, 10, 12, 14, 16, 18, 20, 22, 24, 26, 28, 30, 32, 34, 36, 38 or 40 population doublings. In another specific embodiment of said isolated placental stem cells or populations of cells comprising the isolated placental stem cells, said cells or population are primary isolates. In another specific embodiment of the isolated placental stem cells, or populations of cells comprising isolated placental stem cells, that are disclosed herein, said isolated placental stem cells are fetal in origin (that is, have the fetal genotype).

In certain embodiments, said isolated placental stem cells do not differentiate during culturing in growth medium, i.e., medium formulated to promote proliferation, e.g., during proliferation in growth medium. In another specific embodiment, said isolated placental stem cells do not require a feeder layer in order to proliferate. In another specific embodiment, said isolated placental stem cells do not differentiate in culture in the absence of a feeder layer, solely because of the lack of a feeder cell layer.

In another embodiment, cells useful in the methods and compositions described herein are isolated placental stem cells, wherein a plurality of said isolated placental stem cells are positive for aldehyde dehydrogenase (ALDH), as assessed by an aldehyde dehydrogenase activity assay. Such assays are known in the art (see, e.g., Bostian and Betts, *Biochem. J.*, 173, 787, (1978)). In a specific embodiment, said ALDH assay uses ALDEFLUOR® (Aldagen, Inc., Ashland, Oreg.) as a marker of aldehyde dehydrogenase activity. In a specific embodiment, said plurality is between about 3% and about 25% of cells in said population of cells. In another embodiment, provided herein is a population of isolated umbilical cord cells, e.g., multipotent isolated umbilical cord cells, wherein a plurality of said isolated umbilical cord cells are positive for aldehyde dehydrogenase, as assessed by an aldehyde dehydrogenase activity assay that uses ALDEFLUOR® as an indicator of aldehyde dehydrogenase activity. In a specific embodiment, said plurality is between about 3% and about 25% of cells in said population of cells. In another embodiment, said population of isolated placental stem cells or isolated umbilical cord stem cells shows at least three-fold, or at least five-fold, higher ALDH activity than a population of bone marrow-derived mesenchymal stem cells having about the same number of cells and cultured under the same conditions.

In a specific embodiment of any of the above embodiments of the placental stem cells useful in the methods provided herein, the placental stem cells expresses any one, or any combination of, the flow cytometric markers and/or gene expression markers described herein. In certain embodiments, at least 50%, 55%, 60%, 65%, 70%, 75%, 80%, 85%, 90%, 95% or 98% of placental stem cells in an isolated population of the isolated placental stem cells described herein expresses any one, or any combination of, the flow cytometric markers and/or gene expression markers described herein.

In certain embodiments of any of the populations of cells comprising the isolated placental stem cells described herein, the placental stem cells in said populations of cells are substantially free of cells having a maternal genotype; e.g., at least 40%, 45%, 50%, 55%, 60%, 65%, 70%, 75%, 80%, 85%, 90%, 95%, 98% or 99% of the placental stem cells in said population have a fetal genotype. In certain other embodiments of any of the populations of cells comprising the isolated placental stem cells described herein, the populations of cells comprising said placental stem cells are substantially free of cells having a maternal genotype; e.g., at least 40%, 45%, 50%, 55%, 60%, 65%, 70%, 75%, 80%, 85%, 90%, 95%, 98% or 99% of the cells in said population have a fetal genotype.

In a specific embodiment of any of the above isolated placental stem cells or cell populations of isolated placental stem cells, the karyotype of the cells, or at least about 95% or about 99% of the cells in said population, is normal. In another specific embodiment of any of the above placental stem cells, the placental stem cells, or cells in the population of cells, are non-maternal in origin.

Different populations of isolated placental stem cells bearing any of the above combinations of markers, can be combined in any ratio. Any two or more populations of the above isolated placental stem cells can be combined to form an isolated placental stem cell population. For example, an population of isolated placental stem cells can comprise a first population of isolated placental stem cells defined by one of the marker combinations described above, and a second population of isolated placental stem cells defined by another of the marker combinations described above, wherein said first and second populations are combined in a ratio of about 1:99, 2:98, 3:97, 4:96, 5:95, 10:90, 20:80, 30:70, 40:60, 50:50, 60:40, 70:30, 80:20, 90:10, 95:5, 96:4, 97:3, 98:2, or about 99:1. In like fashion, any three, four, five or more populations of the above-described isolated placental stem cells can be combined.

Isolated placental stem cells useful in the methods and compositions described herein can be obtained, e.g., by disruption of placental tissue, with or without enzymatic digestion (see Section 5.3.3) or perfusion (see Section 5.3.4). For example, populations of isolated placental cells, from which placental stem cells can be isolated, can be produced according to a method comprising perfusing a mammalian placenta that has been drained of cord blood and perfused to remove residual blood; perfusing said placenta with a perfusion solution; and collecting said perfusion solution, wherein said perfusion solution after perfusion comprises a population of placental cells that comprises isolated placental stem cells; and isolating a plurality of said isolated placental cells from said population of cells. In a specific embodiment, the perfusion solution is passed through both the umbilical vein and umbilical arteries and collected after it exudes from the placenta. In another specific embodiment, the perfusion solution is passed through the umbilical vein and collected from the umbilical arteries, or passed through the umbilical arteries and collected from the umbilical vein.

In various embodiments, the isolated placental stem cells, contained within a population of cells obtained from perfusion of a placenta, are at least 50%, 60%, 70%, 80%, 90%, 95%, 99% or at least 99.5% of said population of placental cells. In another specific embodiment, the isolated placental stem cells collected by perfusion comprise fetal and maternal cells. In another specific embodiment, the isolated placental stem cells collected by perfusion are at least 50%, 60%, 70%, 80%, 90%, 95%, 99% or at least 99.5% fetal cells.

In another specific embodiment, provided herein is a composition comprising a population of the isolated placental stem cells, as described herein, collected by perfusion, wherein said composition comprises at least a portion of the perfusion solution used to collect the isolated placental stem cells.

The placental stem cells described herein can also be isolated by digestion of placental tissue with one or more tissue-disrupting enzymes to obtain a population of placental cells comprising the placental stem cells, and isolating, or substantially isolating, the placental stem cells from the remainder of said placental cells. The whole, or part of, the placenta can be digested to obtain the isolated placental stem cells described herein. In other specific embodiment, the tissue-disrupting enzyme is trypsin or collagenase. In various embodiments, the isolated placental stem cells, contained within a population of cells obtained from digesting a placenta, are at least 50%, 60%, 70%, 80%, 90%, 95%, 99% or at least 99.5% of said population of placental cells.

Populations of the isolated placental stem cells described above can comprise about, at least, or no more than, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$ or more of the isolated placental stem cells. Populations of isolated placental stem cells useful in the methods of treatment described herein comprise at least 50%, 55%, 60%, 65%, 70%, 75%, 80%, 85%, 90%, 95%, 98%, or 99% viable isolated placental stem cells, e.g., as determinable by, e.g., trypan blue exclusion.

The placental stem cells described herein, useful in the methods provided herein, display the above characteristics (e.g., combinations of cell surface markers and/or gene expression profiles) in primary culture, or during proliferation in medium comprising 60% DMEM-LG (Gibco), 40% MCDB-201 (Sigma), 2% fetal calf serum (FCS) (Hyclone Laboratories), 1× insulin-transferrin-selenium (ITS), 1× lenolenic-acid-bovine-serum-albumin (LA-BSA), $10^{-9}$ M dexamethasone (Sigma), $10^{-4}$ M ascorbic acid 2-phosphate (Sigma), epidermal growth factor (EGF) 10 ng/ml (R&D Systems), platelet derived-growth factor (PDGF-BB) 10 ng/ml (R&D Systems), and 100 U penicillin/1000 U streptomycin.

5.2.3 Growth in Culture

The growth of the isolated placental stem cells described herein in Section 5.2.2 in certain embodiments depends in part upon the particular medium selected for growth. Under optimum conditions, the isolated placental stem cells typically double in number in about 1-3 days. During culture, the isolated placental stem cells described herein adhere to a substrate in culture, e.g. the surface of a tissue culture container (e.g., tissue culture dish plastic, fibronectin-coated plastic, and the like) and form a monolayer. In specific embodiments, said placental stem cells double in culture when cultured at 37° C. in 95% air/5% $CO_2$ in medium comprising 60% DMEM-LG (Gibco) and 40% MCDB-201 (Sigma) supplemented with 2% fetal calf serum (FCS) (Hyclone Laboratories), 1× insulin-transferrin-selenium (ITS), 1× lenolenic-acid-bovine-serum-albumin (LA-BSA), $10^{-9}$ M dexamethasone (Sigma), $10^{-4}$ M ascorbic acid 2-phosphate (Sigma), epidermal growth factor (EGF) 10 ng/ml (R&D Systems), platelet derived-growth factor (PDGF-BB) 10 ng/ml (R&D Systems), and 100 U penicillin/1000 U streptomycin; or in medium comprising DMEM-LG (Gibco) supplemented with 2%-10% fetal calf serum (FCS) (Hyclone Laboratories), 1×ITS, 1×(LA-BSA), $10^{-9}$ M dexamethasone (Sigma), $10^{-4}$ M ascorbic acid 2-phosphate (Sigma), epidermal growth factor (EGF) 10 ng/ml (R&D Systems), platelet derived-growth factor (PDGF-BB) 10 ng/ml (R&D Systems), and 100 U penicillin/1000 U streptomycin.

5.3 Methods of Obtaining Isolated Placental Stem Cells 5.3.1 Cell Collection Composition Placental stem cells are obtained from a mammalian placenta using a physiologically-acceptable solution, e.g., a cell collection composition. An exemplary cell collection composition is described in detail in related U.S. Patent Application Publication No. 2007/0190042, the disclosure of which is incorporated herein by reference in its entirety The cell collection composition can comprise any physiologically-acceptable solution suitable for the collection and/or culture of cells, e.g., the isolated placental stem cells described herein, for example, a saline solution (e.g., phosphate-buffered saline, Kreb's solution, modified Kreb's solution, Eagle's solution, 0.9% NaCl. etc.), a culture medium (e.g., DMEM, H.DMEM, etc.), and the like.

The cell collection composition can comprise one or more components that tend to preserve isolated placental stem cells, that is, prevent the isolated placental stem cells from dying, or delay the death of the isolated placental stem cells, reduce the number of isolated placental stem cells in a population of cells that die, or the like, from the time of collection to the time of culturing. Such components can be, e.g., an apoptosis inhibitor (e.g., a caspase inhibitor or JNK inhibitor); a vasodilator (e.g., magnesium sulfate, an antihypertensive drug, atrial natriuretic peptide (ANP), adrenocorticotropin, corticotropin-releasing hormone, sodium nitroprusside, hydralazine, adenosine triphosphate, adenosine, indomethacin or magnesium sulfate, a phosphodiesterase inhibitor, etc.); a necrosis inhibitor (e.g., 2-(1H-Indol-3-yl)-3-pentylamino-maleimide, pyrrolidine dithiocarbamate, or clonazepam); a TNF-α inhibitor; and/or an oxygen-carrying perfluorocarbon (e.g., perfluorooctyl bromide, perfluorodecyl bromide, etc.).

The cell collection composition can comprise one or more tissue-degrading enzymes, e.g., a metalloprotease, a serine protease, a neutral protease, an RNase, or a DNase, or the like. Such enzymes include, but are not limited to, collagenases (e.g., collagenase I, II, III or IV, a collagenase from *Clostridium histolyticum*, etc.); dispase, thermolysin, elastase, trypsin, LIBERASE, hyaluronidase, and the like.

The cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefaclor, cefixime or cefadroxil), a clarithromycin, an erythromycin, a penicillin (e.g., penicillin V) or a quinolone (e.g., ofloxacin, ciprofloxacin or norfloxacin), a tetracycline, a streptomycin, etc. In a particular embodiment, the antibiotic is active against Gram (+) and/or Gram(−) bacteria, e.g., *Pseudomonas aeruginosa, Staphylococcus aureus*, and the like. In one embodiment, the antibiotic is gentamycin, e.g., about 0.005% to about 0.01% (w/v) in culture medium The cell collection composition can also comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 μM to about 100 μM); a reducing agent (e.g., N-acetylcysteine present at about 0.1 mM to about 5 mM); an agent that prevents calcium entry into cells (e.g., verapamil present at about 2 μM to about 25 μM); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/l to about 100,000 units/l); or an amiloride containing compound (e.g., amiloride, ethyl isopropyl amiloride, hexamethylene amiloride, dimethyl amiloride or isobutyl amiloride present at about 1.0 μM to about 5 μM).

5.3.2 Collection and Handling of Placenta

Generally, a human placenta is recovered shortly after its expulsion after birth. In a preferred embodiment, the placenta is recovered from a patient after informed consent and after a complete medical history of the patient is taken and is associated with the placenta. Preferably, the medical history continues after delivery. Such a medical history can be used to coordinate subsequent use of the placenta or the isolated placental stem cells harvested therefrom. For example, isolated human placental stem cells can be used, in light of the medical history, for personalized medicine for the infant associated with the placenta, or for parents, siblings or other relatives of the infant.

Prior to recovery of isolated placental stem cells, the umbilical cord blood and placental blood are preferably removed. In certain embodiments, after delivery, the cord blood in the placenta is recovered. The placenta can be subjected to a conventional cord blood recovery process. Typically a needle or cannula is used, with the aid of gravity, to exsanguinate the placenta (see, e.g., Anderson, U.S. Pat. No. 5,372,581; Hessel et al., U.S. Pat. No. 5,415,665). The needle or cannula is usually placed in the umbilical vein and the placenta can be gently massaged to aid in draining cord blood from the placenta. Such cord blood recovery may be performed commercially, e.g., LifeBank USA, Cedar Knolls, N.J. Preferably, the placenta is gravity drained without further manipulation so as to minimize tissue disruption during cord blood recovery.

Typically, a placenta is transported from the delivery or birthing room to another location, e.g., a laboratory, for recovery of cord blood and collection of placental stem cells by, e.g., perfusion or tissue dissociation. The placenta is preferably transported in a sterile, thermally insulated transport device (maintaining the temperature of the placenta between 20-28° C.), for example, by placing the placenta, with clamped proximal umbilical cord, in a sterile zip-lock plastic bag, which is then placed in an insulated container. In another embodiment, the placenta is transported in a cord blood collection kit substantially as described in pending U.S. Pat. No. 7,147,626, the disclosure of which is incorporated by reference herein. Preferably, the placenta is delivered to the laboratory four to twenty-four hours following delivery. In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta.

The placenta, prior to cell collection, can be stored under sterile conditions and at either room temperature or at a temperature of 5° C. to 25° C. The placenta may be stored for a period of for a period of four to twenty-four hours, up to forty-eight hours, or longer than forty eight hours, prior to perfusing the placenta to remove any residual cord blood. In one embodiment, the placenta is harvested from between about zero hours to about two hours post-expulsion. The placenta is preferably stored in an anticoagulant solution at a temperature of 5° C. to 25° C. Suitable anticoagulant solutions are well known in the art. For example, a solution of heparin or warfarin sodium can be used. In a preferred embodiment, the anticoagulant solution comprises a solution of heparin (e.g., 1% w/w in 1:1000 solution). The exsanguinated placenta is preferably stored for no more than 36 hours before placental stem cells are collected.

The mammalian placenta or a part thereof, once collected and prepared generally as above, can be treated in any art-known manner, e.g., can be perfused or disrupted, e.g., digested with one or more tissue-disrupting enzymes, to obtain isolated placental stem cells.

5.3.3 Physical Disruption and Enzymatic Digestion of Placental Tissue

In one embodiment, stem cells are collected from a mammalian placenta by physical disruption of part of all of the organ. For example, the placenta, or a portion thereof, may be, e.g., crushed, sheared, minced, diced, chopped, macerated or the like. The tissue can then be cultured to obtain a population of isolated placental stem cells. Typically, the placental tissue is disrupted using, e.g., culture medium, a saline solution, or a stem cell collection composition (see Section 5.5.1 and below).

Typically, isolated placental stem cells can be obtained by disruption of a small block of placental tissue, e.g., a block of placental tissue that is about 1, 2, 3, 4, 5, 6, 7, 8, 9, 10, 20, 30, 40, 50, 60, 70, 80, 90, 100, 200, 300, 400, 500, 600, 700, 800, 900 or about 1000 cubic millimeters in volume. Any method of physical disruption can be used, provided that the method of disruption leaves a plurality, more preferably a majority, and more preferably at least 60%, 70%, 80%, 90%, 95%, 98%, or 99% of the cells in said organ viable, as determinable by, e.g., trypan blue exclusion.

The isolated placental stem cells can generally be collected from a placenta, or portion thereof, at any time within about the first three days post-expulsion, but preferably between about 8 hours and about 18 hours post-expulsion.

In a specific embodiment, the disrupted tissue is cultured in tissue culture medium suitable for the proliferation of isolated placental stem cells (see, e.g., Section 5.6, below, describing the culture of placental stem cells, e.g., PDACs).

In another specific embodiment, placental stem cells are isolated e.g., in part, by physical disruption of placental tissue, wherein the physical disruption includes enzymatic digestion, which can be accomplished by use of one or more tissue-digesting enzymes. The placenta, or a portion thereof, may also be physically disrupted and digested with one or more enzymes, and the resulting material then immersed in, or mixed into, a cell collection composition.

A preferred cell collection composition comprises one or more tissue-disruptive enzyme(s). Enzymes that can be used to disrupt placenta tissue include papain, deoxyribonucleases, serine proteases, such as trypsin, chymotrypsin, collagenase, dispase or elastase. Serine proteases may be inhibited by alpha 2 microglobulin in serum and therefore the medium used for digestion is usually serum-free. EDTA and DNase are commonly used in enzyme digestion procedures to increase the efficiency of cell recovery. The digestate is preferably diluted so as to avoid trapping cells within the viscous digest.

Any combination of tissue digestion enzymes can be used. Typical concentrations for digestion using trypsin include, 0.1% to about 2% trypsin, e.g., about 0.25% trypsin. Proteases can be used in combination, that is, two or more proteases in the same digestion reaction, or can be used sequentially in order to liberate placental stem cells. For example, in one embodiment, a placenta, or part thereof, is digested first with an appropriate amount of collagenase I at about 1 to about 2 mg/ml for, e.g., 30 minutes, followed by digestion with trypsin, at a concentration of about 0.25%, for, e.g., 10 minutes, at 37° C. Serine proteases are preferably used consecutively following use of other enzymes.

In another embodiment, the tissue can further be disrupted by the addition of a chelator, e.g., ethylene glycol bis(2-aminoethyl ether)-N,N,N'N'-tetraacetic acid (EGTA) or ethylenediaminetetraacetic acid (EDTA) to the stem cell collection composition comprising the stem cells, or to a solution in which the tissue is disrupted and/or digested prior to isolation of the placental stem cells with the stem cell collection composition.

Following digestion, the digestate is washed, for example, three times with culture medium, and the washed cells are seeded into culture flasks. The cells are then isolated by differential adherence, and characterized for, e.g., viability, cell surface markers, differentiation, and the like.

It will be appreciated that where an entire placenta, or portion of a placenta comprising both fetal and maternal cells (for example, where the portion of the placenta comprises the chorion or cotyledons), the placental stem cells isolated can comprise a mix of placental stem cells derived from both fetal and maternal sources. Where a portion of the placenta that comprises no, or a negligible number of, maternal cells (for example, amnion), the placental stem cells isolated therefrom will comprise almost exclusively fetal placental stem cells (that is, placental stem cells having the genotype of the fetus).

Placental stem cells, e.g., the placental stem cells described in Section 5.2.2, above, can be isolated from disrupted placental tissue by differential trypsinization (see Section 5.3.5, below) followed by culture in one or more new culture containers in fresh proliferation medium, optionally followed by a second differential trypsinization step.

5.3.4 Placental Perfusion

Placental stem cells, e.g., the placental stem cells described in Section 5.2.2, above, can also be isolated, e.g., in part, by perfusion of the mammalian placenta. Methods of perfusing mammalian placenta to obtain placental stem cells are disclosed, e.g., in U.S. Pat. Nos. 7,045,148 and 7,255,729, in U.S. Patent Application Publication Nos. 2007/0275362 and 2007/0190042, the disclosures of each of which are incorporated herein by reference in their entireties.

Placental stem cells can be collected, e.g., isolated, by perfusion, e.g., through the placental vasculature, using, e.g., a cell collection composition as a perfusion solution. In one embodiment, a mammalian placenta is perfused by passage of perfusion solution through either or both of the umbilical artery and umbilical vein. The flow of perfusion solution through the placenta may be accomplished using, e.g., gravity flow into the placenta. Preferably, the perfusion solution is forced through the placenta using a pump, e.g., a peristaltic pump. The umbilical vein can be, e.g., cannulated with a cannula, e.g., a TEFLON® or plastic cannula, that is connected to a sterile connection apparatus, such as sterile tubing. The sterile connection apparatus is connected to a perfusion manifold.

In preparation for perfusion, the placenta is preferably oriented (e.g., suspended) in such a manner that the umbilical artery and umbilical vein are located at the highest point of the placenta. The placenta can be perfused by passage of a perfusion fluid through the placental vasculature and surrounding tissue. The placenta can also be perfused by passage of a perfusion fluid into the umbilical vein and collection from the umbilical arteries, or passage of a perfusion fluid into the umbilical arteries and collection from the umbilical vein.

In one embodiment, for example, the umbilical artery and the umbilical vein are connected simultaneously, e.g., to a pipette that is connected via a flexible connector to a reservoir of the perfusion solution. The perfusion solution is passed into the umbilical vein and artery. The perfusion solution exudes from and/or passes through the walls of the blood vessels into the surrounding tissues of the placenta, and is collected in a suitable open vessel from the surface of the placenta that was attached to the uterus of the mother during gestation. The perfusion solution may also be introduced through the umbilical cord opening and allowed to flow or percolate out of openings in the wall of the placenta which interfaced with the maternal uterine wall. Placental stem cells that are collected by this method, which can be referred to as a "pan" method, are typically a mixture of fetal and maternal cells.

In another embodiment, the perfusion solution is passed through the umbilical veins and collected from the umbilical artery, or is passed through the umbilical artery and collected from the umbilical veins. Placental stem cells collected by this method, which can be referred to as a "closed circuit" method, are typically almost exclusively fetal.

It will be appreciated that perfusion using the pan method, that is, whereby perfusate is collected after it has exuded from the maternal side of the placenta, results in a mix of fetal and maternal cells. As a result, the cells collected by this method can comprise a mixed population of placental stem cells, of both fetal and maternal origin. In contrast, perfusion solely through the placental vasculature in the closed circuit method, whereby perfusion fluid is passed through one or two placental vessels and is collected solely through the remaining vessel(s), results in the collection of a population of placental stem cells almost exclusively of fetal origin.

The closed circuit perfusion method can, in one embodiment, be performed as follows. A post-partum placenta is obtained within about 48 hours after birth. The umbilical cord is clamped and cut above the clamp. The umbilical cord can be discarded, or can processed to recover, e.g., umbilical cord stem cells, and/or to process the umbilical cord membrane for the production of a biomaterial. The amniotic membrane can be retained during perfusion, or can be separated from the chorion, e.g., using blunt dissection with the fingers. If the amniotic membrane is separated from the chorion prior to perfusion, it can be, e.g., discarded, or processed, e.g., to obtain stem cells by enzymatic digestion, or to produce, e.g., an amniotic membrane biomaterial, e.g., the biomaterial described in U.S. Application Publication No. 2004/0048796, the disclosure of which is incorporated by reference herein in its entirety. After cleaning the placenta of all visible blood clots and residual blood, e.g., using sterile gauze, the umbilical cord vessels are exposed, e.g., by partially cutting the umbilical cord membrane to expose a cross-section of the cord. The vessels are identified, and opened, e.g., by advancing a closed alligator clamp through the cut end of each vessel. The apparatus, e.g., plastic tubing connected to a perfusion device or peristaltic pump, is then inserted into each of the placental arteries. The pump can be any pump suitable for the purpose, e.g., a peristaltic pump. Plastic tubing, connected to a sterile collection reservoir, e.g., a blood bag such as a 250 mL collection bag, is then inserted into the placental vein. Alternatively, the tubing connected to the pump is inserted into the placental vein, and tubes to a collection reservoir(s) are inserted into one or both of the placental arteries. The placenta is then perfused with a volume of perfusion solution, e.g., about 750 ml of perfusion solution. Cells in the perfusate are then collected, e.g., by centrifugation. In certain embodiments, the placenta is perfused with perfusion solution, e.g., 100-300 mL perfusion solution, to remove residual blood prior to perfusion to collect placental stem cells. In another embodiment, the placenta is not perfused with perfusion solution to remove residual blood prior to perfusion to collect placental stem cells.

In one embodiment, the proximal umbilical cord is clamped during perfusion, and more preferably, is clamped within 4-5 cm (centimeter) of the cord's insertion into the placental disc.

The first collection of perfusion fluid from a mammalian placenta during the exsanguination process is generally colored with residual red blood cells of the cord blood and/or placental blood. The perfusion fluid becomes more colorless as perfusion proceeds and the residual cord blood cells are washed out of the placenta. Generally from 30 to 100 ml (milliliter) of perfusion fluid is adequate to initially exsanguinate the placenta, but more or less perfusion fluid may be used depending on the observed results.

The volume of perfusion liquid used to isolate placental stem cells may vary depending upon the number of cells to be collected, the size of the placenta, the number of collections to be made from a single placenta, etc. In various embodiments, the volume of perfusion liquid may be from 50 mL to 5000 mL, 50 mL to 4000 mL, 50 mL to 3000 mL, 100 mL to 2000 mL, 250 mL to 2000 mL, 500 mL to 2000 mL, or 750 mL to 2000 mL. Typically, the placenta is perfused with 700-800 mL of perfusion liquid following exsanguination.

The placenta can be perfused a plurality of times over the course of several hours or several days. Where the placenta is to be perfused a plurality of times, it may be maintained or cultured under aseptic conditions in a container or other suitable vessel, and perfused with the cell collection composition, or a standard perfusion solution (e.g., a normal saline solution such as phosphate buffered saline ("PBS")) with or without an anticoagulant (e.g., heparin, warfarin sodium, coumarin, bishydroxycoumarin), and/or with or without an antimicrobial agent (e.g., β-mercaptoethanol (0.1 mM); antibiotics such as streptomycin (e.g., at 40-100 μg/ml), penicillin (e.g., at 40 U/ml), amphotericin B (e.g., at 0.5 μg/ml). In one embodiment, an isolated placenta is maintained or cultured for a period of time without collecting the perfusate, such that the placenta is maintained or cultured for 1, 2, 3, 4, 5, 6, 7, 8, 9, 10, 11, 12, 13, 14, 15, 16, 17, 18, 19, 20, 21, 22, 23, or 24 hours, or 2 or 3 or more days before perfusion and collection of perfusate. The perfused placenta can be maintained for one or more additional time(s), e.g., 1, 2, 3, 4, 5, 6, 7, 8, 9, 10, 11, 12, 13, 14, 15, 16, 17, 18, 19, 20, 21, 22, 23, 24 or more hours, and perfused a second time with, e.g., 700-800 mL perfusion fluid. The placenta can be perfused 1, 2, 3, 4, 5 or more times, for example, once every 1, 2, 3, 4, 5 or 6 hours. In a preferred embodiment, perfusion of the placenta and collection of perfusion solution, e.g., cell collection composition, is repeated until the number of recovered nucleated cells falls below 100 cells/ml. The perfusates at different time points can be further processed individually to recover time-dependent populations of cells, e.g., stem cells. Perfusates from different time points can also be pooled. In a preferred embodiment, placental stem cells are collected at a time or times between about 8 hours and about 18 hours post-expulsion.

Placental stem cells can be isolated from placenta by perfusion with a solution comprising one or more proteases or other tissue-disruptive enzymes. In a specific embodiment, a placenta or portion thereof (e.g., amniotic membrane, amnion and chorion, placental lobule or cotyledon, umbilical cord, or combination of any of the foregoing) is brought to 25-37° C., and is incubated with one or more tissue-disruptive enzymes in 200 mL of a culture medium for 30 minutes. Cells from the perfusate are collected, brought to 4° C., and washed with a cold inhibitor mix comprising 5 mM EDTA, 2 mM dithiothreitol and 2 mM beta-mercaptoethanol. The placental stem cells are washed after several minutes with a cold (e.g., 4° C.) stem cell collection composition.

In certain embodiments, perfusion (whether by pan method or closed-circuit method) is carried out open under a sterile hood in, e.g., a pan. In certain other embodiments, perfusion is carried out within a closed environment, e.g., a sterile bag containing the placenta. In certain other embodiments, the placenta is folded, e.g., folded in half, or substantially in half, once or a plurality of times during perfusion. In specific embodiments, the folding is accomplished by hand, or mechanically.

Perfusion, carried out as described above, results in the collection of placental perfusate, a solution comprising a heterogeneous population of different placental cells, which population comprises the tissue culture plastic adhesive placental stem cells described above in Section 5.2.2, as well as hematopoietic placental stem cells, e.g., $CD34^+$ placental stem cells, which are not tissue culture plastic adherent.

5.3.5 Isolation, Sorting, and Characterization of Placental Stem Cells

The isolated placental stem cells, e.g., the tissue culture plastic-adherent cells described in Section 5.2.2, above, whether obtained by perfusion or physical disruption, e.g., by enzymatic digestion, can initially be purified from (i.e., be isolated from) other cells by Ficoll gradient centrifugation. Such centrifugation can follow any standard protocol for centrifugation speed, etc. In one embodiment, for example, cells collected from the placenta are recovered from perfusate by centrifugation at 5000×g for 15 minutes at room temperature, which separates cells from, e.g., contaminating debris and platelets. In certain embodiments, the Ficoll is used at a density of from about 1.070 g/ml to about 1.090 g/mL, e.g., about 1.073 g/mL, 1.077 g/mL, or about 1.084 g/mL; the placental stem cells will collect on top of the gradient at these densities. In another embodiment, placental perfusate is concentrated to about 200 ml, gently layered over Ficoll, and centrifuged at about 1100×g for 20 minutes at 22° C., and the low-density interface layer of cells is collected for further processing.

Cell pellets can be resuspended in fresh stem cell collection composition, or a medium suitable for cell maintenance, e.g., stem cell maintenance, for example, IMDM serum-free medium containing 2 U/ml heparin and 2 mM EDTA (GibcoBRL, NY). The total mononuclear cell fraction can be isolated, e.g., using Lymphoprep (Nycomed Pharma, Oslo, Norway) according to the manufacturer's recommended procedure.

Placental stem cells obtained by perfusion or digestion can, for example, be further, or initially, isolated by differential trypsinization using, e.g., a solution of 0.05% trypsin with 0.2% EDTA (Sigma, St. Louis Mo.). Differential trypsinization is possible because the isolated placental stem cells, which are tissue culture plastic-adherent, typically detach from the plastic surfaces within about five minutes whereas other adherent populations typically require more than 20-30 minutes incubation. The detached placental stem cells can be harvested following trypsinization and trypsin neutralization, using, e.g., Trypsin Neutralizing Solution (TNS, Cambrex). In one embodiment of isolation of adherent cells, aliquots of, for example, about 5-10×10$^6$ cells are placed in each of several T-75 flasks, preferably fibronectin-coated T75 flasks. In such an embodiment, the cells can be cultured with commercially available Mesenchymal Stem Cell Growth Medium (MSCGM) (Cambrex), and placed in a tissue culture incubator (37° C., 5% $CO_2$). After 10 to 15 days, non-adherent cells are removed from the flasks by washing with PBS. The PBS is then replaced by MSCGM.

The number and type of cells collected from a mammalian placenta can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. For example, using antibodies to CD73, one can determine, using the techniques above, whether a cell comprises a detectable amount of CD73; if so, the cell is CD73$^+$. Likewise, if a cell produces enough OCT-4 RNA to be detectable by RT-PCR, or significantly more OCT-4 RNA than an adult (terminally-differentiated) cell (e.g., a dermal fibroblast), the cell is OCT-4$^+$. In a specific embodiment, the cell is positive for a particular mRNA if the mRNA is amplified above background by RT-PCR, using an appropriate primer pair, in 35 cycles or less. Antibodies to cell surface markers (e.g., CD markers such as CD34) and the sequence of stem cell-specific genes, such as OCT-4, are well-known in the art.

Placental stem cells, particularly cells that have been isolated by Ficoll separation, differential adherence, or a combination of both, may be sorted, e.g., using a fluorescence activated cell sorter (FACS). Fluorescence activated cell sorting (FACS) is a well-known method for separating particles, including cells, based on the fluorescent properties of the particles (Kamarch, 1987, Methods Enzymol, 151:150-165). In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In one sorting scheme, placental stem cells, e.g., PDACs, are sorted on the basis of expression of one or more of the markers CD34, CD44, CD45, CD73, CD90, CD105, CD133, CD166, CD200 and/or KDR; that is, the placental stem cells are sorted on the basis of expression of one or more of CD44, CD73, CD90, CD105, CD166 or CD200, and/or lack of expression of CD34, CD45, CD133, or KDR. This can be accomplished in connection with procedures to select such cells on the basis of their adherence properties in culture. For example, tissue culture plastic adherence selection can be accomplished before or after sorting on the basis of marker expression. In one embodiment, for example, cells are sorted first on the basis of their expression of CD34; CD34$^-$ cells are retained, and CD34$^-$ cells that are additionally one or more of CD73$^+$, CD90$^+$ or CD200$^+$ are separated from all other CD34$^-$ cells. In another embodiment, cells from placenta are sorted based on their expression of CD200; for example, cells displaying CD200 are isolated for further use. Cells that express, e.g., CD200 can, in a specific embodiment, be further sorted based on their expression of CD73 and/or CD105, or epitopes recognized by antibodies SH2, SH3 or SH4, or lack of expression of CD34, CD38 or CD45. For example, in another embodiment, placental stem cells are sorted by expression, or lack thereof, of CD200, CD73, CD105, CD34, CD38 and CD45, and placental stem cells that are CD200$^+$, CD73$^+$, CD105$^+$, CD34$^-$, CD38$^-$ and CD45$^-$ are isolated from other placental cells for further use.

Sorting of cells can be used to confirm the identity of a population of placental stem cells. For example, the tissue culture plastic-adherent placental stem cells, e.g., PDACs, described herein can be cultured for one or more passages, then collected and a sample characterized using antibodies to CD34, CD44, CD45, CD73, CD90, CD105, and/or CD200, to determine if, e.g., 70%, 75%, 80%, 85%, 90%, 95% or 98% of the cultured cells are CD34$^-$, CD44$^+$, CD45$^-$, CD73$^+$, CD90$^+$, CD$^+$, and/or CD200$^+$.

In specific embodiments of any of the above embodiments of sorted placental stem cells, at least 50%, 60%, 70%, 80%, 90% or 95% of the cells in a cell population remaining after sorting are said isolated placental stem cells. Placental stem cells can be sorted by one or more of any of the markers described in Section 5.2.2, above. In a specific embodiment, for example, placental cells that are (1) adherent to tissue culture plastic, and (2) CD10$^+$, CD34$^-$ and CD105$^+$ are sorted from (i.e., isolated from) other placental cells. In another specific embodiment, placental cells that are (1) adherent to tissue culture plastic, and (2) CD10$^+$, CD34$^-$, CD105$^+$ and CD200$^+$ are sorted from (i.e., isolated from) other placental cells. In another specific embodiment, placental cells that are (1) adherent to tissue culture plastic, and (2) CD10$^+$, CD34$^-$, CD45$^-$, CD90$^+$, CD105$^+$ and CD200$^+$ are sorted from (i.e., isolated from) other placental cells. Placental stem cells need not be sorted according to a particular cellular marker, or set of cellular markers, to be "isolated," however.

With respect to nucleotide sequence-based detection and/or analysis of placental stem cells, sequences for the markers listed herein are readily available in publicly-available databases such as GenBank or EMBL.

With respect to antibody-mediated detection and sorting of placental stem cells, e.g., placental stem cells or placental multipotent cells, any antibody, specific for a particular marker, can be used, in combination with any fluorophore or other label suitable for the detection and sorting of cells (e.g., fluorescence-activated cell sorting). Antibody/fluorophore combinations to specific markers include, but are not limited to, fluorescein isothiocyanate (FITC) conjugated monoclonal antibodies against HLA-G (available from Serotec, Raleigh, N.C.), CD10 (available from BD Immunocytometry Systems, San Jose, Calif.), CD44 (available from BD Biosciences Pharmingen, San Jose, Calif.), and CD105 (available from R&D Systems Inc., Minneapolis, Minn.); phycoerythrin (PE) conjugated monoclonal antibodies against CD44, CD200, CD117, and CD13 (BD Biosciences Pharmingen); phycoerythrin-Cy7 (PE Cy7) conjugated monoclonal antibodies against CD33 and CD10 (BD Biosciences Pharmingen); allophycocyanin (APC) conjugated streptavidin and monoclonal antibodies against CD38 (BD Biosciences Pharmingen); and Biotinylated CD90 (BD Biosciences Pharmingen). Other antibodies that can be used include, but are not limited to, CD133-APC (Miltenyi), KDR-Biotin (CD309, Abcam), Cytokeratin-Fitc (Sigma or Dako), HLA ABC-Fitc (BD), HLA DR,DQ,DP-PE (BD), β-2-microglobulin-PE (BD), CD80-PE (BD) and CD86-APC (BD). Other antibody/label combinations that can be used include, but are not limited to, CD45-PerCP (peridin chlorophyll protein); CD44-PE; CD10-F (fluorescein); HLA-G-F and 7-amino-actinomycin-D (7-AAD); HLA-ABC-F; and the like. This list is not exhaustive, and other antibodies from other suppliers are also commercially available.

Isolated placental stem cells can be assayed for CD117 or CD133 using, for example, phycoerythrin-Cy5 (PE Cy5) conjugated streptavidin and biotin conjugated monoclonal antibodies against CD117 or CD133; however, using this system, the cells can appear to be positive for CD117 or CD133, respectively, because of a relatively high background.

The isolated placental stem cells can be labeled with an antibody to a single marker and detected and/or sorted. Placental stem cells can also be simultaneously labeled with multiple antibodies to different markers.

In another embodiment, magnetic beads can be used to separate cells, e.g., separate placental stem cells from other placental cells. The cells may be sorted using a magnetic activated cell sorting (MACS) technique, a method for separating particles based on their ability to bind magnetic beads (0.5-100 μm diameter). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

Isolated placental stem cells can also be characterized and/or sorted based on cell morphology and growth characteristics. For example, isolated placental stem cells can be characterized as having, and/or selected on the basis of, e.g., a fibroblastoid appearance in culture. The isolated placental stem cells can also be characterized as having, and/or be selected, on the basis of their ability to form embryoid-like bodies. In one embodiment, for example, placental stem cells that are fibroblastoid in shape, express CD73 and CD105, and produce one or more embryoid-like bodies in culture are isolated from other placental cells. In another embodiment, OCT-4+ placental stem cells that produce one or more embryoid-like bodies in culture are isolated from other placental cells.

The isolated placental stem cells can be assessed for viability, proliferation potential, and longevity using standard techniques known in the art, such as trypan blue exclusion assay, fluorescein diacetate uptake assay, propidium iodide uptake assay (to assess viability); and thymidine uptake assay, MTT (3-(4,5-Dimethylthiazol-2-yl)-2,5-diphenyltetrazolium bromide) cell proliferation assay (to assess proliferation). Longevity may be determined by methods well known in the art, such as by determining the maximum number of population doubling in an extended culture.

Isolated placental stem cells, e.g., the isolated placental stem cells described in Section 5.2.2, above, can also be separated from other placental cells using other techniques known in the art, e.g., selective growth of desired cells (positive selection), selective destruction of unwanted cells (negative selection); separation based upon differential cell agglutinability in the mixed population as, for example, with soybean agglutinin; freeze-thaw procedures; filtration; conventional and zonal centrifugation; centrifugal elutriation (counter-streaming centrifugation); unit gravity separation; countercurrent distribution; electrophoresis; and the like.

5.4 Culture of Isolated Placental Stem Cells 5.4.1 Culture Media

Isolated placental cells, or placental tissue from which placental stem cells grow out, can be used to initiate, or seed, cultures of placental stem cells. Cells are generally transferred to sterile tissue culture vessels either uncoated or coated with extracellular matrix or ligands such as laminin, collagen (e.g., native or denatured), gelatin, fibronectin, ornithine, vitronectin, and extracellular membrane protein (e.g., MATRIGEL® (BD Discovery Labware, Bedford, Mass.)). Similar procedures may be used for BM-MSC culture.

Isolated placental cells, e.g., isolated placental stem cells, can be cultured in any medium, and under any conditions, recognized in the art as acceptable for the culture of cells, e.g., stem cells. Preferably, the culture medium comprises serum, e.g., bovine calf serum, human serum, or the like. The isolated placental stem cells can be cultured in, for example, DMEM-LG (Dulbecco's Modified Essential Medium, low glucose)/MCDB 201 (chick fibroblast basal medium) containing ITS (insulin-transferrin-selenium), LA+BSA (linoleic acid-bovine serum albumin), dexamethasone L-ascorbic acid, PDGF, EGF, IGF-1, and penicillin/streptomycin; DMEM-HG (high glucose) comprising 10% fetal bovine serum (FBS); DMEM-HG comprising 15% FBS; IMDM (Iscove's modified Dulbecco's medium) comprising 10% FBS, 10% horse serum, and hydrocortisone; M199 comprising 1% to 20% FBS, EGF, and heparin; α-MEM (minimal essential medium) comprising 10% FBS, GLUTAMAX™ and gentamicin; DMEM comprising 10% FBS, GLUTAMAX™ and gentamicin, etc.

Other media in that can be used to culture placental stem cells include DMEM (high or low glucose), Eagle's basal medium, Ham's F10 medium (F10), Ham's F-12 medium (F12), Iscove's modified Dulbecco's medium, Mesenchymal Stem Cell Growth Medium (MSCGM), Liebovitz's L-15 medium, MCDB, DMEM/F12, RPMI 1640, advanced DMEM (Gibco), DMEM/MCDB201 (Sigma), and CELL-GRO FREE.

The culture medium can be supplemented with one or more components including, for example, serum (e.g., fetal bovine serum (FBS), preferably about 2-15% (v/v); equine (horse) serum (ES); human serum (HS)); beta-mercaptoethanol (BME), preferably about 0.001% (v/v); one or more growth factors, for example, platelet-derived growth factor (PDGF), epidermal growth factor (EGF), basic fibroblast growth factor (bFGF), insulin-like growth factor-1 (IGF-1), leukemia inhibitory factor (LIF), vascular endothelial growth factor (VEGF), and erythropoietin (EPO); amino acids, including L-valine; and one or more antibiotic and/or antimycotic agents to control microbial contamination, such as, for example, penicillin G, streptomycin sulfate, amphotericin B, gentamicin, and nystatin, either alone or in combination.

In certain embodiments, the placental stem cells suitable for use in the methods described herein can be cultured in medium comprising DMEM medium supplemented with fetal bovine serum (FBS, e.g., 1.9% FBS v/v), linoleic acid-albumin (e.g., 0.01% v/v) (Sigma), insulin-transferrin-selenium (0.97% v/v) (Invitrogen, Carlsbad, Calif.), gentamicin (e.g., 48 µg/mL) (Invitrogen), L-ascorbic acid 2-phosphate sesquimagnesium salt (e.g., 97 µM) (Sigma), dexamethasone 48 nM (Sigma), recombinant human PDGF-BB (e.g., 9.7 ng/ml) (Invitrogen), and recombinant human EGF (e.g., 9.7 ng/ml) (Invitrogen).

The isolated placental stem cells can be cultured in standard tissue culture conditions, e.g., in tissue culture dishes or multiwell plates. The isolated placental stem cells can also be cultured using a hanging drop method. In this method, isolated placental stem cells are suspended at about $1 \times 10^4$ cells per mL in about 5 mL of medium, and one or more drops of the medium are placed on the inside of the lid of a tissue culture container, e.g., a 100 mL Petri dish. The drops can be, e.g., single drops, or multiple drops from, e.g., a multichannel pipetter. The lid is carefully inverted and placed on top of the bottom of the dish, which contains a volume of liquid, e.g., sterile PBS sufficient to maintain the moisture content in the dish atmosphere, and the placental stem cells are cultured.

In one embodiment, isolated placental stem cells are cultured in the presence of a compound that acts to maintain an undifferentiated phenotype in the isolated placental stem cells. In this context, "undifferentiated" does not require complete non-differentiation, e.g., encompasses a relatively undifferentiated phenotype as compared to terminally differentiated cells, or placental stem cells caused to differentiation such as to express one or more characteristics of a terminally differentiated cell. In a specific embodiment, the compound is a substituted 3,4-dihydropyridimol[4,5-d]pyrimidine. In another specific embodiment, the compound is a compound having the following chemical structure:

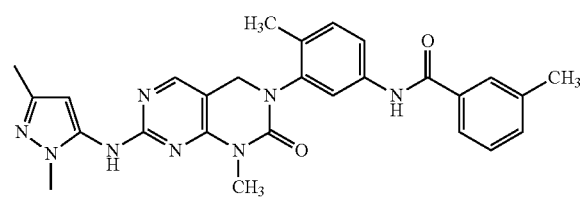

The compound can be contacted with isolated placental stem cells at a concentration of, for example, between about 1 µM to about 10 µM.

5.4.2 Expansion and Proliferation of Placental Stem Cells

Once placental stem cells have been isolated (e.g., separated from at least 50% of the placental cells with which the placental stem cells are normally associated in vivo), the cell or population of cells can be proliferated and expanded in vitro. For example, isolated placental stem cells can be cultured in tissue culture containers, e.g., dishes, flasks, multiwell plates, or the like, for a sufficient time for the cells to proliferate to 70-90% confluence, that is, until the cells and their progeny occupy 70-90% of the culturing surface area of the tissue culture container.

The isolated placental stem cells can be seeded in culture vessels at a density that allows cell growth. For example, the cells may be seeded at low density (e.g., about 1,000 to about 5,000 cells/cm$^2$) to high density (e.g., about 50,000 or more cells/cm$^2$). In a preferred embodiment, the cells are cultured in the presence of about 0 to about 5 percent by volume $CO_2$ in air. In some preferred embodiments, the cells are cultured at about 2 to about 25 percent $O_2$ in air, preferably about 5 to about 20 percent $O_2$ in air. The cells preferably are cultured at about 25° C. to about 40° C., preferably 37° C. The cells are preferably cultured in an incubator. The culture medium can be static or agitated, for example, using a bioreactor. Placental stem cells, in certain embodiments, are grown under low oxidative stress (e.g., with addition of glutathione, ascorbic acid, catalase, tocopherol, N-acetylcysteine, or the like).

Once confluence of less than 100%, for example, 70% to 90% is obtained, the cells may be passaged. For example, the cells can be enzymatically treated, e.g., trypsinized, using techniques well-known in the art, to separate them from the tissue culture surface. After removing the cells by pipetting and counting the cells, about 10,000-100,000 cells/cm$^2$ are passaged to a new culture container containing fresh culture medium. Typically, the new medium is the same type of medium from which the isolated placental stem cells were removed. The isolated placental stem cells can be passaged about, at least, or no more than 1, 2, 3, 4, 5, 6, 7, 8, 9, 10, 12, 14, 16, 18, or 20 times, or more.

5.4.3 Populations of Isolated Placental Stem Cells

Also provided herein are populations of isolated placental stem cells, e.g., the isolated placental stem cells described in Section 5.2.2, above, useful in the methods and compositions described herein. Populations of isolated placental stem cells can be isolated directly from one or more placentas; that is, the cell population can be a population of placental cells comprising the isolated placental cells, wherein the isolated placental stem cells are obtained from, or contained within, perfusate, or obtained from, or contained within, disrupted placental tissue, e.g., placental tissue digestate (that is, the collection of cells obtained by enzymatic digestion of a placenta or part thereof). The isolated placental stem cells described herein can also be cultured and expanded to produce populations of the isolated placental stem cells. Populations of placental cells comprising the isolated placental stem cells can also be cultured and expanded to produce placental stem cell populations.

Placental stem cell populations useful in the methods of treatment provided herein comprise the isolated placental stem cells, for example, the isolated placental stem cells as described in Section 5.2.2 herein. In various embodiments, at least 10%, 20%, 30%, 40%, 50%, 60%, 70%, 80%, 90%, 95%, or 99% of the cells in a placental cell population are the isolated placental stem cells. That is, a population of the isolated placental cells can comprise, e.g., as much as 1%, 5%, 10%, 20%, 30%, 40%, 50%, 60%, 70%, 80%, 90% cells that are not the isolated placental stem cells.

Isolated placental cell populations, comprising the isolated placental stem cells, useful in the methods and compositions described herein can be produced by, e.g., selecting isolated placental cells, whether derived from enzymatic digestion or perfusion, that express particular markers and/or particular culture or morphological characteristics. In various embodiments, for example, provided herein is a method of producing a cell population by selecting placental cells that comprise placental stem cells that (a) adhere to a substrate, and (b)

express any one, or any combination of, the flow cytometric markers and/or gene expression characteristics described herein, e.g., in Section 5.2, above.

In another aspect, populations of placental stem cells, e.g., the placental stem cells described in Section 5.2, above, can be produced by selecting for both marker expression characteristics and the ability of the population of placental stem cells, e.g., a sample of the population of placental stem cells, to suppress, e.g., detectably suppress, the proliferation of cells of a bone-related cancer. In various embodiments, the cells of a bone-related cancer are multiple myeloma cells, chondrosarcoma cells, bone cancer cells, neuroblastoma cells, osteosarcoma cells, Ewing's sarcoma cells, chordoma cells, malignant fibrous histiocytoma of bone cells, prostate cancer cells, or fibrosarcoma of bone cells. Such a selection can be applied, for example, to different populations of placental stem cells, e.g., batches or lots of placental stem cells in order to identify populations that satisfy, for example, certain predetermined criteria for effectiveness.

Selection of cell populations comprising placental stem cells having any of the marker combinations described in Section 5.2.2, above, can be isolated or obtained in similar fashion.

In any of the above embodiments, selection of the isolated cell populations can additionally comprise selecting placental stem cells that express ABC-p (a placenta-specific ABC transporter protein; see, e.g., Allikmets et al., *Cancer Res.* 58(23):5337-9 (1998)). The method can also comprise selecting cells exhibiting at least one characteristic specific to, e.g., a mesenchymal stem cell, for example, expression of CD44, expression of CD90, or expression of a combination of the foregoing.

In the above embodiments, the substrate can be any surface on which culture and/or selection of cells, e.g., isolated placental stem cells, can be accomplished. Typically, the substrate is plastic, e.g., tissue culture dish or multiwell plate plastic. Tissue culture plastic can be coated with a biomolecule, e.g., laminin or fibronectin.

Isolated placental stem cells can be selected by any means known in the art of cell selection. For example, cells can be selected using an antibody or antibodies to one or more cell surface markers, for example, in flow cytometry or FACS. Selection can be accomplished using antibodies in conjunction with magnetic beads. Antibodies that are specific for certain stem cell-related markers are known in the art. For example, antibodies to OCT-4 (Abcam, Cambridge, Mass.), CD200 (Abcam), HLA-G (Abcam), CD73 (BD Biosciences Pharmingen, San Diego, Calif.), CD105 (Abcam; BioDesign International, Saco, Me.), etc. Antibodies to other markers are also available commercially, e.g., CD34, CD38 and CD45 are available from, e.g., StemCell Technologies or BioDesign International.

Isolated placental stem cell populations can comprise placental cells that are not stem cells, or cells that are not placental cells.

The isolated placental stem cell populations provided herein can be combined with one or more populations of non-stem cells or non-placental cells. For example, a population of isolated placental stem cells can be combined with blood (e.g., placental blood or umbilical cord blood), blood-derived stem cells (e.g., stem cells derived from placental blood or umbilical cord blood), umbilical cord stem cells, populations of blood-derived nucleated cells, bone marrow-derived mesenchymal cells, bone-derived stem cell populations, crude bone marrow, adult (somatic) stem cells, populations of stem cells contained within tissue, cultured stem cells, populations of fully-differentiated cells (e.g., chondrocytes, fibroblasts, amniotic cells, osteoblasts, muscle cells, cardiac cells, etc.) and the like. In a specific embodiment, a population of cells useful in the methods and compositions described herein comprises isolated placental stem cells and isolated umbilical cord stem cells. Cells in an isolated placental stem cell population can be combined with a plurality of cells of another type in ratios of about 100,000,000:1, 50,000,000:1, 20,000,000:1, 10,000,000:1, 5,000,000:1, 2,000,000:1, 1,000,000:1, 500,000:1, 200,000:1, 100,000:1, 50,000:1, 20,000:1, 10,000:1, 5,000:1, 2,000:1, 1,000:1, 500:1, 200:1, 100:1, 50:1, 20:1, 10:1, 5:1, 2:1, 1:1; 1:2; 1:5; 1:10; 1:100; 1:200; 1:500; 1:1,000; 1:2,000; 1:5,000; 1:10,000; 1:20,000; 1:50,000; 1:100,000; 1:500,000; 1:1,000,000; 1:2,000,000; 1:5,000,000; 1:10,000,000; 1:20,000,000; 1:50,000,000; or about 1:100,000,000, comparing numbers of total nucleated cells in each population. Cells in an isolated placental stem cell population can be combined with a plurality of cells of a plurality of cell types, as well.

In one embodiment, an isolated population of placental stem cells is combined with a plurality of hematopoietic stem cells. Such hematopoietic stem cells can be, for example, contained within unprocessed placental, umbilical cord blood or peripheral blood; in total nucleated cells from placental blood, umbilical cord blood or peripheral blood; in an isolated population of $CD34^+$ cells from placental blood, umbilical cord blood or peripheral blood; in unprocessed bone marrow; in total nucleated cells from bone marrow; in an isolated population of $CD34^+$ cells from bone marrow, or the like.

In other embodiments, a population of the placental stem cells described herein, e.g., the PDACs described in Section 5.2.2, above, are combined with osteogenic placental adherent cells (OPACs), e.g., the OPACs described in U.S. Patent Application No. 2010/0047214, the disclosure of which is hereby incorporated by reference in its entirety. In other embodiments, a population of the placental stem cells described herein, e.g., the PDACs described in Section 5.2.2, above, are combined with placental perfusate and/or natural killer cells, e.g, natural killer cells from placental perfusate, e.g., placental intermediate natural killer cells, e.g., as described in U.S. Patent application Publication No. 2009/0252710, the disclosure of which is hereby incorporated by reference in its entirety.

5.5 Preservation of Placental Stem Cells

Isolated placental stem cells, e.g., the isolated placental stem cells described above, can be preserved, that is, placed under conditions that allow for long-term storage, or conditions that inhibit cell death by, e.g., apoptosis or necrosis.

Placental stem cells can be preserved using, e.g., a composition comprising an apoptosis inhibitor, necrosis inhibitor and/or an oxygen-carrying perfluorocarbon, as described in related U.S. Application Publication No. 2007/0190042, the disclosure of which is incorporated herein by reference in its entirety. In one embodiment, a method of preserving a population of cells, e.g., placental stem cells, comprises contacting said population of cells with a cell collection composition comprising an inhibitor of apoptosis and an oxygen-carrying perfluorocarbon, wherein said inhibitor of apoptosis is present in an amount and for a time sufficient to reduce or prevent apoptosis in the population of cells, as compared to a population of cells not contacted with the inhibitor of apoptosis. In a specific embodiment, said inhibitor of apoptosis is a caspase inhibitor. In another specific embodiment, said inhibitor of apoptosis is a JNK inhibitor. In another specific embodiment, said JNK inhibitor does not modulate differentiation or proliferation of said cells. In another embodiment, said cell collection composition comprises said inhibitor of apoptosis and said oxygen-carrying perfluorocarbon in separate phases. In another embodiment, said cell collection composition comprises said inhibitor of apoptosis and said oxygen-carrying perfluorocarbon in an emulsion. In another embodiment, the cell collection composition additionally comprises an emulsifier, e.g., lecithin. In another embodiment, said apoptosis inhibitor and said perfluorocarbon are between about 0° C. and about 25° C. at the time of contacting the cells. In another specific embodiment, said apoptosis inhibitor and said perfluorocarbon are between about 2° C. and 10° C., or between about 2° C. and about 5° C., at the time of contacting the cells. In another specific embodiment, said contacting is performed during transport of said population of cells. In another specific embodiment, said contacting is performed during freezing and thawing of said population of cells, e.g., placental stem cells.

Populations of placental useful in the methods and compositions described herein, cells can be preserved, e.g., by a method comprising contacting said population of cells with an inhibitor of apoptosis and an organ-preserving compound, wherein said inhibitor of apoptosis is present in an amount and for a time sufficient to reduce or prevent apoptosis in the population of cells, as compared to a population of cells not contacted with the inhibitor of apoptosis. In a specific embodiment, the organ-preserving compound is UW solution (e.g., as described in U.S. Pat. No. 4,798,824; also known as ViaSpan; see also Southard et al., *Transplantation* 49(2):251-257 (1990)) or a solution described in Stern et al., U.S. Pat. No. 5,552,267, the disclosure of which is hereby incorporated by reference in their entireties. In another embodiment, said organ-preserving compound is hydroxyethyl starch, lactobionic acid, raffinose, or a combination thereof. In another embodiment, the cell collection composition additionally comprises an oxygen-carrying perfluorocarbon, either in two phases or as an emulsion.

In another embodiment of the method, placental stem cells are contacted with a cell collection composition comprising an apoptosis inhibitor and oxygen-carrying perfluorocarbon, organ-preserving compound, or combination thereof, during perfusion. In another embodiment, said cells are contacted during a process of tissue disruption, e.g., enzymatic digestion. In another embodiment, placental stem cells are contacted with said cell collection compound after collection by perfusion, or after collection by tissue disruption, e.g., enzymatic digestion.

Typically, during placental stem cell collection, enrichment and isolation, it is preferable to minimize or eliminate cell stress due to hypoxia and mechanical stress. In another embodiment of the method, therefore, a cell, or population of cells, e.g., placental stem cells, is exposed to a hypoxic condition during collection, enrichment or isolation for less than six hours during said preservation, wherein a hypoxic condition is a concentration of oxygen that is less than normal blood oxygen concentration. In another specific embodiment, said population of cells is exposed to said hypoxic condition for less than two hours during said preservation. In another specific embodiment, said population of cells is exposed to said hypoxic condition for less than one hour, or less than thirty minutes, or is not exposed to a hypoxic condition, during collection, enrichment or isolation. In another specific embodiment, said population of cells is not exposed to shear stress during collection, enrichment or isolation.

Placental stem cells can be cryopreserved, e.g., in cryopreservation medium in small containers, e.g., ampoules. Suitable cryopreservation medium includes, but is not limited to, culture medium including, e.g., growth medium, or cell freezing medium, for example commercially available cell freezing medium, e.g., C2695, C2639 or C6039 (Sigma). Cryopreservation medium preferably comprises DMSO (dimethylsulfoxide), at a concentration of about 2% to about 15% (v/v), e.g., about 10% (v/v). Cryopreservation medium may comprise additional agents, for example, methylcellulose and/or glycerol. Placental stem cells are preferably cooled at about 1° C./min during cryopreservation. Cryopreservation can be accomplished by bringing the cells to a temperature of about −80° C. to about −180° C., preferably about −125° C. to about −140° C. Cryopreserved cells can be transferred to liquid nitrogen prior to thawing for use. In some embodiments, for example, once the ampoules have reached about −90° C., they are transferred to a liquid nitrogen storage area. Cryopreservation can also be done using a controlled-rate freezer. Cryopreserved cells preferably are thawed at a temperature of about 25° C. to about 40° C., preferably to a temperature of about 37° C.

Bone marrow-derived mesenchymal stem cells can be preserved by any of the above methods, as well.

5.6 Compositions Comprising Isolated Placental Stem Cells

The placental stem cells described herein, e.g., in Section 5.2.2, can be combined with any physiologically-acceptable or medically-acceptable compound, composition or device for use in the methods and compositions described herein. In certain embodiments, the composition is a pharmaceutically-acceptable composition, e.g., a composition comprising placental stem cells in a pharmaceutically-acceptable carrier. Any of the compositions described herein can additionally comprise isolated bone marrow-derived mesenchymal stem cells, or bone marrow comprising BM-MSCs, e.g., the BM-MSCs described in U.S. Pat. No. 5,486,359.

In certain embodiments, a composition comprising the isolated placental stem cells additionally comprises a matrix, e.g., a decellularized matrix or a synthetic matrix. In another specific embodiment, said matrix is a three-dimensional scaffold. In another specific embodiment, said matrix comprises collagen, gelatin, laminin, fibronectin, pectin, ornithine, or vitronectin. In another ore specific embodiment, the matrix is an amniotic membrane or an amniotic membrane-derived biomaterial. In another specific embodiment, said matrix comprises an extracellular membrane protein. In another specific embodiment, said matrix comprises a synthetic compound. In another specific embodiment, said matrix comprises a bioactive compound. In another specific embodiment, said bioactive compound is a growth factor, cytokine, antibody, or organic molecule of less than 5,000 daltons.

In another embodiment, a composition useful in the methods of treatment provided herein comprises medium conditioned by any of the foregoing placental stem cells, or any of the foregoing placental stem cell populations.

5.6.1 Cryopreserved Cells

The isolated placental stem cells useful in the methods and compositions described herein can be preserved, for example, cryopreserved for later use. Methods for cryopreservation of cells, such as stem cells, are well known in the art. Isolated placental stem cell populations can be prepared in a form that is easily administrable to an individual, e.g., an isolated placental stem cell population that is contained within a container that is suitable for medical use. Such a container can be, for example, a syringe, sterile plastic bag, flask, jar, or other container from which the isolated placental cell population can be easily dispensed. For example, the container can be a blood bag or other plastic, medically-acceptable bag suitable for the intravenous administration of a liquid to a recipient. The container is preferably one that allows for cryopreservation of the isolated placental stem cells.

The cryopreserved isolated placental stem cells can comprise isolated placental cells derived from a single donor, or from multiple donors. The isolated placental stem cell population can be completely HLA-matched to an intended recipient, or partially or completely HLA-mismatched.

Thus, in one embodiment, isolated placental stem cells can be used in the methods and described herein in the form of a composition comprising a tissue culture plastic-adherent placental stem cell population in a container. In a specific embodiment, the isolated placental stem cells are cryopreserved. In another specific embodiment, the container is a bag, flask, or jar. In another specific embodiment, said bag is a sterile plastic bag. In another specific embodiment, said bag is suitable for, allows or facilitates intravenous administration of said isolated placental stem cell population, e.g., by intravenous infusion. The bag can comprise multiple lumens or compartments that are interconnected to allow mixing of the isolated placental stem cells and one or more other solutions, e.g., a drug, prior to, or during, administration. In another specific embodiment, the composition comprises one or more compounds that facilitate cryopreservation of the placental stem cells. In another specific embodiment, said isolated placental stem cells are contained within a physiologically-acceptable aqueous solution. In another specific embodiment, said physiologically-acceptable aqueous solution is a 0.9% NaCl solution. In another specific embodiment, said isolated placental stem cells comprise placental stem cells that are HLA-matched to a recipient of said placental stem cells. In another specific embodiment, said combined cell population comprises placental stem cells that are at least partially HLA-mismatched to a recipient of said placental stem cells. In another specific embodiment, said isolated stem placental stem cells are derived from a plurality of donors.

In certain embodiments, the isolated placental stem cells in the container are any of the isolated placental stem cells described in Section 5.2.2 herein, wherein said cells have been cryopreserved, and are contained within a container.

In a specific embodiment of any of the foregoing cryopreserved isolated placental stem cells, said container is a bag. In various specific embodiments, said container comprises about, at least, or at most $1 \times 10^6$ said isolated placental stem cells, $5 \times 10^6$ said isolated placental stem cells, $1 \times 10^7$ said isolated placental stem cells, $5 \times 10^7$ said isolated placental stem cells, $1 \times 10^8$ said isolated placental stem cells, $5 \times 10^8$ said isolated placental stem cells, $1 \times 10^9$ said isolated placental stem cells, $5 \times 10^9$ said isolated placental stem cells, $1 \times 10^{10}$ said isolated placental stem cells, or $1 \times 10^{10}$ said isolated placental stem cells. In other specific embodiments of any of the foregoing cryopreserved populations, said isolated placental stem cells have been passaged about, at least, or no more than 5 times, no more than 10 times, no more than 15 times, or no more than 20 times. In another specific embodiment of any of the foregoing cryopreserved isolated placental stem cells, said isolated placental stem cells have been expanded within said container.

5.6.2 Genetically Engineered Placental Stem Cells

Further provided herein are placental stem cells, wherein the placental stem cells have been genetically engineered to produce recombinant or exogenous cytokines associated with tumor suppression. For example, in various embodiments, the placental stem cells are engineered to express detectable amounts of exogenous protein, wherein said exogenous protein is one or more of a bone morphogenetic protein (BMP), activin A, osteonectin, osteoprotegerin, or a connexin. Sequences encoding activin A can be found, e.g., at GenBank Accession No. NM_002191. Sequences encoding osteonectin can be found, e.g., at GenBank Accession No. NM_003118. Sequences encoding osteoprotegerin can be found, e.g., at GenBank Accession No. NM_002546.

In specific embodiments, the connexin is connexin 26 (Cx26) or connexin 43 (Cx43). Sequences encoding Cx26 or Cx43 can be found, e.g., at GenBank Accession Nos. NM_004004 and NM_000165, respectively.

In specific embodiments, said bone morphogenetic protein is one or more of BMP1 (bone morphogenetic protein 1), BMP2, BMP3, BMP4, BMP5, BMP6, BMP7, BMP8a, BMP8b, BMP9 (GDF2; Growth Differentiation Factor-2), BMP10, BMP11 (GDF11), BMP12 (GDF7), BMP13 (GDF6), BMP14 (GDF5), or BMP15, or any combination thereof. Sequences encoding BMPs can be found, e.g., in GenBank, e.g., GenBank Accession No. NM_001199 (BMP1), NM_001200 (BMP2), NM_001201 (BMP3), NM_001202 (BMP4), NM_021073 (BMP5), NM_021073 (BMP6), NM_001719 (BMP7), NM_181809 (BMP8a), NM_001720 (BMP8b), NM_016204 (BMP9/GDF2), NM_014482 (BMP10), NM_005811 (BMP11/GDF11), NM_182828 (BMP12/GDF7), NM_001001557 (BMP13/GDF6), NM_000557 (BMP14/GDF5), or NM_005448 (BMP15).

In other embodiments, provided herein are isolated placental stem cells, wherein the placental stem cells are engineered to express exogenous IFN-β or IL-2. In a specific embodiment, said placental stem cells express exogenous IFN-β or IL-2 in an amount that results in greater, e.g., detectably greater, suppression of tumor cell proliferation, when said tumor cells are contacted with said placental stem cells, compared to placental stem cells not expressing exogenous IFNβ or IL-2.

Methods for genetically engineering cells, for example with retroviral vectors, adenoviral vectors, adeno-associated viral vectors, polyethylene glycol, or other methods known to those skilled in the art, can be used. These include using expression vectors which transport and express nucleic acid molecules in the cells. (See Geoddel; Gene Expression Technology: Methods in Enzymology 185, Academic Press, San Diego, Calif. (1990)). Vector DNA can be introduced into prokaryotic or eukaryotic cells via conventional transformation or transfection techniques. Suitable methods for transforming or transfecting host cells can be found in Sambrook et al. Molecular Cloning: A Laboratory Manual, 2nd Edition, Cold Spring Harbor Laboratory press (1989), and other laboratory textbooks.

Placental stem cells can be genetically modified by introducing DNA or RNA into the cell, e.g., DNA or RNA encoding a protein of interest, by methods including viral transfer, including the use of DNA or RNA viral vectors, such as retroviruses (including lentiviruses), Simian virus 40 (SV40), adenovirus, Sindbis virus, and bovine papillomavirus for example; chemical transfer, including calcium phosphate transfection and DEAE dextran transfection methods; membrane fusion transfer, using DNA-loaded membrane vesicles such as liposomes, red blood cell ghosts, and protoplasts, for example; or physical transfer techniques, such as microinjection, electroporation, or naked DNA transfer. The placental stem cells can be genetically altered by insertion of exogenous DNA, or by substitution of a segment of the cellular genome with exogenous DNA. Insertion of exogenous DNA sequence(s) can be accomplished, e.g., by homologous recombination or by viral integration into the host cell genome, or by incorporating the DNA into the cell, particularly into its nucleus, using a plasmid expression vector and a nuclear localization sequence. The DNA can comprise one or more promoters that allow positive or negative induction of expression of the protein of interest using certain chemicals/drugs, e.g., tetracycline; the promoters can, in other embodiments, be constitutive.

Calcium phosphate transfection can be used to introduce, e.g., plasmid DNA containing a polynucleotide sequence encoding the protein of interest, into a cell, e.g., a placental stem cell. In certain embodiments, DNA is combined with a solution of calcium chloride, then added to a phosphate-buffered solution. Once a precipitate has formed, the solution is added directly to cultured cells. Treatment with DMSO or glycerol can be used to improve transfection efficiency, and levels of stable transfectants can be improved using bis-hydroxyethylamino ethanesulfonate (BES). Calcium phosphate transfection systems are commercially available (e.g., PROFECTION®, Promega Corp., Madison, Wis.). DEAE-dextran transfection may also be used.

Isolated placental stem cells may also be genetically modified by microinjection. In certain embodiments, a glass micropipette is guided into the nucleus of cells under a light microscope to inject DNA or RNA.

Placental stem cells can also be genetically modified using electroporation. In certain embodiments, DNA or RNA is added to a suspension of cultured cells, and the DNA/RNA-cell suspension is placed between two electrodes and subjected to an electrical pulse, causing a transient permeability in the cell's outer membrane that is manifested by the appearance of pores across the membrane.

Liposomal delivery of DNA or RNA to genetically modify the cells can be performed using cationic liposomes, optionally including dioleoyl phosphatidylethanolamine (DOPE) or dioleoyl phosphatidylcholine (DOPC), e.g., LIPOFECTIN® (Life Technologies, Inc.). Other commercially-available delivery systems include EFFECTENE™ (Qiagen), DOTAP (Roche Molecular Biochemicals), FUGENE 6™. (Roche Molecular Biochemicals), and TRANSFECTAM® (Promega).

Viral vectors can be used to genetically alter placental stem cells by delivery of, e.g., target genes, polynucleotides, antisense molecules, or ribozyme sequences into the cells. Retroviral vectors are effective for transducing rapidly-dividing cells, although a number of retroviral vectors have been developed to effectively transfer DNA into non-dividing cells as well. Packaging cell lines for retroviral vectors are known to those of skill in the art. In certain embodiments, a retroviral DNA vector contains two retroviral LTRs such that a first LTR is located 5' to the SV40 promoter, which is operationally linked to the target gene sequence cloned into a multicloning site, followed by a 3' second LTR. Once formed, the retroviral DNA vector is transferred into a packaging cell line using calcium phosphate-mediated transfection, as previously described. Following approximately 48 hours of virus production, the viral vector, now containing the target gene sequence, is harvested. Methods of transfecting cells using lentiviral vectors, recombinant herpes viruses, adenoviral vectors, or alphavirus vectors are known in the art.

Successful transfection or transduction of target cells can be demonstrated using genetic markers, in a technique that is known to those of skill in the art. The green fluorescent protein of *Aequorea victoria*, for example, has been shown to be an effective marker for identifying and tracking genetically modified hematopoietic cells. Alternative selectable markers include the β-Gal gene, truncated nerve growth factor receptor, or drug selectable markers (including but not limited to NEO, MTX, or hygromycin).

Bone marrow-derived mesenchymal stem cells can be genetically modified by any of the methods, and/or by any of the genes, disclosed above.

5.6.3 Pharmaceutical Compositions

Populations of isolated placental stem cells, or populations of cells comprising the isolated placental stem cells, can be formulated into pharmaceutical compositions for use in vivo, e.g., in the methods of treatment provided herein. Such pharmaceutical compositions comprise a population of isolated placental stem cells, or a population of cells comprising isolated placental stem cells, in a pharmaceutically-acceptable carrier, e.g., a saline solution or other accepted physiologically-acceptable solution for in vivo administration. Pharmaceutical compositions comprising the isolated placental stem cells described herein can comprise any, or any combination, of the isolated placental stem cells described elsewhere herein. The pharmaceutical compositions can comprise fetal, maternal, or both fetal and maternal isolated placental stem cells. The pharmaceutical compositions provided herein can further comprise isolated placental stem cells obtained from a single individual or placenta, or from a plurality of individuals or placentae.

The pharmaceutical compositions provided herein can comprise any number of isolated placental stem cells. For example, a single unit dose of isolated placental stem cells can comprise, in various embodiments, about, at least, or no more than $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more isolated placental stem cells, or from $1\times10^5$ to $5\times10^5$, $5\times10^5$ to $1\times10^6$, $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to $1\times10^9$, $1\times10^9$ to $5\times10^9$, $5\times10^9$ to $1\times10^{10}$, $1\times10^{10}$ to $5\times10^{10}$, or $5\times10^{10}$ to $1\times10^{11}$ isolated placental stem cells.

The pharmaceutical compositions provided herein comprise populations of placental stem cells that comprise 50% viable cells or more (that is, at least 50% of the cells in the population are functional or living). Preferably, at least 60% of the cells in the population are viable. More preferably, at least 70%, 80%, 90%, 95%, or 99% of the cells in the population in the pharmaceutical composition are viable.

The pharmaceutical compositions provided herein can comprise one or more compounds that, e.g., facilitate engraftment (e.g., anti-T-cell receptor antibodies, an immunosuppressant, or the like); stabilizers such as albumin, dextran 40, gelatin, hydroxyethyl starch, plasmalyte, and the like.

When formulated as an injectable solution, in one embodiment, the pharmaceutical composition comprises about 1% to 1.5% HSA and about 2.5% dextran. In a preferred embodiment, the pharmaceutical composition comprises from about $5\times10^6$ cells per milliliter to about $2\times10^7$ cells per milliliter in a solution comprising 5% HSA and 10% dextran, optionally comprising an immunosuppressant, e.g., cyclosporine A at, e.g., 10 mg/kg.

In other embodiments, the pharmaceutical composition, e.g., a solution, comprises isolated placental stem cells, wherein said pharmaceutical composition comprises between about $1.0\pm0.3\times10^6$ cells per milliliter to about $5.0\pm1.5\times10^6$ cells per milliliter. In other embodiments, the pharmaceutical composition comprises between about $1.5\times10^6$ cells per milliliter to about $3.75\times10^6$ cells per milliliter. In other embodiments, the pharmaceutical composition comprises between about $1\times10^6$ cells/mL to about $50\times10^6$ cells/mL, about $1\times10^6$ cells/mL to about $40\times10^6$ cells/mL, about $1\times10^6$ cells/mL to about $30\times10^6$ cells/mL, about $1\times10^6$ cells/mL to about $20\times10^6$ cells/mL, about $1\times10^6$ cells/mL to about $15\times10^6$ cells/mL, or about $1\times10^6$ cells/mL to about $10\times10^6$ cells/mL. In certain embodiments, the pharmaceutical composition comprises no visible cell clumps (i.e., no macro cell clumps), or substantially no such visible clumps. As used herein, "macro cell clumps" means an aggregation of cells visible without magnification, e.g., visible to the naked eye, and generally refers to a cell aggregation larger than about 150 microns In some embodiments, the pharmaceutical composition comprises about 2.5%, 3.0%, 3.5%, 4.0%, 4.5%, 5.0%, 5.5%, 6.0%, 6.5%, 7.0%, 7.5% 8.0%, 8.5%, 9.0%, 9.5% or 10% dextran, e.g., dextran-40. In a specific embodiment, said composition comprises about 7.5% to about 9% dextran-40. In a specific embodiment, said composition comprises about 5.5% dextran-40. In certain embodiments, the pharmaceutical composition comprises from about 1% to about 15% human serum albumin (HSA). In specific embodiments, the pharmaceutical composition comprises about 1%, 2%, 3%, 4%, 5%, 65, 75, 8%, 9%, 10%, 11%, 12%, 13%, 14% or 15% HSA. In a specific embodiment, said cells have been cryopreserved and thawed. In another specific embodiment, said cells have been filtered through a 70 µM to 100 µM filter. In another specific embodiment, said composition comprises no visible cell clumps. In another specific embodiment, said composition comprises fewer than about 200 cell clumps per $10^6$ cells, wherein said cell clumps are visible only under a microscope, e.g., a light microscope. In another specific embodiment, said composition comprises fewer than about 150 cell clumps per $10^6$ cells, wherein said cell clumps are visible only under a microscope, e.g., a light microscope. In another specific embodiment, said composition comprises fewer than about 100 cell clumps per $10^6$ cells, wherein said cell clumps are visible only under a microscope, e.g., a light microscope.

In a specific embodiment, the pharmaceutical composition comprises about $1.0\pm0.3\times10^6$ cells per milliliter, about 5.5% dextran-40 (w/v), about 10% HSA (w/v), and about 5% DMSO (v/v).

In other embodiments, the pharmaceutical composition comprises a plurality of isolated placental stem cells in a solution comprising 10% dextran-40, wherein the pharmaceutical composition comprises between about $1.0\pm0.3\times10^6$ cells per milliliter to about $5.0\pm1.5\times10^6$ cells per milliliter, and wherein said composition comprises no cell clumps visible with the unaided eye (i.e., comprises no macro cell clumps). In some embodiments, the pharmaceutical composition comprises between about $1.5\times10^6$ cells per milliliter to about $3.75\times10^6$ cells per milliliter. In a specific embodiment, said cells have been cryopreserved and thawed. In another specific embodiment, said cells have been filtered through a 70 µM to 100 µM filter. In another specific embodiment, said composition comprises fewer than about 200 micro cell clumps (that is, cell clumps visible only with magnification) per $10^6$ cells. In another specific embodiment, the pharmaceutical composition comprises fewer than about 150 micro cell clumps per $10^6$ cells. In another specific embodiment, the pharmaceutical composition comprises fewer than about 100 micro cell clumps per $10^6$ cells. In another specific embodiment, the pharmaceutical composition comprises less than 15%, 14%, 13%, 12%, 11%, 10%, 9%, 8%, 7%, 6%, 5%, 4%, 3%, or 2% DMSO, or less than 1%, 0.9%, 0.8%, 0.7%, 0.6%, 0.5%, 0.4%, 0.3%, 0.2%, or 0.1% DMSO.

Further provided herein are compositions comprising placental stem cells, wherein said compositions are produced by one of the methods disclosed herein. For example, in one embodiment, the pharmaceutical composition comprises cells, e.g., placental stem cells, wherein the pharmaceutical composition is produced by a method comprising filtering a solution comprising cells, e.g., placental stem cells, to form a filtered cell-containing solution; diluting the filtered cell-containing solution with a first solution to about 1 to $50\times10^6$, 1 to $40\times10^6$, 1 to $30\times10^6$, 1 to $20\times10^6$, 1 to $15\times10^6$, or 1 to $10\times10^6$ cells per milliliter, e.g., prior to cryopreservation; and diluting the resulting filtered cell-containing solution with a second solution comprising dextran, but not comprising human serum albumin (HSA) to produce said composition. In certain embodiments, said diluting is to no more than about $15\times10^6$ cells per milliliter. In certain embodiments, said diluting is to no more than about $10\pm3\times10^6$ cells per milliliter. In certain embodiments, said diluting is to no more than about $7.5\times10^6$ cells per milliliter. In other certain embodiments, if the filtered cell-containing solution, prior to the dilution, comprises less than about $15\times10^6$ cells per milliliter, filtration is optional. In other certain embodiments, if the filtered cell-containing solution, prior to the dilution, comprises less than about $10\pm3\times10^6$ cells per milliliter, filtration is optional. In other certain embodiments, if the filtered cell-containing solution, prior to the dilution, comprises less than about $7.5\times10^6$ cells per milliliter, filtration is optional.

In a specific embodiment, the cells, e.g., placental stem cells, are cryopreserved between said diluting with a first dilution solution and said diluting with said second dilution solution. In another specific embodiment, the first dilution solution comprises dextran and HSA. The dextran in the first dilution solution or second dilution solution can be dextran of any molecular weight, e.g., dextran having a molecular weight of from about 10 kDa to about 150 kDa. In some embodiments, said dextran in said first dilution solution or said second solution is about 2.5%, 3.0%, 3.5%, 4.0%, 4.5%, 5.0%, 5.5%, 6.0%, 6.5%, 7.0%, 7.5% 8.0%, 8.5%, 9.0%, 9.5% or 10% dextran. In another specific embodiment, the dextran in said first dilution solution or said second dilution solution is dextran-40. In another specific embodiment, the dextran in said first dilution solution and said second dilution solution is dextran-40. In another specific embodiment, said dextran-40 in said first dilution solution is 5.0% dextran-40. In another specific embodiment, said dextran-40 in said first dilution solution is 5.5% dextran-40. In another specific embodiment, said dextran-40 in said second dilution solution is 10% dextran-40. In another specific embodiment, said HSA in said solution comprising HSA is 1 to 15% HSA. In another specific embodiment, said HSA in said solution comprising HSA is about 1%, 2%, 3%, 4%, 5%, 6%, 7%, 8%, 9%, 10%, 11%, 12%, 13%, 14% or 15% HSA. In another specific embodiment, said HSA in said solution comprising HSA is 10% HSA. In another specific embodiment, said first dilution solution comprises HSA. In another specific embodiment, said HSA in said first dilution solution is 10% HSA. In another specific embodiment, said first dilution solution comprises a cryoprotectant. In another specific embodiment, said cryoprotectant is DMSO. In another specific embodiment, said dextran-40 in said second dilution solution is about 10% dextran-40. In another specific embodiment, said composition comprising cells comprises about 7.5% to about 9% dextran. In another specific embodiment, the pharmaceutical composition comprises from about $1.0\pm0.3\times10^6$ cells per milliliter to about $5.0\pm1.5\times10^6$ cells per milliliter. In another specific embodiment, the pharmaceutical composition comprises from about $1.5\times10^6$ cells per milliliter to about $3.75\times10^6$ cells per milliliter.

In another embodiment, the pharmaceutical composition is made by a method comprising (a) filtering a cell-containing solution comprising placental stem cells prior to cryopreservation to produce a filtered cell-containing solution; (b) cryopreserving the cells in the filtered cell-containing solution at about 1 to $50\times10^6$, 1 to $40\times10^6$, 1 to $30\times10^6$, 1 to $20\times10^6$, 1 to $15\times10^6$, or 1 to $10\times10^6$ cells per milliliter; (c) thawing the cells; and (d) diluting the filtered cell-containing solution about 1:1 to about 1:11 (v/v) with a dextran-40 solution. In certain embodiments, if the number of cells is less than about $10\pm3\times10^6$ cells per milliliter prior to step (a), filtration is optional. In another specific embodiment, the cells in step (b) are cryopreserved at about $10\pm3\times10^6$ cells per milliliter. In another specific embodiment, the cells in step (b) are cryopreserved in a solution comprising about 5% to about 10% dextran-40 and HSA. In certain embodiments, said diluting in step (b) is to no more than about $15\times10^6$ cells per milliliter.

In another embodiment, the pharmaceutical composition is made by a method comprising: (a) suspending placental stem cells in a 5.5% dextran-40 solution that comprises 10% HSA to form a cell-containing solution; (b) filtering the cell-containing solution through a 70 μM filter; (c) diluting the cell-containing solution with a solution comprising 5.5% dextran-40, 10% HSA, and 5% DMSO to about 1 to $50\times10^6$, 1 to $40\times10^6$, 1 to $30\times10^6$, 1 to $20\times10^6$, 1 to $15\times10^6$, or 1 to $10\times10^6$ cells per milliliter; (d) cryopreserving the cells; (e) thawing the cells; and (f) diluting the cell-containing solution 1:1 to 1:11 (v/v) with 10% dextran-40. In certain embodiments, said diluting in step (c) is to no more than about $15\times10^6$ cells per milliliter. In certain embodiments, said diluting in step (c) is to no more than about $10\pm3\times10^6$ cells/mL. In certain embodiments, said diluting in step (c) is to no more than about $7.5\times10^6$ cells/mL.

In another embodiment, the composition comprising cells is made by a method comprising: (a) centrifuging a plurality of cells, e.g., placental stem cells, to collect the cells; (b) resuspending the cells in 5.5% dextran-40; (c) centrifuging the cells to collect the cells; (d) resuspending the cells in a 5.5% dextran-40 solution that comprises 10% HSA; (e) filtering the cells through a 70 μM filter; (f) diluting the cells in 5.5% dextran-40, 10% HSA, and 5% DMSO to about 1 to $50\times10^6$, 1 to $40\times10^6$, 1 to $30\times10^6$, 1 to $20\times10^6$, 1 to $15\times10^6$, or 1 to $10\times10^6$ cells per milliliter; (g) cryopreserving the cells; (h) thawing the cells; and (i) diluting the cells 1:1 to 1:11 (v/v) with 10% dextran-40. In certain embodiments, said diluting in step (f) is to no more than about $15\times10^6$ cells per milliliter. In certain embodiments, said diluting in step (f) is to no more than about $10\pm3\times10^6$ cells/mL. In certain embodiments, said diluting in step (f) is to no more than about $7.5\times10^6$ cells/mL. In other certain embodiments, if the number of cells is less than about $10\pm3\times10^6$ cells per milliliter, filtration is optional.

Other injectable formulations, suitable for the administration of cellular products, may be used.

The pharmaceutical compositions useful in the methods of the invention can comprise any of the placental stem cells described herein, e.g., as described in Section 5.2.2, above. In one embodiment, the pharmaceutical composition comprises isolated placental stem cells that are substantially, or completely, non-maternal in origin, that is, have the fetal genotype; e.g., at least about 90%, 95%, 98%, 99% or about 100% are non-maternal in origin. In certain embodiments, a pharmaceutical composition comprises a population of isolated placental stem cells that are, in non-limiting examples, $CD10^+$, $CD34^-$, $CD105^+$ and $CD200^+$; $CD200^+$ and $HLA-G^-$; $CD73^+$, $CD105^+$, and $CD200^+$; $CD200^+$ and $OCT-4^+$; or $CD73^+$, $CD105^+$ and $HLA-G^-$; or a combination of the foregoing, wherein at least 70%, 80%, 90%, 95% or 99% of said isolated placental stem cells are non-maternal in origin. In another embodiment, a pharmaceutical composition comprises a population of isolated placental stem cells that are $CD10^+$, $CD105^+$ and $CD34^-$; $CD10^+$, $CD105^+$, $CD200^+$ and $CD34^-$; $CD10^+$, $CD105^+$, $CD200^+$, $CD34^-$ and at least one of $CD90^+$ or $CD45^-$; $CD10^+$, $CD90^+$, $CD105^+$, $CD200^+$, $CD34^-$ and $CD45^-$; $CD10^+$, $CD90^+$, $CD105^+$, $CD200^+$, $CD34^-$ and $CD45^-$; $CD200^+$ and $HLA-G^-$; $CD73^+$, $CD105^+$, and $CD200^+$; $CD200^+$ and $OCT-4^+$; $CD73^+$, $CD105^+$ and $HLA-G^-$; one or more of $CD117^-$, $CD133^-$, $KDR^-$, $CD80^-$, $CD86^-$, $HLA-A,B,C^+$, $HLA-DP,DQ,DR^-$ and/or $PDL1^+$; or a combination of the foregoing, wherein at least 70%, 80%, 90%, 95% or 99% of said isolated placental stem cells are non-maternal in origin. In a specific embodiment, the pharmaceutical composition additionally comprises a stem cell that is not obtained from a placenta.

Isolated placental stem cells in the compositions, e.g., pharmaceutical compositions, provided herein, can comprise placental stem cells derived from a single donor, or from multiple donors. The isolated placental stem cells can be completely HLA-matched to an intended recipient, or partially or completely HLA-mismatched.

The pharmaceutical compositions provided herein can further comprise BM-MSCs. In certain embodiments, the placental stem cells and BM-MSCs are present in the pharmaceutical composition at a ratio of, e.g., 99:1, 95:5, 90:10, 85:15, 80:20, 75:25, 70:30, 65:35, 60:40, 55:45, 50:50, 45:55, 40:60, 35:65, 30:70, 25:75, 20:80, 15:85, 10:90, 5:95 or 1:99 by numbers of cells, or between 99:1 and 95:5, between 95:5 and 90:10, between 90:10 and 85:15, between 85:15 and 80:20, between 80:20 and 75:25, between 75:25 and 70:30, between 70:30 and 65:35, between 65:35 and 60:40, between 60:40 and 55:45, between 55:45 and 50:50, between 50:50 and 45:55, between 45:55 and 40:60, between 40:60 and 35:65, between 35:65 and 30:70, between 30:70 and 25:75, between 25:75 and 20:80, between 20:80 and 15:85, between 10:90 and 5:95, or between 5:95 and 1:99, by numbers of cells.

5.6.4 Matrices Comprising Isolated Placental Stem Cells

Further provided herein are compositions comprising matrices, hydrogels, scaffolds, and the like that comprise placental stem cells. Such compositions can be used in the place of, or in addition to, cells in liquid suspension. In certain embodiments, the isolated placental stem cells are combined with platelet rich plasma. In other embodiments, the isolated placental stem cells are combined with alginate.

The isolated placental stem cells described herein can be seeded onto a natural matrix, e.g., a placental biomaterial such as an amniotic membrane material. Such an amniotic membrane material can be, e.g., amniotic membrane dissected directly from a mammalian placenta; fixed or heat-treated amniotic membrane, substantially dry (i.e., <20% $H_2O$) amniotic membrane, chorionic membrane, substantially dry chorionic membrane, substantially dry amniotic and chorionic membrane, and the like. Preferred placental biomaterials on which isolated placental stem cells can be seeded are described in Hariri, U.S. Application Publication No. 2004/0048796, the disclosure of which is incorporated herein by reference in its entirety.

The isolated placental stem cells described herein can be suspended in a hydrogel solution suitable for, e.g., injection. Suitable hydrogels for such compositions include self-assembling peptides, such as RAD16. In one embodiment, a hydrogel solution comprising the cells can be allowed to harden, for instance in a mold, to form a matrix having cells dispersed therein for implantation. Isolated placental stem cells in such a matrix can also be cultured so that the cells are mitotically expanded prior to implantation. The hydrogel is, e.g., an organic polymer (natural or synthetic) that is cross-linked via covalent, ionic, or hydrogen bonds to create a three-dimensional open-lattice structure that entraps water molecules to form a gel. Hydrogel-forming materials include polysaccharides such as alginate and salts thereof, peptides, polyphosphazines, and polyacrylates, which are crosslinked ionically, or block polymers such as polyethylene oxide-polypropylene glycol block copolymers which are crosslinked by temperature or pH, respectively. In some embodiments, the hydrogel or matrix is biodegradable.

In some embodiments, the formulation comprises an in situ polymerizable gel (see., e.g., U.S. Patent Application Publication 2002/0022676, the disclosure of which is incorporated herein by reference in its entirety; Anseth et al., *J. Control Release*, 78(1-3):199-209 (2002); Wang et al., *Biomaterials*, 24(22):3969-80 (2003).

In some embodiments, the polymers are at least partially soluble in aqueous solutions, such as water, buffered salt solutions, or aqueous alcohol solutions, that have charged side groups, or a monovalent ionic salt thereof. Examples of polymers having acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

The isolated placental stem cells described herein or co-cultures thereof can be seeded onto a three-dimensional framework or scaffold and implanted in vivo. Such a framework can be implanted in combination with any one or more growth factors, cells, drugs or other components that, e.g., stimulate tissue formation.

Examples of scaffolds that can be used include nonwoven mats, porous foams, or self assembling peptides. Nonwoven mats can be formed using fibers comprised of a synthetic absorbable copolymer of glycolic and lactic acids (e.g., PGA/PLA) (VICRYL, Ethicon, Inc., Somerville, N.J.). Foams, composed of, e.g., poly(8-caprolactone)/poly(glycolic acid) (PCL/PGA) copolymer, formed by processes such as freeze-drying, or lyophilization (see, e.g., U.S. Pat. No. 6,355,699), can also be used as scaffolds.

In another embodiment, isolated placental stem cells can be seeded onto, or contacted with, a felt, which can be, e.g., composed of a multifilament yarn made from a bioabsorbable material such as PGA, PLA, PCL copolymers or blends, or hyaluronic acid.

The isolated placental stem cells provided herein can, in another embodiment, be seeded onto foam scaffolds that may be composite structures. Such foam scaffolds can be molded into a useful shape, such as that of a portion of a specific structure, e.g., a bone containing a lesion. In some embodiments, the framework is treated, e.g., with 0.1M acetic acid followed by incubation in polylysine, PBS, and/or collagen, prior to inoculation of the cells in order to enhance cell attachment. External surfaces of a matrix may be modified to improve the attachment or growth of cells and differentiation of tissue, such as by plasma-coating the matrix, or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate, etc.), a cellular matrix, and/or other materials such as, but not limited to, gelatin, alginates, agar, agarose, and plant gums, and the like.

In some embodiments, the scaffold comprises, or is treated with, materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as EPTFE, and segmented polyurethaneurea silicones, such as PURSPAN™ (The Polymer Technology Group, Inc., Berkeley, Calif.). The scaffold can also comprise anti-thrombotic agents such as heparin; the scaffolds can also be treated to alter the surface charge (e.g., coating with plasma) prior to seeding with isolated placental stem cells.

The placental stem cells provided herein can also be seeded onto, or contacted with, a physiologically-acceptable ceramic material including, but not limited to, mono-, di-, tri-, alpha-tri-, beta-tri-, and tetra-calcium phosphate, hydroxyapatite, fluoroapatites, calcium sulfates, calcium fluorides, calcium oxides, calcium carbonates, magnesium calcium phosphates, biologically active glasses such as BIOGLASS®, and mixtures thereof. Porous biocompatible ceramic materials currently commercially available include SURGIBONE® (CanMedica Corp., Canada), ENDOBON® (Merck Biomaterial France, France), CEROS® (Mathys, AG, Bettlach, Switzerland), and mineralized collagen bone grafting products such as HEALOS™ (DePuy, Inc., Raynham, Mass.) and VITOSS®, RHAKOSS™, and CORTOSS® (Orthovita, Malvern, Pa.). The framework can be a mixture, blend or composite of natural and/or synthetic materials.

In one embodiment, the isolated placental stem cells are seeded onto, or contacted with, a suitable scaffold at about $0.5 \times 10^6$ to about $8 \times 10^6$ cells/mL.

5.7 Immortalized Placental Stem Cell Lines

The placental stem cells useful in the treatment of a bone-related cancer, suppression of bone related cancer cell proliferation, or suppression of osteoclast progenitor maturation can be conditionally immortalized by transfection with any suitable vector containing a growth-promoting gene, that is, a gene encoding a protein that, under appropriate conditions, promotes growth of the transfected cell, such that the production and/or activity of the growth-promoting protein is regulatable by an external factor. In a preferred embodiment the growth-promoting gene is an oncogene such as, but not limited to, v-myc, N-myc, c-myc, p53, SV40 large T antigen, polyoma large T antigen, E1a adenovirus or E7 protein of human papillomavirus.

External regulation of the growth-promoting protein can be achieved by placing the growth-promoting gene under the control of an externally-regulatable promoter, e.g., a promoter the activity of which can be controlled by, for example, modifying the temperature of the transfected cells or the composition of the medium in contact with the cells. in one embodiment, a tetracycline (tet)-controlled gene expression system can be employed (see Gossen et al., *Proc. Natl. Acad. Sci. USA* 89:5547-5551, 1992; Hoshimaru et al., *Proc. Natl. Acad. Sci. USA* 93:1518-1523, 1996). In the absence of tet, a tet-controlled transactivator (tTA) within this vector strongly activates transcription from $ph_{CMV^*-1}$, a minimal promoter from human cytomegalovirus fused to tet operator sequences. tTA is a fusion protein of the repressor (tetR) of the transposon-10-derived tet resistance operon of *Escherichia coli* and the acidic domain of VP16 of herpes simplex virus. Low, non-toxic concentrations of tet (e.g., 0.01-1.0 μg/mL) almost completely abolish transactivation by tTA.

In one embodiment, the vector further contains a gene encoding a selectable marker, e.g., a protein that confers drug resistance. The bacterial neomycin resistance gene ($neo^R$) is one such marker that may be employed within the present methods. Cells carrying $neo^R$ may be selected by means known to those of ordinary skill in the art, such as the addition of, e.g., 100-200 μg/mL G418 to the growth medium.

Transfection can be achieved by any of a variety of means known to those of ordinary skill in the art including, but not limited to, retroviral infection. In general, a cell culture may be transfected by incubation with a mixture of conditioned medium collected from the producer cell line for the vector and DMEM/F12 containing N2 supplements. For example, a placental stem cell culture prepared as described above may be infected after, e.g., five days in vitro by incubation for about 20 hours in one volume of conditioned medium and two volumes of DMEM/F12 containing N2 supplements. Transfected cells carrying a selectable marker may then be selected as described above.

Following transfection, the cells are passaged onto a surface that permits proliferation, e.g., allows at least 30% of the cells to double in a 24 hour period. Preferably, the substrate is a polyornithine/laminin substrate, consisting of tissue culture plastic coated with polyornithine (10 µg/mL) and/or laminin (10 µg/mL), a polylysine/laminin substrate or a surface treated with fibronectin. Cultures are then fed every 3-4 days with growth medium, which may or may not be supplemented with one or more proliferation-enhancing factors. Proliferation-enhancing factors may be added to the growth medium when cultures are less than 50% confluent.

The conditionally-immortalized placental stem cell lines can be passaged using standard techniques, such as by trypsinization, when 80-95% confluent. Up to approximately the twentieth passage, it is, in some embodiments, beneficial to maintain selection (by, for example, the addition of G418 for cells containing a neomycin resistance gene). Cells may also be frozen in liquid nitrogen for long-term storage.

Clonal cell lines can be isolated from a conditionally-immortalized human placental stem cell line prepared as described above. In general, such clonal cell lines may be isolated using standard techniques, such as by limit dilution or using cloning rings, and expanded. Clonal cell lines may generally be fed and passaged as described above.

Conditionally-immortalized human placental stem cell lines, which may, but need not, be clonal, may generally be induced to differentiate by suppressing the production and/or activity of the growth-promoting protein under culture conditions that facilitate differentiation. For example, if the gene encoding the growth-promoting protein is under the control of an externally-regulatable promoter, the conditions, e.g., temperature or composition of medium, may be modified to suppress transcription of the growth-promoting gene. For the tetracycline-controlled gene expression system discussed above, differentiation can be achieved by the addition of tetracycline to suppress transcription of the growth-promoting gene. In general, 1 µg/mL tetracycline for 4-5 days is sufficient to initiate differentiation. To promote further differentiation, additional agents may be included in the growth medium.

BM-MSCs may also be immortalized using any of the above methods.

5.8 Kits

In another aspect, provided herein are kits, suitable for the treatment of an individual who has a bone-related cancer, e.g., multiple myeloma or chondrosarcoma, or one of the other bone-related cancers listed elsewhere herein, comprising, in a container separate from remaining kit contents, tissue culture plastic placental stem cells, e.g., the isolated placental stem cells described in Section 5.2.2, above, and/or isolated bone marrow-derived mesenchymal stem cells, and instructions for use. Preferably, the placental stem cells and/or BM-MSCs are provided in a pharmaceutically-acceptable solution, e.g., a solution suitable for intralesional administration or a solution suitable for intravenous administration.

In certain embodiments, the kits comprise one or more components that facilitate delivery of the placental stem cells and/or BM-MSCs to the individual. For example, in certain embodiments, the kit comprises components that facilitate intralesional delivery of the cells to the individual. In such embodiments, the kit can comprise, e.g., syringes and needles suitable for delivery of cells to the individual, and the like. In such embodiments, the placental stem cells may be contained in the kit in a bag, or in one or more vials. In certain other embodiments, the kit comprises components that facilitate intravenous or intra-arterial delivery of the placental cells to the individual. In such embodiments, the placental stem cells may be contained, e.g., within a bottle or bag (for example, a blood bag or similar bag able to contain up to about 1.5 L solution comprising the cells), and the kit additionally comprises tubing and needles suitable for the delivery of cells to the individual.

Additionally, the kit may comprise one or more compounds that reduce pain or inflammation in the individual (e.g., an analgesic, steroidal or non-steroidal anti-inflammatory compound, or the like. The kit may also comprise an antibacterial or antiviral compound (e.g., one or more antibiotics), a compound to reduce anxiety in the individual (e.g., alaprazolam), a compound that reduces an immune response in the individual (e.g., cyclosporine A), an antihistamine (diphenhydramine, loratadine, desloratadine, quetiapine, fexofenadine, cetirizine, promethazine, chlorepheniramine, levocetirizine, cimetidine, famotidine, ranitidine, nizatidine, roxatidine, lafutidine, or the like).

Additionally, the kit can comprise disposables, e.g., sterile wipes, disposable paper goods, gloves, or the like, which facilitate preparation of the individual for delivery, or which reduce the likelihood of infection in the individual as a result of the administration of the placental stem cells.

6. EXAMPLES 6.1 Example 1

Placental Stem Cells Promote Bone Formation In Vivo

This Example demonstrates the ability of isolated tissue culture plastic-adherent placental stem cells to promote bone formation.

Placental stem cells were obtained as follows. Briefly, placental tissue measuring approximately 1×2×1 cm was obtained and minced into approximately 1 mm$^3$ pieces. These pieces were digested with collagenase IA (2 mg/ml, Sigma) for 30 minutes, followed by digestion with trypsin-EDTA (0.25%, GIBCO BRL) for 10 minutes, at 37° C. in a water bath. The resulting solution was centrifuged at 400 g for 10 minutes at room temperature, followed by removal of the digestion solution. The pellet was resuspended to approximately 10 volumes with PBS, and centrifuged at 400 g for 10 minutes at room temperature. The tissue/cell pellet was resuspended in 130 mL culture medium, and the cells were seeded at 13 ml per fibronectin-coated T-75 flask. Cells were incubated at 37° C. with a humidified atmosphere with 5% $CO_2$. Cells used in the studies described herein, and in following Examples, were cultured to passage 6 before use. Such isolated placental stem cells are generally $CD34^-$, $CD10^+$, $CD105^+$, and $CD200^+$. Examination with antibodies to CD44 and CD90 further showed the cells to be $CD34^-$, $CD10^+$, $CD44^+$, $CD90^-$, $CD105^+$, and $CD200^+$.

Rats used in this study were approximately 6 weeks old at the time of the study, and sixteen rats were assigned to each group. Bilateral cranial defects (left and right; approximately 3 mm×5 mm) were created in 96 male Hsd:RH-Foxn$^{rnu}$ athymic rats (Charles River, Wilmington, Mass.). Briefly, in the central cranial area between the ears a transverse skin incision was made, and a tissue expander was placed into the central region of the rostral margin of the incision (skin flap). The expander opened the incision and exposed the cranium. The periosteum was removed from the parietal bones after the incision was made. The defect sites were marked, and a Dremel drill at a medium speed was used to gently carve out the margin of both defects, approximately 3 mm by 5 mm in area, in each parietal bone. The edges of the defect were checked and gently smoothed using forceps if needed. Once cleaned and cleared of excess fluid, the defect was treated intralesionally, as described below. The dermis was then pulled back over the cranium and the dermal incision closed using sutures.

The treatment groups were as follows. One defect per rat was repaired with HEALOS® (sponge-like biomimetic matrix comprising cross-linked collagen and hydroxyapatite; DuPuy Spine, Inc., Raynham, Mass.) seeded with placental stem cells ($5 \times 10^6$ cells in 500 µL), bone marrow-derived mesenchymal stem cells (BM-MSCs; obtained from fresh bone marrow aspirate (AllCells, Emeryville, Calif.)) ($5 \times 10^6$ cells in 500 µL), HEALOS® alone as a negative control, or HEALOS® supplemented with bone morphogenetic protein 2 (BMP-2) (5 µg per explant) as a positive control. In other negative control rats, the defect was not repaired. The remaining defect in each rat was repaired using HEALOS® alone.

Three weeks after implantation, rats receiving HEALOS®+BMP-2, HEALOS®+placental stem cells, and HEALOS®+BM-MSCs all showed approximately the same level of healing, and significantly greater healing of the cranial defect than rats receiving HEALOS® alone, or receiving no repair. See FIG. 1.

Thus, PDACs have the capacity to promote the healing of bone lesions, one symptom of multiple myeloma progression.

6.2 Example 2

Placental Stem Cells Suppress Osteoclast Maturation

This Example demonstrates that tissue culture plastic-adherent placental stem cells (PDACs) inhibit maturation of osteoclast precursors. Suppression of osteoclast precursors would provide a benefit to multiple myeloma patients suffering from bone lesions (and attendant symptoms) caused by myeloma-induced osteoclast overproduction.

Human osteoclast precursors, obtained by enriching $CD14^+$ cells from peripheral blood mononuclear cells (PB-MCs) using an EASYSEP® Human CD14 Positive Selection Kit (Cat#18058), were prepared in 24 well plates and cultured in the medium αMEM supplemented with macrophage colony stimulating factor (M-CSF) and Receptor Activator for Nuclear Factor κ B Ligand (RANKL; see Yaccoby et al., *Cancer Research* 64(6):2016-2023 (2004)). Placental stem cells, isolated as described in Example 1, or fetal mesenchymal stem cells (MSC), were cultured with osteoclast precursors in noncontact conditions by seeding the cells on 1 µm TRANSWELLs® (COSTAR®; CORNING®, New York) (10,000 cells/TRANSWELL®) and coculturing the placental stem cells or MSCs with the osteoclast precursors for 5-6 days. At the end of the culturing, the TRANSWELLs® were removed and osteoclast precursors and/or osteoclasts were examined for evidence of apoptosis by staining for annexin V and propidium iodide (PI) using an annexin V/PI kit (Caltag Labs., Burlingame, Calif.). Annexin V binds phosphatidylserine, which is transported from the inner leaflet of the plasma membrane to the outer leaflet during apoptosis; cells with intact plasma membranes exclude propidium iodide. Thus, cells that are positive for annexin staining but not PI staining are early apoptotic cells; cells positive for both annexin staining and PI staining are late apoptotic cells.

The placental stem cells were found to significantly induce apoptosis and reduce viability of osteoclast precursors compared to controls in which multiple myeloma cells were grown without placental stem cells, as shown by increased Annexin V and propidium iodide staining.

Cells in the TRANSWELLs® were fixed with formalin and stained for tartrate resistant acid phosphatase (TRAP; an osteoclast marker). The numbers of multinucleated TRAP-expressing osteoclasts were counted in each well. Placental stem cells, isolated as described in Example 1, inhibited differentiation of osteoclasts, as indicated by a lessening of TRAP staining in histological sections, and by a significant ($p<0.05$) decrease in the number of TRAP-positive osteoclasts (FIG. 2).

Thus, placental stem cells can not only repair bone lesions, but can reduce the number and activity of osteoclasts that would create or contribute to such lesions.

6.3 Example 3

Placental Stem Cells Inhibit the Growth of Multiple Myeloma Cells

This Example demonstrates that tissue culture plastic-adherent placental stem cells (PDACs) are able to suppress the proliferation of multiple myeloma cells both in vitro and in vivo.

6.3.1 PDAC Suppression of Multiple Myeloma Cell Proliferation In Vitro

Human multiple myeloma cell lines BN, JB, DNC and HLE (see Li et al., *Br. J. Haematol.* 138(6):802-11 (2007)), and ARP1 were established at the Myeloma Institute for Research and Therapy at the University of Arkansas for Medical Sciences. The multiple myeloma cell line U266 (Nilsson et al., *Clin. Exp. Immunol.* 7:477 (1970)) was obtained from the American type Culture Collection. These cell lines were transfected with a luciferase/GFP lentiviral construct by established methods (see Li et al., ibid.) to facilitate tracking and analysis of tumor growth in the presence of placental stem cells in cell-to-cell contact conditions. BN, JB and DNC are stroma-dependent cell lines. Placental stem cells, fetal MSC (FB-MSC), and MSC generated from bone marrow of patients with multiple myeloma (Pt-MSC) were cultured in 96 well plates at about 10,000 cells/well). Multiple myeloma cells (10,000 cells/well) were co-cultured with placental stem cells or MSCs for a week in RPMI media supplemented with 10% FBS and antibiotics. At the end of culture, growth of the multiple myeloma cells was determinable by measurement of luciferase activity.

The results of this study are summarized in FIG. 3, showing fold growth of multiple myeloma cells in the presence of placental stem cells compared to growth in the presence of FB-MSC and Pt-MSCs. Multiple myeloma cell growth in the presence of placental stem cells varied depending on the particular cell line, but growth for each cell line was significantly lower for cell lines co-cultured with placental stem cells than for cell lines co-cultured with fetal MSCs or patient MSCs.

MSCs, and placental stem cells isolated as described in Example 1, were also induced to differentiate into osteoblasts through incubation with DMEM/10% fetal bovine serum (FBS) conditioned by osteoblast osteogenesis factors (e.g., ascorbic acid, beta glycerophosphate and dexamethasone) for approximately 3-3.5 weeks (see Yaccoby et al., *Haemato-*

*logica* 91(2):192-199 (2006)). For testing effects on growth of multiple myeloma cell lines, the plates were washed with PBS to remove osteoblastic factors. Multiple myeloma cell growth in co-culture with osteoblasts generated from FB-MSC or Pt-MSC was reduced as compared to growth of multiple myeloma cells in co-culture with FB-MSC or Pt-MSC. Differentiation of placental stem cells into osteoblasts had no effect on growth of, or slightly reduced the growth of, multiple myeloma cell lines as compared to co-culture with placental stem cells. The experiment was repeated 3 times for most of the cell lines.

To study the possible effect of cell-cell contact, cells were cultured in a system in which cell-cell contact is prevented. In particular, MSCs (FB-MSCs or BM-MSCs), or placental stem cells isolated as described in Example 1, were cultured in a TRANSWELL® system on the back side of 24-well TRANSWELL® membranes, while multiple myeloma plasma cells were cultured on the upper chamber of the TRANSWELL®. See FIG. 4. Primary multiple myeloma cells from 6 patients were isolated using CD138-immunomagnetic bead separation and co-cultured at 500,000 multiple myeloma cells/well with MSCs or placental stem cells (100,000 cells/TRANSWELL®) for 6-10 days. CD138 is a marker of plasma cells.

The effects of co-cultures on multiple myeloma cell viability were determined by trypan blue exclusion and by an MTT (3-(4,5-dimethylthiazol-2-yl)-2,5-diphenyltetrazolium bromide) assay. The MTT assay is a colorimetric assay for measuring the activity of enzymes that reduce MTT to formazan, giving a purple color. This reduction takes place only when mitochondrial reductase enzymes are active, and therefore conversion is often used as a measure of viable cells. In one experiment, multiple myeloma cells were also subjected to annexin V/PI flow analysis, as described in Example 2, above. Survival of primary multiple myeloma cells was reduced in the TRANSWELL® co-culture with placental stem cells as compared to survival in TRANSWELL® co-culture with fetal MSC, for myeloma cells from most patients tested. See FIG. 5.

6.3.2 Placental Stem Cell Suppression of Multiple Myeloma Cell Proliferation and Increase in Bone Mass In Vivo The pLEGFP retroviral vector containing an Enhanced Green Fluorescent Protein (EGFP) coding sequence (Clontech, Palo Alto, Calif., USA) was used to transiently transfect the packaging cell line Phoenix Eco (ecotropic) using SuperFect (QIAGEN Inc., Valencia, Calif., USA). EGFP is a red-shifted variant of wild-type *Aequorea victoria* green fluorescent protein that has been optimized for brighter fluorescence and higher expression in mammalian cells. Supernatants containing retroviral particles were collected 24-48 hours after transfection. To facilitate tracking, placental stem cells were infected with the retroviral particles in the presence of 8 μg/ml polybrene for 12 hours at which time the media were replaced with fresh culture medium. In some experiments, cells were exposed to the supernatants containing the viral particles once more before being selected by culturing them in the presence of 200-400 μg/ml of G418 for 2-3 weeks.

As an alternative to using human bone tissue in a SCID-hu model of primary human myeloma, a system in which rabbit bones were implanted into SCID mice (SCID-rab mice), followed by introduction of myeloma cells directly into the implanted bone, was used. Myelomatous SCID-rab mice were constructed as previously described. See Yata, K. and Yaccoby, S., et al, Leukemia 2004; 18:1891-1897. CB.17/Icr-SCID mice (6-8-week old) were obtained from Harlan Sprague Dawley (Indianapolis, Ind., USA) and pregnant New Zealand rabbits from Myrtle Rabbitry (Thompson Station, Tenn., USA). The 3-4-week-old rabbits were deeply anesthetized with a high dose of pentobarbital sodium and killed by cervical dislocation. The rabbit femora and tibiae were cut into two pieces, with the proximal and distal ends kept closed, while the vertebrae were cut into small fragments (1×2 cm$^2$).

For bone implantation, the right or left side of the SCID mouse was rinsed with alcohol and blotted with sterile gauze. The rabbit bone was inserted subcutaneously through a small (5 mm) incision. The incision was then closed with sterile surgical staples, and engraftment of the bones was allowed to take place for 6-8 weeks. In some experimental mice, two bones were simultaneously implanted contralaterally in the same mouse. For each experiment, 10-50×10$^6$ unseparated human patient-derived myeloma bone marrow cells containing 17+/−8% plasma cells (PCs) or 3.3+/−1.6×10$^6$ PCs in 50 μl of phosphate-buffered saline (PBS) were injected directly into the implanted rabbit bone. At least two mice were used for each experiment. Mice were periodically bled from the tail vein to measure changes in levels of circulating human immunoglobulin (Ig) of the M-protein isotype.

Establishment of myeloma growth was demonstrated by increased levels of human monoclonal immunoglobulins (hIg) in mouse sera, as seen by ELISA, and by radiographic evaluation of lytic bone lesions. 5×10$^5$ EGFP-expressing placental stem cells, isolated as described in Example 1 prior to transformation, were collected with the use of trypsin-EDTA and resuspended in 50 μl PBS. The placental stem cells were injected directly into the implanted bones in the SCID-rab mice. Experiments were continued for 8-16 weeks post-injection. Changes in the bone mineral density (BMD) of the implanted bones were determined using a PIXImus DEXA densitometer (GE Medical Systems LUNAR, Madison, Wis.). The effect of the placental stem cells on multiple myeloma cell proliferation was determined by tracking the levels of human monoclonal immunoglobulins (hIg) in mouse sera, as seen by ELISA.

Multiple myeloma cells from one patient (designated Patient 1) were found to grow in SCID-rab/SCID-hu mice, and could be passaged to newly constructed SCID-rab/SCID-hu mice; however, they were not able to grow independently or on stromal layer in vitro. Six SCID-rab mice successfully engrafted with the multiple myeloma cells were administered transfected placental stem cells intralesionally, and six were administered a control (phosphate buffered saline).

Growth of multiple myeloma cells was found to be significantly inhibited at two and four weeks after injection of placental stem cells, but not PBS, by detection of human monoclonal immunoglobulins (hIg) in sera from the mice, as seen by ELISA (p<0.007; FIG. 6). Bioluminescence analysis in live animals detected luciferase-expressing placental stem cells in these mice; bioluminescence intensity at 14 days was reduced in all mice administered placental stem cells (Table 1B). Further, X-rays taken before administration of placental stem cells and 4 weeks after treatment revealed increased bone mass following placental stem cell injection into myelomatous bones, but reduced bone mass in control PBS-treated bones (FIG. 7).

TABLE 1B

Results of live bioluminescence assays - numbers of counts per animal.

| Mouse | 1 | 2 | 3 | 4 | 5 |
|---|---|---|---|---|---|
| 3 days | $5.20 \times 10^6$ | $6.50 \times 10^5$ | $8.3 \times 10^6$ | $2.30 \times 10^7$ | $3.30 \times 10^6$ |
| 14 days | $2.68 \times 10^4$ | ND | $2.80 \times 10^5$ | $1.10 \times 10^6$ | $2.00 \times 10^4$ |

To test the effect of placental stem cells on the bone mass density of nonmyelomatous bone, placental stem cells ($1 \times 10^6$ cells/mouse) or vehicle were injected directly into the implanted nonmyelomatous bones in SCID-rab mice. Injection of the placental stem cells, but not vehicle, resulted in marked increased of BMD of the implanted bone from pretreatment levels. These data indicate that direct injection of placental stem cells into myelomatous or nonmyelomatous bone resulted in increased local bone mass, and that increased bone formation by placental stem cells was associated with reduced myeloma burden.

Next we utilized myeloma cells from a second patient, designated Patient 2, which are molecularly classified as a high risk, MMSET subtype (associated with aggressive multiple myeloma and a poor prognosis) and express moderate level of DKK1. Patient 2 myeloma cells did not grow in culture but were successfully passaged in the SCID-rab model described above. Treatment was initiated when myeloma growth was well established and osteolytic lesions were evident. Placental stem cells were injected intralesionally into the implanted bone ($0.1$-$1 \times 10^6$ placental stem cells/bone, 7 hosts/group) or subcutaneously using a HyStem-C hydrogel carrier ($5 \times 10^6$ placental stem cells/mouse, 6 mice). Analyzed 4 weeks after treatment, intralesional injection of 0.5 and $1 \times 10^6$ placental stem cells resulted in increased BMD of the implanted bones from pretreatment levels ($p<0.01$) or prevention of bone loss compared to control group ($p<0.02$) (FIG. 8). Increased bone mass by injection of $1 \times 10^6$ placental stem cells was additionally associated with reduced myeloma growth at near significant level ($p<0.08$, FIG. 9).

The effect of placental stem cells and human fetal MSCs on myeloma bone disease and tumor growth was also compared. Cells were injected ($1 \times 10^6$ cells/mouse) directly into the implanted bones of SCID-rab mice engrafted with Patient 2 myeloma cells (7 hosts/group). Placental stem cells and MSC treatment resulted in increased BMD of the implanted bone as compared to pretreatment level, however the effect of placental stem cells was more profound (FIG. 10). Both placental stem cells and MSC treatment significantly inhibited growth of patient #2 myeloma cells in the SCID-rab model (FIG. 11).

These results suggest that, while both MSCs and placental stem cells are effective in increasing BMD of myeloma-affected bones, placental stem cells have higher bone anabolic potential than fetal MSCs.

Thus, this Example demonstrates that placental stem cells can significantly reduce the viability of multiple myeloma cells, particularly when administered intralesionally into myelomatous individuals. Placental stem cells also reduce the viability of multiple myeloma cells in vitro in conditions allowing cell-cell contact, and in conditions preventing cell-cell contact. Coupled with the ability of placental stem cells to repair bone, e.g., bone lesions that are symptomatic of multiple myeloma, and to inhibit osteoclast maturation, a major cause of the development of multiple myeloma-related bone lesions, these results indicate that placental stem cells can be a useful anti-multiple myeloma therapeutic.

6.4 Example 4

Placental Stem Cells Promote Multiple Myeloma Cell Cycle Arrest

This Example demonstrates that tissue culture plastic-adherent placental stem cells (PDACs) suppress the growth of multiple myeloma cells.

6.4.1 Placental Stem Cells Suppress Multiple Myeloma Cell Proliferation

To study the effect of placental stem cells on the growth of multiple myeloma cells, placental stem cells, isolated as described in Example 1, were co-cultured with 6 multiple myeloma cell lines (MMCLs), designated U-266 (American Type Culture Collection (ATCC) Catalog No. TIB-196), RPMI-8226 (ATCC Catalog No. CCL-155), L-363 (Deutsche Sammlung von Mikroorganismen and Zellkulturen GmbH (DSMZ) Catalog No. ACC49), H929 (Gazdar, *Blood* 67:1542-1549 (1986)), LP-1 (DSMZ Catalog No. ACC41) and OPM-2 (DSMZ Catalog No. ACC-50). The four multiple myeloma cell lines selected for these experiments represent the heterogeneity of multiple myeloma cells, as seen by differences in the production of immunoglobulins (see Table 2) and differences in cellular marker expression (see Tables 3A-3C).

TABLE 2

Production of immunoglobulin types by multiple myeloma cell lines

| Cell line | IgA | IgG | Kappa chain | Lambda chain |
|---|---|---|---|---|
| H-929 | 0.0 | 0.1 | 98.9 | 0.9 |
| OPM-2 | 0.6 | 0.1 | 3.5 | 97.3 |
| RPMI-8226 | 0.0 | 0.0 | 0.9 | 85.8 |
| U266 | 0.0 | 0.1 | 1.2 | 99.5 |

Table 3A-3C: Cellular markers expressed by multiple myeloma cell lines (expressed as percentage of cells expressing a marker).

TABLE 3A

| Sample | CD38+ | CD56+ | CD19+ | CD45+ | CD11b+ | CD40+ | CD138+ |
|---|---|---|---|---|---|---|---|
| H929 | 97.7 | 98.6 | 0.74 | 2.3 | 7.56 | 0.18 | 72.9 |
| OPM-2 | 13.2 | 21.2 | 0.062 | 0.21 | 56.9 | 0.14 | 7.33 |
| RPMI-8226 | 96.7 | 64.4 | 0.093 | 0.3 | 29.4 | 18.3 | 16.7 |
| U266 | 4.39 | 3.39 | 0.64 | 91.5 | 2.51 | 0.84 | 16.6 |

TABLE 3B

| Cell line | CD58+ | CXCR4 (CD184)+ | CD44+ | CD49e (VLA5)+ | CD117+ | CD20+ |
|---|---|---|---|---|---|---|
| H929 | 99.8 | 0.65 | 99.7 | 51.1 | 27.1 | 0.54 |
| OPM-2 | 29 | 8.14 | 21.2 | 0.35 | 0.53 | 0.31 |

TABLE 3B-continued

| Cell line | CD58+ | CXCR4 (CD184)+ | CD44+ | CD49e (VLA5)+ | CD117+ | CD20+ |
|---|---|---|---|---|---|---|
| RPMI-8226 | 95.8 | 4.2 | 6.48 | 67.6 | 7.73 | 0.057 |
| U266 | 100 | 83.5 | 48.3 | 0.55 | 0.28 | 1.21 |

TABLE 3C

| Cell line | CD33+ | CD54+ | CD28+ | CD49d (VLA4)+ | CD106+ | CD11a+ |
|---|---|---|---|---|---|---|
| H929 | 0.76 | 99.2 | 95.3 | 99.6 | 0.2 | 12.4 |
| OPM-2 | 0.2 | 1.01 | 2.44 | 0.059 | 0.2 | 0.1 |
| RPMI-8226 | 26.2 | 99.9 | 99.7 | 2.75 | 6.39 | 46.5 |
| U266 | 6.83 | 100 | 99.9 | 99.5 | 0.58 | 5.77 |

Passage 6 placental stem cells, isolated as described in Example 1, were thawed with DMEM+10% fetal calf serum (FCS). $5 \times 10^4$ placental stem cells were plated in 24-well plate per well. After the placental stem cells grew to confluency, with a one time medium change, $5 \times 10^4$ MMCL cells per well were plated on the top of the placental stem cells, and incubated at 37° C. under 5% $CO_2$ for 4-5 days. MMCL cells were harvested on days 1, 2 and 5 of culture for further analysis. Cells were counted using the EASYCOUNT™ System (Immunicon).

Results indicated that the placental stem cells achieved significant growth inhibition of multiple myeloma cell lines U266 ($p<0.001$ at day 5 of co-culture), RPMI-8226 ($p<0.03$ at day 5 of co-culture), H929 ($p<0.003$ at day 4 of co-culture), and OPM-2 ($p<0.01$ at day 5 of co-culture), compared to these multiple myeloma cells cultured alone. See FIG. 12. In separate experiments, co-culture of L-363 cells with placental stem cells resulted in substantial inhibition of growth ($p<0.06$ at day 5 of co-culture), and co-culture of LP-1 cells with placental stem cells also resulted in inhibition of growth.

6.4.2 Placental Stem Cells Downregulate Multiple Myeloma Cell Expression of Genes Encoding Proteins that Play Key Roles in NF-κB Signaling and B Cell Activation To further characterize the growth inhibition of the placental stem cells on the multiple myeloma cell lines, the placental stem cells, isolated as described in Example 1, were co-cultured with U-266, RPMI-8226, OPM-2 and H929 cells for 4 days, then multiple myeloma cells co-cultured with placental stem cells, or multiple myeloma cells cultured alone were collected by gentle pipetting without disturbing placental stem cells followed by RNA preparation and quantitative real-time PCR (qRT-PCR) analysis. qRT-PCR was performed using 384-well microfluidic cards (TAQMAN® Custom Array, Applied Biosystems), which enable simultaneous realtime PCR reactions. The cards contained 300 genes involved in cell cycle regulation, cellular growth and proliferation, and hormonal immune response, including genes involved in B cell signaling and NF-θB signaling. qRT-PCR was performed using 7900HT Fast Real-Time PCR System (Applied Biosystems), and data was analyzed using REALTIME STAT-MINER® software.

Co-culture with the placental stem cells significantly downregulated genes encoding key components of B cell activation, including TRAF1 (TNF Receptor Associated Factor 1), TRAF6, and genes encoding key components of the NF-θB signaling pathway, including TIRAP (Toll-Interleukin 1 Receptor TIR domain containing Adaptor Protein); p65/RelA, and RelB. See Table 4, below.

DKK1, a protein produced by multiple myeloma cells, inhibits the activity of osteoblasts and tips the balance between osteoblasts and osteoclasts in favor of bone resorption. After co-culture with placental stem cells as above, DKK1 expression in OPM-2 cells was downregulated as well. See Table 4.

TABLE 4

Fold change of gene expression in OPM-2 co-cultured with placental stem cells in comparison with OPM-2 alone.

| Gene | Fold Change | STDEV |
|---|---|---|
| DKK1 | 0.34 | 0.09 |
| RELA | 0.72 | 0.03 |
| RELB | 0.27 | 0.08 |
| TIRAP | 0.49 | 0.05 |
| TRAF1 | 0.44 | 0.07 |
| TRAF6 | 0.50 | 0.12 |

Standard deviation was calculated for means of fold change for 2 replicates.
STDEV: Standard Deviation.

6.4.3 Placental Stem Cells Downregulate Multiple Myeloma Cell Expression of Genes Encoding Cyclins and CDKs, and Upregulate Genes Encoding CDK Inhibitors The effect of the placental stem cells (PDACs), isolated as described in Example 1, on the expression of cyclins (CCNs) and cyclin-dependent kinases (CDKs) was analyzed by qRT-PCR using 384-well microfluidic cards containing genes involved in cell cycle regulation, as described above, and analyzed using Ingenuity Pathways Analysis (INGENUITY® Systems, www.ingenuity.com). The placental stem cells were found to decrease expression in the multiple myeloma cell lines of genes encoding certain CCNs and CDKs, and to increase expression of genes for certain CDK inhibitors in a cell type-specific manner. For example, in multiple myeloma cell line OPM-2, the CDKs CDK3, CDK5, and CDK7 were downregulated; in multiple myeloma cell lines RPMI-8226 and U-266, CDK4 was downregulated. In contrast, in multiple myeloma cell line OPM-2, CDK inhibitors p16, and p19, and CDK inhibitor 3 were upregulated; in multiple myeloma cell line RPMI-8226, CDK inhibitor p19 was upregulated; in multiple myeloma cell line U266 p21 was upregulated; and in multiple myeloma cell line H929, p19, p21 and p27 were all upregulated.

A summary of changes in expression of cell cycle-related genes is presented below in Tables 5A-5D.

Tables 5A-5D. Fold change of gene expression in multiple myeloma cells co-cultured with placental stem cells in comparison with multiple myeloma cells alone for multiple myeloma cell lines OPM-2, U-266, RPMI-8226, and H929. Standard deviation was calculated for means of fold change for 2 replicates.

TABLE 5A

OPM-2

| | Fold Change | STDEV |
|---|---|---|
| CCNB3 | 0.39 | 0.07 |
| CCNC | 0.63 | 0.02 |
| CCND1 | 0.01 | 0.00 |
| CDK3 | 0.82 | 0.05 |
| CDK5 | 0.82 | 0.00 |
| CDK7 | 0.73 | 0.05 |
| CDKN2A (p16) | 1.55 | 0.26 |
| CDKN2D (p19) | 1.61 | 0.25 |
| CDKN3 | 4.41 | 0.27 |

TABLE 5B

U-266

| | Fold Change | STDEV |
|---|---|---|
| CCNB1 | 0.16 | 0.01 |
| CCNB2 | 0.16 | 0.03 |
| CCND1 | 0.23 | 0.01 |
| CCND2 | 0.08 | 0.00 |
| CDK4 | 0.38 | 0.01 |
| CDKN1A (p21) | 1.45 | 0.14 |
| E2F3 | 0.80 | 0.02 |
| E2F4 | 0.44 | 0.00 |
| E2F5 | 0.30 | 0.00 |
| E2F6 | 0.22 | 0.00 |

TABLE 5C

RPMI-8226

| | Fold Change | STDEV |
|---|---|---|
| CCNB1 | 0.61 | 0.03 |
| CCNB2 | 0.82 | 0.14 |
| CCND1 | 0.64 | 0.06 |
| CCND2 | 0.68 | 0.05 |
| CDK2AP1 | 0.56 | 0.02 |
| CDK4 | 0.56 | 0.03 |
| CDKN2D (p19) | 1.41 | 0.13 |
| E2F3 | 0.67 | 0.02 |
| E2F4 | 0.75 | 0.10 |
| E2F5 | 0.52 | 0.02 |
| E2F6 | 0.63 | 0.07 |

TABLE 5D

H929

| | Fold Change | STDEV |
|---|---|---|
| CCNB1 | 0.52 | 0.03 |
| CCNB2 | 0.71 | 0.07 |
| CCNB3 | 0.54 | 0.37 |
| CCNC | 0.64 | 0.02 |
| CDK10 | 0.40 | 0.00 |
| CDK3 | 0.84 | 0.06 |
| CDK5 | 0.83 | 0.09 |
| CDK9 | 0.82 | 0.03 |
| CDKN1A (p21) | 3.71 | 0.99 |
| CDKN1B (p27) | 1.12 | 0.18 |
| CDKN2D (p19) | 1.18 | 0.08 |

Placental stem cells, isolated as described in Example 1, were also found to decrease expression in the multiple myeloma cell lines of genes encoding E2F family members 3, 4, 5 and 6 (proteins that play a major role in the transition from $G_1$ to S phase) and phosphorylated Rb (Retinoblastoma protein). This finding is significant because in the hypophosphorylated state, Rb acts as tumor suppressor by inhibiting the factors of E2F family; phosphorylated Rb, however, has little inhibitory function on cell cycle progression.

To further investigate the effect of the placental stem cells on multiple myeloma cell proliferation, the phosphorylation state of Retinoblastoma protein (Rb) was analyzed by flow cytometry using the J146-35 monoclonal antibody (BD Pharmingen, Cat#558549) and the J112-906 monoclonal antibody (Cat#558549, BD). Antibody J146-35 recognizes Rb phosphorylated at serine 780 (pS780), which affects Rb binding to E2F, and antibody J112-906 recognizes Rb phosphorylated at serines 807 and 811 (pS807/pS811), which regulate c-Abl binding and cell cycle progression. H929, LP1 and OPM2 co-cultured with the placental stem cells showed decreased RB phosphorylation at pS780, and at pS807/pS811, relative to cells cultured alone. See FIGS. 13A-13C.

The effect of the placental stem cells on the proliferation of multiple myeloma cell lines was further assayed using fluorescent the dyes BrdU and 7-AAD using an APC BrdU flow kit (Cat#552598, BD biosciences). Co-culture with the placental stem cells resulted in an increased percentage of multiple myeloma cells in G0/G1 phase, and a decreased percentage of such cells in S phase, for cell lines RPMI-8226, OPM-2 and U266, as compared to the multiple myeloma cells cultured alone. See Table 6.

TABLE 6

Cell analysis from MMCL: placental stem cell co-culture

| | G0/G1 | S phase |
|---|---|---|
| H929 | 63.5 | 27.0 |
| H929 + Placental Stem Cells | 53.9 | 28.9 |
| RPMI-8226 | 45.3 | 11.6 |
| RPMI-8226 + Placental Stem Cells | 64.9 | 9.9 |
| OPM2 | 49.2 | 42.8 |
| OPM2 + Placental Stem Cells | 78.4 | 11.5 |
| U266 | 43.0 | 19.2 |
| U266 + Placental Stem Cells | 65.9 | 9.3 |

Multiple myeloma cells secrete aberrantly high levels of immunoglobulins. To study the effect of the placental stem cells on immunoglobulin production by multiple myeloma cell lines, surface or intracellular immunoglobulin production by MMCLs co-cultured with the placental stem cells, or MMCLs cultured alone, was analyzed by flow cytometry. Decreased immunoglobulin production was observed from multiple myeloma cell lines H929, OPM2 and LP1 when co-cultured with the placental stem cells as compared to the multiple myeloma cells cultured alone. For example, co-cultured H929 cells showed decreased Kappa (κ) immunoglobulin production; co-cultured OPM2 cells showed decreased Lambda (λ) production; and co-cultured LP1 showed decreased surface and intracellular Lambda and IgG and intracellular Kappa production, compared to the cells when cultured alone. See Table 7.

TABLE 7

Change of geometric mean of Ig production in MMCL: placental stem cell co-culture system

| Cell Line | Ig | Location | Day 1 | Day 2 | Day 4 |
|---|---|---|---|---|---|
| H929 | Kappa | | — | N/A | −81.0% |
| OPM2 | Lambda | | — | −4.2% | −52.2% |
| LP1 | Lambda | surface | −9.6% | −17.9% | −48.7% |
| | Lambda | intracellular | −31.6% | −16.5% | −13.5% |
| LP1 | IgG | surface | −7.3% | −10.0% | −36.4% |
| | IgG | intracellular | −20.0% | −21.3% | −13.7% |
| LP1 | Kappa | intracellular | −15.1% | −11.4% | −13.4% |

Ig: Immunoglobulin type

The results above demonstrating that placental stem cells reduce the proliferation of multiple myeloma cells were not due to a general effect of placental stem cell co-culture with other cell types, but were specific to multiple myeloma cells. For example, the placental stem cells were found to augment expansion of $CD34^+$ hematopoietic cells when co-cultured at three different ratios (10:1, 1:1, and 1:10) over 7 days.

Thus, the above studies demonstrate that the placental stem cells, when co-cultured with multiple myeloma cell lines, reduce the growth rate of the multiple myeloma cells, down-regulate expression of multiple myeloma cell line genes encoding cell cycle proteins needed for progression through the cell cycle, and upregulate genes encoding inhibitors of cell cycle progression. As such, the placental stem cells would be useful in the reduction of proliferation of multiple myeloma cells in vivo.

6.5 Example 5

Use of Placental Stem Cells to Suppress Growth of Chondrosarcoma Cells

This Example demonstrates that placental stem cells (PDACs) suppress the proliferation of chondrosarcoma cells in culture.

TRANSWELL® culture: To examine the effects of placental stem cells, isolated as described in Example 1, on tumor cell growth in a TRANSWELL® co-culture system, $1\times10^4$ or $5\times10^4$ PDACs were seeded on the bottom chamber of the TRANSWELL® system in 600 µL, of growth medium and $1\times10^4$ chondrosarcoma cells (ATCC® No. CRL-7891; 400 µL in growth medium) were seeded on the top chamber of TRANSWELLs® (3 µm in diameter). Chondrosarcoma cells were cultured alone without placental stem cells as a control. All TRANSWELL® co-cultures were set up in 24-well plate, and each condition was set up in triplicate. After 7 days of culture in cell culture incubator at 37° C. under 5% $CO_2$, chondrosarcoma cells on the top chamber were examined using a Leica microscope.

Chondrosarcoma is a cancer characterized by the production of cartilage matrix around the tumor cells. Consistent with this symptomology, in the TRANSWELL® experiment, the chondrosarcoma cells grew as distinct aggregates, clearly visible under the microscope, in the absence of placental stem cells. In the presence of placental stem cells both ratios tested, there were visibly fewer chondrosarcoma cells, and the cells were characterized by a complete absence of cell aggregates that characterized the growth of the tumor cells alone. As such, placental stem cells clearly inhibited the growth of the chondrosarcoma cells.

6.6 Example 6

Inhibition of Osteoclastogenesis Using Lenalidomide

This Example demonstrates that the small molecule lenalidomide (sold under the trade name REVLIMID®; 3-(4-amino-1-oxo 1,3-dihydro-2H-isoindol-2-yl) piperidine-2,6-dione) can be used to suppress osteoclastogenesis.

Lenalidomide has a profound anti-osteoclastogenic effect at concentrations around 1 µM, generating a steep decline in the number of osteoclasts formed (FIG. 14). When osteoclast precursors cultured with the placental stem cells, isolated as in Example 1, and 0.1 µM or 1 µM lenalidomide, were compared to osteoclasts grown with placental stem cells or bone marrow-derived mesenchymal stem cells (BM-MSC), lenalidomide was found to further decrease the number of osteoclasts that differentiated from the osteoclast precursors. FIG. 15. Therefore, there is a possible synergistic or additive anti-osteoclastogenic effect of PDACs and lenalidomide at concentration of between about 0.1 µM to 1 µM.

Therefore, both lenalidomide alone and lenalidomide in combination with placental stem cells are effective at reducing the number of osteoclast precursors, and therefore should be therapeutic in reducing the number and/or severity of bone lesions adjunct to a bone-related cancer, such as multiple myeloma.

EQUIVALENTS

The present disclosure is not to be limited in scope by the specific embodiments described herein. Indeed, various modifications of the subject matter provided herein, in addition to those described, will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

What is claimed:

1. An in vitro method of suppressing the proliferation of cells of a bone-related cancer, comprising contacting said cells of a bone-related cancer with a plurality of placental stem cells for a time sufficient for said placental stem cells to suppress proliferation of said cells of a bone-related cancer, as compared to a plurality of said cells of a bone-related cancer not contacted with placental stem cells, wherein said placental stem cells are $CD34^-$, $CD\ 10^+$, $CD\ 105^+$ and $CD200^+$ as detectable by flow cytometry, and are not trophoblasts, cytotrophoblasts or bone marrow-derived mesenchymal stem cells, and wherein said cells of a bone-related cancer are multiple myeloma cells, chondrosarcoma cells, osteosarcoma cells, Ewing sarcoma cells, chordoma cells, cells of a malignant fibrous histiocytoma of bone, or cells of a fibrosarcoma of bone not prostate cancer cells.

2. The method of claim 1, wherein said placental cells are $CD34^-$, $CD45^-$, $CD10^+$, $CD90^+$, $CD105^+$ and $CD200^+$, as detectable by flow cytometry.

3. The method of claim 1, wherein said placental cells are $CD34^-$, $CD45^-$, $CD10^+$, $CD80^-$, $CD86^-$, $CD90^+$, $CD105^-$ and $CD200^+$, as detectable by flow cytometry.

4. The method of claim 1, wherein said placental cells suppress proliferation of said cells of a bone-related cancer by at least 50% compared to proliferation of an equivalent number of cells of a bone-related cancer in the absence of said placental cells.

5. A method of treating a bone related cancer, comprising administering to a subject having a bone-related cancer a plurality of placental stem cells for a time sufficient for said placental stem cells to suppress proliferation of cells of said bone-related cancer,
wherein said placental stem cells are $CD34^-$, $CD\ 10^+$, $CD\ 105^+$ and $CD200^+$ as detectable by flow cytometry, and are not trophoblasts, cytotrophoblasts or bone marrow-derived mesenchymal stem cells,
and wherein said cells of a bone-related cancer are multiple myeloma cells, chondrosarcoma cells, osteosarcoma cells, Ewing sarcoma cells, chordoma cells, a malignant fibrous histiocytoma of bone, or a fibrosarcoma of bone.

6. The method of claim 5, wherein said placental cells are $CD34^-$, $CD45^-$, $CD10^+$, $CD\ 90^+$, $CD\ 105^+$ and $CD200^+$, as detectable by flow cytometry.

7. The method of claim 5, wherein said placental cells are $CD34^-$, $CD45^-$, $CD10^+$, $CD80^-$, $CD86^-$, $CD\ 90^+$, $CD\ 105^+$ and $CD200^+$, as detectable by flow cytometry.

8. The method of claim 5, wherein said subject is human.

9. The method of claim 5, wherein said placental stem cells are administered at or adjacent to a bone lesion caused by said bone-related cancer.

10. The method of claim 5, wherein at least $1\times10^8$ placental stem cells are administered to said individual.

* * * * *